(12) United States Patent
Conrad

(10) Patent No.: US 10,542,861 B2
(45) Date of Patent: Jan. 28, 2020

(54) SURFACE CLEANING APPARATUS

(71) Applicant: Omachron Intellectual Property Inc., Hampton (CA)

(72) Inventor: Wayne Ernest Conrad, Hampton (CA)

(73) Assignee: Omachron Intellectual Property Inc., Hampton, Ontario (CA)

( * ) Notice: Subject to any disclaimer, the term of this patent is extended or adjusted under 35 U.S.C. 154(b) by 119 days.

(21) Appl. No.: 15/852,477

(22) Filed: Dec. 22, 2017

(65) Prior Publication Data

US 2019/0082907 A1 Mar. 21, 2019

Related U.S. Application Data

(60) Provisional application No. 62/559,151, filed on Sep. 15, 2017.

(51) Int. Cl.
*A47L 11/40* (2006.01)
*A47L 11/30* (2006.01)
(Continued)

(52) U.S. Cl.
CPC .......... *A47L 11/4088* (2013.01); *A47L 5/38* (2013.01); *A47L 7/0004* (2013.01); *A47L 7/009* (2013.01);
(Continued)

(58) Field of Classification Search
CPC ...... A47L 11/4088; A47L 7/02; A47L 11/302; A47L 11/4041; A47L 11/4044; A47L 11/4083; A47L 5/38; A47L 7/0023; A47L 9/248; A47L 11/4036; A47L 11/4016; A47L 11/4027; A47L 5/225; A47L 5/24; A47L 5/30; A47L 5/32; A47L 5/36; A47L 7/0028; A47L 9/122; A47L 9/127; A47L 9/1641; A47L 9/242; A47L 11/4005; A47L 7/0004; A47L 11/4091; A47L 7/0009; A47L 9/1625; A47L 11/34; A47L 9/2826; A47L 9/2847; A47L 9/2857; A47L 11/30; A47L 7/0038; A47L 9/1608; A47L 9/1683; A47L 9/18; A47L 7/0014; A47L 9/165; A47L 9/1666; A47L 11/201; A47L 7/009;
(Continued)

(56) References Cited

U.S. PATENT DOCUMENTS 3,543,325 A 12/1970 Hamrick
4,559,666 A 12/1985 Duncan et al.
(Continued)

FOREIGN PATENT DOCUMENTS

CA 978485 A1 11/1975
CN 1212095 C 7/2005
(Continued)

OTHER PUBLICATIONS

Machine English Translation of the Abstract of CN1212095, published on Jul. 27, 2005.

*Primary Examiner* — David Redding
(74) *Attorney, Agent, or Firm* — Philip C. Mendes da Costa; Bereskin & Parr LLP/S.E.N.C.R.L., s.r.l.

(57) ABSTRACT

An upright surface cleaning apparatus, such as an extractor, has an upright section moveably mounted to a surface cleaning head and a recline limiter system adapted to inhibit the upright section reclining to a positon at which recovered water enters the separator.

19 Claims, 97 Drawing Sheets

(51) Int. Cl.
| | |
|---|---|
| B01D 36/00 | (2006.01) |
| B01D 45/16 | (2006.01) |
| A47L 11/20 | (2006.01) |
| B04C 9/00 | (2006.01) |
| A47L 7/02 | (2006.01) |
| A47L 5/38 | (2006.01) |
| A47L 7/00 | (2006.01) |
| A47L 9/24 | (2006.01) |
| B01D 29/35 | (2006.01) |
| B04C 3/06 | (2006.01) |
| A47L 9/16 | (2006.01) |
| A47L 11/34 | (2006.01) |
| A47L 9/28 | (2006.01) |
| A47L 9/18 | (2006.01) |
| A47L 9/06 | (2006.01) |
| A47L 11/202 | (2006.01) |
| B01D 45/12 | (2006.01) |
| B04C 3/00 | (2006.01) |
| B01D 45/08 | (2006.01) |
| B01D 50/00 | (2006.01) |

(52) U.S. Cl.
CPC ........... *A47L 7/0009* (2013.01); *A47L 7/0014* (2013.01); *A47L 7/0023* (2013.01); *A47L 7/0038* (2013.01); *A47L 7/02* (2013.01); *A47L 9/0633* (2013.01); *A47L 9/165* (2013.01); *A47L 9/1608* (2013.01); *A47L 9/1625* (2013.01); *A47L 9/1666* (2013.01); *A47L 9/1683* (2013.01); *A47L 9/18* (2013.01); *A47L 9/248* (2013.01); *A47L 9/2826* (2013.01); *A47L 9/2847* (2013.01); *A47L 9/2857* (2013.01); *A47L 11/201* (2013.01); *A47L 11/202* (2013.01); *A47L 11/30* (2013.01); *A47L 11/302* (2013.01); *A47L 11/34* (2013.01); *A47L 11/4013* (2013.01); *A47L 11/4016* (2013.01); *A47L 11/4027* (2013.01); *A47L 11/4036* (2013.01); *A47L 11/4041* (2013.01); *A47L 11/4044* (2013.01); *A47L 11/4083* (2013.01); *A47L 11/4091* (2013.01); *A47L 11/4094* (2013.01); *B01D 29/35* (2013.01); *B01D 36/003* (2013.01); *B01D 45/16* (2013.01); *B04C 3/06* (2013.01); *B04C 9/00* (2013.01); *B01D 45/08* (2013.01); *B01D 45/12* (2013.01); *B01D 50/002* (2013.01); *B01D 2279/55* (2013.01); *B04C 2003/006* (2013.01); *B04C 2009/002* (2013.01); *B04C 2009/008* (2013.01)

(58) Field of Classification Search
CPC .. A47L 9/0633; A47L 11/202; A47L 11/4013; A47L 11/4094; B04C 2003/006; B04C 2009/002; B04C 2009/008; B04C 3/06; B04C 9/00; B01D 45/08; B01D 50/002; B01D 2279/55; B01D 29/35; B01D 36/003; B01D 45/16; B01D 45/12
See application file for complete search history.

(56) References Cited

U.S. PATENT DOCUMENTS

| | | | | |
|---|---|---|---|---|
| 4,896,142 | A | * | 1/1990 | Aycox .................. A47L 11/34 340/604 |
| 5,135,552 | A | | 8/1992 | Weistra |
| 6,344,064 | B1 | | 2/2002 | Conrad |
| 6,832,407 | B2 | * | 12/2004 | Salem .................. A47L 7/0028 15/319 |
| 7,048,783 | B2 | * | 5/2006 | Ponjican .............. A47L 7/0004 15/353 |
| 7,247,181 | B2 | | 7/2007 | Hansen et al. |
| 7,293,324 | B2 | * | 11/2007 | Chui .................... A47L 7/0028 15/319 |
| 7,473,289 | B2 | | 1/2009 | Oh et al. |
| 7,887,613 | B2 | | 2/2011 | Ruben |
| 8,695,159 | B2 | | 4/2014 | Van Der Kooi et al. |
| 8,850,654 | B2 | | 10/2014 | Nolan et al. |
| 2008/0148512 | A1 | * | 6/2008 | Beskow ................ A47L 9/04 15/350 |
| 2011/0056044 | A1 | * | 3/2011 | Reed, Jr. .............. A47L 11/34 15/320 |
| 2014/0059983 | A1 | | 3/2014 | Ho |
| 2017/0119225 | A1 | | 5/2017 | Xia et al. |

FOREIGN PATENT DOCUMENTS

| | | |
|---|---|---|
| EP | 1707094 B1 | 4/2012 |
| GB | 539973 A | 10/1941 |
| GB | 2522658 B | 4/2016 |

* cited by examiner

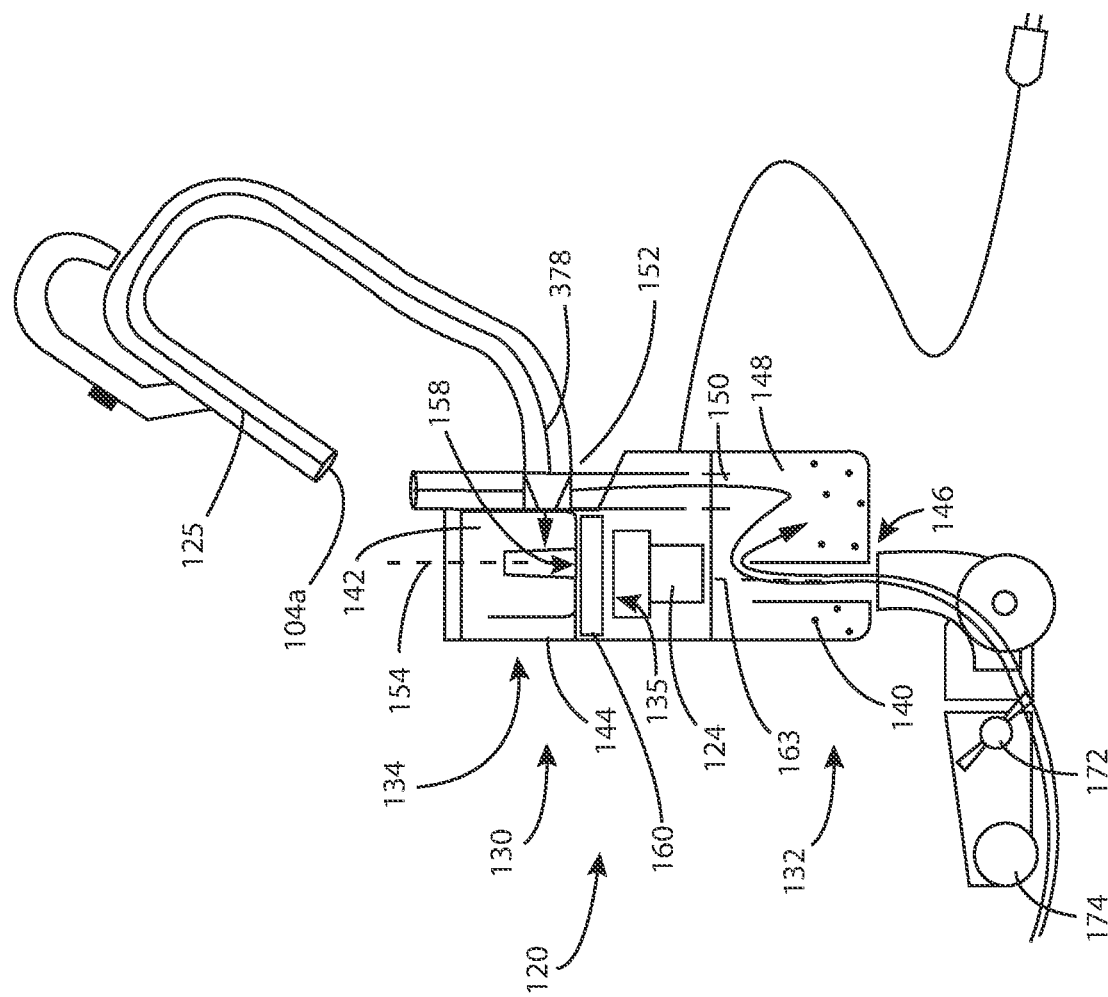

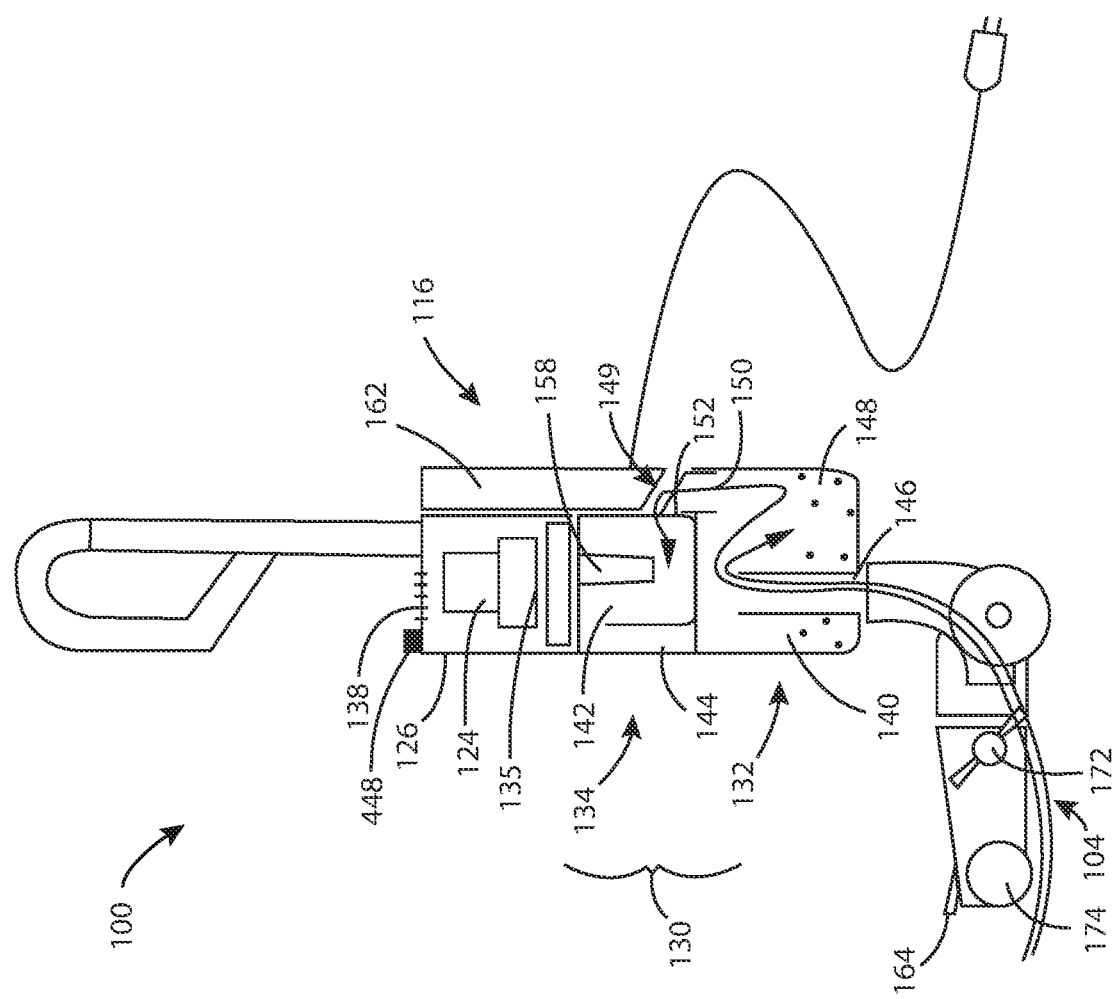

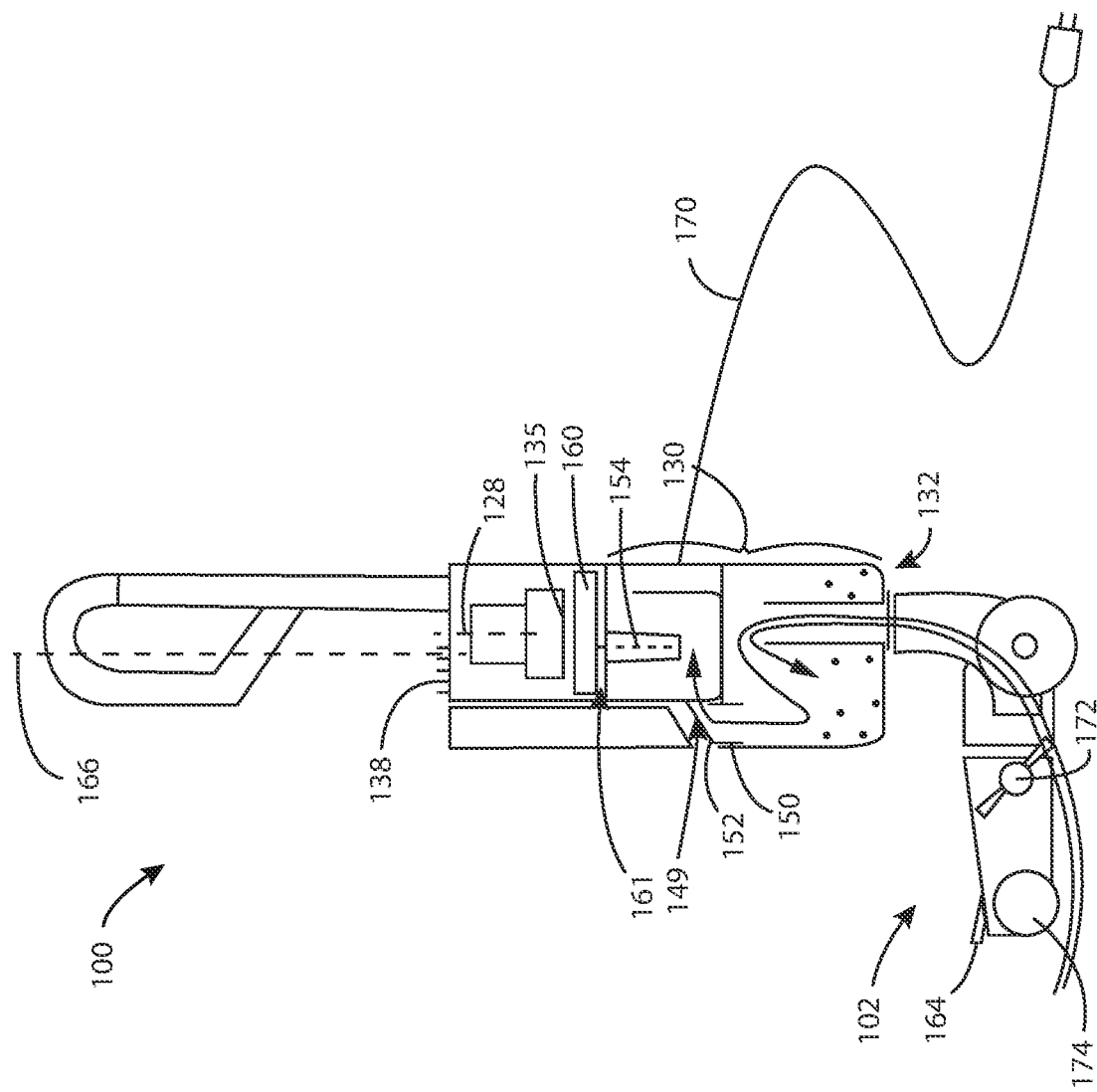

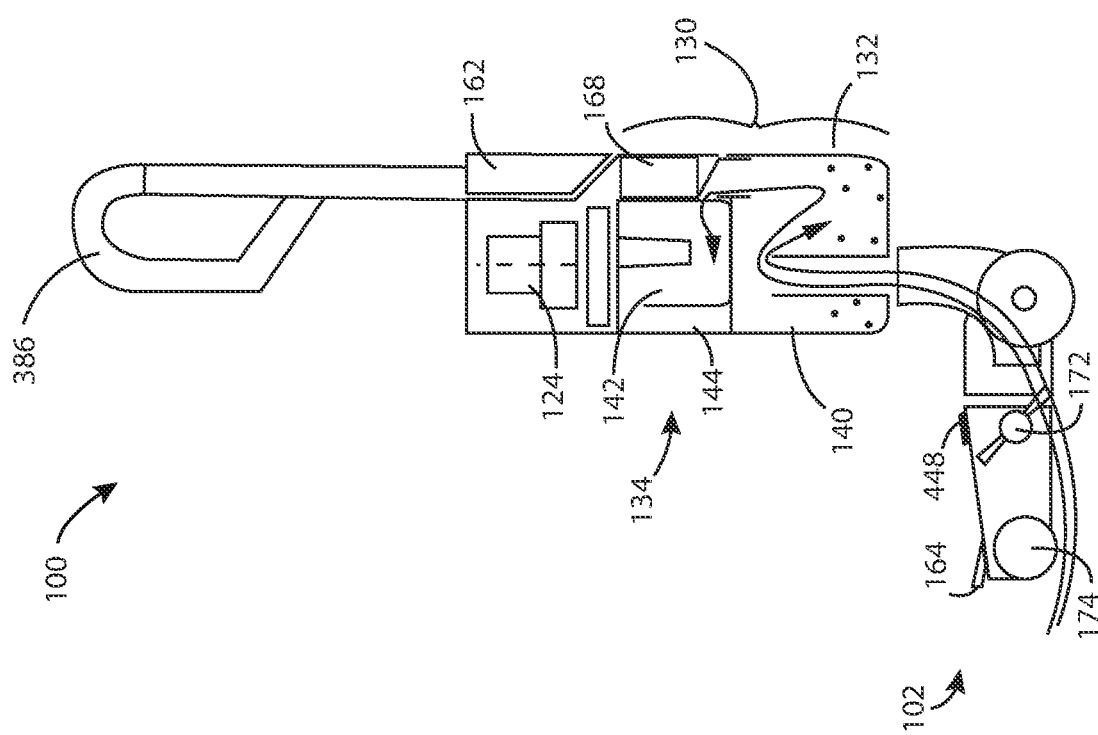

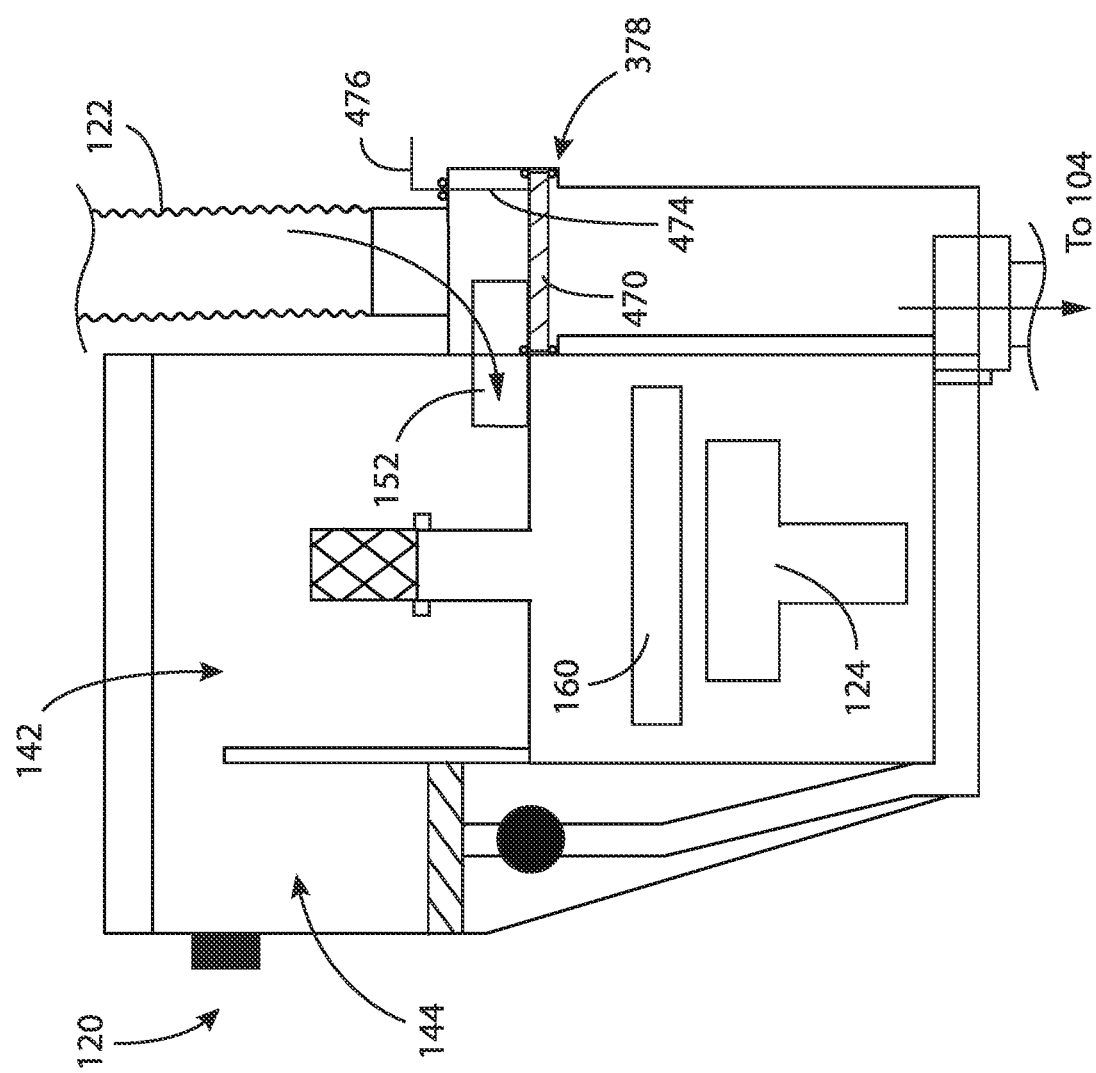

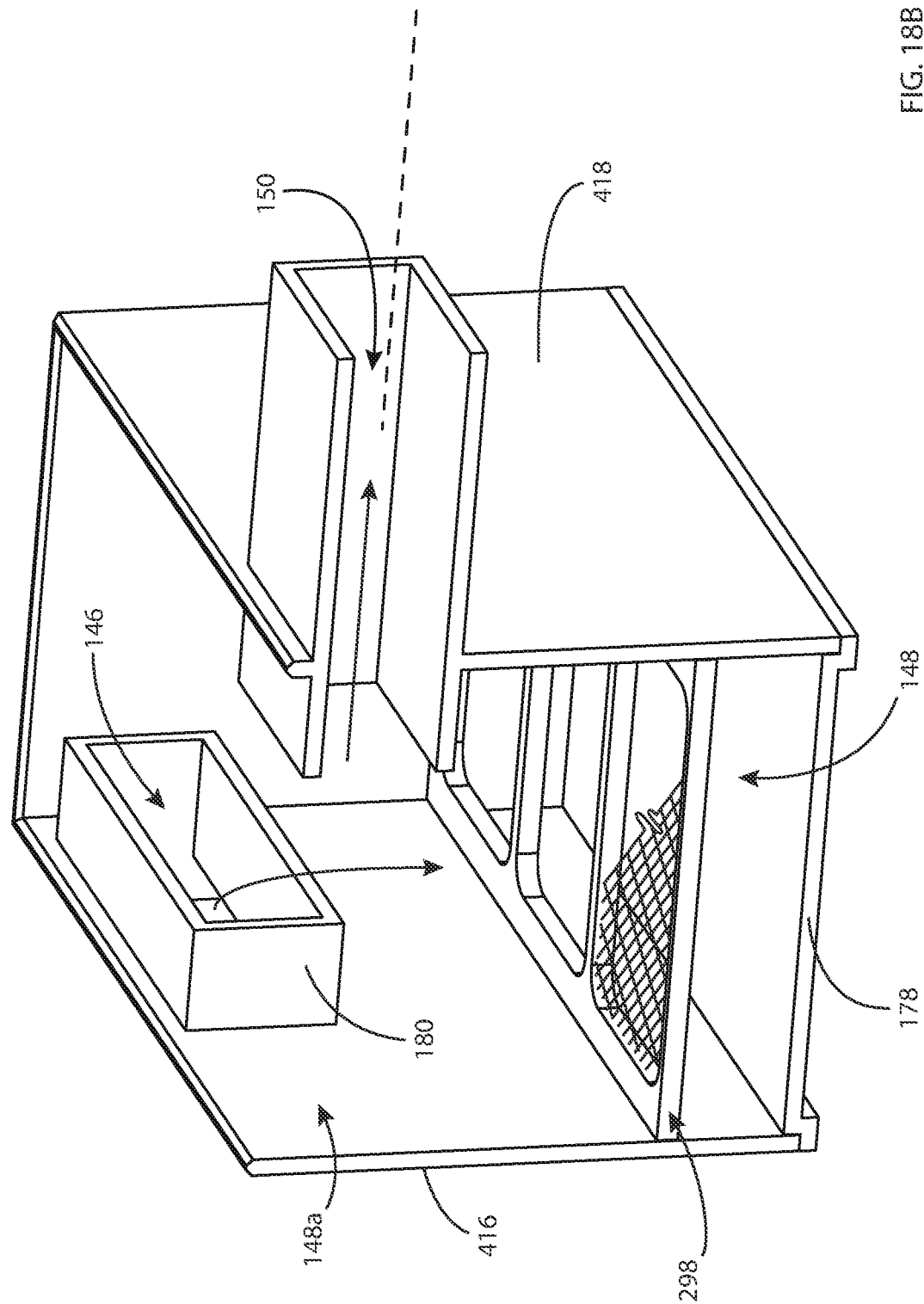

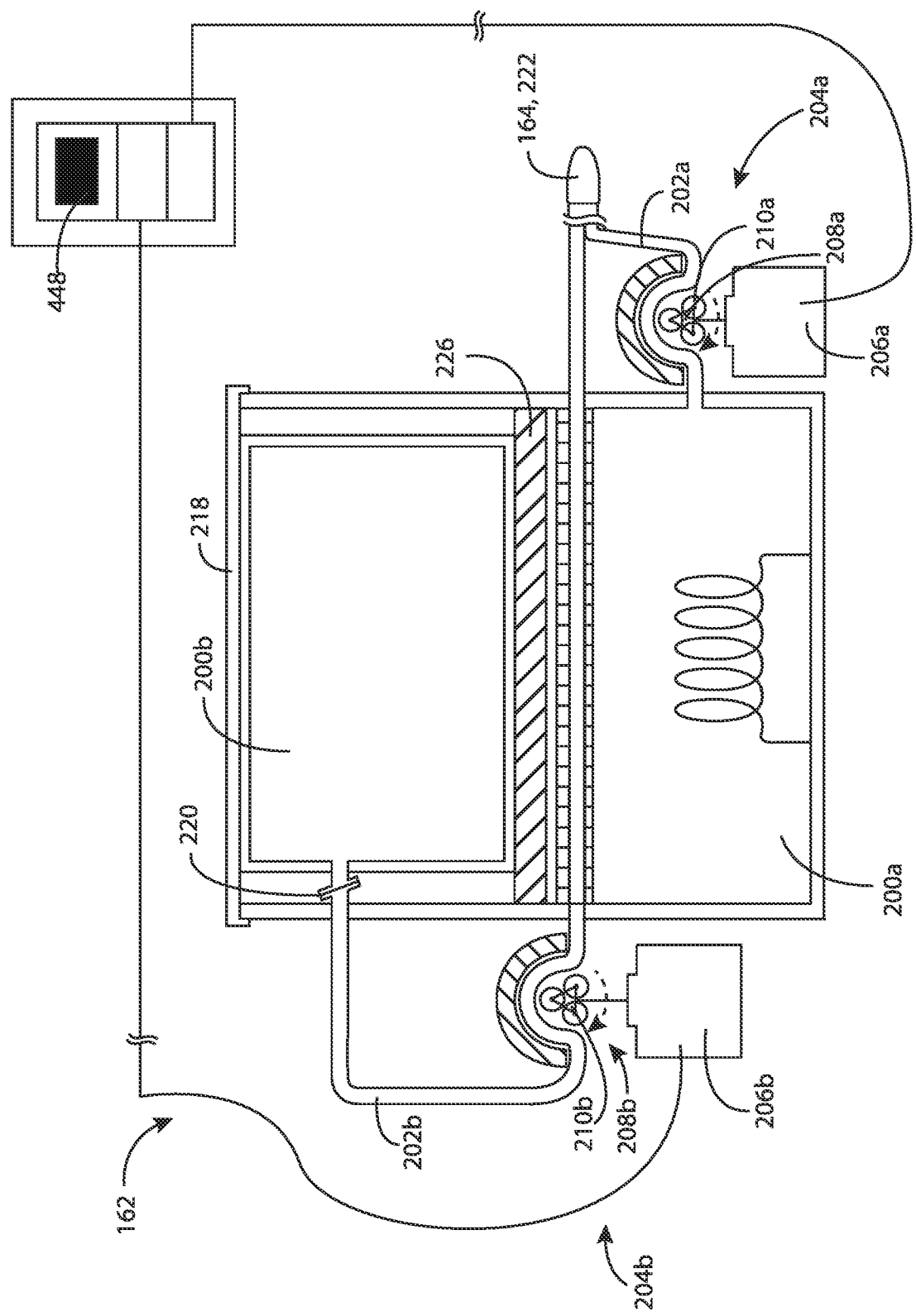

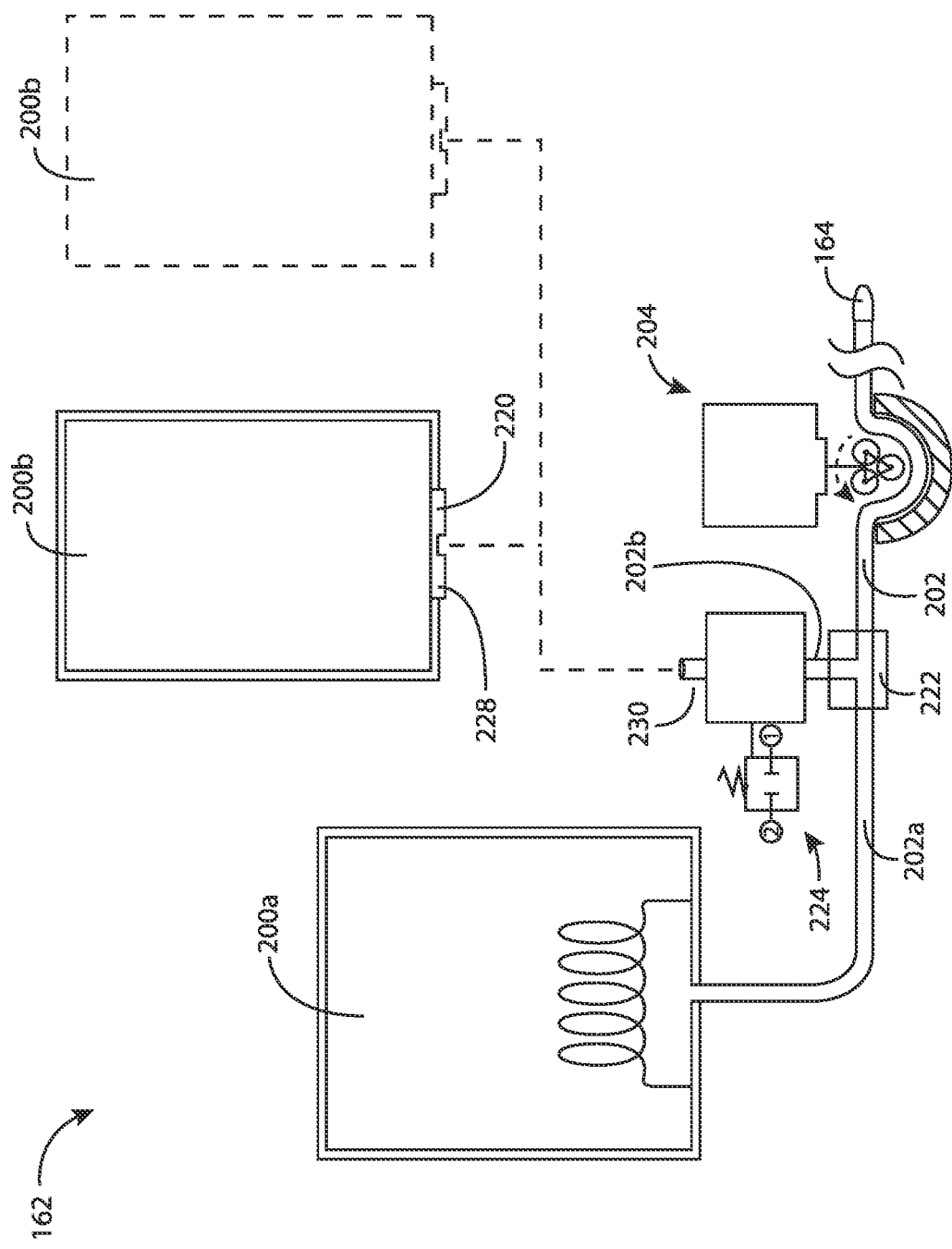

FIG. 56

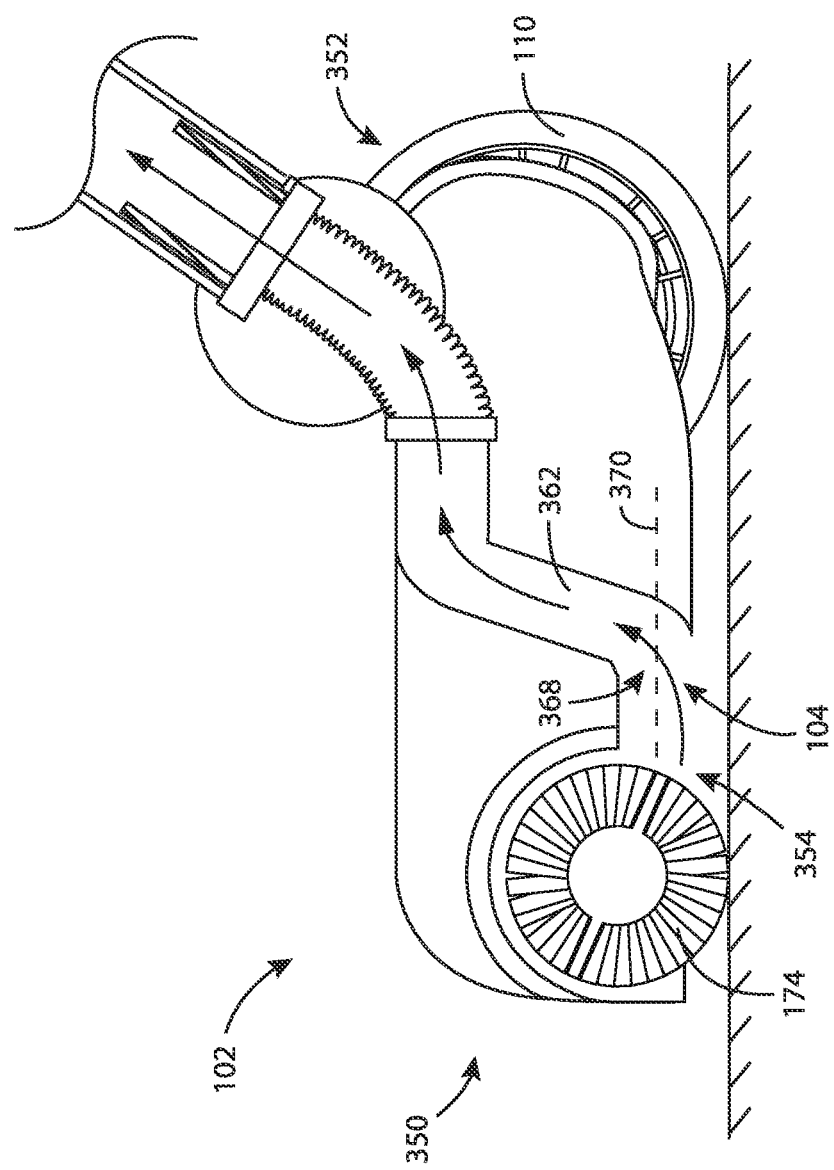

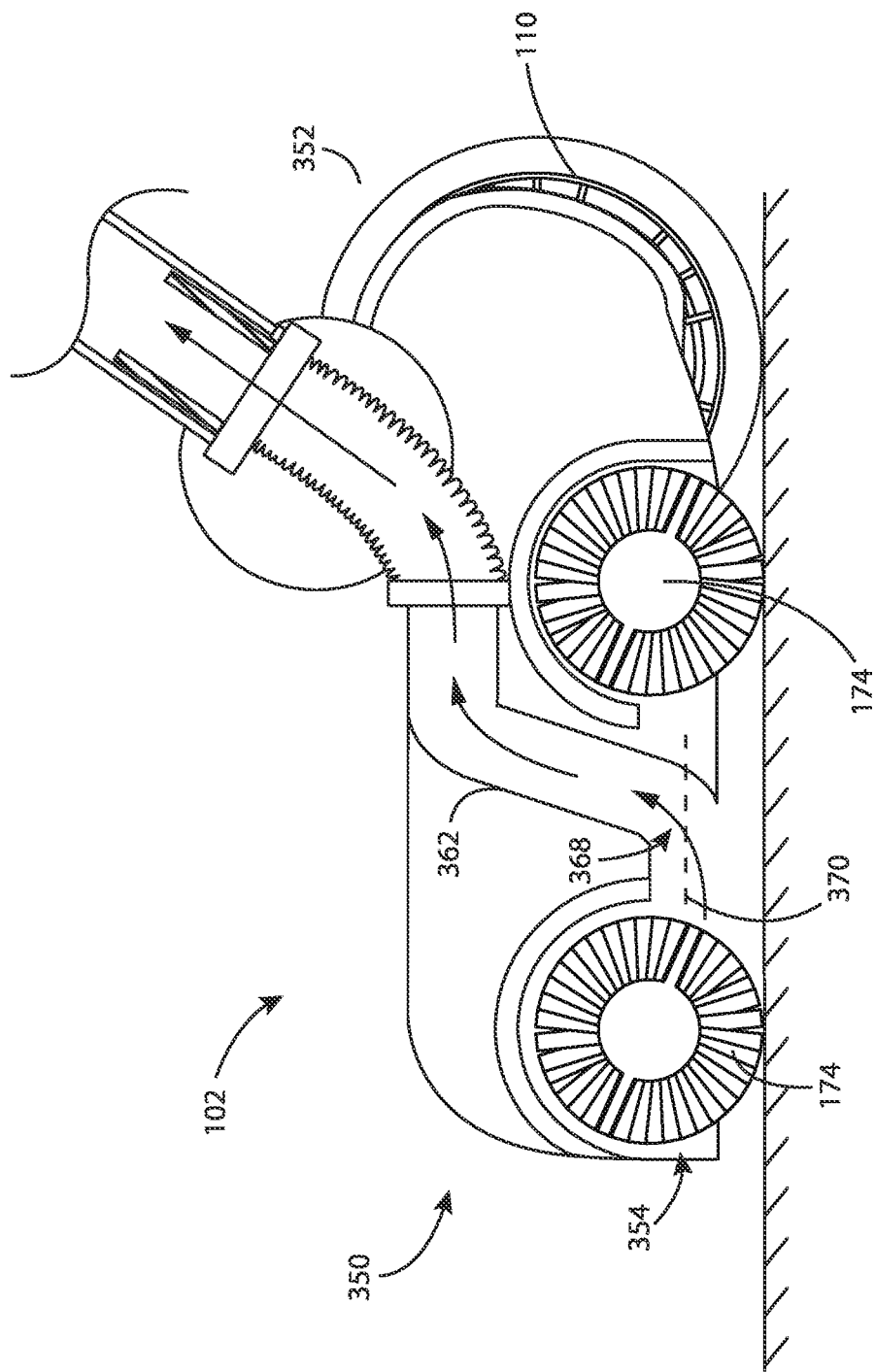

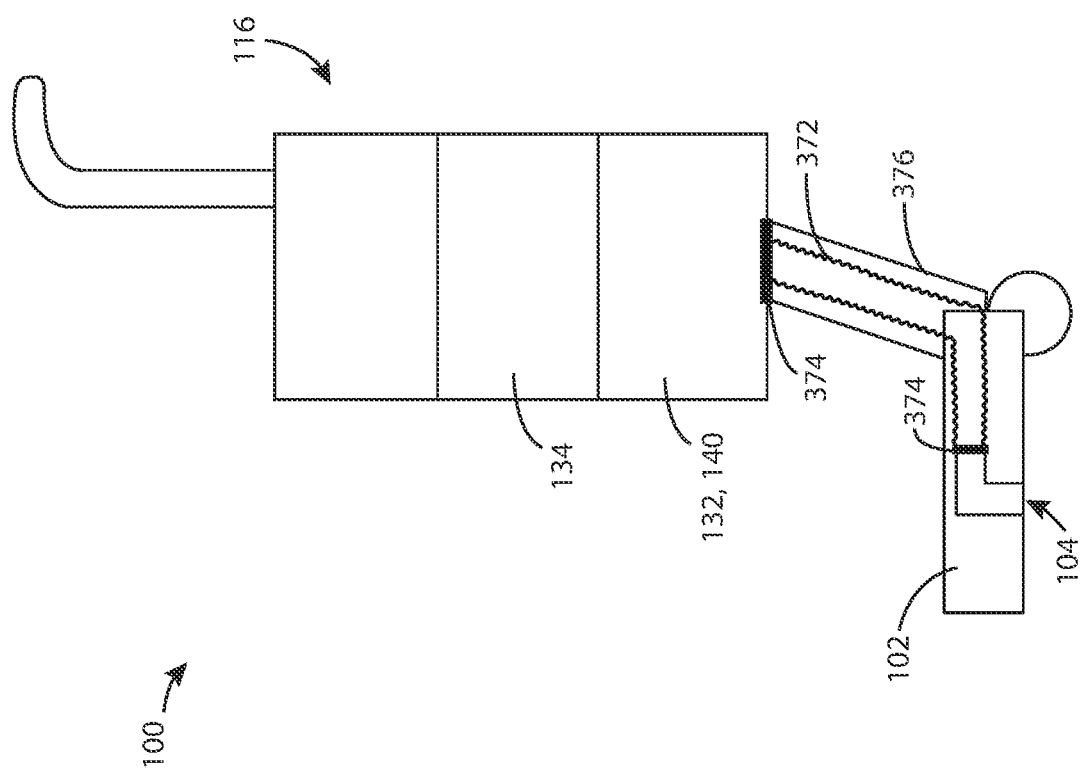

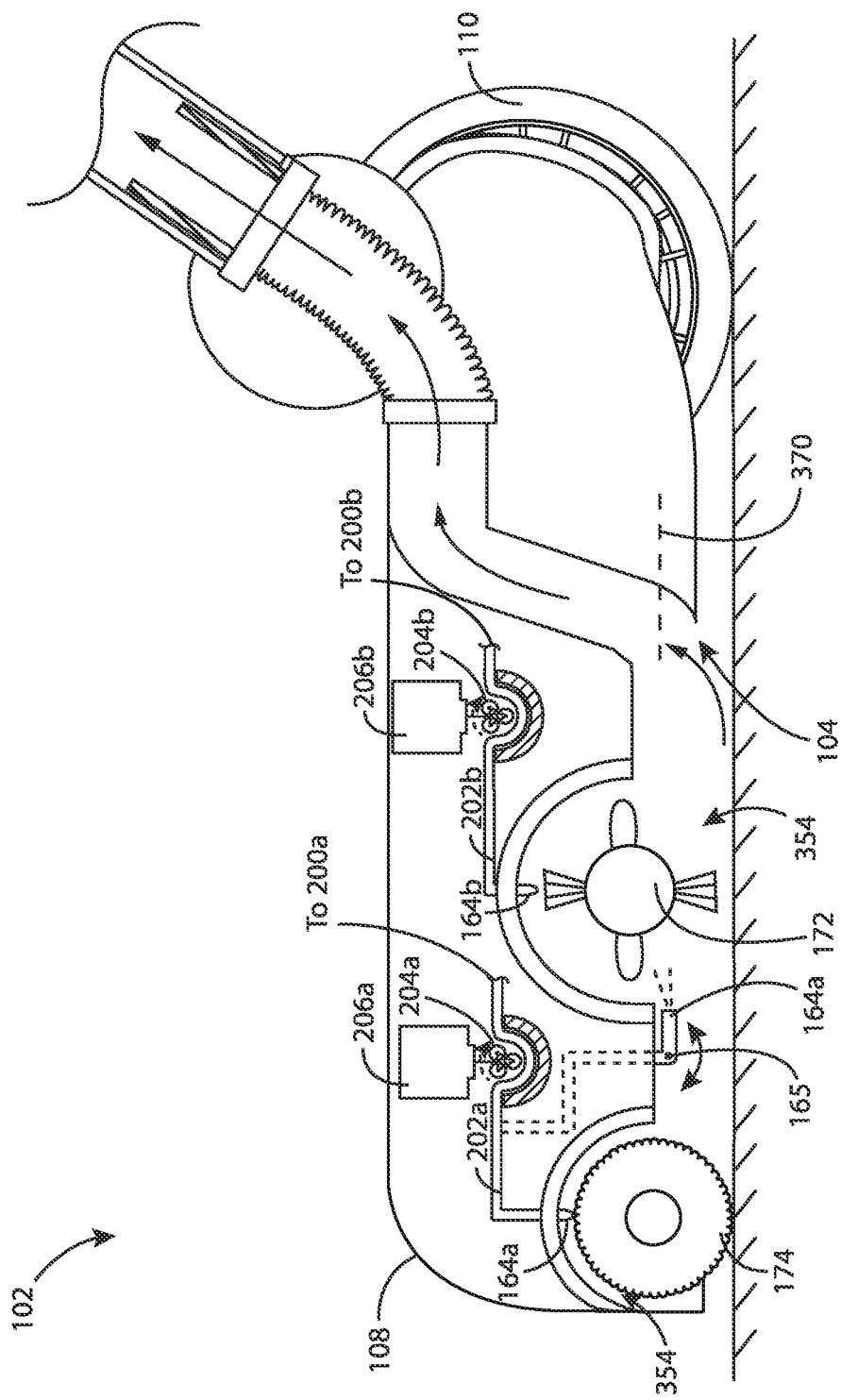

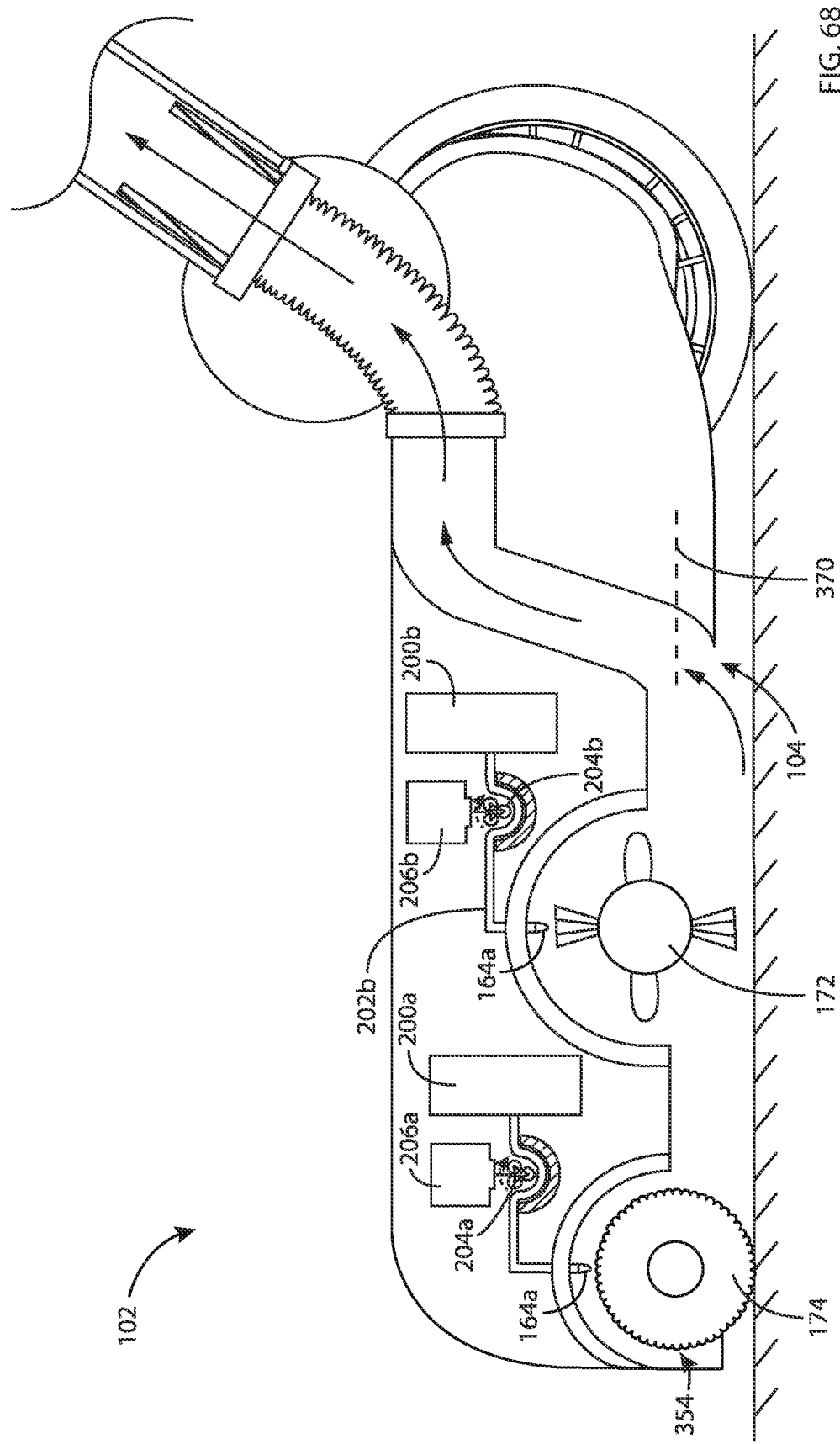

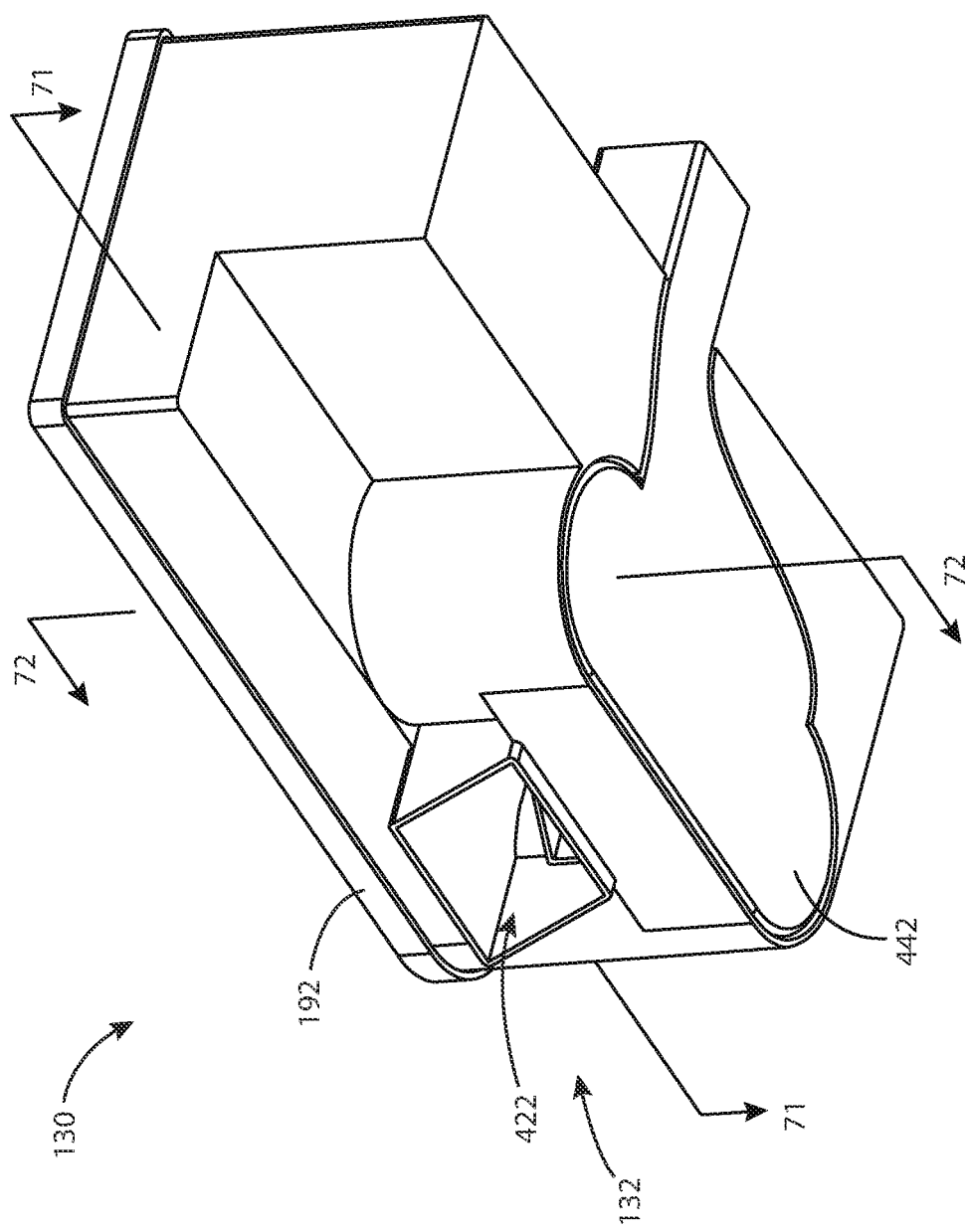

SURFACE CLEANING APPARATUS

CROSS REFERENCE TO RELATED APPLICATIONS

This application claims the benefit of the filing date of U.S. Provisional Patent Application Ser. No. 62/559,151, filed Sep. 15, 2017, the specification of which is incorporated herein by reference.

FIELD OF THE INVENTION

The present subject matter of the teachings described herein relates to a surface cleaning apparatus which may be operable as at least one of a sweeper, a vacuum cleaner, a hard floor cleaning apparatus and an extractor and optionally, the surface cleaning apparatus may be operable as two or more of these apparatus.

BACKGROUND OF THE INVENTION

Extractors are a type of surface cleaning apparatus which have a reservoir to apply a cleaning solution to, e.g., carpet and a nozzle to extract the used cleaning solution from the carpet. A separation system is provided to separate the used cleaning solution, which is entrained in dirty air that is drawn into the extractor, and to store the used cleaning solution in a used reservoir. Typically, the nozzle of an extractor is not designed to remove large particulate matter from carpet (e.g., popcorn) and accordingly, a carpet may have to be cleaned using a vacuum cleaner prior to using an extractor to clean the carpet.

Various different surface cleaning apparatus are known which use different cleaning stages that are arranged in series. These include EP 1707094 (Kim et al.), U.S. Pat. No. 7,473,289 (Oh et at.) and U.S. Pat. No. 5,135,552 (Weistra). Various different extractor designs are also known.

SUMMARY OF THE INVENTION

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

According to one aspect of this disclosure, a surface cleaning apparatus may be operable as a traditional vacuum cleaner (e.g., the dirty air inlet may be configured as a traditional vacuum cleaner dirty air inlet to draw in particulate matter, including larger particulate matter, which may then be removed from an air stream. This may be referred to as a vacuum cleaning mode or a dry cleaning mode as a cleaning solution may not yet have been applied to the surface being cleaned. The surface cleaning apparatus may also be operable in an extractor or wet cleaning mode, in which it is operable to treat an incoming dirty fluid stream that contains liquid and may also include dirt and other solid debris. Providing a single apparatus that can be operable in both wet and dry cleaning modes may allow a user to use a single apparatus to clean a surface (e.g., carpet) prior to applying a cleaning solution to clean the surface and then to use the same apparatus to apply a cleaning solution to the surface and to remove the cleaning solution from the surface. An advantage of this design is that a user need not use or store two separate machines.

In order to operate in an extractor mode, the surface cleaning apparatus may include a liquid distribution system, including an onboard liquid reservoir and a spray or application nozzle, whereby the apparatus may apply one or more of water, a carpet cleaning solution, a hard floor cleaning solution and/or any other desired liquid to the floor or surface to be cleaned. Accordingly, prior to applying the liquid, the same surface cleaning apparatus may be used to vacuum the surface to help remove at least some of the solid debris before the liquid is applied. The liquid may then be applied and, as needed, allowed to remain on the surface for a pre-determined period of time, and the surface cleaning apparatus may then be used in its extractor mode to extract the liquid from the surface. If the apparatus is not configured to include an onboard liquid distribution system, liquid may be applied to the surface using a separate apparatus.

In accordance with one broad aspect of the teachings describe herein, which may be used alone or in combination with any other aspects described herein, a surface cleaning apparatus may be provided with two treatment stages. The first treatment stage may be designed to remove liquid from an air stream (e.g., a momentum separator). The second treatment stage may be designed to remove solid particulate matter from the air stream (e.g., one or more cyclones in parallel). It will be appreciated that some solid particulate matter may be removed in the first treatment stage and that some liquid may be removed in the second treatment stage. In accordance with this aspect, the second or solid particulate matter treatment stage may be positioned above the first or liquid treatment stage. An advantage of this design is that the liquid treatment stage may be located at a lower elevation on the surface cleaning apparatus. Due to the volume of liquid an extractor is designed to remove, liquid requires substantially more energy to be drawn upwardly to a liquid treatment stage than entrained solid particulate matter. Accordingly, the energy requirement of a surface cleaning apparatus may be reduced by positioning the liquid treatment stage below the solid particulate matter treatment stage. Such a design is particularly advantageous if the surface treatment apparatus is an upright surface treatment apparatus wherein the treatment stages are provided on the upright section. A further advantage is that, if the treatment stages are at least partially or fully stacked on each other in a generally vertical arrangement, the overall foot print of the surface cleaning apparatus may be reduced.

In accordance with this broad aspect, there is provided a surface cleaning apparatus comprising:
- (a) a surface cleaning head having a front end having a dirty fluid inlet; and,
- (b) an upright section moveably mounted to the surface cleaning head, the upright section moveable between an upright storage position and a reclined surface cleaning position, the upright section comprising a front side, a rear side, a first stage liquid separator having a liquid separator fluid inlet downstream from the dirty fluid inlet and a liquid separator fluid outlet, a second stage cyclone separator comprising a cyclone chamber having a cyclone chamber fluid inlet and a cyclone chamber fluid outlet and a suction motor downstream from the second stage cyclone separator, the suction motor having a suction motor inlet end, wherein the cyclone separator is positioned above and downstream from the first stage liquid separator when the upright section is in the storage position.

In any embodiment, the first stage liquid separator may include a momentum separator.

In any embodiment, the suction motor may be positioned above the cyclone separator.

In any embodiment, the liquid separator fluid outlet may be positioned at an upper end of the liquid separator and the cyclone chamber fluid outlet may be positioned at an upper end of the cyclone chamber and the suction motor inlet end may face towards the cyclone chamber fluid outlet.

In any embodiment, the liquid separator fluid inlet may be provided in a lower surface of the liquid separator.

In any embodiment, the second stage cyclone separator may include a dirt collection chamber exterior to the cyclone chamber and the cyclone chamber has a dirt outlet at an upper end of the cyclone chamber.

In any embodiment, when the upright section is in the storage position, at least a portion of the dirt collection chamber may be positioned at a same elevation as a separated liquid reservoir (separated liquid container) of the liquid separator.

In any embodiment, a fluid passage may extend from the liquid separator fluid outlet to the cyclone chamber fluid inlet, and at least a portion of the fluid passage that extends upwardly when the upright section is in the storage position may be located at the front side of the upright section.

In accordance with this broad aspect, there is also provided a surface cleaning apparatus comprising:
  (a) a surface cleaning head having a front end having a dirty fluid inlet; and,
  (b) an upright section moveably mounted to the surface cleaning head, the upright section moveable between an upright storage position and a reclined surface cleaning position, the upright section comprising a front side, a rear side, a first stage liquid separator having a liquid separator fluid inlet downstream from the dirty fluid inlet and a liquid separator fluid outlet, a second stage cyclone separator positioned downstream from the liquid separator and comprising a cyclone chamber having a cyclone chamber fluid inlet and a cyclone chamber fluid outlet and a suction motor downstream from the second stage cyclone separator, the suction motor having a suction motor inlet end and a suction motor axis of rotation,
  wherein the upright section includes a fluid passage from the liquid separator fluid outlet to the cyclone chamber fluid inlet, wherein at least a portion of the fluid passage that extends upwardly when the upright section is in the storage position is located at the front side of the upright section.

In any embodiment, the first stage liquid separator may include a momentum separator.

In any embodiment, the cyclone separator may be positioned above the first stage liquid separator and the suction motor is positioned above the cyclone separator.

In any embodiment, the cyclone separator may be positioned above the first stage liquid separator and the liquid separator fluid outlet may be positioned at an upper end of the liquid separator. The cyclone chamber fluid outlet may be positioned at an upper end of the cyclone chamber and the suction motor inlet end may face towards the cyclone chamber fluid outlet.

In any embodiment, the liquid separator fluid inlet may be provided in a lower surface of the liquid separator.

In any embodiment, the second stage cyclone separator may include a dirt collection chamber exterior to the cyclone chamber and the cyclone chamber may have a dirt outlet at an upper end of the cyclone chamber.

In any embodiment, when the upright section is in the storage position, at least a portion of the dirt collection chamber may be positioned at a same elevation as a separated liquid reservoir of the liquid separator.

In any embodiment, the cyclone separator may be positioned above the first stage liquid separator.

In any embodiment, the cyclone separator may be positioned overlying the first stage liquid separator.

In any embodiment, the suction motor axis of rotation may intersect the first stage liquid separator and the second stage cyclone separator.

In accordance with another broad aspect of the teachings describe herein, which may be used alone or in combination with any other aspects described herein, a liquid collection chamber for receiving liquid separated by the first treatment stage and a solid collection chamber for receiving solid particulate matter separated by the second treatment stage are emptyable concurrently. An advantage of this design is that it may facilitate emptying of the treatment unit (which comprises the first and second treatment stages). For example, the solid collection chamber and the liquid collection container may be simultaneously openable. Optionally, a cyclone chamber in the treatment unit may also be openable simultaneously with the solid collection chamber and the liquid collection container.

In accordance with this aspect, there is provided a surface cleaning apparatus comprising:
  (a) a surface cleaning head having a front end having a dirty fluid inlet; and,
  (b) an upright section moveably mounted to the surface cleaning head, the upright section moveable between an upright storage position and a reclined surface cleaning position, the upright section comprising:
    (i) a first stage liquid separator having a liquid collection container, a separated liquid separator fluid inlet downstream from the dirty fluid inlet and a liquid separator fluid outlet;
    (ii) a second stage cyclone separator comprising a cyclone chamber and a solid collection chamber exterior to the cyclone chamber, the cyclone chamber having a cyclone chamber fluid inlet, a cyclone chamber dirt outlet in communication with the solid collection chamber and a cyclone chamber fluid outlet; and,
    (iii) a suction motor downstream from the second stage cyclone separator,
  wherein the liquid collection container and the solid collection chamber are emptyable concurrently.

In any embodiment, when the upright section is in the storage position, the solid collection chamber may be positioned at a same elevation as the liquid collection container.

In any embodiment, the solid collection chamber may be positioned laterally beside the liquid collection container.

In any embodiment, the solid collection chamber and the liquid collection container may be removable concurrently from the upright section.

In any embodiment, the solid collection chamber and the liquid collection container may be removable from the upright section in a closed configuration.

In any embodiment, the first stage liquid separator and the second stage cyclone separator may be removable concurrently from the upright section.

In any embodiment, the solid collection chamber and the separated liquid container are of a unitary construction.

In any embodiment, the solid collection chamber and the separated liquid collection container may be integrally formed.

In any embodiment, the first stage liquid separator and the second stage cyclone separator may be removable in a sealed configuration other than the liquid separator fluid inlet and the cyclone chamber fluid outlet.

In any embodiment, the solid collection chamber and the separated liquid collection container may have an openable top.

In any embodiment, the openable top may include the cyclone chamber.

In any embodiment, the solid collection chamber may be positioned laterally beside the separated liquid collection container and the cyclone chamber may have a cyclone axis of rotation that intersects the separated liquid collection container.

In any embodiment, the solid collection chamber may be positioned laterally beside the liquid collection container and the cyclone chamber overlies the liquid collection container.

In accordance with this aspect, there is also provided a surface cleaning apparatus comprising
- (a) a first stage liquid separator having a liquid collection container, a separated liquid separator fluid inlet downstream from the dirty fluid inlet and a liquid separator fluid outlet;
- (b) a second stage cyclone separator comprising a cyclone chamber and a solid collection chamber exterior to the cyclone chamber, the cyclone chamber having a cyclone chamber fluid inlet, a cyclone chamber dirt outlet in communication with the solid collection chamber and a cyclone chamber fluid outlet; and,
- (c) a suction motor downstream from the second stage cyclone separator,
wherein the liquid collection container and the solid collection chamber are emptyable concurrently.

In any embodiment, the solid collection chamber may be positioned laterally beside the liquid collection container.

In any embodiment, the solid collection chamber and the separated liquid collection container may be removable concurrently from the surface cleaning apparatus.

In any embodiment, the solid collection chamber and the separated liquid collection container may be removable from the surface cleaning apparatus in a closed configuration.

In any embodiment, the first stage liquid separator and the second stage cyclone separator may be removable concurrently from the surface cleaning apparatus.

In any embodiment, the first stage liquid separator and the second stage cyclone separator may be removable in a sealed configuration other than the separated liquid separator fluid inlet and the cyclone chamber fluid outlet.

In any embodiment, the solid collection chamber and the separated liquid collection container may have an openable top and the openable top may include the cyclone chamber.

In accordance with another broad aspect of the teachings describe herein, which may be used alone or in combination with any other aspects described herein, a surface cleaning apparatus has two or more different brushes (e.g., a hard floor cleaning brush and a carpet cleaning brush) and a liquid (e.g., water or a cleaning solution) may be applied to a selected brush. Further, a different liquid may be applied to each brush. For example, in a hard floor cleaning mode a liquid, which may be a hard floor cleaning solution, may be applied to the hard floor cleaning brush and in a carpet cleaning mode a liquid, which may be a carpet cleaning solution, may be applied to the carpet cleaning brush.

In accordance with this aspect, there is provided a surface cleaning apparatus comprising:
- (a) a surface cleaning head having a hard floor cleaning brush and a carpet cleaning brush; and,
- (b) a liquid delivery system comprising at least one spray nozzle that delivers at least one liquid,
wherein surface cleaning apparatus is operable in a hard floor cleaning configuration in which the liquid is delivered from the at least one nozzle to the soft brush bar, and a carpet cleaning configuration in which the liquid is delivered from the at least one nozzle to the carpet cleaning brush In any embodiment, the at least one spray nozzle may include at least one first nozzle that delivers the liquid to the hard floor cleaning brush and at least one second nozzle that delivers the liquid to the carpet cleaning brush.

In any embodiment, the liquid may include a hard floor cleaning solution and a carpet cleaning solution, wherein the at least one first nozzle delivers the hard floor cleaning solution to the hard floor cleaning brush and the at least one second nozzle delivers the carpet cleaning solution to the carpet cleaning brush.

In any embodiment, the at least one first nozzle may be positioned to deliver the hard floor cleaning solution to the hard floor cleaning brush and the at least one second nozzle may be positioned to deliver the carpet cleaning solution to the carpet cleaning brush.

In any embodiment, an actuator may be operably connected to the cleaning solution delivery system wherein, in a hard floor cleaning actuation mode, the at least one first nozzle delivers the liquid to the hard floor cleaning brush and in a carpet cleaning actuation mode, the at least one second nozzle delivers the liquid to the carpet cleaning brush.

In any embodiment, the liquid may include a hard floor cleaning solution and a carpet cleaning solution wherein, in a hard floor cleaning actuation mode, the at least one first nozzle delivers the hard floor cleaning solution to the hard floor cleaning brush and in a carpet cleaning actuation mode, the at least one second nozzle delivers the carpet cleaning solution to the carpet cleaning brush.

In any embodiment, in the hard floor cleaning actuation mode, the hard floor cleaning brush may be rotated and the carpet cleaning brush may be stationary, and in the carpet cleaning actuation mode, the hard floor cleaning brush may be stationary and the carpet cleaning brush may be rotated.

In any embodiment, in both the hard floor cleaning actuation mode and the carpet cleaning actuation mode, both the hard floor cleaning brush and the carpet cleaning brush may be rotated.

In any embodiment, the at least one spray nozzle may be moveably mounted whereby, in the hard floor cleaning configuration, the at least one spray nozzle is positioned to deliver the liquid to the soft brush bar, and in the carpet cleaning configuration, the at least one spray nozzle is positioned to deliver the liquid to the carpet cleaning brush.

In any embodiment, the liquid may include a hard floor cleaning solution and a carpet cleaning solution and the at least one spray nozzle may be moveably mounted whereby, in the hard floor cleaning configuration, the at least one spray nozzle is positioned to deliver the hard floor cleaning solution to the soft brush bar, and in the carpet cleaning configuration, the at least one spray nozzle is positioned to deliver the carpet cleaning solution to the carpet cleaning brush.

In any embodiment, an actuator may be operably connected to the cleaning solution delivery system wherein, in a hard floor cleaning actuation mode, the at least one nozzle may deliver the liquid to the hard floor cleaning brush and in a carpet cleaning actuation mode, the at least one nozzle may deliver the liquid to the carpet cleaning brush.

In any embodiment, in the hard floor cleaning configuration the liquid may delivered at a first rate, and in the carpet cleaning configuration the liquid may be delivered at a second rate that is faster than the first rate. For example, in the hard floor cleaning configuration, the liquid may be delivered at a rate of 10-100 mL/min and in the carpet cleaning configuration, the liquid may be delivered at a rate of at least 100 mL/min.

In any embodiment, in the hard floor cleaning configuration, the hard floor cleaning brush and the carpet cleaning brush may be rotated at a first rate of rotation and in the carpet cleaning configuration, the hard floor cleaning brush and the carpet cleaning brush may be rotated at a second rate of rotation that is faster than the first rate of rotation. For example, in the hard floor cleaning configuration, the hard floor cleaning brush and the carpet cleaning brush may be rotated at a rate of rotation of between about 1000-2400 RPM and in the carpet cleaning configuration, the hard floor cleaning brush and the carpet cleaning brush may be rotated at a rate of rotation of between about 2400-5000 RPM.

In any embodiment, the liquid may include a hard floor cleaning solution and a carpet cleaning solution and the cleaning solution delivery system may include a hard floor cleaning solution reservoir and a carpet cleaning solution reservoir.

In any embodiment, the liquid may include a hard floor cleaning solution and a carpet cleaning solution and the cleaning solution delivery system may include a clean water reservoir and a mixing system for selectively preparing carpet the hard floor cleaning solution and the carpet cleaning solution.

In accordance with another broad aspect of the teachings describe herein, which may be used alone or in combination with any other aspects described herein a surface cleaning apparatus may have one or more liquid delivery system operable to alternately deliver different liquids (e.g., a carpet cleaning solution and a hard floor cleaning solution). Optionally, the liquid delivery system may have different conduits (which may be removable) for the different liquids which may be delivered (e.g., a water delivery line, a hard floor cleaning solution line and/or a carpet cleaning solution line). An advantage of this design is that different solutions may not be mixed.

In accordance with this aspect, there is provided surface cleaning apparatus comprising:
(a) a liquid delivery system operable to alternately deliver a carpet cleaning solution and a hard floor cleaning solution; and,
(b) an actuator operably connected to the cleaning solution delivery system wherein, in a hard floor cleaning actuation mode, the cleaning solution delivery system delivers the hard floor cleaning solution to at least one delivery nozzle and in a carpet cleaning actuation mode, the cleaning solution delivery system delivers the carpet cleaning solution to the at least one delivery nozzle.

In any embodiment, the actuator may be manually operated by a user.

In any embodiment, the actuator may include a detector operable to determine a surface that is being cleaned.

In any embodiment, the liquid delivery system may include a carpet cleaning solution reservoir and a hard floor cleaning solution reservoir.

In any embodiment, the liquid delivery system may include a carpet cleaning solution delivery line extending from the carpet cleaning solution reservoir to the at least one delivery nozzle and a hard floor cleaning solution delivery line extending from the hard floor solution reservoir to the at least one delivery nozzle.

In any embodiment, the at least one delivery nozzle may include at least one hard floor delivery nozzle and at least one carpet delivery nozzle. The carpet cleaning solution delivery line may extend from the carpet cleaning solution reservoir to the at least one carpet delivery nozzle and the hard floor cleaning solution delivery line may extend from the hard floor solution reservoir to the at least one hard floor delivery nozzle.

In any embodiment, each of the carpet cleaning solution reservoir and the hard floor cleaning solution reservoir may be removable from the surface cleaning apparatus.

In any embodiment, the carpet cleaning solution reservoir may be removable from the surface cleaning apparatus with the carpet cleaning solution delivery line and the hard floor cleaning solution reservoir may be removable from the surface cleaning apparatus with the hard floor cleaning solution delivery line.

In any embodiment, the liquid delivery system may include a water reservoir, a hard floor cleaning concentrate container and a carpet cleaning concentrate container.

In any embodiment, the liquid delivery system may include a mixer chamber, a carpet cleaning concentrate delivery line extending from the carpet cleaning concentrate container, a hard floor cleaning concentrate delivery line extending from the hard floor concentrate container and a water delivery line extending from the water reservoir. The carpet cleaning concentrate delivery line, the hard floor cleaning concentrate delivery line and the water delivery line may be in fluid communication with the mixer nozzle.

In any embodiment, the carpet cleaning concentrate delivery line, the hard floor cleaning concentrate delivery line and the water delivery line may each extend to a position selected from an inlet end of the mixer chamber or a position adjacent the inlet end of the mixer chamber.

In any embodiment, the mixer chamber may be upstream of the at least one delivery nozzle.

In any embodiment, the at least one delivery nozzle may include the mixer chamber.

In any embodiment, at least one pump may be operably coupled to an exterior of each of the carpet cleaning concentrate delivery line and the hard floor cleaning concentrate delivery line. The at least one pump may include a peristaltic pump.

In any embodiment, the liquid delivery system may mix the hard floor cleaning concentrate with water at a first concentrate to water rate and may mix the carpet cleaning concentrate container with water at a second concentrate to water rate that differs to the first rate.

In any embodiment, the cleaning solution delivery system may also be operable to deliver clean water to the at least one delivery nozzle.

In accordance this broad aspect, there is also provided a surface cleaning apparatus comprising a liquid delivery system comprising a water reservoir, a first compartment for receiving a first cleaning solution concentrate, a mixer chamber, a first cleaning solution concentrate delivery line extending from the first compartment and a water delivery line extending from the water reservoir, wherein the first cleaning solution concentrate delivery line and the water delivery line are in fluid communication with the mixer nozzle In any embodiment, an actuator may be operably connected to the cleaning solution delivery system. In a first actuation mode, the cleaning solution delivery system may deliver a cleaning solution prepared from water and the first cleaning solution concentrate to at least one delivery nozzle and in a second actuation mode, the cleaning solution delivery system may deliver water to the at least one delivery nozzle.

In any embodiment, a second compartment for receiving a second cleaning solution concentrate and a second cleaning solution concentrate delivery line may extend from the second compartment. The second cleaning solution concentrate delivery line may be in fluid communication with the mixer nozzle.

In any embodiment, an actuator may be operably connected to the cleaning solution delivery system. In a hard floor cleaning actuation mode, the cleaning solution delivery system may deliver a hard floor cleaning solution prepared from water and the first cleaning solution concentrate to at least one delivery nozzle and, in a carpet cleaning actuation mode, the cleaning solution delivery system may deliver a carpet cleaning solution prepared from the water and the second cleaning solution concentrate to the at least one delivery nozzle.

In any embodiment, the first compartment may be a refillable compartment.

In any embodiment, the first compartment may removably receive a first cartridge containing the first cleaning solution concentrate.

In any embodiment, the first cartridge may be removable with the first cleaning solution concentrate delivery line.

In any embodiment, at least one pump may be operably coupled to an exterior of each of the first cleaning solution concentrate delivery line and water delivery line. The at least one pump may be a peristaltic pump.

In accordance with this aspect, there is also provided a surface cleaning apparatus which may include a liquid delivery system having a first compartment for receiving a first cleaning solution, a first cleaning solution delivery line extending from the first compartment and at least one pump operably coupled to an exterior of the first cleaning solution delivery line.

In any embodiment, the at least one pump may include a peristaltic pump.

In any embodiment, the first compartment may removably receive a first cartridge containing the first cleaning solution.

In any embodiment, the first cartridge may be removable with the first cleaning solution delivery line.

In accordance with another broad aspect of the teachings describe herein, which may be used alone or in combination with any other aspects described herein a surface cleaning apparatus may have a solid and liquid separation stage including a combined solid and liquid separator and a collection chamber that receives both solids and liquids from the combined solid and liquid separator. The collection chamber may be subdivided by a water permeable member, such as a screen, so as to enable the separated liquid to be stored separate from the separated solid particulate matter. An advantage of this design is that a single reservoir may not have a build-up of sludge like material.

In accordance with this aspect, there is provided a surface cleaning apparatus having a solid and liquid separation stage comprising:
  (a) a combined solid and liquid separator having a separated element outlet; and,
  (b) a solid and liquid collection chamber in communication with the separated element outlet, the solid and liquid separation chamber including a screen provided therein, when the surface cleaning apparatus is in a floor cleaning orientation, the solid and liquid collection chamber has a lower region comprising a liquid collection region whereby, in operation, liquid passes through the screen and solid material collects on the screen.

In any embodiment, the combined solid and liquid separation member may include a cyclone having a cyclone wall, a cyclone fluid inlet and a cyclone fluid outlet and, when the surface cleaning apparatus is in the floor cleaning orientation, the separated element outlet may be at an upper end of the cyclone.

In any embodiment, a baffle may be provided on an outer surface of the cyclone wall proximate the separated element outlet and may be located below the separated element outlet when the surface cleaning apparatus is in the floor cleaning orientation.

In any embodiment, when the surface cleaning apparatus is in the floor cleaning orientation, the cyclone fluid inlet and the cyclone fluid outlet may be at a lower end of the cyclone.

In any embodiment, when the surface cleaning apparatus is in the floor cleaning orientation, the lower region may extend to a position at a lower elevation than a lower end of the combined solid and liquid separation member.

In any embodiment, the screen may be oriented such that a first direction of flow of liquid through the screen is at an angle to the first direction of flow through the separated element outlet.

In any embodiment, the screen may be configured such that an additional direction of flow of liquid through the screen is at an angle to first direction of flow of liquid through the screen In any embodiment, the screen may generally L-shaped In any embodiment, the surface cleaning apparatus may include at least one additional screen.

In any embodiment, when the surface cleaning apparatus is in the floor cleaning orientation, the solid and liquid collection chamber may have an upper end and the upper end is openable.

In any embodiment, when the surface cleaning apparatus is in the floor cleaning orientation, the solid and liquid separation member may have an upper end and the upper end that is openable concurrently with the upper end of the solid and liquid collection chamber.

In any embodiment, the surface cleaning apparatus may be an upright surface cleaning apparatus comprising a surface cleaning head and an upright section moveably mounted thereto between a storage position and a reclined surface cleaning position and the solid and liquid separation stage may be provided in the upright section. When the upright section is in the storage position, the separated element outlet may be provided at an upper end of the combined solid and liquid separation member, the lower region may extend to a position at a lower elevation than a lower end of the combined solid and liquid separation member and the solid and liquid collection chamber may have an upper end and the upper end is openable.

In any embodiment, when the surface cleaning apparatus is in a floor cleaning orientation, the surface cleaning apparatus may have a drive handle located rearwardly on the surface cleaning apparatus and the separated element outlet is located on a rear side of the combined solid and liquid separation member.

In accordance with this aspect, there is also provided a surface cleaning apparatus having a solid and liquid separation stage comprising:
  (a) a combined solid and liquid separation member having a separation member wall having a separated element outlet; and, (b) a solid and liquid collection chamber in communication with the separated element outlet,
wherein, when the surface cleaning apparatus is in a floor cleaning orientation, the separated element outlet is provided at an upper end of the combined solid and liquid separation member, a lower end of the solid and liquid collection chamber extends to a position at a lower elevation than a lower end of the combined solid and liquid separation member and the solid and liquid collection chamber has an upper end and the upper end is openable.

In any embodiment, when the surface cleaning apparatus is in the floor cleaning orientation, the solid and liquid separation member has an upper end and the upper end may be openable concurrently with the upper end of the solid and liquid collection chamber.

In any embodiment, the solid and liquid separation chamber further may include a screen provided therein and, when the surface cleaning apparatus is in the floor cleaning orientation, the solid and liquid collection chamber may have a lower region including a liquid collection region whereby, in operation, liquid passes through the screen and solid material collects on the screen.

In any embodiment, a baffle may be provided on an outer surface of the separation member wall proximate the separated element outlet and may be located below the separated element outlet when the surface cleaning apparatus is in the floor cleaning orientation.

In any embodiment, the combined solid and liquid separation member may include a cyclone having a cyclone fluid inlet and a cyclone fluid outlet. When the surface cleaning apparatus is in the floor cleaning orientation, the cyclone fluid inlet and the cyclone fluid outlet are at a lower end of the cyclone.

In any embodiment, when the surface cleaning apparatus is in a floor cleaning orientation, the surface cleaning apparatus may have a drive handle located rearwardly on the surface cleaning apparatus and the separated element outlet may be located on a rear side of the combined solid and liquid separation member.

In accordance with another aspect of the teachings describe herein, which may be used alone or in combination with any other aspects described herein, an upright surface cleaning apparatus may be configured as an upright surface cleaning apparatus with an above floor cleaning mode (e.g., a wand and a flexible hose may be removable for above floor cleaning) and/or a cleaning unit may be removably mounted to the upright apparatus with or without a wand and flexible hose. An advantage of these embodiments is that additional cleaning modes may be provided in a single apparatus. In such an embodiment, when used in an extractor mode or without the wand and hose deployed, the wand and hose may not be part of the fluid flow path through the apparatus. An advantage of this design is that the flow path is shorter in an extractor mode, thereby reducing the energy requirement and also reducing the water that may build up in the hose.

In accordance with this aspect, there is provided an upright surface cleaning apparatus comprising:
(a) a surface cleaning head having a first dirty fluid inlet;
(b) at least one treatment unit comprising a first separator;
(c) an upright section moveably mounted to the surface cleaning head, the upright section moveable between an upright storage position and a reclined surface cleaning position, the upright section having the first separator and an above floor cleaning member comprising a second dirty fluid inlet and a flexible hose;
(d) a liquid deliver system extending from at least one fluid reservoir to at least one applicator nozzle;
(e) a floor cleaning fluid flow path extending from the first dirty fluid inlet to a clean air outlet, the first fluid flow path including the first separation stage and a suction motor; and,
(f) an above floor fluid flow path extending from the second dirty fluid inlet to the clean air outlet and including the first separator, the suction motor and the above floor cleaning member,
wherein the upright surface cleaning apparatus is operable in a floor cleaning mode which utilizes the floor cleaning fluid flow path and an above floor cleaning mode which utilizes the above floor fluid flow path. The flexible hose may be isolated from the floor cleaning fluid flow path.

In any embodiment, a valve may alternately connect the first dirty fluid inlet and the second dirty fluid inlet in flow communication with the first separator.

In any embodiment, the floor cleaning fluid flow path may have a portion which extends from the first dirty fluid inlet to an outlet end that is upstream of the at least one cleaning stage and the above floor fluid flow path has a portion which extends from the second dirty fluid inlet to an outlet end that is upstream of the at least one cleaning stage and the outlet end of each of the floor cleaning and above floor fluid flow paths is located at an inlet portion of the valve.

In any embodiment, a valve actuator may be drivingly connected to the valve and the above floor cleaning member may be drivingly connected to the valve actuator whereby the valve is moved to a floor cleaning position in which the at least one cleaning stage is in flow communication with the first dirty fluid inlet when an inlet end of the above floor cleaning member is mounted to the upright surface cleaning apparatus and the valve is moved to an above floor cleaning position in which the at least one cleaning stage is in flow communication with the second dirty fluid inlet when the inlet end of the above floor cleaning member is removed from the upright surface cleaning apparatus.

In any embodiment, the upright section may include a portable surface cleaning unit which is removably mounted to the upright surface cleaning apparatus and the portable surface cleaning unit may include the at least one cleaning stage and the suction motor.

In any embodiment, the portable surface cleaning unit may be removable without the at least one fluid reservoir.

In any embodiment, the at least one fluid reservoir may be part of the surface cleaning head.

In any embodiment, the at least one separation stage may include a second separation stage that is upstream from the first separation stage and the portable surface cleaning unit may be removable without the second separation stage.

In any embodiment, the at least one separation stage may include a second separation stage that is upstream from the first separation stage and the portable surface cleaning unit may be removable without the second separation stage.

In any embodiment, the second separation stage may be part of the surface cleaning head.

In any embodiment, the second separation stage may include a liquid separator.

In any embodiment, the flexible hose may be isolated from the floor cleaning fluid flow path.

In accordance this aspect, there is also provided an upright surface cleaning apparatus comprising:
(a) a surface cleaning head having a first dirty fluid inlet;
(b) at least one separation stage comprising a first separation stage;

(c) an upright section moveably mounted to the surface cleaning head, the upright section moveable between an upright storage position and a reclined surface cleaning position, the upright section having a portable surface cleaning unit which is removably mounted to the upright surface cleaning apparatus, wherein the portable surface cleaning unit comprises the first separation stage and an above floor cleaning member, the above floor cleaning member comprising a second dirty fluid inlet and a flexible hose;

(d) a cleaning solution delivery system extending from at least one fluid reservoir to at least one applicator nozzle;

(e) a floor cleaning fluid flow path extending from the first dirty fluid inlet to a clean air outlet, the first fluid flow path including the first separation stage and a suction motor; and, (f) an above floor fluid flow path extending from the second dirty fluid inlet to the clean air outlet and including the first separation stage, the suction motor and the above floor cleaning member, wherein the upright surface cleaning apparatus is operable in a floor cleaning mode which utilizes the floor cleaning fluid flow path and an above floor cleaning mode which utilizes the above floor fluid flow path.

In any embodiment, the portable surface cleaning unit may be removable without the at least one fluid reservoir.

In any embodiment, the at least one fluid reservoir may be part of the surface cleaning head.

In any embodiment, the at least one separation stage may include a second separation stage that is upstream from the first separation stage and the portable surface cleaning unit may be removable without the second separation stage.

In any embodiment, the at least one separation stage may include a second separation stage that is upstream from the first separation stage and the portable surface cleaning unit may be removable without the second separation stage.

In any embodiment, the at least one separation stage may include a second separation stage that is upstream from the first separation stage and the second separation stage may be part of the surface cleaning head.

In any embodiment, the second separation stage may include a liquid separator.

In any embodiment, the flexible hose may be isolated from the floor cleaning fluid flow path.

In accordance with another aspect of the teachings describe herein, which may be used alone or in combination with any other aspects described herein an upright surface cleaning apparatus having a surface cleaning apparatus which removes water from a surface is provided with a fluid flow path upstream from the separation stage (which may be any separation stage known in the art or disclosed herein) wherein at least a portion of the fluid flow path upstream from the separation stage is removable. An advantage of this design is that the removable portion may be removed and washed and/or dried to reduce the build-up of odors in the apparatus.

In accordance with this aspect, there is provided a surface cleaning apparatus comprising:

(a) a cleaning solution delivery system comprising a liquid reservoir and a fluid flow path extending from the liquid reservoir to at least one delivery nozzle;

(b) a fluid flow path extending from a dirty fluid inlet head to a clean air outlet; and, (c) a separation stage positioned in the fluid flow path, wherein the fluid flow path upstream of the separation member comprises a removable portion.

In any embodiment, the removable portion may have an absence of a treatment member.

In any embodiment, the removable portion may comprise a flexible hose.

In any embodiment, the removable portion may comprise a plurality of individual segments.

In any embodiment, at least one of the segments may be rigid.

In any embodiment, one or more of the segments may be removable without removing all of the segments concurrently.

In any embodiment, the removable portion may comprise a pivot joint.

In any embodiment, the removable portion may extend through a pivot joint.

In any embodiment, the removable portion may comprise at least a portion of the removable portion is transparent.

In any embodiment, the surface cleaning apparatus may be an all in the head surface cleaning apparatus comprising a surface cleaning head and the removable portion is provided in the surface cleaning head.

In any embodiment, the surface cleaning apparatus may be an upright surface cleaning apparatus having a surface cleaning head and an upright section moveably mounted to the surface cleaning head, the surface cleaning head including a moveable joint whereby the upright section is moveable between an upright storage position and a reclined surface cleaning position, the upright section comprising the separation stage and the removable portion comprises the moveable joint.

In any embodiment, the surface cleaning apparatus may be an upright surface cleaning apparatus having a surface cleaning head and an upright section moveably mounted to the surface cleaning head, the surface cleaning head including a moveable joint whereby the upright section is moveable between an upright storage position and a reclined surface cleaning position, the upright section comprising the separation stage and the removable portion extends through the moveable joint.

In any embodiment, the dirty fluid inlet may comprise a brush chamber and the removable portion extends from the brush chamber to the separation stage.

In any embodiment, the separation stage may comprise a liquid separator.

In any embodiment, the removable portion may be removable with the separation stage.

In any embodiment, the separation stage may be removable as a sealed unit other than the fluid inlet and the fluid outlet.

In any embodiment, the removable portion may be removable with the separation stage.

In any embodiment, the surface cleaning apparatus may be an all in the head surface cleaning apparatus comprising a surface cleaning head and the removable portion is provided in the surface cleaning head.

In accordance with another aspect of the teachings describe herein, which may be used alone or in combination with any other aspects described herein an upright surface cleaning apparatus having a surface cleaning apparatus has one or more of a liquid separator, a liquid collection container and a cleaning liquid reservoir in the surface cleaning head. An advantage of this design is that, in the case of an upright surface cleaning apparatus or an all in the head surface cleaning apparatus, the experienced handle weight (the weight of the handle experienced by a user when a cleaning solution or recovered dirty water is stored in the unit, is reduced by storing at least some of the liquid other than on the upright section. This may also help reduce the distance and elevation that liquid is conveyed within the fluid flow path of the apparatus, which may help reduce power requirements, and may lower the center of gravity of the apparatus when in use.

In accordance with this aspect, there is provided an upright surface cleaning apparatus comprising:
- (a) a surface cleaning head having a first dirty fluid inlet and a first stage liquid separator;
- (b) an upright section moveably mounted to the surface cleaning head, the upright section moveable between an upright storage position and a reclined surface cleaning position, the upright section comprising a second stage solid separator downstream from the first stage liquid separator;
- (c) a liquid delivery system comprising a cleaning liquid reservoir and a fluid flow path extending from the cleaning liquid reservoir to at least one delivery nozzle; and,
- (d) a fluid flow path extending from the dirty fluid inlet head to a clean air outlet and comprising the first stage liquid separator, the second stage solid separator and a suction motor.

In any embodiment, the cleaning liquid reservoir may be part of the surface cleaning head.

In any embodiment, the cleaning solution delivery system may be part of the surface cleaning head.

In any embodiment, the second stage solid separator may comprise a cyclone.

In any embodiment, a portion of the fluid flow path located between the first dirty fluid inlet and the first stage liquid separator may be removable. Optionally, the portion of the fluid flow path and the first stage liquid separator may be concurrently removable.

In any embodiment, the upright section may have a portable surface cleaning unit which is removably mounted to the upright surface cleaning apparatus, wherein the portable surface cleaning unit comprises the second stage solid separator, the suction motor and an above floor cleaning member, the above floor cleaning member comprising a second dirty fluid inlet and a flexible hose. Optionally the cleaning liquid reservoir may be part of the surface cleaning head. Alternately, or in addition, a portion of the fluid flow path located between the first dirty fluid inlet and the first stage liquid separator may be removable and the portion of the fluid flow path and the first stage liquid separator may be concurrently removable.

In accordance with this aspect, there is also provided a surface cleaning apparatus comprising:
- (a) a surface cleaning head having a first dirty fluid inlet;
- (b) at least one separation stage comprising a first separation stage provided in the surface cleaning head, the first separation stage comprising a liquid collection container;
- (c) an upright section moveably mounted to the surface cleaning head, the upright section moveable between an upright storage position and a reclined surface cleaning position, the upright section having a drive handle;
- (d) a cleaning solution deliver system extending from at least a cleaning liquid reservoir to at least one delivery nozzle; and,
- (e) a floor cleaning fluid flow path extending from the first dirty fluid inlet to a clean air outlet, the first fluid flow path including the first separation stage and a suction motor.

In any embodiment, the at least one separation stage may comprise a second separation stage that is downstream from the first separation stage. Optionally, the second separation stage may be part of the surface cleaning head.

In any embodiment, the surface cleaning apparatus may be an all in the head surface cleaning apparatus.

In any embodiment, the surface cleaning apparatus may be an upright surface cleaning apparatus having an upright section moveably mounted to the surface cleaning head, the upright section moveable between an upright storage position and a reclined surface cleaning position and the second separation stage is part of the upright section.

In accordance with this aspect, there is also provide an upright surface cleaning apparatus comprising:
- (a) a surface cleaning head having a first dirty fluid inlet;
- (b) at least one separation stage comprising a first stage liquid separator comprising a liquid collection container;
- (c) an upright section moveably mounted to the surface cleaning head, the upright section moveable between an upright storage position and a reclined surface cleaning position;
- (d) a cleaning solution delivery system comprising a cleaning liquid reservoir and a fluid flow path extending from the cleaning liquid reservoir to at least one delivery nozzle; and,
- (e) a fluid flow path extending from the first dirty fluid inlet head to a clean air outlet and comprising the first stage liquid separator and a suction motor,
- wherein at least one of the liquid collection container and the cleaning liquid reservoir is part of the surface cleaning head.

In any embodiment, both of the liquid collection container and the cleaning liquid reservoir may be part of the surface cleaning head.

In any embodiment, the at least one separation stage may comprise a second separation stage that is downstream from the first separation stage and the second separation stage is part of the surface cleaning head.

In any embodiment, the liquid collection container may be in flow communication with the first stage liquid separator and the first stage liquid separator is part of the upright section.

In any embodiment, the liquid collection container may be part of the surface cleaning head.

In accordance with another aspect of the teachings describe herein, which may be used alone or in combination with any other aspects described herein, an upright surface cleaning apparatus is provided with a cleaning head having two different types of rollers or brushes (e.g., a hard floor cleaning brush and a carpet cleaning brush). The hard floor cleaning brush may be positioned forward of the carpet cleaning brush. The two brushes may be rotatable at different speeds. An advantage of this design is that the cleaning head may be used to treat both hard floors and carpet.

In accordance with this aspect, there is provided a surface cleaning head comprising:
- (a) a body having a front end having a dirty fluid inlet, a rear end and a brush chamber;
- (b) a front hard floor cleaning brush and a rotatable carpet cleaning brush positioned rearward of the front hard floor cleaning brush, each brush having a generally horizontally extending axis of rotation when the surface cleaning head is positioned on a generally horizontal floor;

(c) a debriding member which engages an upper rearward portion of the front hard floor cleaning brush; and, (d) the front end having a front wall which extends to a position spaced at least 0.25" above a hard surface floor when the surface cleaning head is positioned on the hard surface floor, wherein the front hard floor cleaning brush extends to the hard surface floor when the surface cleaning head is positioned on the hard surface floor, and wherein the front hard floor cleaning brush engages at least a portion of an inner surface of a forward portion of the brush chamber.

In any embodiment, engagement of the front hard floor cleaning brush with the inner portion of the brush chamber may essentially inhibit air travelling upwardly over the brush into the brush chamber.

In any embodiment, the front wall may extend to a position spaced between 0.25" and 1.5" above a hard surface floor when the surface cleaning head is positioned on the hard surface floor.

In any embodiment, the front wall may extend to a position spaced between 0.5" and 1.25", and optionally 0.75"-1", above a hard surface floor when the surface cleaning head is positioned on the hard surface floor.

In any embodiment, the debriding member may extend forwardly and downwardly from an upper surface of the brush chamber.

In any embodiment, the front hard floor cleaning brush may comprise microfibers.

In any embodiment, the front hard floor cleaning brush may have an absence of self-supporting bristles.

In any embodiment, the front hard floor cleaning brush may comprise a plurality of generally radially extending elastomeric paddles.

In any embodiment, the carpet brush may comprise a plurality of spaced apart rows of bristles positioned circumferentially around the carpet brush wherein some of the rows of bristles have a lower stiffness compared to other rows of bristles that have a higher stiffness.

In any embodiment, a row of bristles having the lower stiffness may be positioned between two circumferentially spaced apart rows of bristles having the higher stiffness.

In any embodiment, the front rotatable brush may have a diameter that is from 75% to 125% of a diameter of the carpet brush and, optionally, the front rotatable brush and the carpet brush have approximately the same diameter.

In any embodiment, the front rotatable brush and the carpet brush may have approximately the same diameter.

In any embodiment, the front rotatable brush and the carpet brush may operate at different speeds.

In any embodiment, the front rotatable brush may have a radially outer portion which travels at a speed which is from 75% to 125% a speed of the surface cleaning head when travelling over carpet.

In any embodiment, the front rotatable brush may have a radially outer portion which travels at a speed which is proximate the speed of the surface cleaning head when travelling over carpet.

In accordance with this aspect, there is also provided a surface cleaning head comprising:

(a) a body having a front end having a dirty fluid inlet, a rear end and a brush chamber;

(b) a front hard floor cleaning brush and a rotatable carpet cleaning brush positioned rearward of the front hard floor cleaning brush, each brush having a generally horizontally extending axis of rotation when the surface cleaning head is positioned on a generally horizontal floor; and, (c) the front end having a front wall which extends to a positioned spaced above a hard surface floor when the surface cleaning head is positioned on the hard surface floor, wherein the front rotatable brush and the carpet brush operate at different speeds.

In any embodiment, the front rotatable brush may have a radially outer portion which travels at a speed which is from 75% to 125% a speed of the surface cleaning head when travelling over carpet.

In any embodiment, the front rotatable brush may have a radially outer portion which travels at a speed which is proximate the speed of the surface cleaning head when travelling over carpet.

In any embodiment, the front rotatable brush may have a diameter that is from 0.75% to 1.25 percent of a diameter of the carpet brush.

In any embodiment, the front rotatable brush and the carpet brush may have approximately the same diameter.

In accordance with another aspect of the teachings describe herein, which may be used alone or in combination with any other aspects described herein an upright surface cleaning apparatus having a surface cleaning apparatus is provided with a cyclone having a liquid blocking collar (e.g., an annular ring), which inhibits and, optionally essentially prevents or prevents liquid separated from an air stream exiting the cyclone chamber via the cyclone air outlet of the cyclone chamber. An advantage of this design is that a single stage cyclone may be used to separate both liquid and particulate matter entrained in an air stream.

In accordance with this aspect, there is provided a surface cleaning apparatus comprising:

(a) a liquid delivery system comprising at least one spray nozzle that delivers at least one liquid, (b) an inverted cyclone comprising, when the surface cleaning apparatus is in a floor cleaning orientation, a lower end, a lower end wall, an upper end and an upper end wall, the lower end having a cyclone fluid inlet and a cyclone air outlet and the upper end has a separated element outlet, wherein the cyclone air outlet comprises a treated air outlet conduit and a liquid blocking collar is provided on an outer surface of the treated air outlet conduit below an inlet to the treated fluid outlet conduit; and, (c) a solid and liquid collection chamber in communication with the separated element outlet.

In any embodiment, the inverted cyclone may have a cyclone sidewall and the separated element outlet is provided in a sidewall of the inverted cyclone.

In any embodiment, the cyclone fluid inlet may have a height extending away from the lower end wall and the liquid blocking collar may be located above a mid-point of the height when the surface cleaning apparatus is in the floor cleaning orientation.

In any embodiment, the surface cleaning apparatus may further comprise an outlet screen covering the inlet to the treated air outlet conduit.

In any embodiment, the outlet screen may be frusto-conical in shape and the outlet screen may have a lower end that is wider than an upper end of the outlet screen when the surface cleaning apparatus is in the floor cleaning orientation.

In any embodiment, the surface cleaning apparatus may further comprise an outlet conduit screen wherein the outlet conduit screen may be positioned around the treated air outlet conduit at a position below the liquid blocking collar when the surface cleaning apparatus is in the floor cleaning orientation.

In any embodiment, the liquid blocking collar may extend a first lateral distance outward from the treated air outlet conduit and the outlet conduit screen may extend a second lateral distance outward from the treated air outlet conduit and the second lateral distance is less than the first lateral distance.

In any embodiment, the cyclone fluid inlet may have a radial inner end and the outlet conduit screen may be spaced inwardly from the radial inner end whereby a gap is provided between the cyclone fluid inlet and the outlet conduit screen.

In accordance with this aspect, there is also provided a surface cleaning apparatus comprising:
  (a) a liquid delivery system comprising at least one spray nozzle that delivers at least one liquid,
  (b) an inverted cyclone comprising, when the surface cleaning apparatus is in a floor cleaning orientation, a first end, a first end wall, a second end and a second end wall, the first end having a cyclone fluid inlet and a cyclone air outlet and the second end has a separated element outlet, wherein the cyclone air outlet comprises a treated air outlet conduit and a liquid blocking collar is provided on an outer surface of the treated air outlet conduit below an inlet to the treated air outlet conduit; and,
  (c) a solid and liquid collection chamber in communication with the separated element outlet.

In any embodiment, the inverted cyclone may have a cyclone sidewall and the separated element outlet is provided in a sidewall of the inverted cyclone.

In any embodiment, the cyclone fluid inlet may have a height extending away from the first end wall and the liquid blocking collar may be spaced further from the first end wall than a mid-point of the height of the cyclone fluid inlet.

In any embodiment, the surface cleaning apparatus may further comprise an outlet screen covering the inlet to the treated air outlet conduit.

In any embodiment, the outlet screen may be frusto-conical in shape and the outlet screen may have a first end that is positioned closer to the inlet of the treated air outlet conduit than a second end of the outlet screen and the first end of the outlet screen may be wider than a second end of the outlet screen.

In any embodiment, the surface cleaning apparatus may further comprise an outlet conduit screen wherein the outlet conduit screen may be positioned around the treated air outlet conduit and extends between the first end wall and the liquid blocking collar.

In any embodiment, the outlet conduit screen may be frusto-conical in shape and may have a first end that is positioned closer to the first end wall a second end of the outlet conduit screen and the first end of the outlet conduit screen may be wider than the second end of the outlet conduit screen.

In any embodiment, the liquid blocking collar may extend a first lateral distance outward from the treated air outlet conduit and the outlet conduit screen may extend a second lateral distance outward from the treated air outlet conduit and the second lateral distance may be less than the first lateral distance.

In any embodiment, the cyclone fluid inlet may have a radial inner end and the outlet conduit screen may be spaced inwardly from the radial inner end whereby a gap is provided between the cyclone fluid inlet and the outlet conduit screen.

In any embodiment, the cyclone fluid inlet may have a radial inner end and the outlet conduit screen may be spaced inwardly from the radial inner end whereby a gap is provided between the cyclone fluid inlet and the outlet conduit screen.

In accordance with another aspect of the teachings describe herein, which may be used alone or in combination with any other aspects described herein, recovered liquid may be transferred from a collection chamber to a separated liquid collection container which may be remote from the collection chamber. For example, the separated liquid collection container may be provided at a location spaced from the treatment unit, such as in a surface cleaning head of an upright surface cleaning apparatus. An advantage of this design is that, in the case of an upright surface cleaning apparatus or an all in the head surface cleaning apparatus, the experienced handle weight experienced by a user when a cleaning solution or recovered dirty water is stored in the unit is reduced by storing at least some of the liquid other than on the upright section. This may also help lower the center of gravity of the apparatus when in use.

In accordance with this aspect, there is provided a surface cleaning apparatus comprising:
  (a) a liquid delivery system comprising at least one spray nozzle that delivers at least one liquid;
  (b) a separator having a separated element outlet;
  (c) a collection chamber in communication with the separated element outlet;
  (d) a separated liquid collection container downstream from the collection chamber; and,
  (e) a fluid flow path from the collection chamber to the separated liquid collection container.

In any embodiment, when the surface cleaning apparatus is in the floor cleaning orientation, the separated liquid collection container may be positioned below the collection chamber.

In any embodiment, separated liquid may pass to the separated liquid collection container by gravity flow.

In any embodiment, the surface cleaning apparatus may further comprise a pump wherein the pump transfers separated fluid from the collection chamber to the separated liquid collection container.

In any embodiment, the surface cleaning apparatus may further comprise a sensor which issues a signal when water is detected in the surface cleaning apparatus and the pump is actuated in response to the signal.

In any embodiment, the pump may be actuated when the liquid delivery system is actuated and/or when the surface cleaning apparatus is actuated.

In any embodiment, the collection chamber may comprise a screen positioned between an inlet to the fluid flow path and the separated element outlet.

In any embodiment, the surface cleaning apparatus may further comprise a valve positioned to prevent fluid passing from the separated liquid collection container to the separated element outlet. The valve may be provided in the fluid flow path.

In any embodiment, the separator may comprise a cyclone.

In any embodiment, the surface cleaning apparatus may further comprise a surface cleaning head having a dirty fluid inlet and an upright section moveably mounted to the surface cleaning head, the upright section moveable between an upright storage position and a reclined surface cleaning position, the upright section comprising the separator and the surface cleaning head comprising the separated liquid collection container. Optionally, separated liquid passes to the separated liquid collection container by gravity flow. Alternately, or in addition, the surface cleaning apparatus may further comprise a pump wherein the pump transfers separated fluid from the collection chamber to the separated liquid collection container.

In any embodiment, the separated liquid collection container may comprise an inflatable bladder. Optionally, the liquid delivery system may comprise a clean liquid container and the inflatable bladder may be provided in the clean liquid container.

In any embodiment, the liquid delivery system may comprise a clean liquid container and the clean liquid container may comprise a deflatable bladder in the separated liquid collection container, wherein the clean liquid container deflates as clean liquid is withdrawn by the liquid delivery system.

In any embodiment, the separated liquid collection container may be a disposable container.

In accordance with another aspect of the teachings describe herein, which may be used alone or in combination with any other aspects described herein, an upright surface cleaning apparatus, which may be a hand held surface cleaning apparatus, is provided with a system to inhibit, essentially prevent or prevent water from exiting a liquid collection chamber and travelling to a suction motor. For example, if the surface cleaning apparatus is an upright surface cleaning apparatus, the surface cleaning apparatus may include a tilt or recline sensor which inhibits the upright section recline past a certain point when the surface cleaning apparatus is operated in an extractor mode and/or a sensor, such as a moisture sensor which issues a signal when water is detected in, e.g., a liquid collection chamber, the treatment unit or the flow path upstream of the suction motor. It will be appreciated that, surface cleaning apparatus, such as a hand held surface cleaning apparatus, may also incorporate a moisture sensor which issues a signal when water is detected in, e.g., a liquid collection chamber, the treatment unit or the flow path upstream of the suction motor. An advantage of this design is that the unit is inhibited from operating in a manner whereby water may be drawn into the suction motor.

In accordance with this aspect, there is provided a an upright surface cleaning apparatus comprising:
  (a) a surface cleaning head having a dirty fluid inlet;
  (b) an upright section moveably mounted to the surface cleaning head, the upright section moveable between an upright storage position and a reclined surface cleaning position;
  (c) a separator and a liquid collection chamber that receives recovered water, wherein the liquid collection chamber is provided on the upright section;
  (d) a fluid flow path extending from the dirty fluid inlet to a clean air outlet, the first fluid flow path including the separator and a suction motor; and, (e) a recline limiter system adapted to inhibit the upright section reclining to a position at which recovered water enters the separator.

In any embodiment, the recline limiter system may comprise a moisture sensor which issues a signal upon detecting water and a blocking member which, upon issuance of the signal, deploys to inhibit rearward inclination of the upright section further than a particular inclination. The particular rearward inclination of the upright section may be an angle of from 15 to 30° from the floor.

In any embodiment, the auto shut off control system may comprise an inclination sensor which issues a signal upon detecting a particular rearward inclination of the upright section and a blocking member which, upon issuance of the signal, deploys to inhibit rearward inclination of the upright section further than a particular inclination. The particular rearward inclination of the upright section may be an angle of from 15 to 30° from the floor.

In any embodiment, the upright surface cleaning apparatus may further comprise a cleaning solution delivery system comprising at least one spray nozzle that delivers at least one cleaning solution and the recline limiter system is actuated when the cleaning solution delivery system is actuated.

In any embodiment, the recline limiter system may comprise a moisture sensor which issues a water detection signal upon detecting water and an inclination sensor which issues an inclination signal upon detecting a particular rearward inclination of the upright section and the recline limiter system deploys a blocking member that inhibits rearward inclination of the upright section further than a particular inclination upon issuance of the signals.

In any embodiment, the upright surface cleaning apparatus may further comprise a solenoid which is actuated to deploy the blocking member upon issuance of the signals.

In any embodiment, the separator may comprise an inverted cyclone comprising, when the surface cleaning apparatus is in a floor cleaning orientation, a lower end and an upper end, the lower end having a cyclone fluid inlet and a cyclone fluid outlet and the upper end has a separated element outlet in communication with the collection chamber.

In accordance with this aspect, there is also provided a surface cleaning apparatus comprising:
  (a) a surface cleaning head having a dirty fluid inlet;
  (b) an upright section moveably mounted to the surface cleaning head, the upright section moveable between an upright storage position and a reclined surface cleaning position;
  (c) a separator and a liquid collection chamber that receives recovered water, wherein the liquid collection chamber is provided on the upright section;
  (d) a fluid flow path extending from the dirty fluid inlet to a clean air outlet, the first fluid flow path including the separator and a suction motor; and,
  (e) an auto shut off control system adapted to shut the suction motor off prior to the upright section reclining to a position at which recovered water enters the separator.

In any embodiment, the auto shut off control system may comprise a moisture sensor which issues a signal upon detecting water and the auto shut off control system de-actuates the suction motor upon receipt of the signal.

In any embodiment, the auto shut off control system may comprise an inclination sensor which issues a signal upon detecting a particular rearward inclination of the upright section and the auto shut off control system de-actuates the suction motor upon receipt of the signal.

In any embodiment, the particular rearward inclination of the upright section may be an angle of from 15 to 30° from the floor.

In any embodiment, the surface cleaning apparatus may further comprise a cleaning solution delivery system comprising at least one spray nozzle that delivers at least one cleaning solution and the auto shut off control system is actuated when the cleaning solution delivery system is actuated.

In any embodiment, the auto shut off control system may comprise a moisture sensor which issues a water detection signal upon detecting water and an inclination sensor which issues an inclination signal upon detecting a particular rearward inclination of the upright section and the auto shut off control system de-actuates the suction motor when both signals are issued.

In any embodiment, the separator may comprise an inverted cyclone comprising, when the surface cleaning apparatus is in a floor cleaning orientation, a lower end and an upper end, the lower end having a cyclone fluid inlet and a cyclone fluid outlet and the upper end has a separated element outlet in communication with the collection chamber.

In any embodiment, the surface cleaning apparatus may further comprise a cleaning solution delivery system comprising at least one spray nozzle that delivers at least one cleaning solution and the auto shut off control system comprises an inclination sensor which issues a first inclination signal that inhibits the actuation of the suction motor until the upright section has been reclined beyond an initial angular degree of rotation of the upright section from the upright storage position.

In any embodiment, the auto shut off control system may comprise a moisture sensor which issues a water detection signal upon detecting water and the inclination sensor issues a second inclination signal upon detecting a particular rearward inclination of the upright section and the auto shut off control system de-actuates the suction motor when both the water detection signal and the second inclination signals are issued.

In any embodiment, the inclination sensor may comprise a single inclination sensor which issues both the first and second inclination signals.

In any embodiment, the surface cleaning apparatus may be a hand held surface cleaning apparatus.

In accordance with another aspect of the teachings describe herein, which may be used alone or in combination with any other aspects described herein, in order to inhibit, essentially prevent or prevent water from exiting a liquid collection chamber and travelling to a suction motor, a valve may be provided to close a flow path back into a separator, such as a cyclone. Alternately, or in addition the separated liquid container may be configured to provide a reservoir to store separated liquid when the orientation of a surface cleaning apparatus is changed from, e.g., a cleaning orientation to a horizontal orientation or a storage orientation to a reclined cleaning orientation.

In accordance with this aspect, there is provided a surface cleaning apparatus comprising:
 (a) a liquid delivery system comprising at least one spray nozzle that delivers at least one liquid;
 (b) a separation stage comprising a separator and a separated liquid container in communication with a separated element outlet of the separator; and,
 (c) a fluid flow path extending from a dirty fluid inlet to a clean air outlet, the fluid flow path including the separator and a suction motor,
 wherein, when the surface cleaning apparatus is in a vertical orientation, the separated liquid container has a first portion underlying the separator, a second portion laterally spaced from the first portion and positioned below the separator and a third portion positioned above the second portion, and the third portion has a volume that is at least 80% of a volume of the first portion.

In any embodiment, the separation stage may further comprise a solid collection chamber and the first portion underlies the solid collection chamber, the second portion is laterally spaced from the first portion and is positioned below the solid collection chamber and the third portion is positioned above the second portion, and the third portion has a volume that is at least 80% of a volume of the first portion.

In any embodiment, the third portion may be positioned adjacent the solid collection chamber.

In any embodiment, the third portion may extend along a side of the solid collection chamber.

In any embodiment, the third portion may be in flow communication with the solid collection chamber and the second portion is in flow communication with the third portion.

In any embodiment, the first and second portions may comprise a contiguous volume.

In any embodiment, the separator may comprise an inverted cyclone comprising, when the surface cleaning apparatus is in a floor cleaning orientation, a lower end and an upper end, the lower end having a cyclone fluid inlet and a cyclone fluid outlet and the upper end has the separated element outlet, wherein the third portion has a volume whereby, when the surface cleaning apparatus is in a vertical orientation, the first and second portions are full with separated liquid and the third portion is empty and when the surface cleaning apparatus is then moved to a horizontal orientation, an upper surface of the separated liquid is positioned below the separated element outlet.

In any embodiment, the surface cleaning apparatus may be an upright surface cleaning apparatus comprising:
 (a) a surface cleaning head having the dirty fluid inlet;
 (b) an upright section moveably mounted to the surface cleaning head, the upright section moveable between an upright storage position and a reclined surface cleaning position; and,
 (c) a recline limiter system adapted to inhibit the upright section reclining beyond a particular angle of inclination,
 wherein the third portion has a volume whereby, when the surface cleaning apparatus is in a vertical orientation, the first and second portions are full with separated liquid and the third portion is empty and when the surface cleaning apparatus is then moved to the particular angle of inclination, an upper surface of the separated liquid is positioned below the separated element outlet.

In any embodiment, the surface cleaning apparatus may further comprise a valve in a flow connection between the third portion and the solid collection chamber.

In accordance with this aspect, there is also provided a surface cleaning apparatus comprising:
 (a) a liquid delivery system comprising at least one spray nozzle that delivers at least one liquid;
 (b) a separation stage comprising a separator and a separated liquid container in communication with a separated element outlet of the separator; and,
 (c) a fluid flow path extending from a dirty fluid inlet to a clean air outlet, the fluid flow path including the separator and a suction motor,
 wherein, when the surface cleaning apparatus is in a vertical orientation, the separated liquid container has a first portion underlying the separator, a second portion laterally spaced from the first portion and positioned below the separator and a third portion positioned above the second portion, and the third portion has a volume whereby, when the surface cleaning apparatus is in a vertical orientation, the first and second portions are full with separated liquid and the third portion is empty and when the surface cleaning apparatus is then moved to a horizontal orientation, an upper surface of the separated liquid is positioned below the separated element outlet.

In any embodiment, the separation stage may further comprise a solid collection chamber and the first portion underlies the solid collection chamber, the second portion is laterally spaced from the first portion and is positioned below the solid collection chamber and the third portion is positioned above the second portion, and the third portion has a volume that is at least 80% of a volume of the first portion.

In any embodiment, the third portion may be positioned adjacent the solid collection chamber.

In any embodiment, the third portion may extend alone a side of the solid collection chamber.

In any embodiment, the third portion may be in flow communication with the solid collection chamber and the second portion is in flow communication with the third portion.

In any embodiment, the first and second portions may comprise a contiguous volume.

In any embodiment, the separator may comprise an inverted cyclone comprising, when the surface cleaning apparatus is in a floor cleaning orientation, a lower end and an upper end, the lower end having a cyclone fluid inlet and a cyclone fluid outlet and the upper end has the separated element outlet.

In any embodiment, the surface cleaning apparatus may be an upright surface cleaning apparatus comprising:
 (a) a surface cleaning head having the dirty fluid inlet;
 (b) an upright section moveably mounted to the surface cleaning head, the upright section moveable between an upright storage position and a reclined surface cleaning position; and,
 c) a recline limiter system adapted to inhibit the upright section reclining beyond a particular angle of inclination,
wherein the third portion has a volume whereby, when the surface cleaning apparatus is in a vertical orientation, the first and second portions are full with separated liquid and the third portion is empty and when the surface cleaning apparatus is then moved to the particular angle of inclination, an upper surface of the separated liquid is positioned below the separated element outlet.

In any embodiment, the surface cleaning apparatus may further comprise a valve in a flow connection between the third portion and the solid collection chamber.

In accordance with this aspect, there is also provided a surface cleaning apparatus comprising:
 (a) a liquid delivery system comprising at least one spray nozzle that delivers at least one liquid;
 (b) a separation stage comprising a separator, a solid collection chamber in communication with a separated element outlet of the separator and a separated liquid container in communication with the solid collection chamber;
 (c) a fluid flow path extending from a dirty fluid inlet to a clean air outlet, the fluid flow path including the separator and a suction motor; and,
 (d) a valve in a flow connection between the solid collection chamber and the separated liquid container.

In any embodiment, the separated liquid container may have a first portion underlying the solid collection chamber, a second portion laterally spaced from the first portion and positioned below the solid collection chamber and a third portion positioned above the second portion and adjacent the solid collection chamber and the third portion is in flow communication with the solid collection chamber.

In any embodiment, the third portion may have a volume that is at least 80% of a volume of the first portion In any embodiment, the separator may comprise an inverted cyclone comprising, when the surface cleaning apparatus is in a floor cleaning orientation, a lower end and an upper end, the lower end having a cyclone fluid inlet and a cyclone fluid outlet and the upper end has the separated element outlet.

In accordance with another aspect of the teachings describe herein, which may be used alone or in combination with any other aspects described herein, an upright surface cleaning apparatus may be a hand held surface cleaning apparatus. The hand held cleaning apparatus may use any of the embodiments of the various aspects disclosed herein which are not limited to designs of an upright or all in the head surface cleaning apparatus.

In accordance with this aspect, there is provided a hand held surface cleaning apparatus comprising:
 (a) a fluid flow path extending from a dirty fluid inlet provided at a front end of the hand held surface cleaning apparatus to a clean air outlet, the fluid flow path including a separator and a suction motor, wherein the suction motor is positioned rearward of the dirty fluid inlet;
 (b) a separation stage comprising the separator, a solid collection chamber in communication with a separated element outlet of the separator and a separated liquid reservoir in communication with the solid collection chamber wherein the solid collection chamber is positioned rearward of the separated liquid reservoir, the separator is positioned rearward of the solid collection chamber; and,
 (c) a handle.

In any embodiment, the suction motor may be positioned rearward of the separator.

In any embodiment, the separated liquid reservoir may be positioned at the front end.

In any embodiment, the handle may be provided at a rear end of the hand held surface cleaning apparatus.

In any embodiment, a plane may intersect the separated liquid reservoir, the solid collection chamber and the separator.

In any embodiment, the fluid flow path may include an inlet passage that extends from the dirty fluid inlet to an inlet to the separator and a portion of the inlet passage extends through the separated liquid reservoir.

In any embodiment, the fluid flow path may include a downstream portion extending from a separator outlet to the suction motor and the suction motor has an axis of rotation that is generally parallel to the flow axis of the downstream portion.

In any embodiment, the flow axis of the downstream portion may be generally parallel to a flow axis of the inlet passage.

In any embodiment, the separator may comprise an inverted cyclone comprising, when the surface cleaning apparatus is in a floor cleaning orientation, a lower end and an upper end, the lower end having a cyclone fluid inlet and a cyclone fluid outlet and the upper end having the separated element outlet.

In any embodiment, the fluid flow path may include an inlet passage that extends from the dirty fluid inlet to an inlet to the cyclone and the cyclone has an axis of rotation that is generally perpendicular to a flow axis of the inlet passage.

In any embodiment, the hand held surface cleaning apparatus may further comprise an on board power source wherein the on board power source is positioned rearward of the separator.

In any embodiment, the hand held surface cleaning apparatus may further comprise an on board power source wherein the on board power source is positioned rearward of the suction motor.

In any embodiment, the fluid flow path may include an inlet passage that extends from the dirty fluid inlet to an inlet to the separator and the hand held surface cleaning apparatus may further comprise an on board power source wherein at least a portion of the on board power source is positioned above of the suction motor when a flow axis of the inlet passage extends generally horizontally.

In any embodiment, the hand held surface cleaning apparatus may further comprise a cleaning solution delivery system comprising at least one spray nozzle that delivers at least one cleaning solution.

In any embodiment, the handle may extend from the separator to a position rearward of an inlet end of the suction motor.

In any embodiment, the handle may extend from the separator to a position adjacent a rear end of the suction motor.

In any embodiment, the fluid flow path may include an inlet passage that extends from the dirty fluid inlet to an inlet to the separator and when a flow axis of the inlet passage extends generally horizontally, all operating components of the hand held surface cleaning apparatus are positioned below the separated element outlet.

In accordance with another aspect of the teachings describe herein, which may be used alone or in combination with any other aspects described herein, an upright surface cleaning apparatus may include an open cell material, such as a sponge, which may be positioned between an entrance to a separated liquid reservoir and a portion of the separated liquid reservoir which retains separated liquid. An advantage of this design is that stored separated liquid may be inhibited from reversing direction and travelling from a liquid reservoir to a separator (e.g., cyclone) and then to the suction motor.

In accordance with this aspect, there is provided a surface cleaning apparatus comprising:
(a) a fluid flow path extending from a dirty fluid inlet a clean air outlet, the fluid flow path including a separator and a suction motor; and,
(b) a separation stage comprising the separator and a separated liquid reservoir
wherein the separated liquid reservoir includes a liquid sequestering member.

In any embodiment, the liquid sequestering member may comprise an open cell material. The open cell material may comprise an open cell foam.

In any embodiment, the liquid sequestering member may be deformable and reusable.

In any embodiment, the separated liquid reservoir may comprise a container with an openable lid wherein the liquid sequestering member remains in the container when the lid is opened.

In any embodiment, the surface cleaning apparatus may further comprise a compression member which is moveable between a first position in which the liquid sequestering member is uncompressed and a second position in which the liquid sequestering member is deformed. The compression member may comprise a plunger.

In any embodiment, the separated liquid reservoir may have a liquid outlet positioned below the compression member when the separated liquid reservoir is positioned in an emptying orientation, whereby, when the liquid outlet is opened and the liquid sequestering member is compressed, liquid trapped in the liquid sequestering member exits the separated liquid reservoir through the liquid outlet while the liquid sequestering member remains in the separated liquid reservoir.

In any embodiment, the separated liquid reservoir may have a separated liquid outlet, the liquid sequestering member may be deformable and reusable, and the surface cleaning apparatus may further comprise a compression member which is moveable between a first position in which the liquid sequestering member is uncompressed and a second position in which the liquid sequestering member is deformed.

In accordance with this aspect, there is also provided a surface cleaning apparatus comprising:
(a) a fluid flow path extending from a dirty fluid inlet a clean air outlet, the fluid flow path including a separator and a suction motor; and,
(b) a separation stage comprising the separator and a separated liquid reservoir wherein the separated liquid reservoir includes baffle members.

In any embodiment, the baffle members may comprise an open cell material.

In any embodiment, the baffle members may comprise an open cell foam.

In any embodiment, the baffle members may be deformable.

In any embodiment, the separated liquid reservoir may comprise a container with an openable lid wherein the baffle members remain in the container when the lid is opened.

In any embodiment, the surface cleaning apparatus may further comprise a compression member which is moveable between a first position in which the baffle members are uncompressed and a second position in which the baffle members are deformed. The compression member may comprise a plunger.

In any embodiment, the separated liquid reservoir may have a liquid outlet positioned below the compression member when the separated liquid reservoir is positioned in an emptying orientation, whereby, when the liquid outlet is opened and the open cell material is compressed, liquid trapped in the open cell material exits the separated liquid reservoir through the liquid outlet while the open cell material remains in the separated liquid reservoir.

In any embodiment, the separated liquid reservoir may have a separated liquid outlet, the baffle members are deformable, and the surface cleaning apparatus further comprises a compression member which is moveable between a first position in which the baffle members are uncompressed and a second position in which the baffle members are deformed.

DRAWINGS

The drawings included herewith are for illustrating various examples of articles, methods, and apparatuses of the teaching of the present specification and are not intended to limit the scope of what is taught in any way.

In the drawings:

FIG. 6 is a schematic, cross-sectional view of the surface cleaning apparatus of FIG. 5, in an above floor cleaning configuration;

FIG. 7 is a schematic, cross-sectional view of another embodiment of a surface cleaning apparatus;

FIG. 8 is a schematic, cross-sectional view of another embodiment of a surface cleaning apparatus;

FIG. 9 is a schematic, cross-sectional view of yet another embodiment of a surface cleaning apparatus;

FIG. 16B is a schematic, cross-sectional view of a portion of the surface cleaning apparatus with a valve in a first configuration;

FIG. 18B is a cross-sectional view of the liquid separator of FIG. 18A, taken along line 18B-18B;

FIG. 23A is a top view of another embodiment of a liquid blocking collar;

FIG. 23B is a cross-sectional view taken along line B-B in FIG. 23A;

FIGS. 23C and 23D are cross-sectional views of alternative configurations for the blocking collar of FIG. 23a;

FIG. 51A is a schematic representation of another embodiment of a liquid reservoir unit;

FIG. 53 is a representation of the liquid reservoir unit of FIG. 52, with a tank removed;

FIG. 56 is a schematic, cross-sectional representation of one embodiment of a surface cleaning head;

FIGS. 59 to 61 are schematic, cross-sectional representations of other embodiments of a surface cleaning head, having a front facing dirty fluid inlet;

FIG. 62 is a schematic cross-sectional view of a portion of another embodiment of a surface cleaning apparatus with a removable air flow path segment;

FIG. 67A is a cross-sectional view of one embodiment of a surface cleaning head;

FIG. 68 is a cross-sectional view of another embodiment of a surface cleaning head;

FIG. 69 is a bottom perspective view of one embodiment of a treatment unit;

FIG. 79 is a cross-sectional, schematic representation of another embodiment of a surface cleaning apparatus in a first configuration; and.

DETAILED DESCRIPTION OF THE INVENTION

Figure 1:
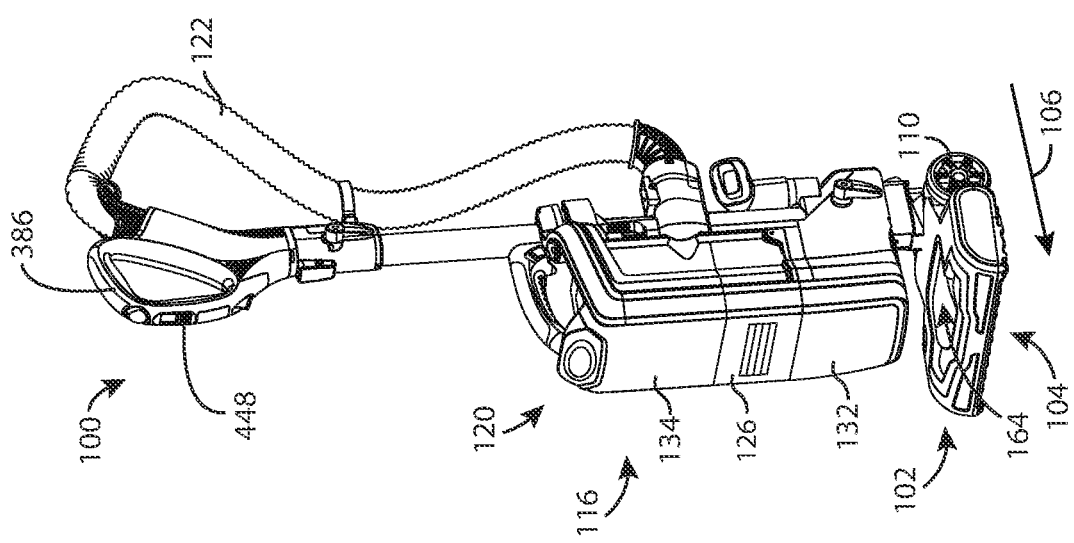
FIG. 1 is a front perspective view of one embodiment of a surface cleaning apparatus in an upright position.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. As used herein, two or more parts are said to be "rigidly coupled", "rigidly connected", "rigidly attached", or "rigidly fastened" where the parts are coupled so as to move as one while maintaining a constant orientation relative to each other. None of the terms "coupled", "connected", "attached", and "fastened" distinguish the manner in which two or more parts are joined together.

Description of a Surface Cleaning Apparatus

Referring to FIGS. 1 to 4, a first embodiment of a surface cleaning apparatus 100 is shown. The following is a general discussion of this embodiment which provides a basis for understanding several of the features which are discussed herein. As discussed in detail subsequently, each of the features may be used by themselves in a surface cleaning apparatus or in combination with one or more of the other features.

In the embodiment shown, the surface cleaning apparatus is an upright surface cleaning apparatus that can be operated in a vacuum cleaner mode and optionally in an extractor mode. In alternate embodiments, the surface cleaning apparatus may be another suitable type of surface cleaning apparatus, such as a canister type vacuum cleaner, and hand vacuum cleaner, a stick vacuum cleaner or a carpet extractor.

In the illustrated example, the surface cleaning apparatus 100 includes a surface cleaning head 102 that is configured to travel (e.g., roll) across a surface to be cleaned, such as a floor. The surface cleaning head 102 includes at least one dirty fluid inlet 104, which may be positioned proximate the floor when the surface cleaning head 102 is in the surface cleaning position. The dirty fluid inlet 104 may be configured to receive relatively dry air, dirt, debris and the like, as would any vacuum cleaner. Dirty fluid inlet 104 may optionally be configured to receive liquids, such as water, cleaning solutions and other liquids that may be on the surface, as would any extractor. It will be appreciated that two different dirty fluid inlets 104 may be provided, one for each function. For example, the surface cleaning head 102 may include a dirty air inlet, configured to receive air and solid debris entrained within the air, and a separate dirty liquid inlet, configured to receive liquids.

The dirty air inlet and dirty liquid inlet, and any other inlets, may be spaced apart from each other, or optionally may be at least partially nested within each other. For example, the dirty air inlet may be positioned forward of the dirty liquid inlet, in a direction of travel of the apparatus 100—indicated by arrow 106 in FIG. 1. This may help ensure that the dirty air inlet reaches and draws in solid material from the surface before the dirty liquid inlet travels over that portion of the surface. This may help prevent fouling of the dirty liquid inlet. An advantage of this design is that a user may use the same surface cleaning head to vacuum and then extract and may do so in a single operation.

Alternately, a single dirty fluid inlet 104 may be configured to receive both relatively dry and relatively wet materials. For example, a single dirty fluid inlet may be reconfigurable (e.g., by reducing the cross-sectional area of part of the flow path through a nozzle in a direction transverse to a direction of air flow therethrough) to have increased air flow at the inlet when used to draw in relatively wet materials (e.g., when operated in an extractor mode).

Except as required by an embodiment using a particular feature disclosed herein, the surface cleaning head 102 may be of any suitable design (including any of those described herein), and may include a variety of features, such as rotating brushes, static brushes, squeegees, liquid application nozzles or sprayers, treatment units, motors, lights and the like.

Figure 2:
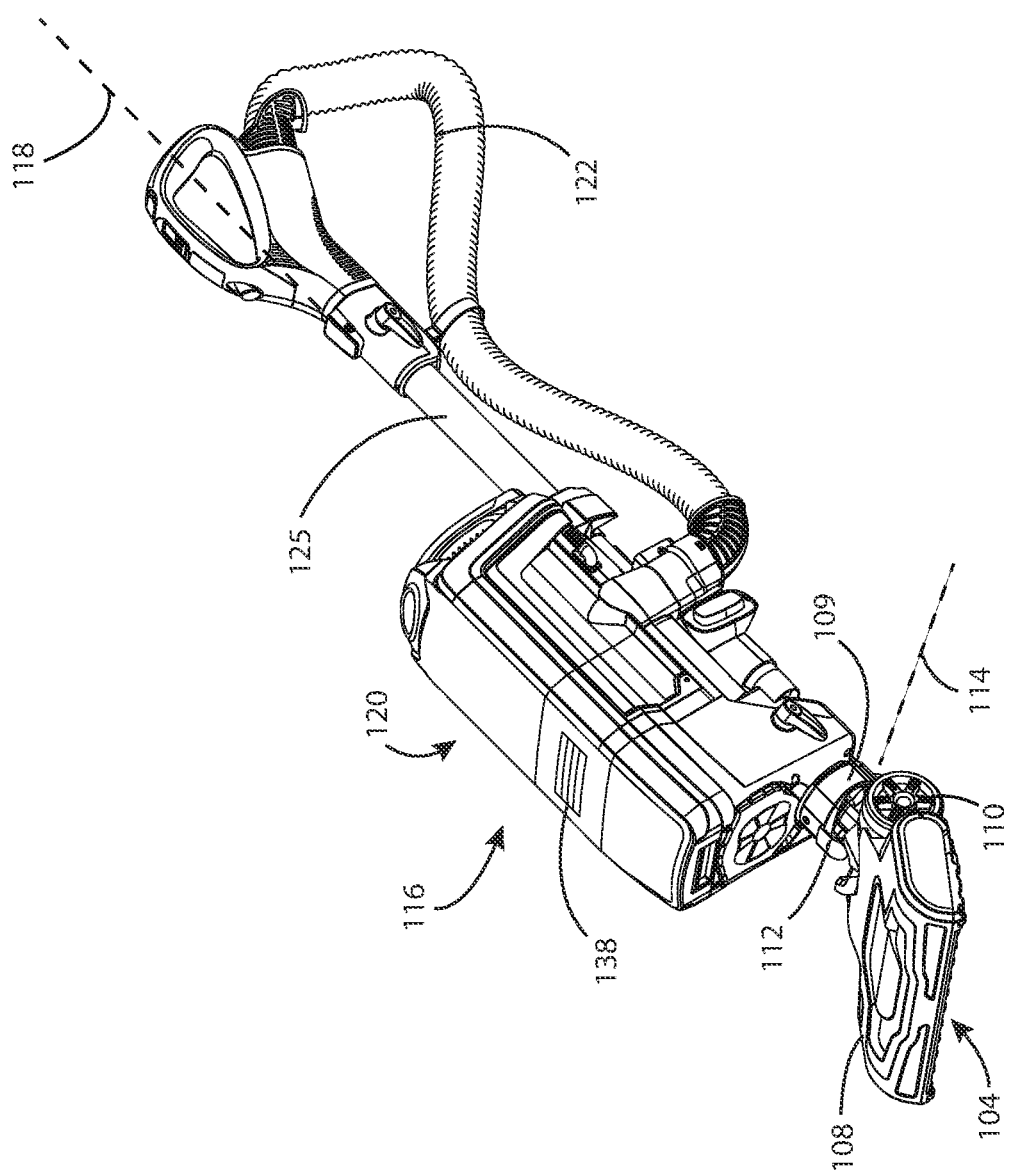
FIG. 2 is a front perspective view of the surface cleaning apparatus of FIG. 1, in a reclined, surface cleaning position.

Referring also to FIG. 2, in the illustrated example, the surface cleaning head may include a body 108, a pair of rear wheels 110 connected to the body to rollingly support the surface cleaning head 102 above a surface to be cleaned and, optionally a pair of front wheels or glides. If the surface cleaning apparatus is an upright surface cleaning apparatus, then the surface cleaning head 102 may also include a support member 112 that is moveably (e.g., pivotally) connected to the body 108 by, e.g., a pivot joint 109 so as to be able to pivot about an axis 114, between an upright, storage position (FIG. 1) and an inclined, surface cleaning position (FIG. 2) and an upright section 116 that is mounted to the support member 112. Upright section 116 may be optionally removably mounted to support member 112.

Optionally, the upright section 116 may also be steeringly connected to the surface cleaning head 102. For example the upright section 116 may be movable in at least one other degree of freedom relative to the surface cleaning head 102 to help facilitate steering of the surface cleaning head 102. For example, the upright section 116 may be rotatably connected to the support member 112 so that it can rotate about its longitudinal axis 118 relative to the surface cleaning head 102. Alternatively, or in addition, the upright section 116 may be pivotable about a different, second (e.g., a forwardly extending horizontal) pivot axis relative to the surface cleaning head 102. A drive handle 386 may be provided on the upright section 116, optionally toward its upper end, and a user may grasp the drive handle 386 to maneuver and/or steer the surface cleaning apparatus 100 across a surface.

As exemplified, the upright section 116 may include a cleaning unit 120 (which as exemplified in FIG. 4 may be a portable cleaning unit) which may optionally be fluidly connected to the dirty fluid inlet 104 via a fluid flow path or passage when removed from the upright section. As exemplified, the fluid flow path may include at least one flexible fluid flow conduit member, in the form of a hose 122, and at least one rigid fluid flow conduit member (a wand) 125.

At least one suction motor, provided in a motor housing, and at least one fluid treatment unit are provided in the fluid flow path to separate dirt, debris, and/or liquids from the fluid traveling through the apparatus 100. In the illustrated example, the suction motor, motor housing and the treatment unit are both provided in the cleaning unit 120.

The fluid treatment unit may include any suitable treatment apparatuses, including one or more momentum separators, one or more cyclonic separators, one or more filters, bags and the like. Preferably, at least one treatment apparatus is provided in the fluid flow path upstream from the suction motor.

Upright Embodiment with Stacked Configuration

In accordance with one aspect of the teachings described herein, which may be used in combination with any other aspects described herein, an exemplary embodiment of a surface cleaning apparatus 100 may be configured as a generally, upright-style cleaning apparatus and may be arranged so that at least some of its operating components are generally vertically stacked on top of each other. Optionally, the surface cleaning apparatus may also be configured so that at least a portion of the fluid passage extending between its first stage liquid separator and its second stage cyclone separator is located toward the front side of the upright section.

In accordance with this aspect, two or more, and optionally three or more, operational components of the apparatus are vertically stacked, and optionally vertically aligned, in the upright section 116. The operating components may be one or more separators, and optionally two or more separators (e.g., a liquid separator and a downstream dry separator), and a suction motor.

An advantage of stacking the components is that it may help reduce the overall size of the cleaning unit 120. It may also help simplify the fluid flow path within the cleaning unit 120, which may help reduce backpressure in the fluid flow path or otherwise help improve the efficiency of the cleaning unit 120. Further, this will enable a liquid separator to be provided at a lower elevation and reduce the energy required during operation of the apparatus as the water need not be raised to atop of the upright surface cleaning apparatus.

Figure 5:
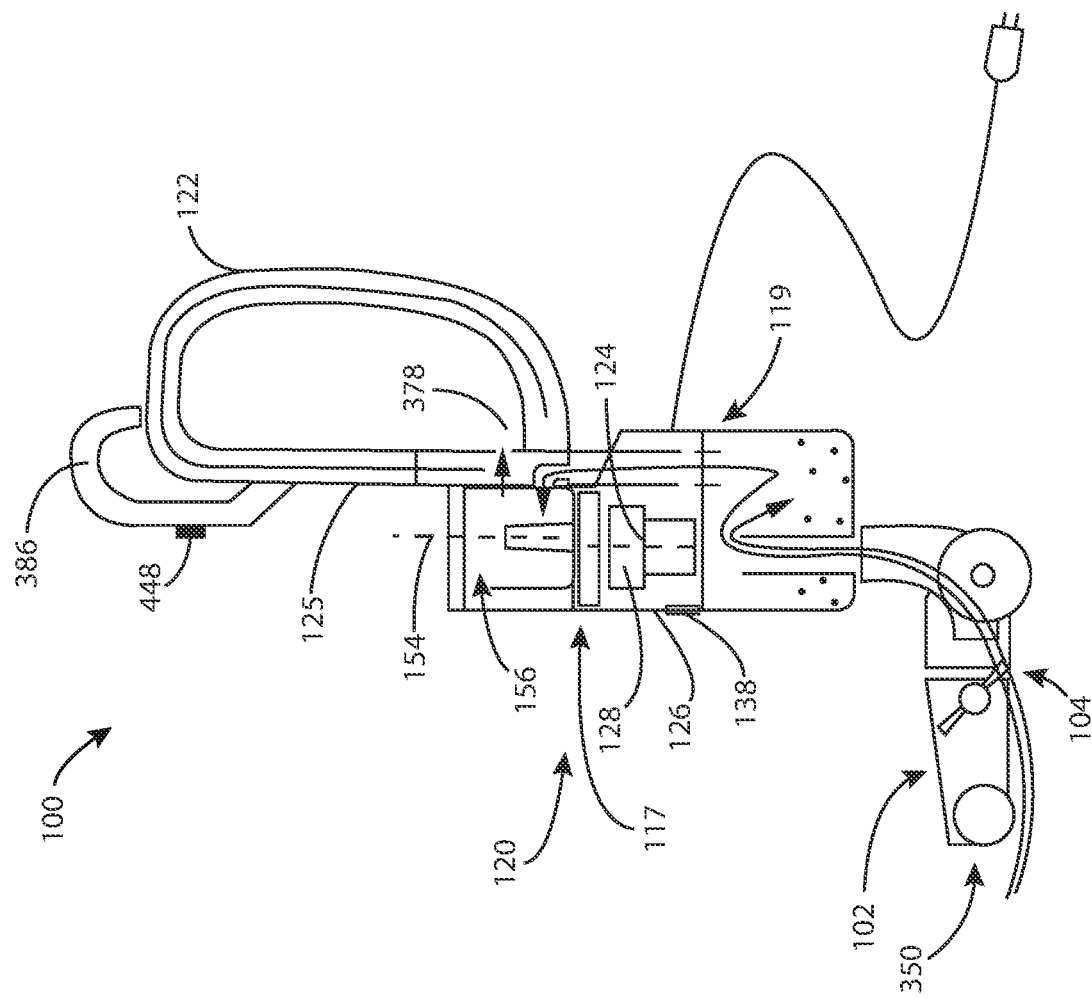
FIG. 5 is a schematic, cross-sectional view of another embodiment of a surface cleaning apparatus.

As exemplified in FIGS. 5 and 6, the cleaning unit 120 includes a suction motor 124 that is positioned in a motor housing 126. The motor 124 has a motor axis of rotation 128 for a fan blade (not shown), which optionally extends generally vertically as exemplified. In the illustrated example, the cleaning unit 120 also includes a downstream separation stage that is operable to separate debris and/or entrained liquid from the air that is flowing through the cleaning unit 120. The separation stage also includes a separator that operable to separate solid particulate matter or debris form the air flow. It will be appreciated that the upright section 116 may include one or more liquid separators for removing liquid from the air flow, one or more dry separators for removing dirt and other dry debris from the air flow, and/or one or more combination separators that is operable to simultaneously separate liquid and dry debris. All of these may be including in cleaning unit 120.

As exemplified in FIGS. 5 and 6, the separation stage includes a treatment unit 130 which is configured as a two stage treatment unit having a first stage separator 132 and a second stage separator 134 positioned in the fluid flow path downstream from the first stage separator 132, and upstream from the suction motor 124.

In this embodiment, the surface cleaning apparatus 100 includes a surface cleaning head 102 (having a front end 350 including the dirty fluid inlet 104) and the upright section 116 is moveably mounted to the surface cleaning head 102, between an upright storage position (FIG. 5) and a reclined surface cleaning position (like that shown in FIG. 2). The upright section 116 has a front side 117, an opposing rear side 119, the first stage liquid separator 132 has a liquid separator fluid inlet 146 downstream from the dirty fluid inlet 104 and a liquid separator fluid outlet 150. A second stage cyclone separator 134 includes a cyclone chamber 142 that has a cyclone chamber fluid inlet 152 and a cyclone chamber air outlet 158. The suction motor 124 is downstream from the second stage cyclone separator 134 and has a suction motor inlet end 135. It will be appreciated that any momentum separator and cyclone may be used.

As exemplified, the first stage liquid separator 132 is positioned such that the outlet of the first stage liquid separator 132 is below the inlet of the second stage separator 134. It will be appreciated that the first stage liquid separator 132 may be below, and may underlie, the second stage separator 134. Accordingly, in accordance with this aspect, at least a portion of a fluid passage 149 that fluidly connects the liquid separator fluid outlet 150 to the cyclone chamber fluid inlet 152 may extend generally upwardly when the upright section 116 is in the storage position (FIG. 5).

In the embodiment of FIGS. 5 and 6, the fluid passage 149 is located at the rear side 119 of the upright section 116. In this embodiment, the cyclone separator 134 is positioned above and downstream from the first stage liquid separator 132 when the upright section is in the storage position (FIG. 5). However, as exemplified in FIG. 8, fluid passage 149 may be located at the front side, or on a lateral side on cleaning unit 120 towards the front side.

Optionally, each of the first and second stage separators 132, 134 may include a single separating apparatus (e.g. a single cyclone chamber, a single liquid separator such as a momentum separator) and/or two or more separating apparatuses arranged in parallel with each other (e.g. two or more cyclone chambers arranged in parallel). Alternatively, instead of having two separating stages, the treatment unit 130 may include only a single stage separator (with one or more separating apparatuses) or three or more separating stages in series with each other.

In the embodiment of FIGS. 5 and 6, the first stage separator 132 is a momentum separator 140 (of any suitable configuration) that is configured to help separate water and other liquids from the incoming dirty fluid flow, and the second stage separator 134 is a single cyclonic separator that includes a cyclone chamber 142 and an external solid collection chamber 144 and that is configured to help separate dust, dirt and other solid debris from the dirty fluid flow.

In the embodiment of FIGS. 5 and 6, the momentum separator 140 includes a momentum separator fluid inlet 146 that is provided in a lower surface 147 of the liquid separator 132, at least one liquid collection reservoir, which in this embodiment is a liquid collection container or reservoir 148 and a momentum separator fluid outlet 150. Any momentum separator may be used. The momentum separator fluid inlet 146 can be fluidly connected to the surface cleaning head 102 to receive the incoming dirty fluid. Liquid separated from the fluid flow can be retained in the liquid collection container 148. After at least some, and preferably when a majority and/or substantially all of the liquid entrained in the air entering via a dirty fluid inlet has been separated from the dirty fluid flow drawn in via the dirty air inlet, the remaining dirty fluid flow can exit via the momentum separator fluid outlet 150 and travel through a suitable fluid passage (which may but optionally does not include the hose 122 and wand 125 in this embodiment) to a dirty air inlet 152 of the cyclone chamber 142. Any cyclone separator may be used. The dirty fluid may then circulate within the cyclone chamber 142 about a longitudinal cyclone axis 154 (which may extend generally vertically as exemplified) which can help disentrain dirt and other solid debris (which may be wet from exposure to a liquid applied by the apparatus) from the fluid flow. The cyclone may comprise a solid collection chamber 114 that is external to the cyclone chamber 142. The separated debris can exit the cyclone chamber 142 via a separated element outlet 156 (FIG. 5) and accumulate in the solid collection chamber 144. The fluid can then exit the cyclone chamber 142 via the cyclone chamber air outlet 158 and flow downstream toward the suction motor. Depending on the configuration of the separator, the separated element outlet 156 may receive dry dirt and debris particles, separated liquid and/or a combination of dry debris and liquid.

In this embodiment, and in several other embodiments described herein, the second stage separator 134 (e.g. the cyclone separator) overlies at least a portion of, and optionally all of, the first stage liquid separator 132 (e.g. the momentum separator 140 as illustrated). This may help reduce the overall lateral size of the cleaning unit 120.

It will be appreciated that, in an alternate embodiment (such as shown in FIG. 7 or 8), the remaining dirty fluid flow after exiting via the momentum separator fluid outlet 150 may travel via a conduit to the cyclone air inlet without passing through the hose 122 and wand 125. An advantage of such embodiments is that wand 125 and hose 122 may only be used for dry cleaning activities, and therefore may not have water or wet particulate matter travel therethrough.

As exemplified, a pre-motor filter 160 may positioned in the fluid flow path (optionally within a pre-motor filter housing or pre-motor chamber 161), between the treatment unit 130 and the suction motor 124, to further filter air exiting the treatment unit 130 before it enters the suction motor 124. The pre-motor filter 160 may be any suitable filter member, including one or more layers of porous media filters (such as foam, felt and the like). An optional post-motor filter (not shown) may alternately or in addition be provided in the fluid flow path, between the suction motor 124 and the clean air outlet 138 of the apparatus 100 (see also FIG. 2).

In this example, suction motor housing 126 is positioned above the first stage separator 132 and below the second stage separator 134. This may help reduce the overall front/back and/or side to side width of the cleaning unit 120, for example as compared to a configuration in which the suction motor housing is positioned forward, rearward or laterally beside the treatment unit 130 or portions thereof. In the illustrated arrangement, the suction motor 124 is oriented vertically, such that the motor axis 128 is substantially parallel to the cyclone axis 154, and to the direction the dirty fluid flow is travelling as it enters the momentum separator 140 (illustrated by axis 163 in FIG. 6). In some configurations two or more of these axes 128, 154 and 163 may be co-axial with each other. In this embodiment, and in others described herein, the suction motor axis of rotation 128 intersects both the first stage liquid separator 132 and the second stage cyclone separator 134.

Preferably, if the treatment unit 130 is configured to include a liquid separator, such as the momentum separator 140, the liquid separator may be provided toward the lower end of the treatment unit 130 and/or cleaning unit 120. As liquid is relatively heavy, as compared to air, positioning any liquid separators relatively low in the apparatus 100 may help lower the centre of gravity of the cleaning unit 120 and/or apparatus 100. This may help reduce help improve the hand feel of the apparatus 100 when in use, and may help reduce the amount of lifting and/or rotational forces exerted on the user's hand/wrist when pushing and steering the apparatus. Positioning any liquid separators relatively low in the apparatus 100 may also reduce the distance/elevation that water and other liquids will travel from the surface cleaning head 102 to the liquid separator. Reducing the elevation that the liquids travel within the fluid flow path may help reduce the amount of energy required to motivate the dirty fluid flow. The dirty fluid that has had its liquids substantially removed can then continue to travel further upwardly within the apparatus 100, such as to the second stage separator 134 provided toward the top of the cleaning unit 120. Positioning liquid separators toward the bottom of the cleaning unit 120 may also help reduce the likelihood that liquids other operating components of the apparatus 100 will come in to contact with the liquid, such as, for example if liquid happens to leak from the liquid collection container 148.

In the embodiment illustrated in FIGS. 5 and 6, the suction motor 124 and its housing 126 are positioned above the momentum separator 140 and below the cyclonic separator. That is, between the first stage separator 132 and second stage separator 134. This configuration is preferred if the cyclone is an inverted cyclone as exemplified. In such a configuration, the air may exit the cyclone and travel axially downwardly to the suction motor. This configuration may further help lower the centre of gravity of the apparatus 100, as the suction motor 124 can be relatively heavy, as compared to the cyclonic separator. Alternatively, the apparatus may be configured so that the suction motor 124 is positioned above or below the treatment unit 130, rather than between two separators. For example, as exemplified in FIGS. 7 and 8, if the cyclone is not an inverted cyclone and has an air outlet at the upper end, the air may exit the cyclone and travel upwardly to the suction motor. In this embodiment, the suction motor 124 is positioned above the entire treatment unit 130, i.e. above both the first separator 132 and the second separator 134.

In the embodiment of FIG. 7, the fluid flow path is configured such that dirty fluid is conveyed from the surface cleaning head 102 to the first separator 132, and then into the second separator 134 without travelling through a flexible hose or elongate conduit section that extends past the suction motor housing 126, or other intervening portions of the cleaning unit 120. In this embodiment, the liquid separator fluid outlet 150 is positioned at an upper end of the liquid separator and the cyclone chamber air outlet 158 is positioned at an upper end of the cyclone chamber 142 and the suction motor inlet end 135 faces towards the cyclone chamber air outlet 158. In this embodiment, the cyclone separator 134 is positioned above the first stage liquid separator 132 and the suction motor 124 is positioned above the cyclone separator 134. The cleaning unit 120 is also configured so that in this embodiment (and in the embodiment of FIG. 8), the liquid separator fluid outlet 150 is positioned at an upper end of the momentum separator 132,140, the cyclone chamber air outlet 158 is positioned at an upper end of the cyclone chamber 142 and the suction motor inlet end 135 faces towards the cyclone chamber air outlet 158, while the optional pre-motor filter 160 is positioned between the suction motor inlet end 135 and the cyclone chamber air outlet 158.

Referring to FIG. 8, another embodiment of a surface cleaning apparatus 100 is configured so that some or all of the flow path from the momentum separator air outlet to the cyclone air inlet 152 is provided towards the front side of the treatment unit 130. In this embodiment, at least a portion of a fluid passage 149 that fluidly connects the liquid separator fluid outlet 150 to the cyclone chamber fluid inlet 152 extends generally upwardly when the upright section 116 is in the storage position (FIG. 5, and is located at the front side 119 of the upright section 116.

When the upright section 116 is reclined in the surface cleaning position, liquid that is contained in the liquid collection container 148 may tend to collect along the rear portion of the first separator 132, as the rear portion will tend to be at a lower elevation than the front portion of the first separator 132. In the embodiment of FIG. 7, for example, this may tend to direct the liquid toward the momentum separator fluid outlet 150, and the cyclone air inlet 152 that is connected thereto. If the liquid reaches the cyclone air inlet 152 (or is close enough to be drawn in by the fluid flow), the liquid may enter the cyclone chamber 142 and/or continue through the fluid flow path and possibly reaching the suction motor 124. This may damage or otherwise interfere with the operation of the cyclone chamber 142 and/or suction motor 124. The higher the level of the liquid within the liquid collection container 148, the more likely it may be for the liquid to flow out via the momentum separator fluid outlet 150. Positioning some or all of the flow path from the momentum separator air outlet to the cyclone air inlet 152 towards the front of the treatment unit 130, such as on the front side, may help reduce the likelihood that liquid will flow into the cyclone air inlet 152 when the upright section is reclined.

As exemplified in FIG. 8, the cyclone air inlet 152 may be provided at the forward most portion of the treatment unit 130. Alternatively, the cyclone air inlet 152 may be positioned at another location that is generally in the front/forward half of the treatment unit 130, i.e. that is forward of a central dividing plane 166, and optionally that is forward of the motor axis 128 and cyclone axis 154.

As exemplified in FIG. 8, providing the momentum separator fluid outlet 150 towards the front of the treatment unit 130 may help facilitate a relatively direct connection between the momentum separator fluid outlet 150 and the cyclone air inlet 152 (e.g. a relatively short fluid flow path with few to no bends), even when the cyclone air inlet 152 is provided in the forward half of the treatment unit 130. Alternatively, the momentum separator fluid outlet 150 may remain at the rear, or in the rear half, of the treatment unit 130 and may be connected to the cyclone air inlet via a forwardly extending conduit or other portion of the fluid flow path. In such an arrangement, the momentum separator fluid outlet 150 and the cyclone air inlet 152 may be provided on opposing halves (front half, back half) of the treatment unit 130, while still permitting the cyclone air inlet 152 to be in the forward half, and helping to prevent the flow of liquid into the cyclone air inlet 152.

In the embodiment of FIG. 8, the liquid separator fluid outlet 150 is positioned at an upper end of the liquid separator and the cyclone chamber air outlet 158 is positioned at an upper end of the cyclone chamber 142 and the suction motor inlet end 135 faces towards the cyclone chamber air outlet 158.

Optionally, some embodiments of the surface cleaning apparatus 100 (including those shown in FIGS. 1-12) may be configured so that at least a portion of the solid collection chamber is positioned laterally beside, and generally at the same elevation as a separated liquid reservoir of the liquid separator.

Figure 17A:
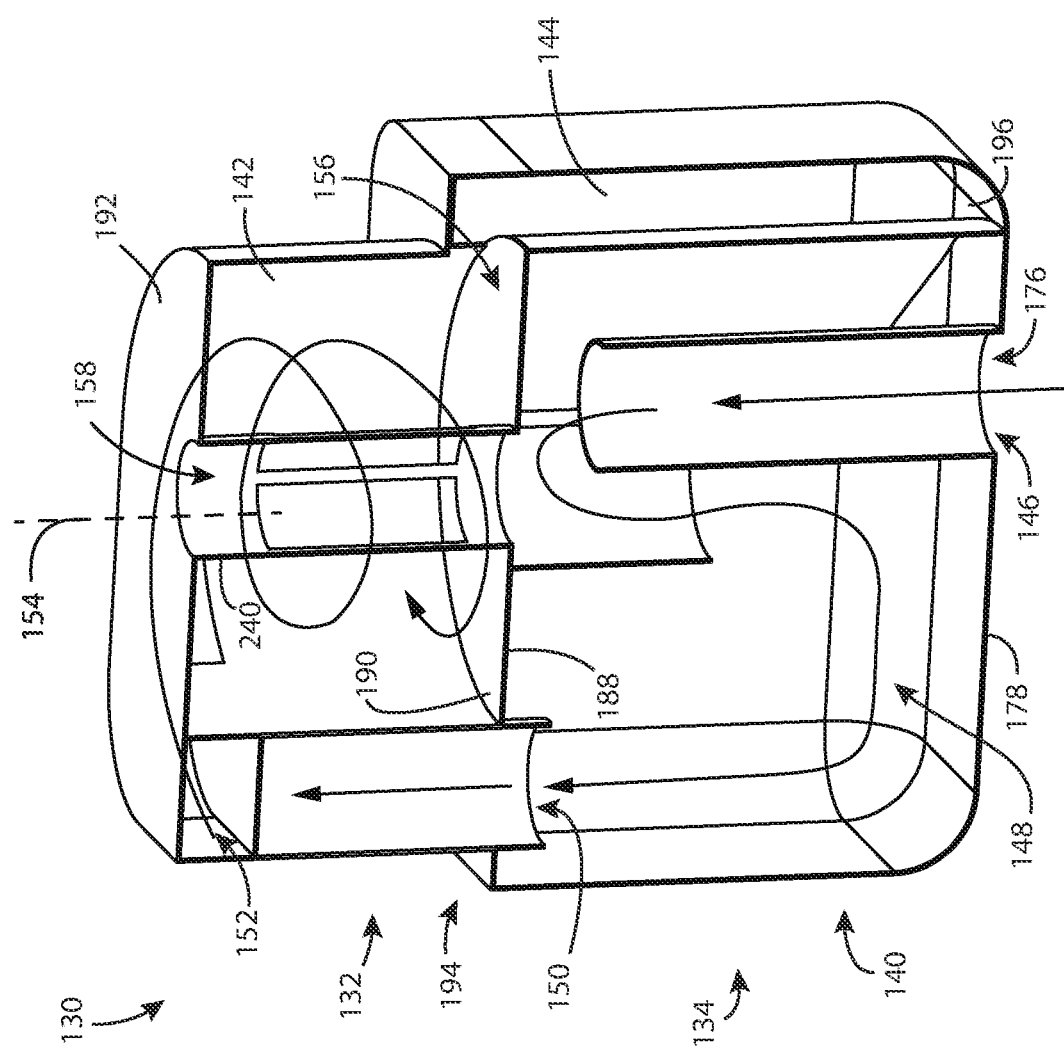
FIG. 17A is a cross-sectional view of one example of a two stage treatment unit.
Figure 17B:
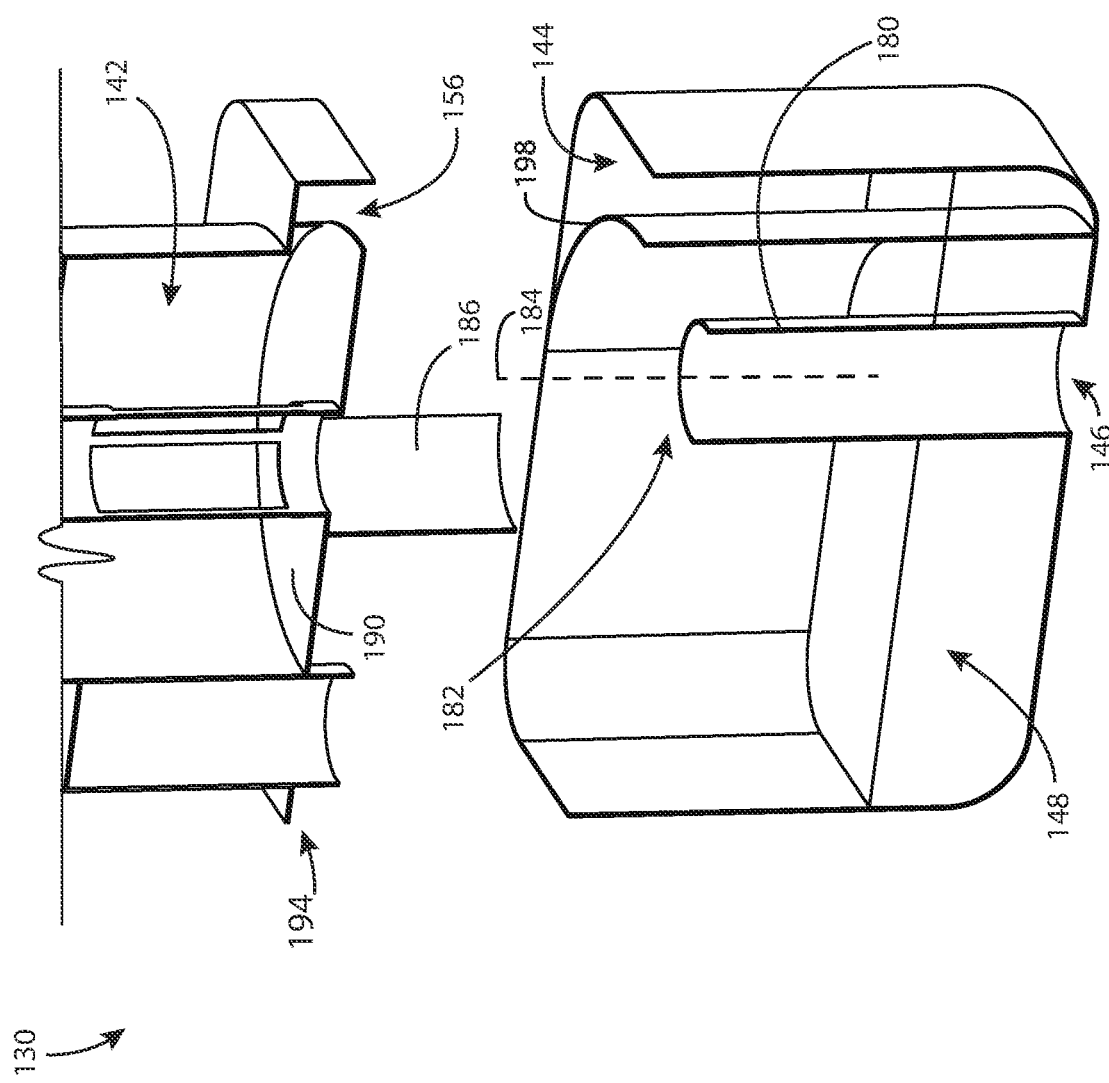
FIG. 17B is a cross-sectional view of the treatment unit of FIG. 17A, with a lid or upper section removed.

Optionally, the cleaning unit 120 may be configured so that at least a portion of the solid collection chamber of the second separator stage is positioned at about the same elevation as the separated liquid reservoir of the first separation unit. This may help reduce the overall size of the cleaning unit 120. Referring also to FIGS. 17A and 17B, an example of a two stage separator is shown in which the solid collection chamber 144 associated with the cyclone chamber 142 of the second separator stage 134 is configured to extend beyond the lower end of the cyclone chamber 142 and to be at the same elevation (i.e. to at least partially axially overlap) as the liquid collection container 148, such that a portion of the solid collection chamber 144 is laterally adjacent and at least partially laterally surrounds the liquid collection container 148.

It will be appreciated that a stacked configuration as disclosed herein may also be used for, e.g., a canister style apparatus or a hand help apparatus.

Momentum Separator with Two Inlets

In accordance with one aspect of the teachings described herein, which may be used in combination with any other aspects described herein, a momentum separator may have one or more side wall inlets.

Figure 18A:
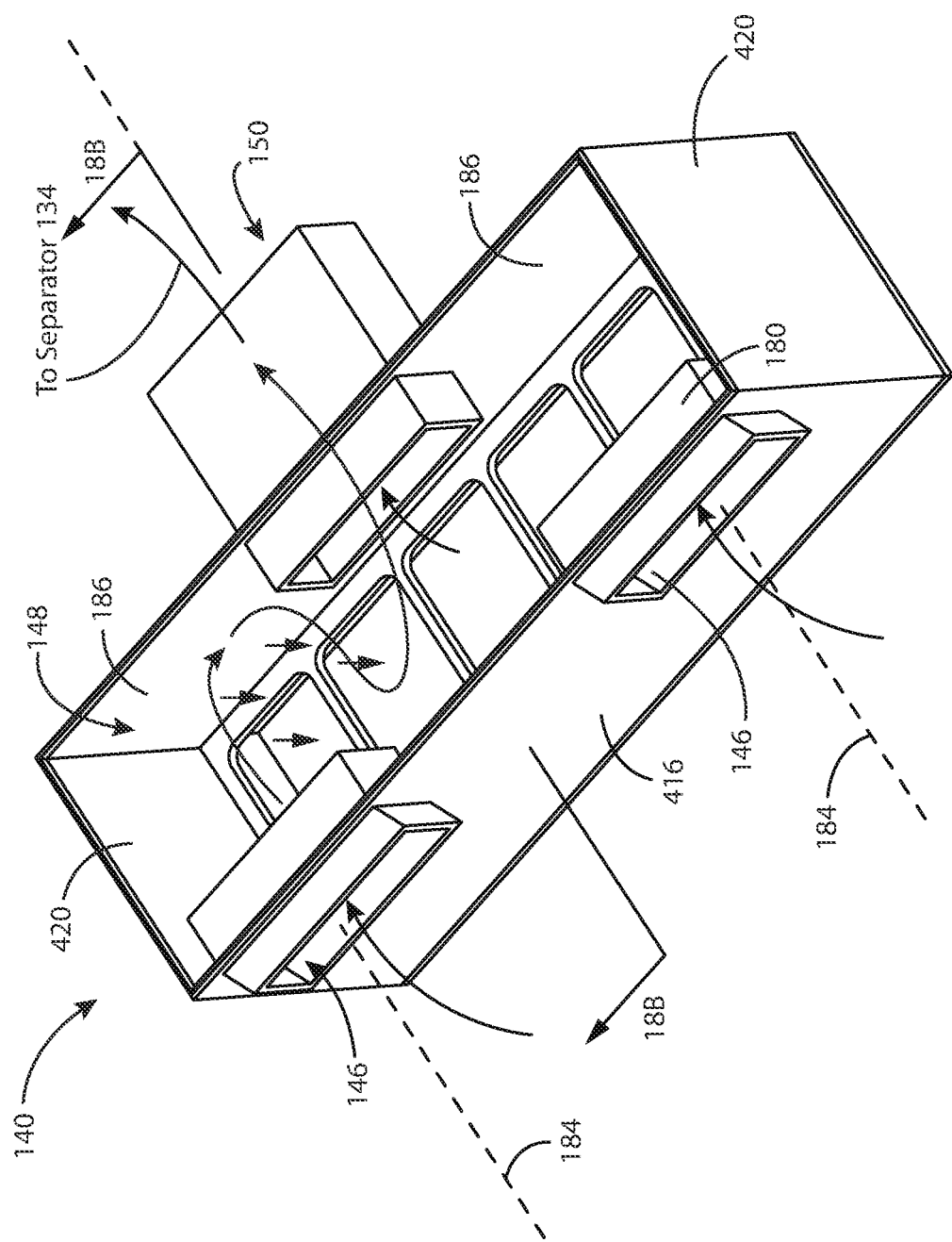
FIG. 18A is a perspective view of one embodiment of a liquid separator with an upper lid removed.

As exemplified in FIGS. 18A and 18B, a momentum separator has an optional openable lid removed to reveal the interior of the separator 140. This embodiment of the momentum separator 140 may be positionable in the surface cleaning head 102, for example as an alternative to the liquid separator shown in the embodiments of FIGS. 13 and 14. In this embodiment, the momentum separator 140 is generally rectangular in shape, and include a front wall 416, rear wall 418 spaced rearwardly from the front wall 416, opposing sidewalls 420 and a lower wall 178. The upper end of the momentum separator 140 can be enclosed by a removable upper lid 194 (not shown in FIGS. 18A and 18B). Together, the walls help define a generally rectangular liquid collection container 148.

In this embodiment, two, separate dirty fluid inlets 146 are provided in a front wall 416 of the separator 140 to receive incoming dirty fluid flows. If the momentum separator 140 is provided in a surface cleaning head 102, each dirty fluid inlet 146 may be in fluid communication with the brush chamber (such as brush chamber 354 described herein) and dirty fluid inlet 104. Extending inwardly from each dirty fluid inlet 146 is a respective inlet conduit 180, extending along generally forward/rearwardly extending conduit axes 184, that helps direct the incoming fluid flow in the generally rearward direction as it enters the momentum separator 140. When travelling rearwardly, at least some of the incoming dirty fluid, and liquid entrained therein, may impact an internal wall portion 186 which may help separate the liquid from the air flow. As exemplified, the internal wall portions 186 may be integrally formed with the rear wall 418, instead of being provided as a separate member projecting downwardly from the lid. In other embodiments, the lid for this momentum separator may include downwardly depending members that provide the internal walls 186 to be engaged by the incoming fluid.

Liquid that is separated from the dirty fluid flow can then fall downwardly into, and be retained in, the liquid collection container 148 and the relatively drier air flow can continue out via the liquid separator fluid outlet 150 and travel downstream to a suitable second separator 134 (such as a cyclone chamber 142).

Optionally, a liquid porous divider, such as an embodiment of a screen 298 can be provided within the liquid collection container 148, and may sub-divide the liquid collection container 148 into a lower portion (below/downstream from the screen 298) and an upper portion 148a (similar to that shown in other embodiments herein). Preferably, most of the separated liquid can pass through the screen 298 and be collected in the lower portion of the liquid collection container 148. The screen 298 may help filter solid particles from the separated liquid (for optional, separate removal) and/or may help reduce the amount of sloshing or splashing of liquid that is contained in the liquid collection container 148 as the momentum separator 140 is moved forward and backward or otherwise jostled while in use. This may be preferable in configurations in which the momentum separator 140 is provided in the surface cleaning head 102, where it may be prone to repeated forward and backward motion as the surface cleaning head 102 is moved over a surface. The screen 298 may include a frame supporting a wire mesh, as shown in this example, or may be of any other suitable, liquid permeable configuration. The screen 298 may optionally be removable, such as by lifting it upwardly and out of the open top of the momentum separator 140, to help facilitate cleaning and/or emptying of the liquid collection container 148 or the screen 298 itself.

Solid and Liquid Collection Regions Emptyable Concurrently

In accordance with one aspect of the teachings described herein, which may be used in combination with any other aspects described herein, dual stage treatment units may be configured so that a solid collection region (e.g., the solid collection chamber 144) and the liquid collection reservoir or region (e.g., liquid collection container 148) may be openable and/or may be emptied concurrently. In some embodiments, the solid collection chamber and the liquid collection reservoir may be openable via a single operation. This may help facilitate emptying of the two stage treatment unit.

FIGS. 17A and 17B exemplify a treatment unit 130 having a first separator 132 that includes a momentum separator 140, and a second separator 134 that includes a cyclone chamber 142 wherein both collection regions are emptyable concurrently.

As exemplified, the momentum separator 140 is configured so that separator fluid inlet 146 includes an upstream end 176 provided in a lower wall 178, and an inlet conduit 180 that extends upwardly along an inlet conduit axis 184, from the upstream end 176 to a downstream end 182. The momentum separator 140 also optionally includes at least one baffle or deflecting member that is position adjacent the downstream end 182 of the separator fluid inlet 146. In this example, the deflecting member includes a portion of the upper end wall 188 of the momentum separator that overlies that downstream end 182, as well as an internal wall 186 that depends inwardly from the upper end wall 188 of the momentum separator 140. The deflecting member is preferably positioned such that an incoming stream of dirty fluid will impact the deflecting member, i.e., will contact the upper end wall 188 and internal wall 186, upon entering the momentum separator 140. This may help cause the dirty fluid stream to change direction relatively quickly, which may tend to help separate liquids from the fluid flow. To exit the momentum separator 140, in the illustrated embodiment, the fluid can travel through the momentum separator fluid outlet 150 which is, in this configuration, provided in the upper end wall 188 and preferably at the front side if the momentum separator is provided on an upper section. The separated liquids, and any other solids and debris, may tend to collect in the liquid collection container 148, while the remaining portion of the incoming dirty fluid flow can continue downstream to the second separator 134.

From the momentum separator fluid outlet 150, the dirty fluid can flow into the cyclone chamber 142 via the cyclone air inlet 152. Debris separated from the air flow via the cyclonic swirling (about cyclone axis 154) can travel through the cyclone separated element outlet 156 and fall into the solid collection chamber 144. In the illustrated example, the solid collection chamber 144 is external the cyclone chamber 142 and is positioned generally beside, and at least partially surrounding the momentum separator 140. This may help reduce the overall size of the treatment unit 130 and facilitate the concurrent emptying of the collection regions. For example, referring to FIG. 17B, in the illustrated embodiment the second separator 134 is removably mounted to the upper end of the first separator 132.

As exemplified in FIGS. 17A and 17B, at least a portion, and optionally the entire upper end wall 192 of the cyclone chamber 142 can be openable to help facilitate emptying of the cyclone chamber 142. Optionally, the upper wall 192 may be openable at the same time as the cyclone chamber 142 is detached from the momentum separator 140, such that the liquid collection container 148, solid collection chamber 144 and cyclone chamber 142 can be open at the same time. In some arrangements, an actuator may be provided so that the upper wall 192 is openable.

In this configuration, the cyclone chamber 142 forms part of an openable lid 194 of the momentum separator 140, wherein a lower cyclone end wall 190 and the upper end wall 188 of the momentum separator 140 are part of a common lid structure 194. This lid 194 also includes the momentum separator fluid outlet 150 and the cyclone separated element outlet 156, as well as the internal wall 186. When the cyclone chamber 142 is removed, the liquid collection container 148 and the solid collection chamber 144 are simultaneously opened for emptying, maintenance and the like and are emptyable concurrently. In this configuration, both the solid collection chamber 144 and the separated liquid collection container 148 have an openable top, but in other embodiments may have openable bottoms, sidewalls and the like.

In the illustrated example, the cyclone chamber 142 overlies the liquid collection container 148 portion of the momentum separator 140, and is laterally offset from (i.e. does not overlie) the solid collection chamber 144, such that the momentum separator is at least partially nested beneath the cyclone chamber 142 and beside the solid collection chamber 144. In other embodiments, at least a portion of the solid collection chamber 144 can extend beneath the cyclone chamber 142, such that the cyclone chamber 142 overlies at least a portion of the solid collection chamber 144 and the momentum separator 140.

In this embodiment, the top of the liquid collection container 148 is configured to have an openable lid 194 for emptying. Alternatively, other portions of the liquid collection container 148 may be openable, including, for example, the lower wall 178, and/or an openable port or drain opening may be provide in one of the walls instead of having an openable wall. Providing an openable lid 194 may be preferable in some instances, as it may help reduce the likelihood of leaks developing around the perimeter of an openable lower wall 178. In this embodiment, the openable top of the liquid collection container 148 includes the cyclone chamber 142.

In this embodiment, the solid collection chamber 144 is positioned laterally beside the liquid collection container 148 and the cyclone chamber 142 is positioned above and overlies the liquid collection container 148 (and optionally, as shown, my not overlie the solid collection chamber 144). In this arrangement, the cyclone axis of rotation 154 intersects the liquid collection container 148, but does not intersect the solid collection chamber 144.

Optionally, the liquid collection container 148 and the solid collection chamber 144 can be at least partially formed from integral, one-piece construction, in which the lower wall 178 is integrally formed with a bottom wall 196 of the solid collection chamber 144, and the two collection regions 148 and 144 are bounded by a common, integrally formed sidewall portion 198 (FIG. 16). This may help reduce the chances of leakage, and may help reduce the overall size of the treatment unit 130.

In accordance with the exemplified embodiment, removing the cyclone chamber opens the upper end of the two collection regions 148 and 144, thereby permitting both collection regions to be emptied concurrently. Alternately, each collection region may have its one lid or openable upper end, which would still permit the two collection regions 148 and 144 to be emptied concurrently. It will be appreciated that the two collection regions 148 and 144 may be remote from the separators but may still be emptied concurrently.

Optionally, the treatment unit 130 may be removable from the cleaning unit 120 (or wherever it is mounted to the apparatus 100) as a single, generally sealed unit. This may help simplifying the emptying process and/or may help reduce the likelihood of the contents of the liquid collection container 148 and solid collection chamber 144 from spilling. For example, in the illustrated embodiment, the treatment unit 130 may be separated from the surface cleaning apparatus 100 while in its closed configuration (other than fluid inlet and outlet conduits). In this arrangement, the treatment unit 130 is substantially sealed, but for the momentum separator fluid inlet 146 and the cyclone chamber air outlet 158. This can allow the liquid collection container 148, solid collection chamber 144 and cyclone chamber 142 remain generally sealed while the treatment unit 130 is removed and transported to a sink, garbage can or the like for emptying. In this arrangement, the solid collection chamber 144 and liquid collection container 148 are removable in their closed configuration.

Alternatively, instead of being configured to open simultaneously, the liquid collection container 148 and the solid collection chamber 144 may be separately openable. For example, the liquid collection container 148 may have an independently openable lid, and may be emptied (e.g. poured into a sink or drain) without also dumping the dry dirt and debris from the solid collection chamber 144 at the same time—or vice versa. This may help prevent unwanted mixing of wet and dry debris when emptying the treatment unit 130.

Single Stage Separator with a Liquid Blocking Member

The following is a description of one example of a treatment unit that is configured to separate liquid and solid debris from an incoming dirty fluid flow using a single treatment stage, such as a cyclonic separation apparatus. This treatment unit may be suitable for use with the surface cleaning apparatuses described herein, for example as an alternative to the dual stage cleaning units.

Figure 19:
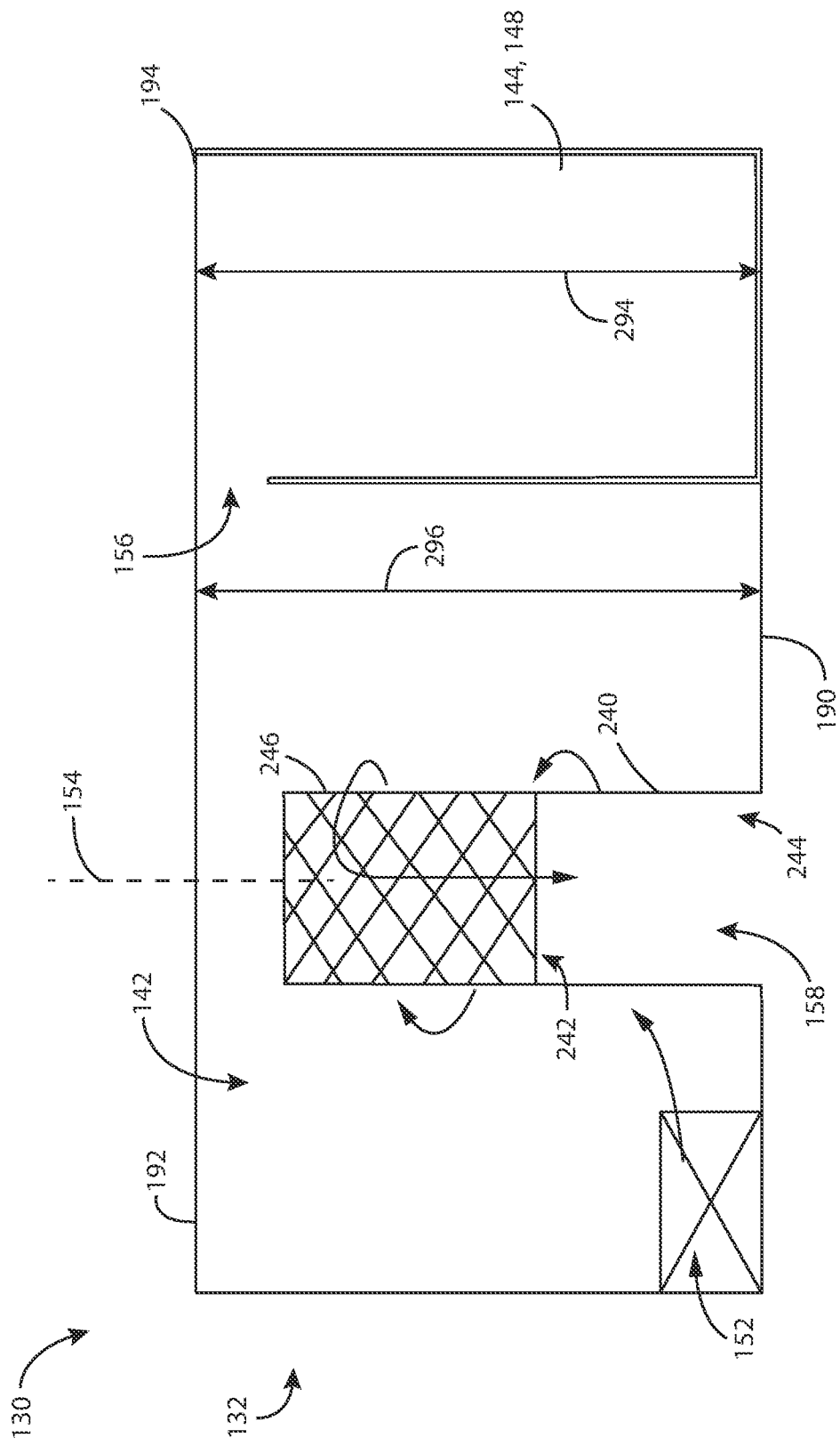
FIG. 19 is a schematic, cross-sectional view of one embodiment of a single stage treatment unit.
Figure 20:
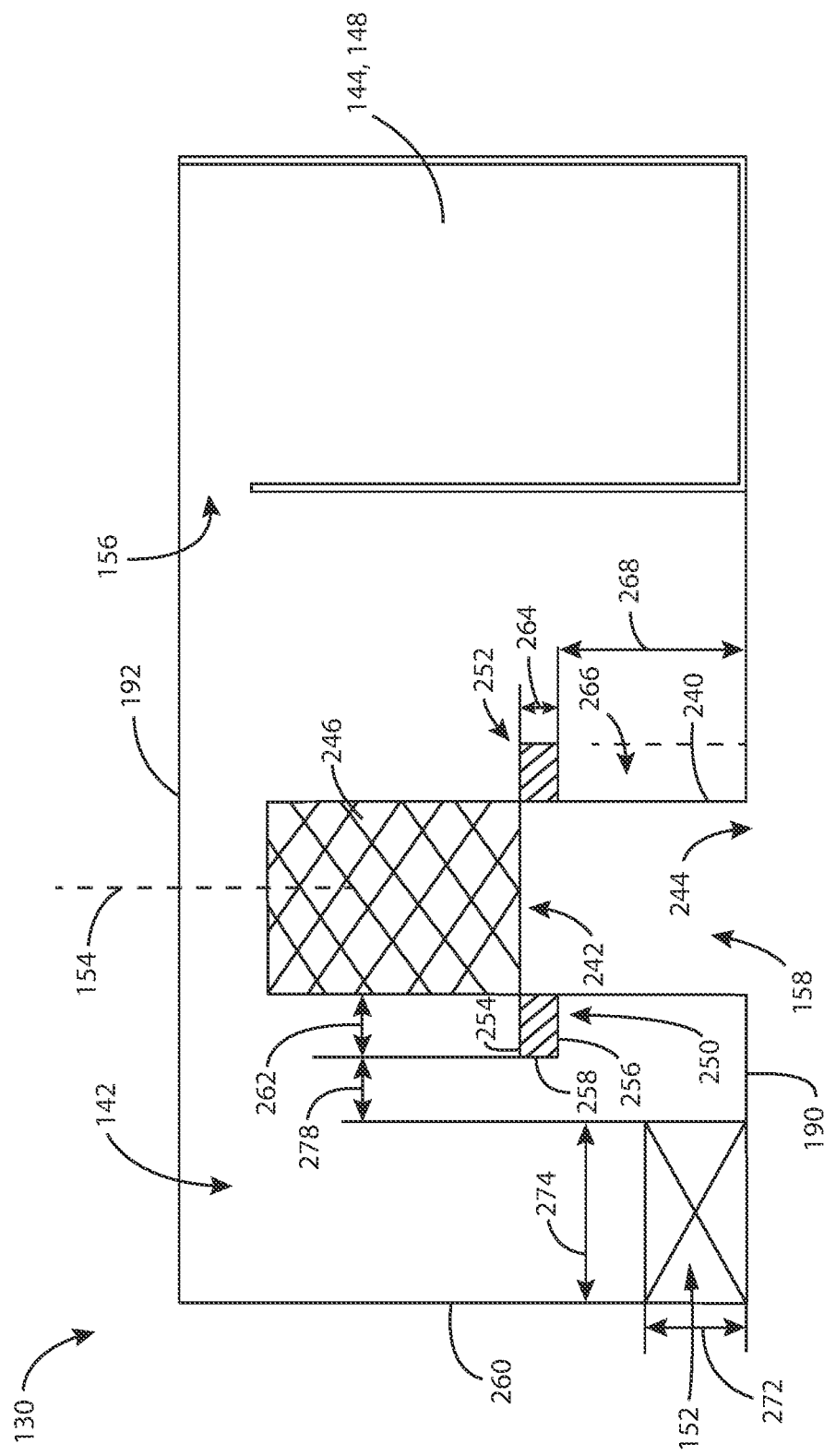
FIG. 20 is a schematic, cross-sectional view of another embodiment of a single stage treatment unit.

Referring to FIGS. 19 and 20, a schematic representation of one example of a treatment unit 130 is configured to include a first separator 132 that is a combined solid and liquid separator, and need not include a second separator 134. In this example, the first separator 132 includes a cyclone chamber 142, having a dirty fluid inlet 152 that is configured to accommodate an incoming dirty fluid stream that may include a combination of liquid and solid debris/contaminants, and a cyclone chamber air outlet 158. As the fluid swirls around the cyclone axis 154, at least some of the liquid and solid debris can become disentrained from the fluid flow. Relatively cleaner and/or dryer fluid can then exit via the cyclone chamber air outlet 158, and proceed downstream to a pre-motor filter, suction motor and the like.

Debris that is separated from the fluid flow can exit the cyclone chamber 142 via a separated element outlet 156, that is analogous to the separated element outlet 156 described in relation to a "dry" cyclone separator, but that is also configured to convey separated liquid (e.g. water) and other wet debris. The separated debris is then collected in a combined solid and liquid collection container which, in this example, functions as both a solid collection chamber 144 and the liquid collection container 148 described herein.

A single stage treatment unit 130 having some or all of the features of the embodiments shown in FIGS. 19-41 (or other suitable features) may be arranged in a variety of suitable orientations on the upright section 116 or other location on the surface cleaning apparatus 100. For example the treatment unit 130 may be oriented so that the cyclone air inlet 152 and cyclone chamber air outlet 158 are generally at the lower end of the cyclone chamber 142 when the upright section 116 is in the storage position and floor cleaning positions. In such arrangements the separated element outlet 156 could be located toward the upper end of the cyclone chamber 142. The separated element outlet 156 may also be positioned so that is generally toward the front side of the surface cleaning apparatus 100 (or cleaning unit 120), toward the rear side of the surface cleaning apparatus 100 (or cleaning unit 120) or facing one of the left or right lateral sides of the surface cleaning apparatus 100 (or cleaning unit 120). For example, if the a single stage treatment unit 130 were used in combination with the surface cleaning apparatus 100 of FIGS. 1-4, it may be oriented so that the separated element outlet 156 is located on the rear side of the cyclone chamber 142. Similarly, if a single stage treatment unit 130 were used in a hand held surface cleaning apparatus 100, such as in the embodiments of FIGS. 64-66, the separated element outlet 156 may be provided toward the rear end of the hand held apparatus, which is the same end that includes the drive handle 386 for the hand held apparatuses 100.

In the illustrated embodiment, the cyclone chamber air outlet 158 includes an axially extending outlet conduit 240, also referred to as a vortex finder, extending between an inner, inlet end 242 and an outlet end 244. A relatively coarse mesh or screen 246 may be provided to cover the inlet end 242 of the conduit 240, which may help prevent hair, fluff and other debris from exiting the cyclone chamber 142 via the cyclone chamber air outlet 158.

The treatment unit 130 of FIGS. 19 and 20 may be useable for treating fluid containing both liquid and solid debris, but under some operating conditions liquid, such as dirty water that has been disentrained from the fluid flow and has accumulated on the lower end wall 190 of the cyclone chamber 142, and may tend to swirl around the base of the outlet conduit 240. In some circumstances, some of the liquid swirling around the outlet conduit 240 may tend to creep up the outer surface of the outlet conduit 240 toward the open, inlet end 242 and may pass through the screen 246 and flow out via the cyclone chamber air outlet 158. Under such conditions, liquid may continue downstream in the fluid flow path, beyond the treatment unit 130 and may soil or clog other downstream filters (such as the pre-motor filter) and/or may interfere with or damage the suction motor. Accordingly, if substantial amounts of liquid are to be collected, the embodiment of FIG. 19 may be preferably used as a second stage separator.

Preferably, the solid collection chamber 144 and liquid collection container 148 (which in FIG. 19 is exemplified as a single container) can be openable for emptying. In the illustrated example, the upright section of the treatment unit 130 can be configured as an openable lid 194 that can be pivoted, detached or otherwise opened to empty the solid collection chamber 144 and liquid collection container 148. Optionally, as illustrated in FIG. 19, the upper end wall 192 of the cyclone chamber 142 may also be part of the openable lid 194. In this arrangement, opening the lid 194 may simultaneously open the solid collection chamber 144, the liquid collection container 148 and the cyclone chamber 142. This may help facilitate emptying of the first separator 132.

Optionally, as exemplified in FIGS. 20-27, to help prevent the liquid from escaping the cyclone chamber 142 via the cyclone chamber air outlet 158, the treatment unit 130 may include one or more liquid blocking members to help impeded the flow and/or escape of liquids. The liquid blocking member may be of any suitable configuration.

Referring to FIG. 20, an embodiment of a single stage treatment unit 130 is schematically illustrated and is configured an inverted cyclone chamber 142 similar to the embodiment of FIG. 19. This embodiment also includes one example of a liquid blocking member that comprises a blocking collar 248 that is provided on, and extends generally radially outwardly from an outer surface of the outlet conduit 240. The presence of the blocking collar 248 may help inhibit the creep/progression of liquids along the outer surface of the outlet conduit 240 before it reaches the inlet end 242. The liquids reaching the blocking collar 248 may tend to fall off of the outlet conduit 240, back toward the lower end wall 190. Without being limited by theory, the blocking collar 248 may create a sub circulation zone that inhibits or prevents fluid travelling upwardly above blocking collar 248. Some of this liquid may remain in the cyclone chamber 142 (to be emptied when the cyclone chamber 142 is opened) and some of the liquid may become re-entrained and exit the cyclone chamber 142 via the separated element outlet 156.

As exemplified, the blocking collar 248 is, in this example, a generally annular, ring-like member having an inner end 250 abutting or attached to the outlet conduit 240, and a free, radially outer end 252 that is spaced from the inner end 250 by a collar width 262, taken in the radial direction (i.e. orthogonal to the cyclone axis 154). The collar width 262 can be any suitable distance, and may be, for example between about 0.01 inches and about 0.75 inches, between about 0.04 inches and about 0.25 inches and may be between about 0.08 inches and about 0.125 inches.

The blocking collar 248 also includes, in this example, a first end surface 254 (an upper surface as illustrated in FIG. 20) that is spaced from and faces the upper end wall 192, and an opposing second end surface 256 (a lower surface as illustrated in FIG. 20) that is spaced from and faces the lower end wall 190. A radially outer side wall 258 extends between the end walls 254 and 256, and is spaced radially inwardly from a side wall 260 of the cyclone chamber 142. End walls 254 and 256 may be, planar, concave or convex. Side wall 258 may be planar, curved or angled with respect to the cyclone axis.

The first and second end surfaces 254 and 256 are separated from each other by a collar height 264, taken in the axial direction. The collar height 264 may be any suitable distance and may be, for example, between about 0.01 inches and about 0.75 inches, between about 0.04 inches and about 0.25 inches and may be between about 0.08 inches and about 0.125 inches. In some embodiments, the collar width 262 may be equal to the collar height 264. In other embodiments, the collar width 262 and collar height 264 may be different.

In the illustrated configuration, a generally annular overhang region 266 is defined as a portion of the interior of the cyclone chamber 142 that is axially between the lower end wall 190 and the second end surface 256.

The blocking collar 248 may be positioned at any suitable location along the length of the outlet conduit 240, including toward (and/or at) the inlet end 242, such that the first end surface 254 is generally flush with the inlet end 242, below the inlet end 242 of the outlet conduit 240 or at an intermediate location along the height (in the axial direction) of the outlet conduit 240. Referring to FIG. 20, the blocking collar 248 is positioned at the inlet end 242 of the conduit 240, and is spaced from the lower end wall 190 by a lower spacing distance 268, that may be any suitable distance and may be greater than the height of the cyclone inlet 152. Referring to the embodiment shown in FIG. 21, the blocking collar 248 is spaced from the inlet end 242 by an upper spacing distance 270.

Figure 21:
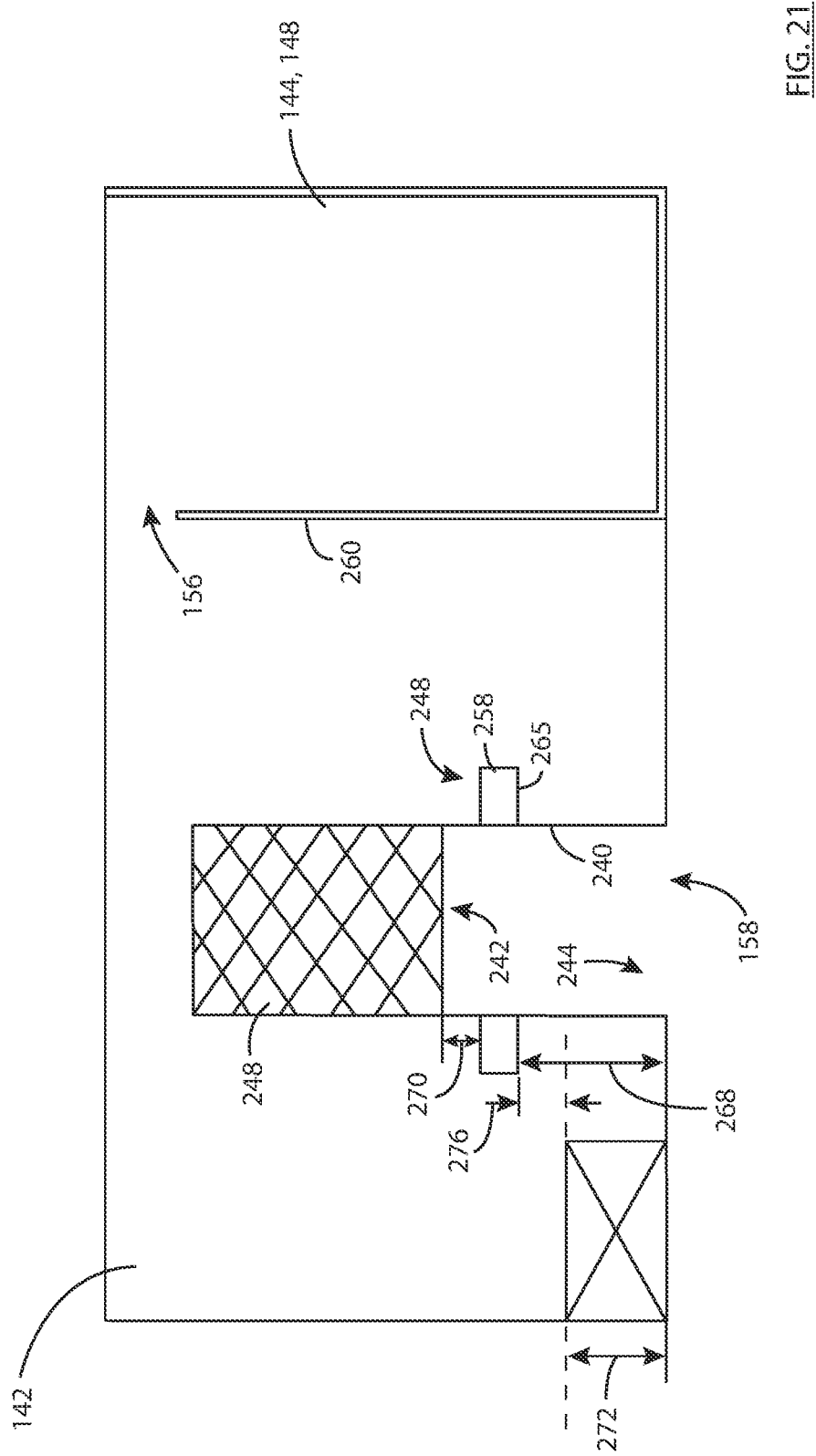
FIG. 21 is a schematic, cross-sectional view of another embodiment of a single stage treatment unit.
Figure 22:
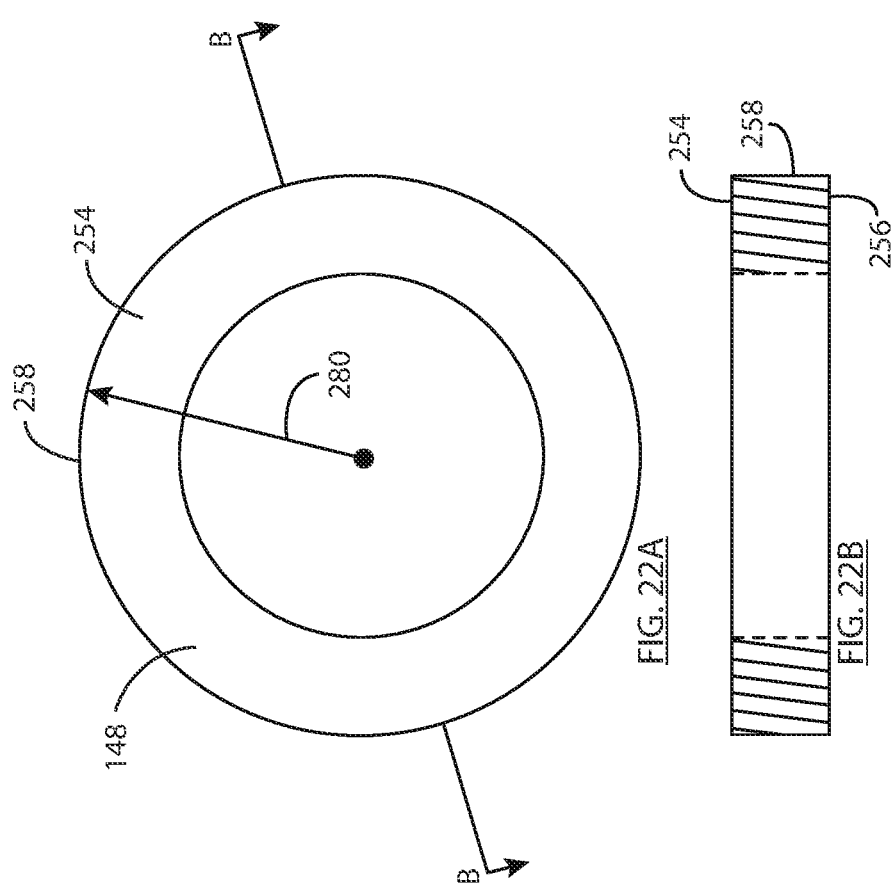
FIG. 22A is a top view of one embodiment of a liquid blocking collar.
FIG. 22B is a cross-sectional view taken along line B-B in FIG. 22A.

Optionally, the blocking collar 248 can be positioned so that it is between the cyclone air inlet 152 and the inlet end 242 of the outlet conduit 240 in the axial direction. Referring again to FIG. 20, in this embodiment, the cyclone fluid inlet 152 has a height 272 in the axial direction and a corresponding width 274 in the radial/lateral direction. The blocking collar 248 may be positioned so that it is located at least above a mid-point of the height 272, and optionally may be positioned so that it is spaced from the fluid inlet 152 in the axial direction, and the lower spacing distance 268 may be greater than the inlet height 272. This is also shown in the embodiment of FIG. 21, where the blocking collar 248 is closer to, but still spaced from the fluid inlet 152 (i.e. the distance 268 is still greater than 272). An inlet spacing distance 276 can also be defined, which can be the axial distance between the fluid inlet 152 and the second end surface 256. This spacing 276 can be any suitable distance, and may be between about 0.5 and about 3 times the inlet height 272, and may be between about 1 and about 1.25 times the inlet height 272.

Alternately, or in addition, the blocking collar 248 may be configured so that its side wall 258 is radially spaced inwardly from the fluid inlet 152. Referring to the embodiment of FIG. 20, a radial offset distance 278 can be configured to be any suitable distance, and may be, for example, between about 0 inches and about 0.5 inches, and may be between about 0.05 inches and about 0.25 inches in some embodiments.

The blocking collar 248 may be of any suitable configuration, including the generally annular, ring-like shape shown in the embodiments of FIGS. 20, 21 and 22a and 22b. In this embodiment, the side wall 258 is generally smooth and has a constant radius 280 (FIG. 22). The side wall 258 is also configured to be generally axially extending, such that relatively sharp corners are formed at the intersection between the side wall 258 and both the first and second end surfaces 254 and 256. This may help disrupt the flow of liquid past the blocking collar.

Figure 23:
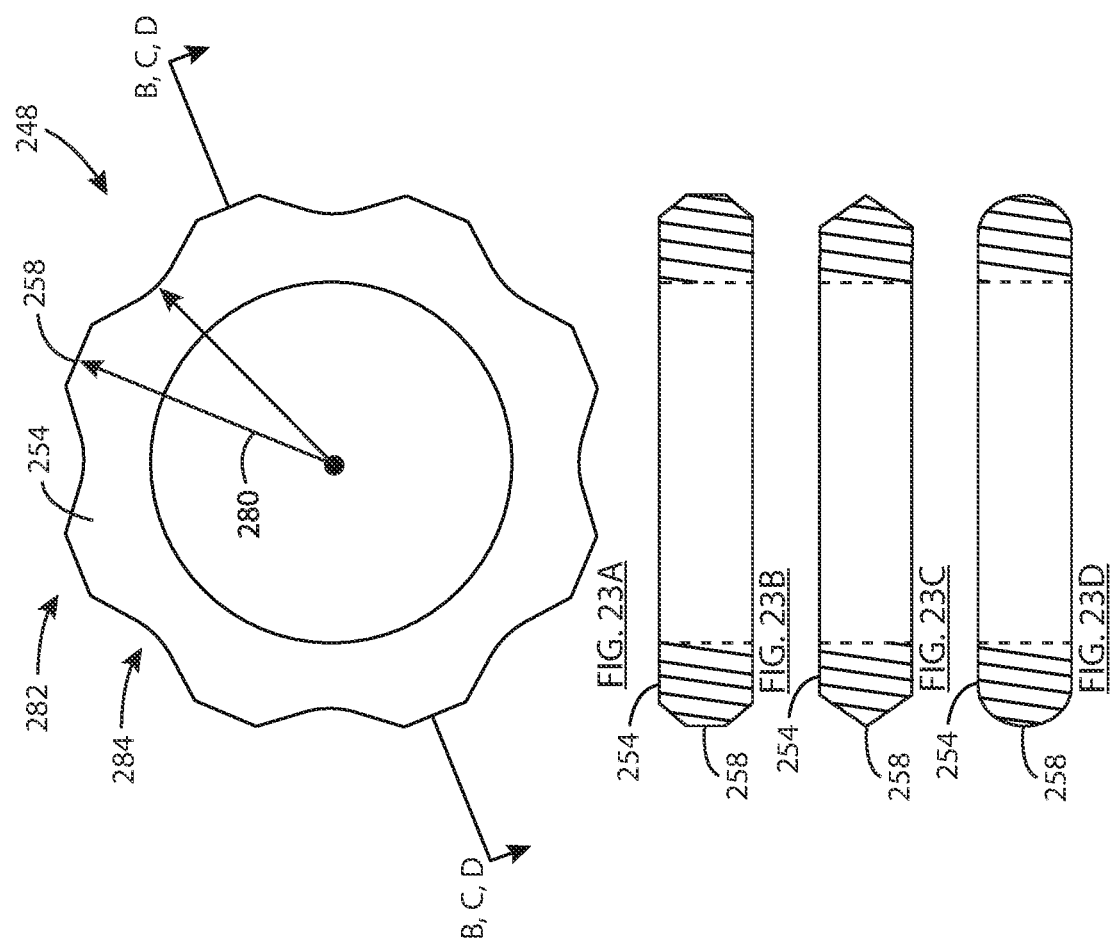
Figure 24:
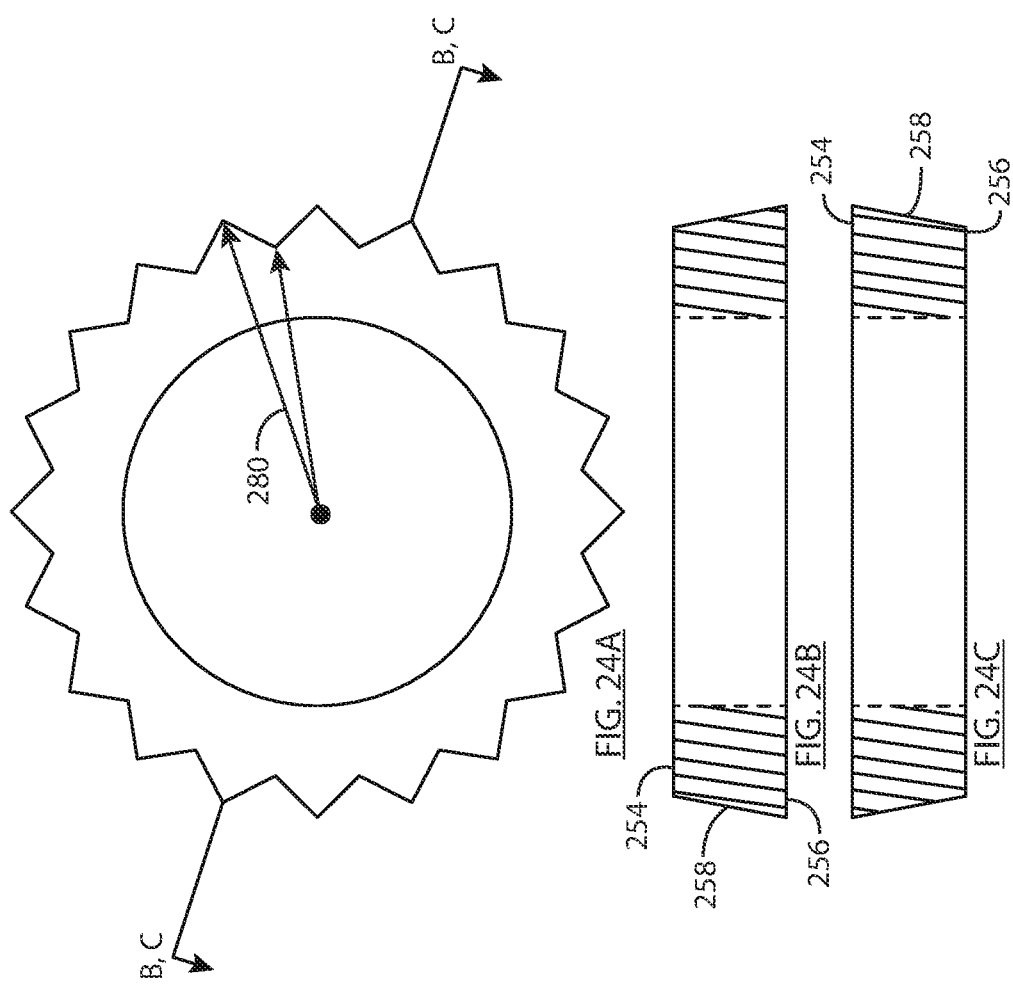
FIG. 24A is a top view of another embodiment of a liquid blocking collar.
FIG. 24B is a cross-sectional view taken along line B-B in FIG. 24A.
FIG. 24C is a cross-sectional view of an alternative configuration for the blocking collar of FIG. 24A.

Alternatively, the blocking collar 248 may have a different configuration. Referring to FIG. 23a, another embodiment of a blocking collar 248 is configured so that the side wall 238 does not extend as a continuous smooth surface, but instead includes alternating wide and narrow regions 282 and 284, with different radii 280. Referring also to FIGS. 23b to 23d, the side wall 258 need not be axially extending, and instead may have a chambered shape (FIG. 23b), may taper to a point (FIG. 23c) and/or may have a curved or radiused shape (FIG. 23d). In another embodiment, as shown in FIGS. 24a to 24c, the blocking collar 248 may have a generally toothed or saw-blade like shape, with a side wall 258 that includes a plurality of teeth having alternating roots 286 and tips 288 spaced around the perimeter of the side wall 258. The blocking collar 248 may also be configured so that the first and second end surfaces 254 and 256 are not symmetrical. For example, the first end surface 254 may be smaller than the second end surface 256 (FIG. 24b) such that the blocking collar 248 generally tapers toward the first end surface 254, or the first end surface 254 may be larger than the second end surface 256 (FIG. 24c) such that the blocking collar 248 generally tapers toward the second end surface 254. While shown in different embodiments, an embodiment of the blocking collar 248 may include any combination of the shapes and features described in any of FIGS. 23a to 24c.

When the treatment units 130 shown in FIG. 19, 20 or 21 are in use, hair, string and other such debris may become wrapped around the outer surface of the outlet conduit 240. As such debris accumulates it may absorb some liquid, and may have the effect of generally increasing the width of the lower portion of the outlet conduit 240. As this occurs, the effective width 262 of the blocking collar 248 may be reduced. Overtime, this may lead to some liquid travelling past the blocking collar 248. To help inhibit such occurrences, the treatment unit 130 may be provided with additional screens, deflectors and the like.

Figure 25:
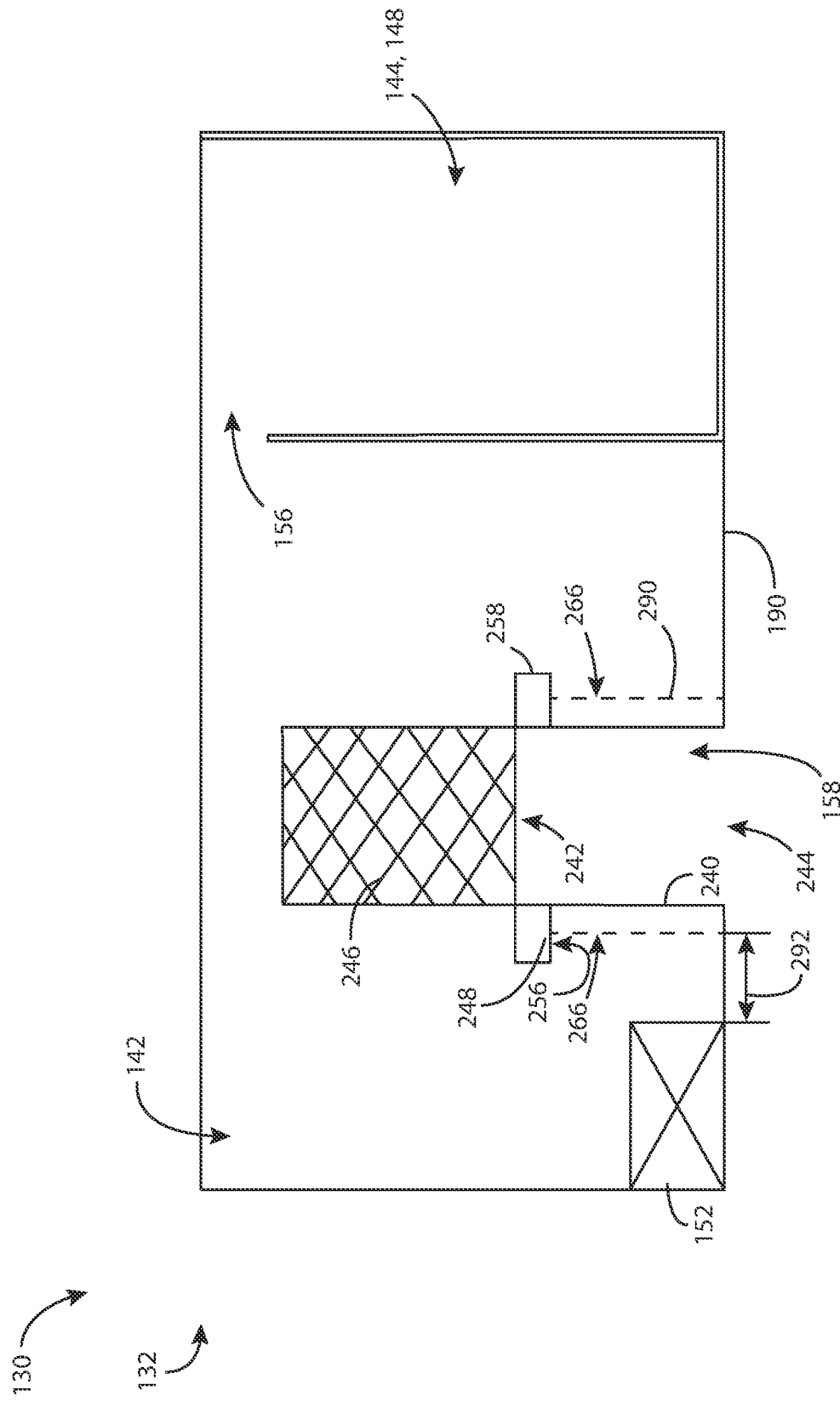
FIGS. 25 to 41 are schematic, cross-sectional views of yet other embodiments of a single stage treatment unit.

Referring to FIG. 25, another embodiment of a treatment unit 130 is shown including an optional lower, mesh or outlet conduit screen 290 that is positioned between the blocking collar 248 and the lower end wall 190 and generally surrounds a lower portion of the outlet conduit 240. This screen 290 may prevent hair from becoming wound around the outer surface of the outlet conduit 240, and instead hair may be wound around the outer surface of the screen 290. As the screen 290 is configured to have openings, and to generally be liquid permeable, liquid in the cyclone chamber 142 may tend to flow radially inwardly through the hair wound around the screen 290, and through the screen 290 itself and into the overhang region 266. The liquid may then circulate within the overhang region 266 and creep up the outer surface of the outlet conduit 240, where it will encounter the blocking collar 248 as described previously.

The lower screen 290 may be generally axially extending, as shown in FIG. 25, and the screen 246 may have an analogous, axial shape. Alternatively, the screens 290 and/or 246 may have different configurations as exemplified in FIGS. 26 and 27.

Figure 26:
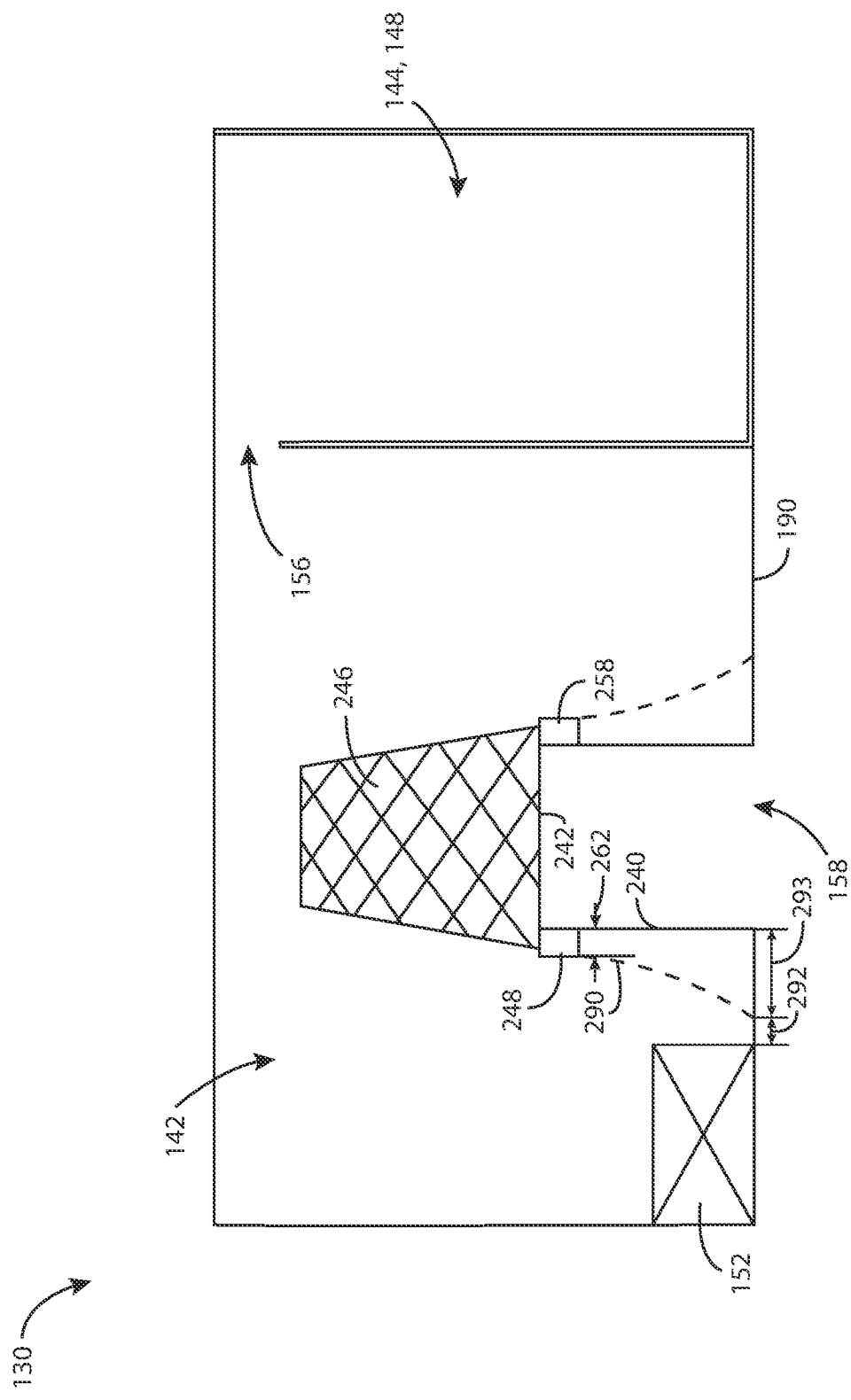

Referring to FIG. 26, in this embodiment of a treatment unit 130, the upper screen 246 covering the inlet end 242 of the outlet conduit 240 is generally frusto-conical in shape and is tapered so that its lower end (seated on the inlet to the outlet conduit 240) is wider in the lateral direction than the upper end of the screen 246. In this embodiment, the lower screen 290 also has a generally flared type configuration in which it is wider toward the lower end wall 190 than it is toward its upper end (i.e. adjacent the blocking collar 248). In this embodiment, the lower end of the lower screen 290 extends outwardly a lateral (e.g. radial) distance 293 from the outer surface of the outlet conduit 240, that is greater than the collar width 262 (see also the embodiment of FIG. 27). It will be appreciated that lower screen 290 may be frusto-conical in shape or otherwise tapered.

Figure 27:
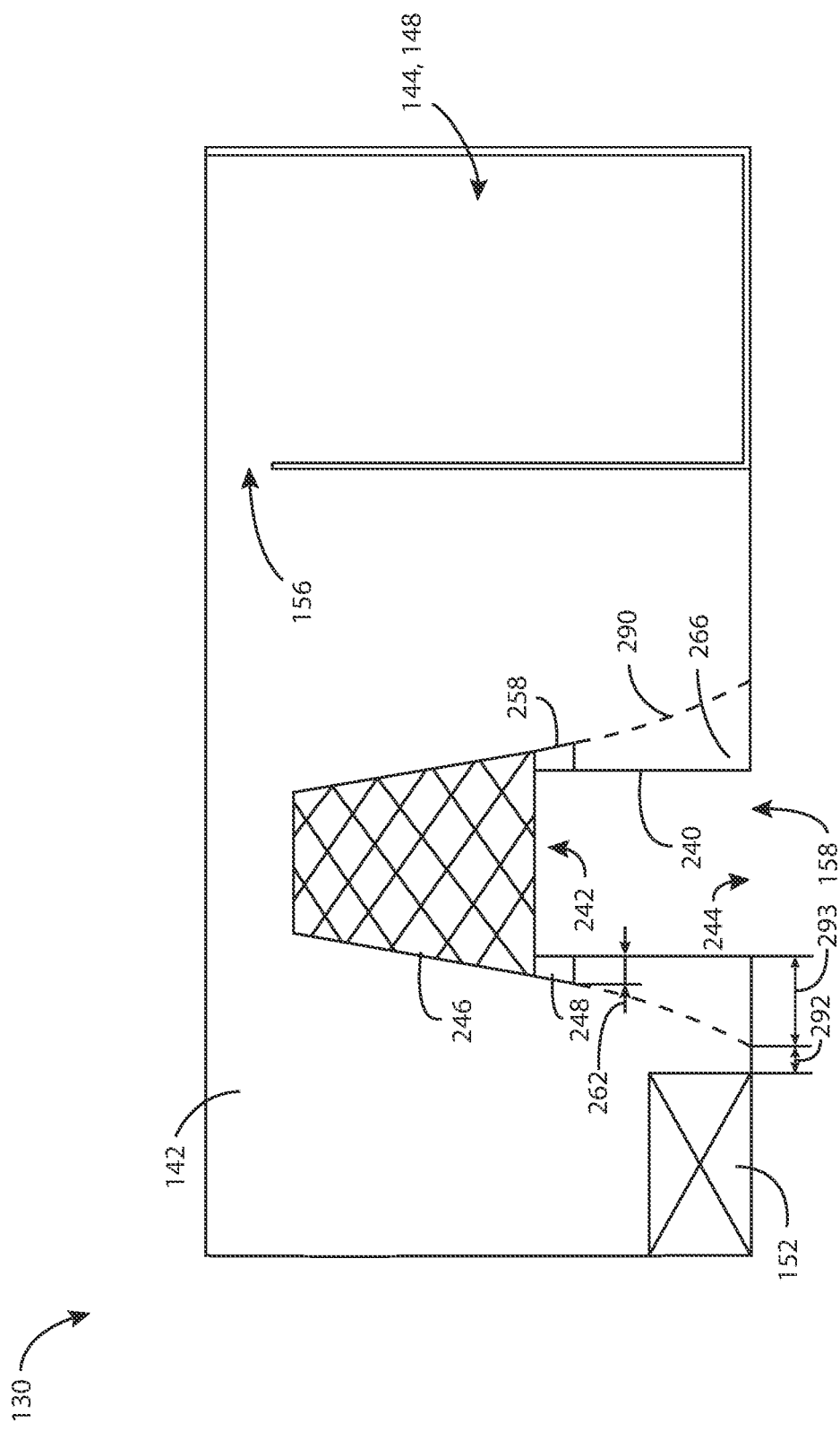

This generally tapered configuration may help facilitate the removal of hair and other such debris, as a user may be able to more easily slide the hair axially along the narrowing screen 290 and/or 246. In the embodiment of FIG. 26, the side wall 258 of the blocking ring is generally axial. Alternatively, as shown in the embodiment of FIG. 27, the side wall 258 may also be tapered so generally match the curvature/tapering of the screens 290 and 246, such that a generally continuous outer surface is provided from the lower end of the screen 290 (adjacent the end wall 190) to the free end of the screen 246. This may help facilitate the sliding removal of wound hair and other debris.

Optionally, the lower screen 290 can be arranged so that is spaced radially inwardly from the radially inner end of the cyclone fluid inlet 152 by a radial screen offset distance 292. This distance 292 may be any suitable distance, and may be, for example, between about 0 and about 0.5 inches, and may be between about 0.05 inches and about 0.25 inches, and between about 0.1 inches and about 0.15 inches. This may help prevent hair and other debris accumulating on the lower screen from blocking the fluid inlet 152.

Single Stage Treatment Unit

The following is a description of a collection region for a treatment unit that is configured to separate liquid and solid debris from an incoming dirty fluid flow using a single treatment stage, such as a cyclonic separation apparatus. This treatment unit may be suitable for use with the surface cleaning apparatuses described herein, for example as an alternative to the dual stage cleaning units. In accordance with this aspect, a single collection region may extend to a position below the separation chamber (e.g., it may be longer than the separation chamber). Alternately, or in addition, the collection region may be subdivided, such as by a screen or other water permeable material, into a liquid collection region at a lower end and a solid collection region above the screen.

In the embodiments of FIG. 19, the treatment unit 130 is configured such that the axial height 294 of the collection chamber (which essentially functions as a combined solid collection chamber 144 and liquid collection container 148) is generally the same as the axial height 296 of the cyclone chamber 142. This may help reduce the overall axial height of the treatment unit 130.

Figure 28:
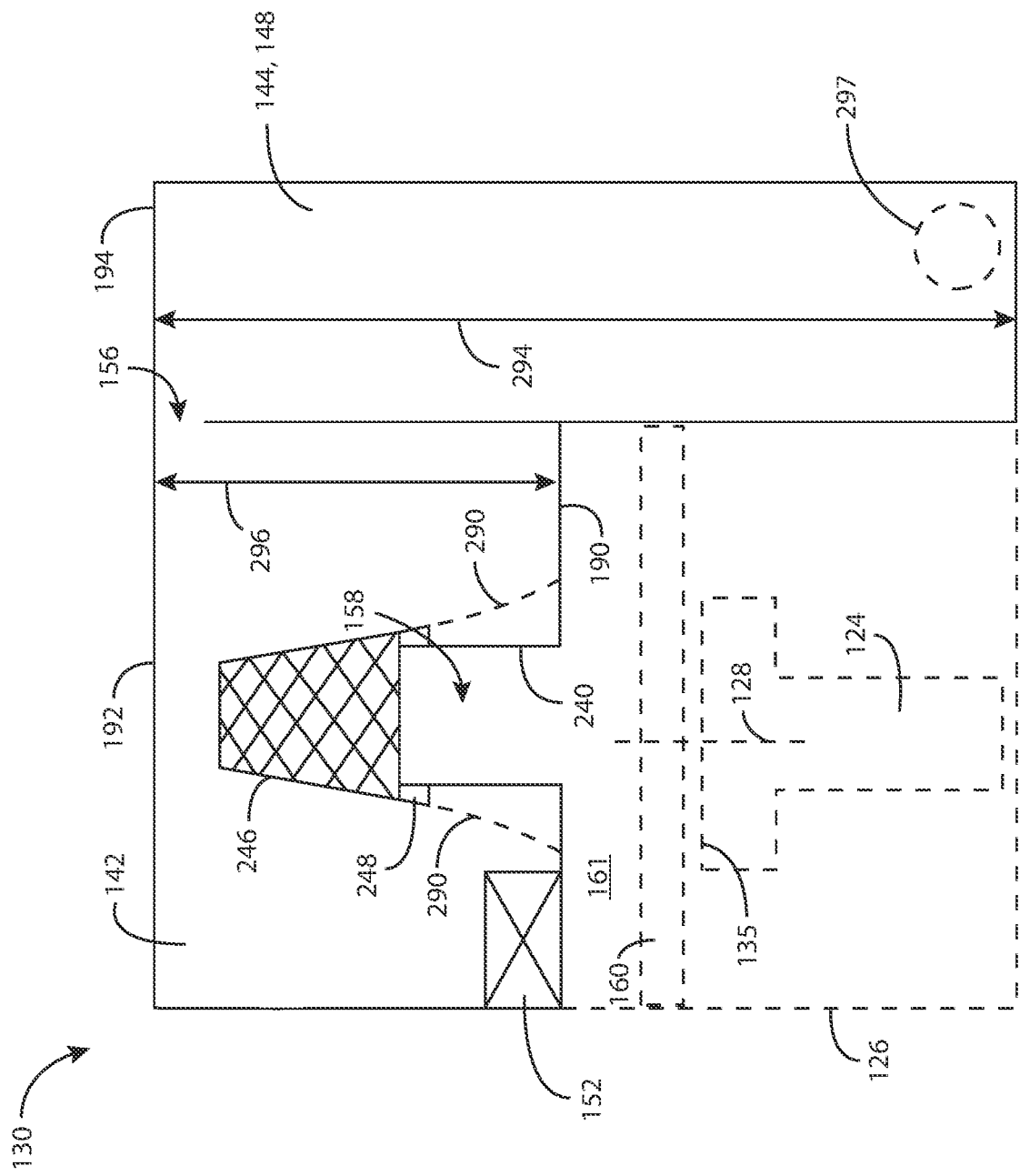

Alternatively, as exemplified in FIG. 28, a combined collection chamber 144, 148 may have a greater axial height 294 than the cyclone chamber axial height 296. When this treatment unit 130 is in use, the solid and liquid exiting the cyclone chamber will enter into the combined collection chamber 144, 148. The separated material may tend to separate and/or stratify, with liquid tending to collect toward the lower end of the area, and some types of solid debris remaining toward the upper end and denser material falling to the bottom. This debris collection area may be emptied by opening the lid 194, and an optional drain port 297 may be provided if desired.

An advantage of providing a combined collection chamber 144, 148 with a greater axial height is that liquid is less likely to slosh or otherwise travel back into the cyclone chamber when the apparatus is in use, particularly if the apparatus is an upright apparatus and the upright section containing the combined collection chamber 144, 148 is reclines.

In addition to having an increased axial height, or if the axial heights of the cyclone chamber and combined collection chamber 144, 148 are the same, a divider may be positioned in the combined collection chamber 144, 148 to help separate the liquid and solid debris that is ejected from the separated element outlet 156. The divider may be liquid permeable, such as a screen or mesh, such that liquid debris may tend to flow through the divider due to gravity while solid debris of a given size is caught by the divider. This may help segregate the liquid and solid debris.

Figure 29:
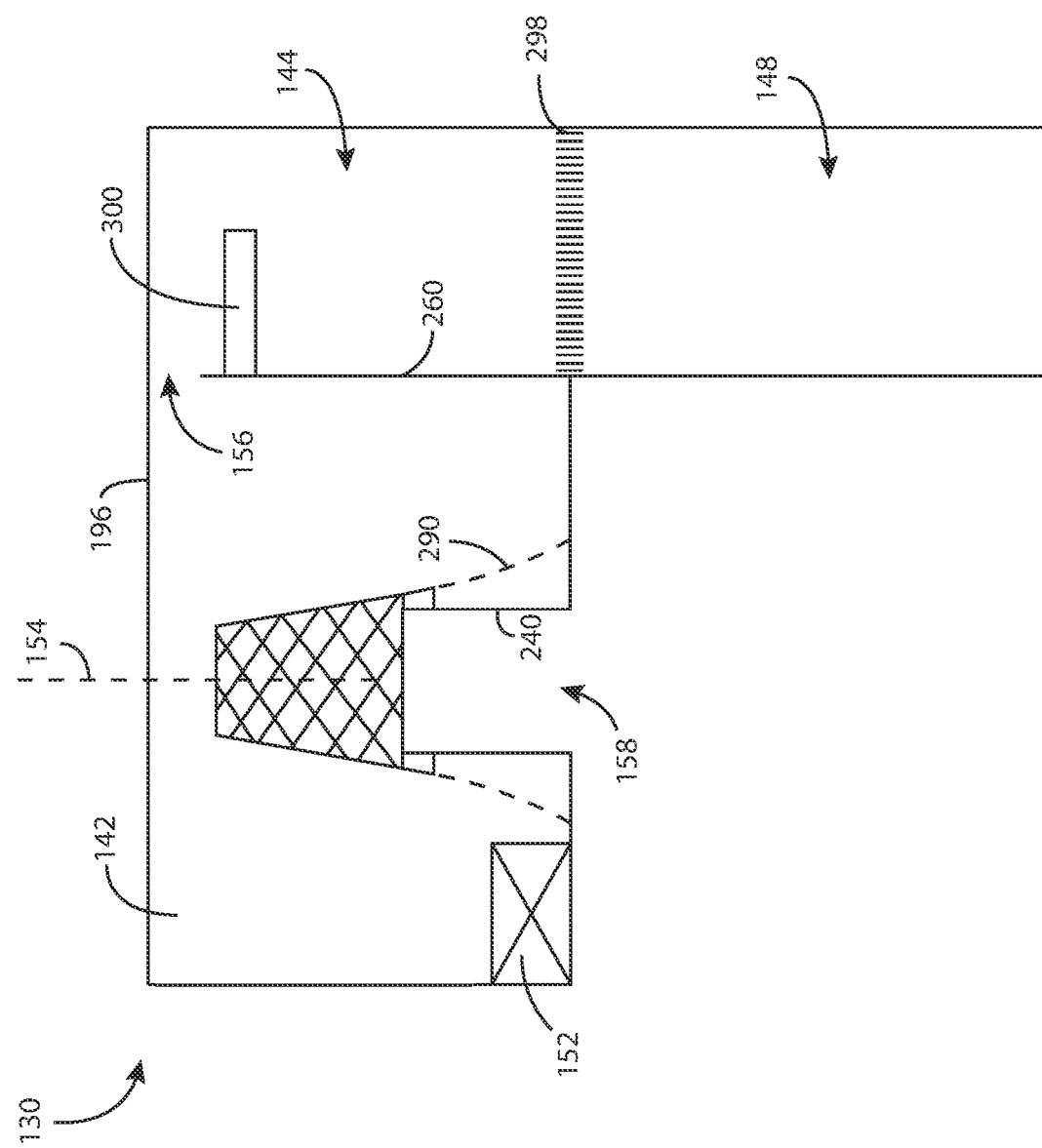

Referring to FIG. 29, this embodiment of the treatment unit 130 includes a debris divider, comprising a porous screen 298, that is positioned in the debris collection region and helps define an upper region that functions as a solid collection chamber 144 and a lower region that functions as a liquid collection container 148 (with upper and lower describing the position of the regions when the surface cleaning apparatus is in a floor cleaning orientation). The screen 298 may be located at any suitable elevation and may be of any desired configuration. In the embodiment of FIG. 29 it extends generally horizontally or rearwardly from an outer surface of the side wall 260 of the cyclone chamber 142 to an outer rear wall of the combined collection chamber 144, 148.

In this embodiment, the debris divider 298 functions as a porous/permeable a lower wall of solid collection chamber 144. Also in this configuration, liquid exiting the cyclone chamber 142 travels through the solid collection chamber 144 before reaching the liquid collection container 148. That is, the liquid collection container 148 is generally downstream from the solid collection chamber 144.

The divider 298 may also function, in some embodiments, as a backflow inhibiting apparatus. For example, while illustrated in a generally upright configuration in FIG. 29 (i.e. with the cyclone axis 154 generally vertical), the treatment unit 130 may tend to be inclined when the surface cleaning apparatus 100 is in use. If, for example, the treatment unit 130 is provided on the upright section 116 of an upright style surface cleaning apparatus 100, it may be inclined at angles of up to 45 degrees, 65 degrees, 75 degrees, 80 degrees, 85 degrees and about 90 degrees from vertical (i.e. it may extend substantially horizontal). When the treatment unit 130 is inclined, liquid that has accumulated in the liquid collection container 148 may tend to slosh and splash around, and in some configurations may tend to flow backwards towards the cyclone chamber 142 as the upright section is reclined. That is, the liquid may tend to flow from the liquid collection container 148 through the solid collection chamber 144 (if applicable) and the separated element outlet 156 and into the cyclone chamber 142. This may interfere with operation of the cyclone chamber 142, and/or may allow liquid to escape through the cyclone chamber 142 and continue downstream in the fluid flow path.

Figure 30:
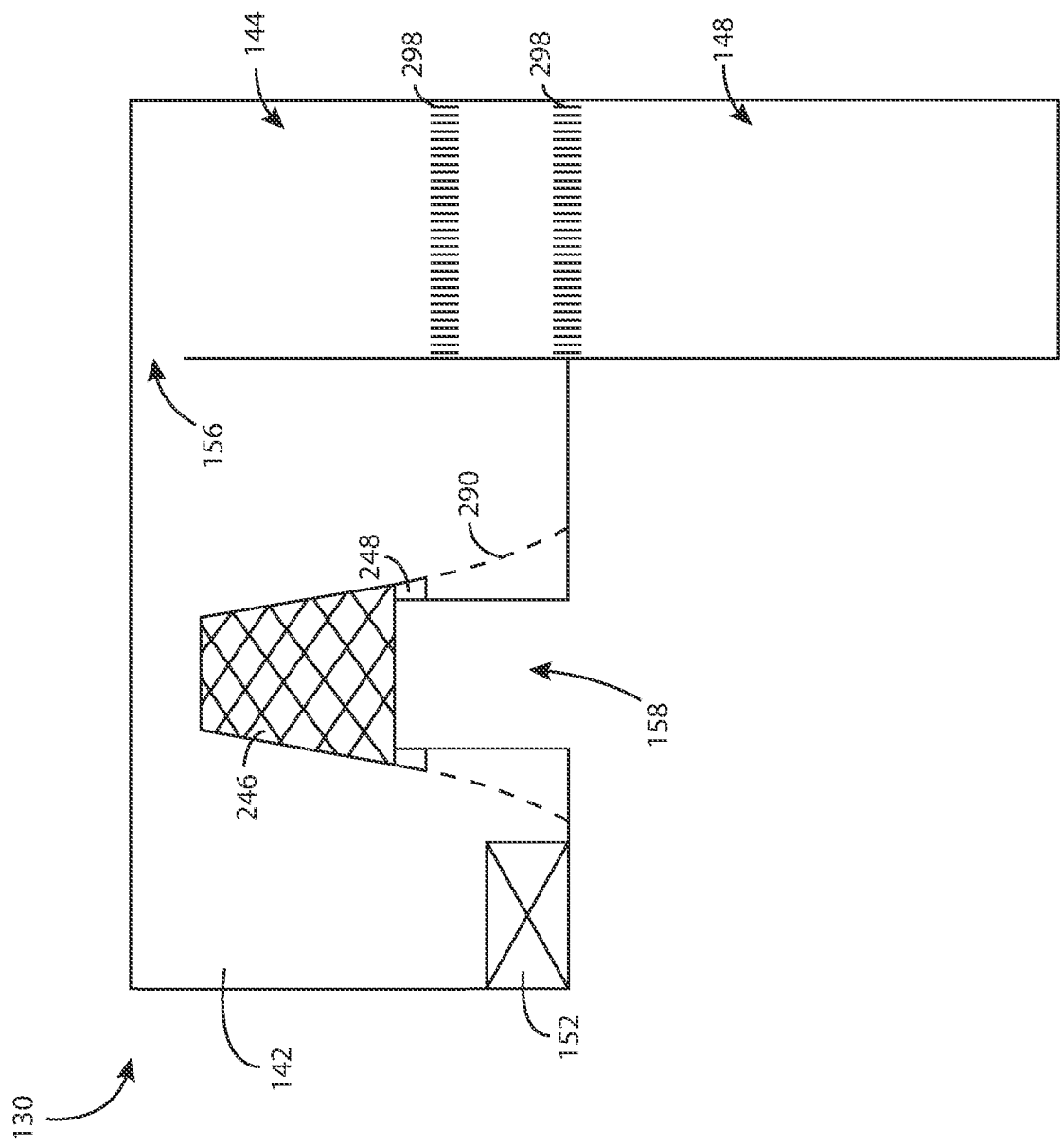

Providing a divider 298 as shown in FIG. 29 may help impede the back flow of liquid from the liquid collection container 148 into the solid collection chamber 144 and/or cyclone chamber 142. Optionally, more than one divider 298 can be provided, as shown in the embodiment of FIG. 30, which may help to further dampen splashing and/or backflow of the liquid held in the liquid collection container 148.

Figure 31:
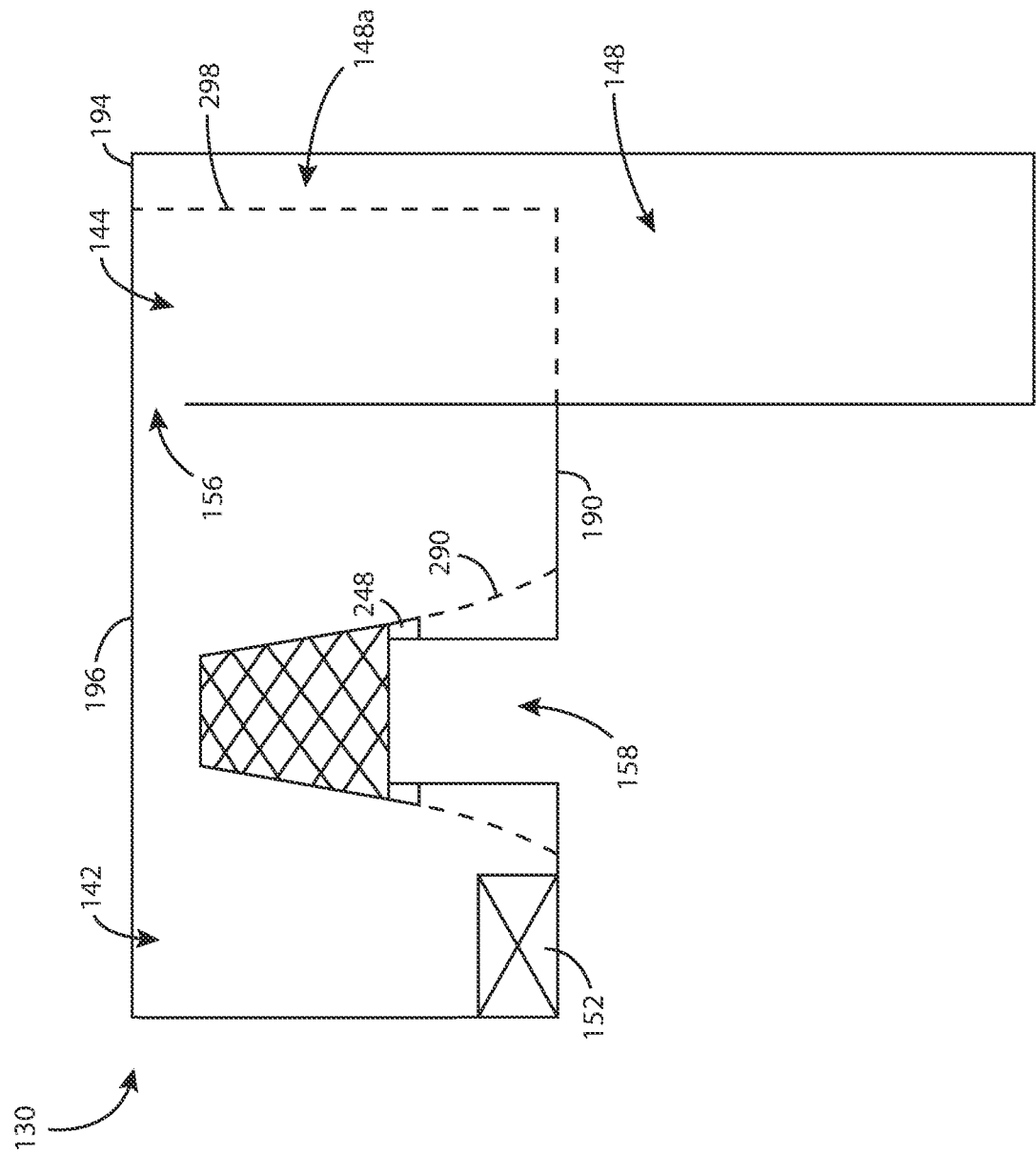

Optionally, the divider 298 may be configured to extend both horizontally and axially. This may help provide an arrangement in which the screen has a larger surface area. Referring to FIG. 31, for example, one embodiment of the treatment unit 130 includes a divider screen 298 that is generally L-shaped and extends horizontally across most of the solid collection chamber, and then extends axially and optionally can extend to the openable lid 194. In this embodiment, the liquid collection container 148 includes an upright section 148a that axially overlaps the solid collection chamber 144, and two walls of the solid collection chamber 144 (the lower wall and the right side wall as illustrated) are formed from liquid pervious mesh. This can help facilitate drainage of the liquid from the solid collection chamber 144, as liquid can be drawn by gravity through the lower end of the solid collection chamber 144 when the treatment unit 130 is upright (as shown in FIG. 31), and may be drawn by gravity through the rear side wall of the solid collection chamber 144 when the treatment unit 130 is inclined in a surface cleaning position.

The upright section 148a may also provide a region into which liquid can flow/slosh when the treatment unit 130 is reclined. The upright section 148a may also help facilitate emptying of the liquid collection container 148, as it can provide a passage from the lower portion to the open upper end of the treatment unit 130 (e.g. when the lid 194 is removed) through which liquid can flow without having to pass through the divider 298 or solid debris in the solid collection chamber 144.

Figure 32:
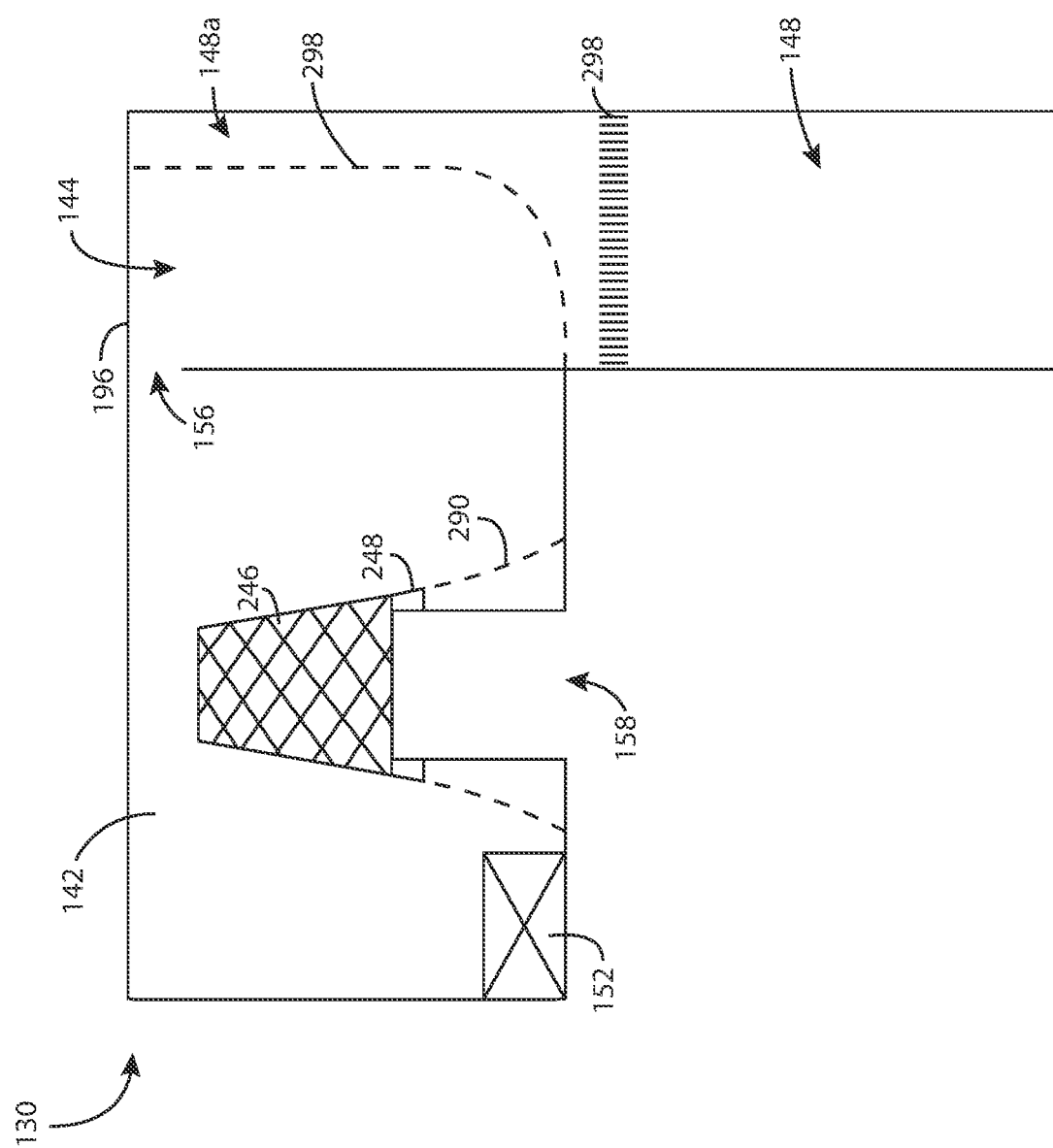

Optionally, as shown in the embodiment of FIG. 32, the treatment unit 130 may include a divider 298 that includes both horizontal and axial portions that are connected by a generally curved juncture surface, instead of a relatively sharp corner, while still being considered generally L-shaped. A divider 298 of this design may be used in any of the embodiments described herein. This embodiment also includes an optional second horizontal divider 298 positioned below and downstream from the first, L-shaped divider 298 and extending across the entire width of the liquid collection container 148. In this configuration, the upper divider 298 may serve to help separate the solid collection chamber 144 from the liquid collection container 148, while the lower divider 298 is positioned substantially entirely within the liquid collection container 148 and may function primarily as a baffle or flow limiting device.

In the embodiments in which the divider 298 includes both lateral and axial portions, dirty fluid, liquid and debris can travel through the screen in two or more different directions. For example, referring to the embodiment of FIG. 31, separated liquid and solid debris may exit via the separated element outlet 156 and may tend to be travelling in a generally lateral or horizontal direction (i.e. from left to right as illustrated) when exiting the separated element outlet 156. Under the effects of gravity, and possibly other factors, some portions of the liquid may reach the divider 298 while still travelling in the lateral direction, and may pass through the divider 298 in a first transmission direction (from left to right). Once through the divider 298, liquid that has been collected in the upper region 148a may then tend to travel axially (downwardly) into the lower portion 148b of the liquid collection container. Other portions of the separated liquid may change direction while within the solid collection chamber 144, and may be travelling generally axially when it reaches the laterally extending portion of the divider 298 (i.e. downwardly as illustrated in this example), and may travel through the divider 298 in a second transmission direction, that is not parallel to the first transmission direction (i.e. is at an angle to first transmission direction, which in this example would be about 90 degrees.). In this embodiment, the liquid may also pass through the second, laterally extending divider 298 in the second transmission direction (i.e. generally axially or downwardly as illustrated).

It will be appreciated that, in these embodiment, the cyclone chamber and the solid and wet storage chambers may be concurrently emptied by opening a lid or top surface 196 of the treatment unit (see FIG. 31).

Single Stage Separator with Dual Separators

In accordance with another aspect, that may be used with one or more of the other aspects disclosed herein, a single separator stage may include two or more separators arranged in parallel with each other in the fluid flow path. Such a separator may be considered a single stage separator as the multiple separators, such as two or more cyclone chambers 142, are arranged in parallel and not in series with each other (i.e. one cyclone chamber 142 is not downstream from the other cyclone chamber 142). Providing multiple separators in a single stage may help increase the efficiency of the separator stage and/or may help increase the total amount of incoming fluid that can be treated by the separator stage. This may also allow each individual separator to be smaller than a single separator that is configured to handle the same volume of fluid flow, which may help reduce some of the dimensions of the separator stage (e.g. it may be relatively shorter than a comparable single separator).

Referring to FIGS. 69-72, an embodiment of a treatment unit 130 that is suitable for use with any surface cleaning apparatuses 100 described herein (e.g., either mounted in the surface cleaning head 102 or on the upright section 116) and includes a separator stage (such may be a first stage, a second stage or optionally may be a single stage as exemplified in FIG. 20) having two separate cyclone chambers 142 arranged in parallel with each other. As exemplified, each cyclone chamber has a liquid blocking collar 248 so that they are suitable to separate both solids and liquids and operable in a single stage separator. Accordingly, this embodiment may use any of the combined collection chambers 144, 148 disclosed herein.

Figure 71:
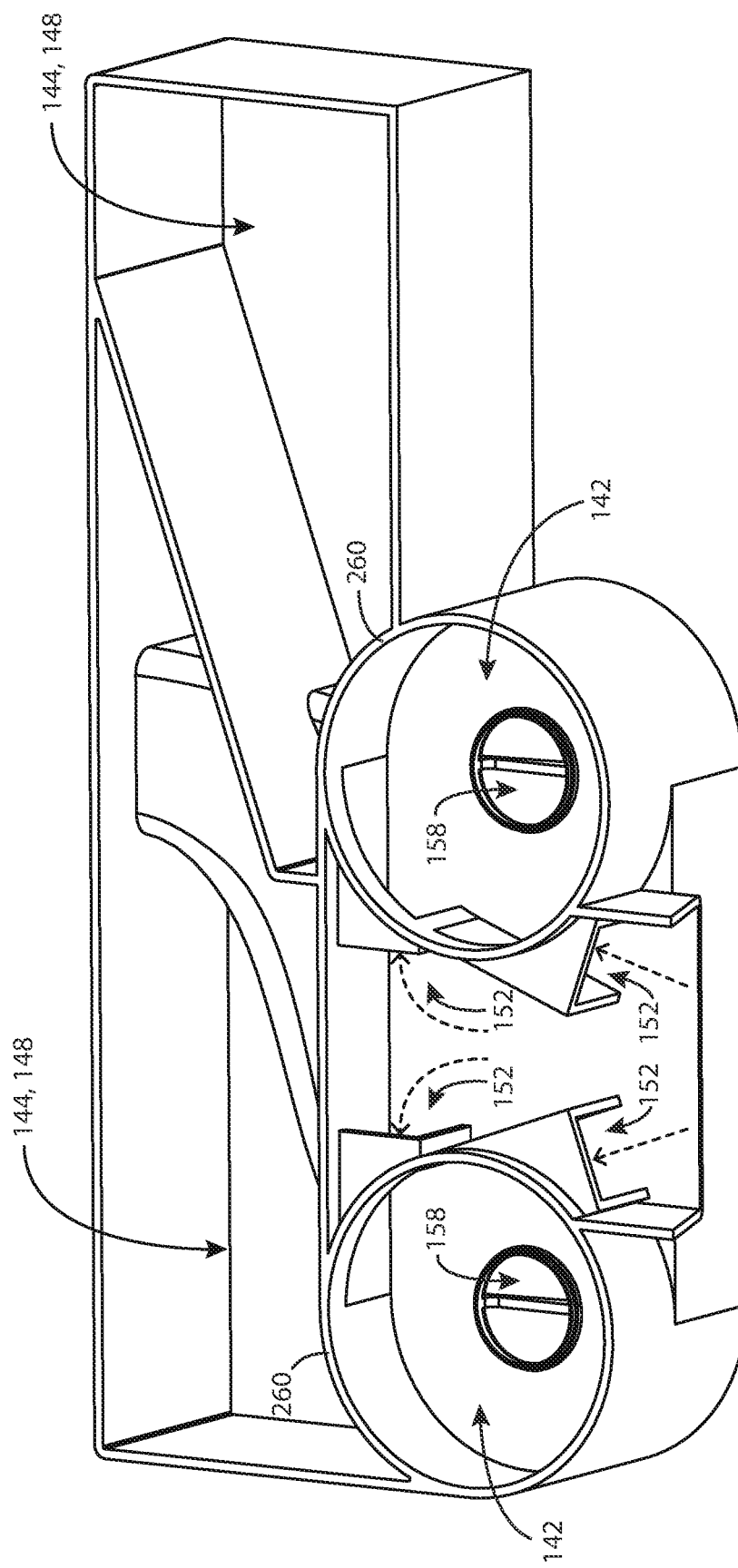
FIG. 71 is a cross-sectional view of the treatment unit of FIG. 69 taken along line 71-71.

In this embodiment, dirty fluid can enter the separator stage 132 via a stage inlet passage 422, and the cyclone chamber fluid inlets 152 of each cyclone chamber 142 are in communication with the stage inlet passage 422. Each cyclone chamber 142 may include a single fluid inlet 152 as shown in other embodiments herein or, as illustrated in FIG. 71, may include two separate fluid inlets 152, each of which is in fluid communication with the stage inlet passage 422.

Figure 70:
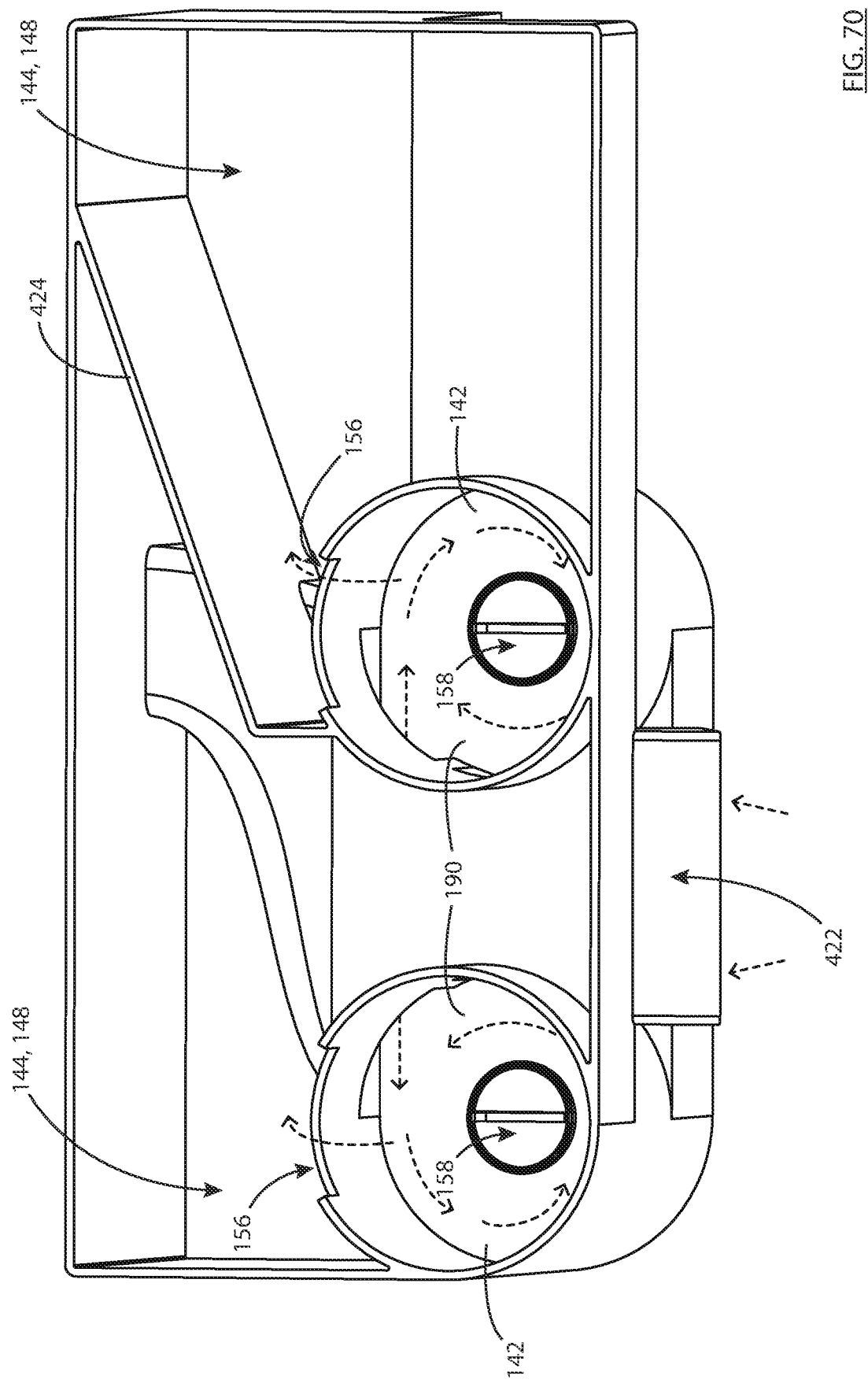
FIG. 70 is a top perspective view of the treatment unit of FIG. 69 with its lid removed.

Referring also to FIG. 70, in which the upper lid (including upper walls 192 and 194) has been removed from the separator stage 132, each cyclone chamber 142 also includes a separated element outlet 156, formed as a slot toward the upper end of the cyclone chamber 142, that is in communication with an associated collection region, which as exemplified in this embodiment, may be a combined solid and liquid collection region 144 and 148 (but in other embodiments may have any suitable configuration, including those described herein). The two combined collection chambers 144, 148 in this embodiment are fluidly isolated by a divider wall 424, but are arranged such that their upper walls 194, and the upper walls 192 of each cyclone chamber 142, are provided by a common, openable lid. In this arrangement, the cyclones 142 and combined collection chambers 144, 148 can be opened simultaneously for emptying.

Single Stage Separator with Dual Separated Element Outlets

In accordance with another aspect, that may be used with one or more of the other aspects disclosed herein, instead of including a single separated element outlet through which both solid and liquid debris and travel from the cyclone chamber to the collection chamber (as shown in FIGS. 69-73), a separator may include two or more discrete separated element outlets, which can optionally be axially spaced apart from each other (and preferably may be positioned toward opposing ends of the separator). Each separated element outlet may be in communication with a separate, discrete collection region/chamber, or alternatively may be in communication with a common collection region/chamber.

Optionally, the separated element outlets may be provided at different locations/positions within the cyclone chamber, which may help facilitate separated debris to exit the cyclone chamber. Optionally, one separated element outlet may be provided toward a first or upper end of the cyclone chamber, and another separated element outlet may be provided toward an opposing second or lower end of the cyclone chamber. In such configurations, the upper separated element outlet may receive mostly solid debris, while separated liquid may tend to collect toward the bottom of the cyclone chamber and may tend to exit via the lower separated element outlet. Providing a separated element outlet toward the lower end of the cyclone chamber may help separate water to drain from the cyclone chamber, and may help reduce the likelihood of the separated liquid becoming re-entrained, creeping up the outside of the outlet conduit 240 or otherwise being drawn into the cyclone chamber air outlet 158.

Figure 74:
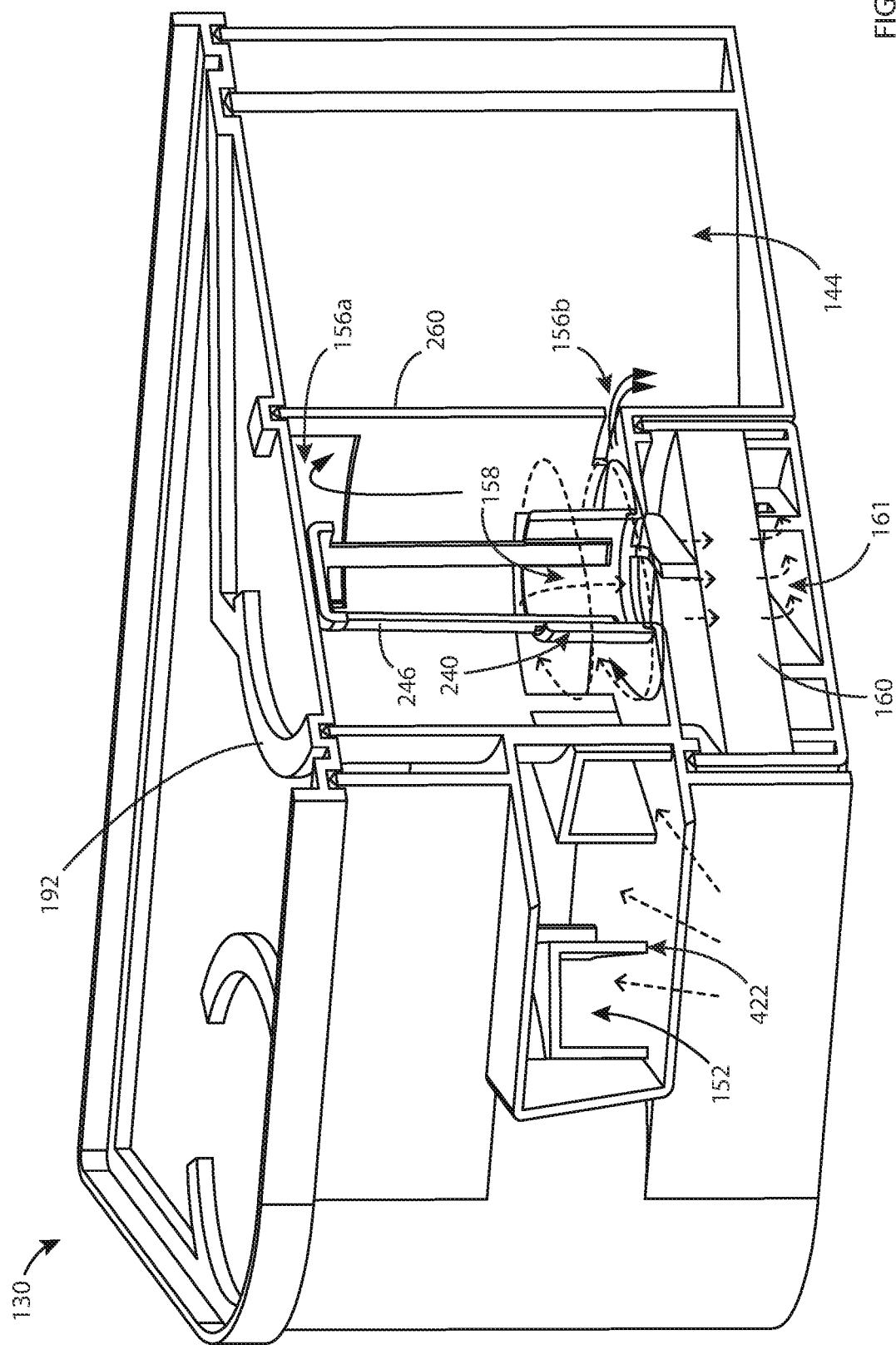
FIG. 74 is a cross-sectional view of another embodiment of a treatment unit.

Referring to FIG. 74, this embodiment of a treatment unit 130 includes a cyclone chamber 142 having an upper separated element 156a provided toward the upper end of the cyclone chamber 142, and a lower separated element 156b provided toward the lower end of the cyclone chamber 142.

When this cyclone chamber is in use, solid debris may tend to be separated from the air stream and travel toward the upper end of the cyclone chamber 142, while at least some of the liquid separated from the incoming dirty fluid (and possibly some solid debris) may tend to collect on the bottom wall 190 of the cyclone chamber. In this arrangement, solid debris may tend to be discharged from the cyclone chamber 142 via the upper separated element 156a, in much the same manner as occurs with other examples of cyclone chambers 142 described herein, while liquid accumulating on the lower wall 190 (or generally toward the lower end of the cyclone chamber 142) may tend to drain out of the cyclone chamber 142 via the lower separated element 156b. This may help provide a relatively low resistance path for separate liquid to exit the cyclone chamber 142, and may reduce the need for the relatively heavy liquid particles to be lifted to the upper separated element 156a via the air flow. This may help improve separation efficiency. This arrangement may also help prevent the separated liquid from accumulating in the lower end of the cyclone chamber 142, and may help prevent the liquid from climbing the outlet conduit 240 and escaping via the cyclone chamber air outlet 158.

The exemplified cyclone chamber is suitable for use with any surface cleaning apparatuses 100 described herein (e.g., either mounted in the surface cleaning head 102 or on the upright section 116). The cyclone chamber may be a first stage, a second stage or optionally may be a single stage as exemplified in FIG. 20. As exemplified, the cyclone chamber has a liquid blocking collar 248 so that it is suitable to separate both solids and liquids and operable in a single stage separator. Accordingly, this embodiment may use any of the combined collection chambers 144, 148 disclosed herein.

Single Stage Separator with Uniflow Cyclone Chamber

In accordance with another aspect, that may be used with one or more of the other aspects disclosed herein, the cyclone chamber(s) 142 may configured such that the cyclone chamber fluid inlet 152 and the cyclone chamber air outlet 158 are positioned toward the same end of the cyclone chamber 142. Embodiments in which the cyclone chamber fluid inlet 152 and the cyclone chamber air outlet 158 are at a lower end may be referred to as inverted cyclones. Alternatively, the cyclone chamber 142 may be configured with the cyclone chamber fluid inlet 152 and the cyclone chamber air outlet 158 at different ends of the cyclone chamber 142 and may be referred to as a uniflow cyclone chamber.

Figure 75:
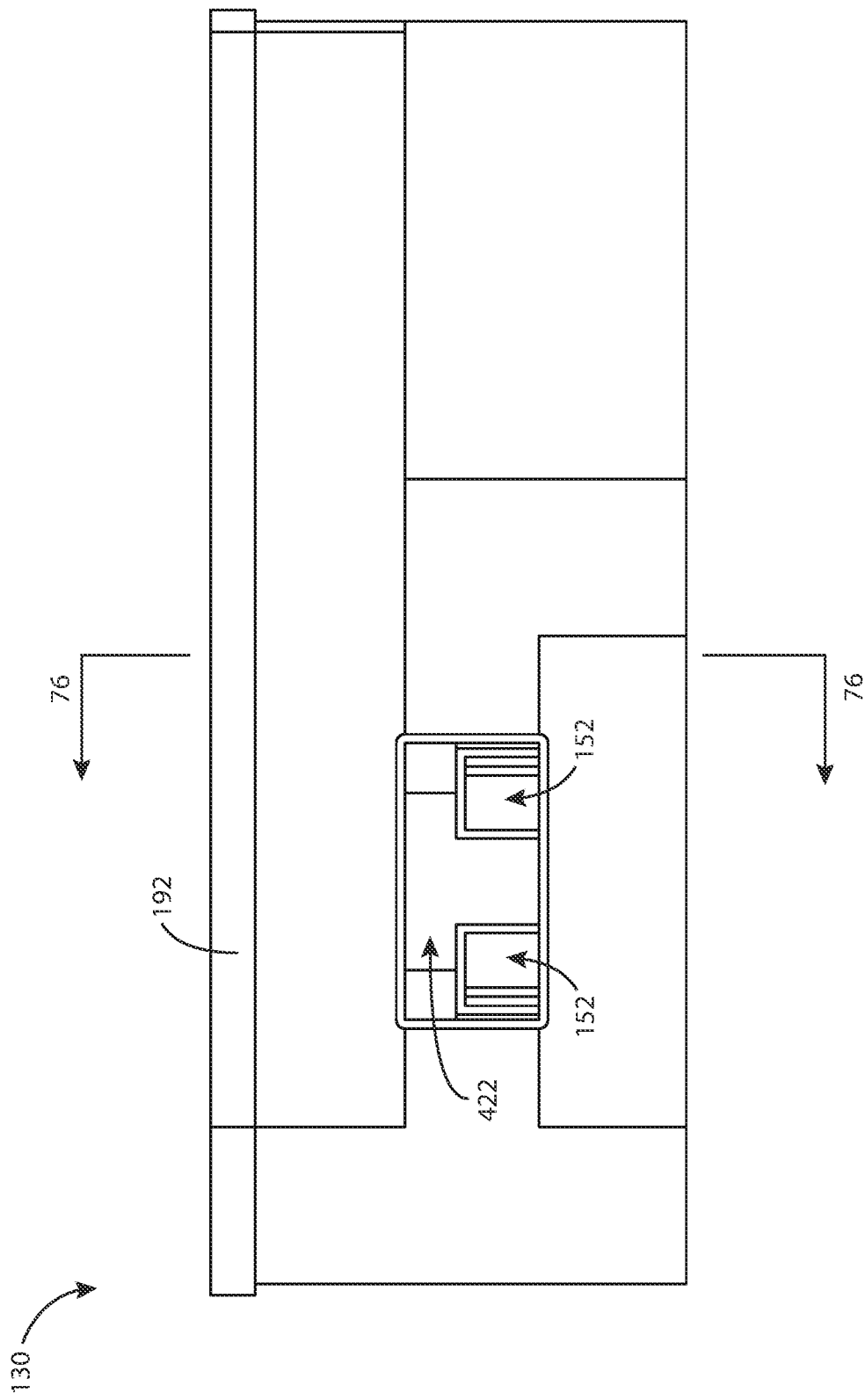
FIG. 75 is a front view of another embodiment of a treatment unit.
Figure 76:
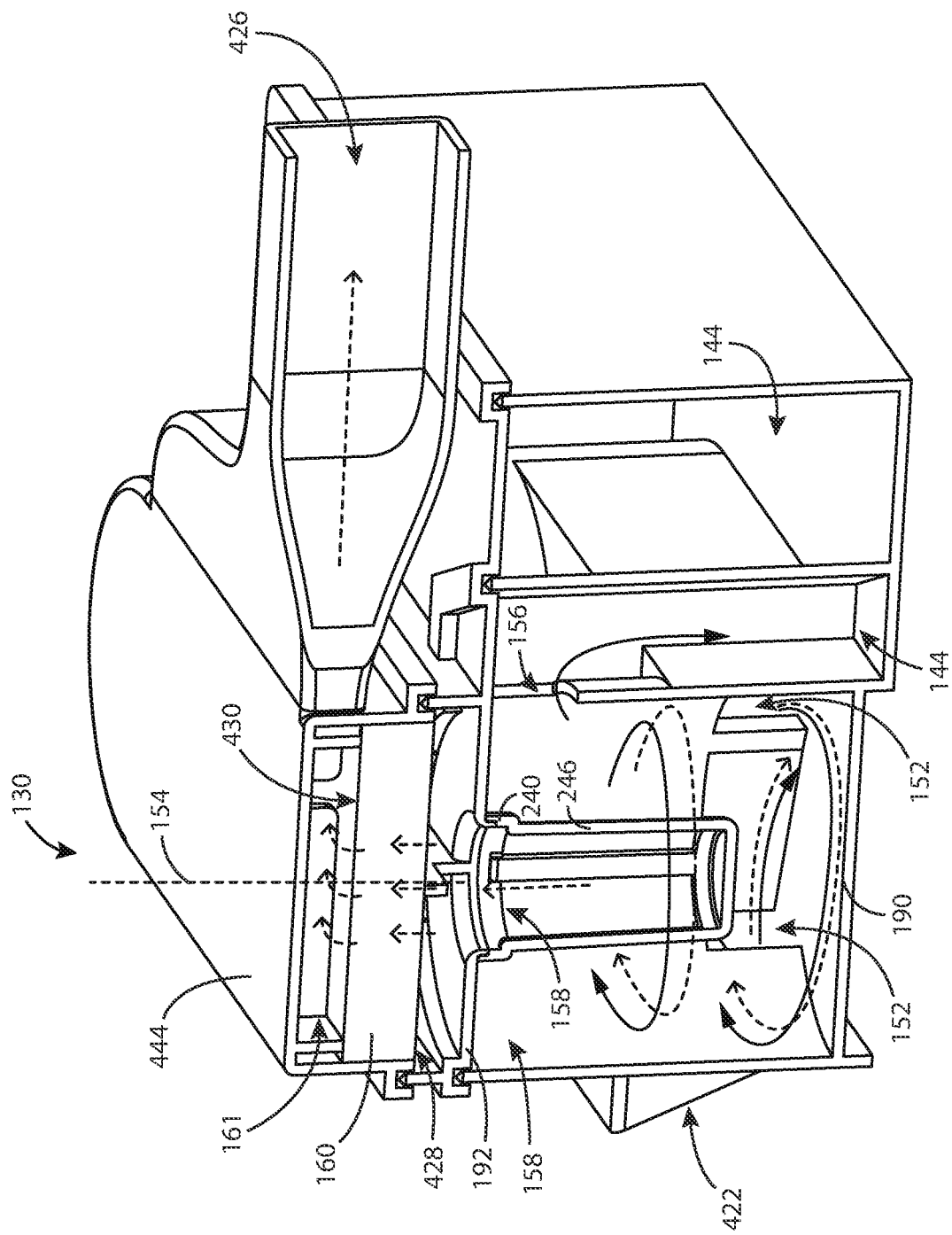
FIG. 76 is a cross-sectional view of the treatment unit of FIG. 75, taken along line 76-76.
Figure 77:
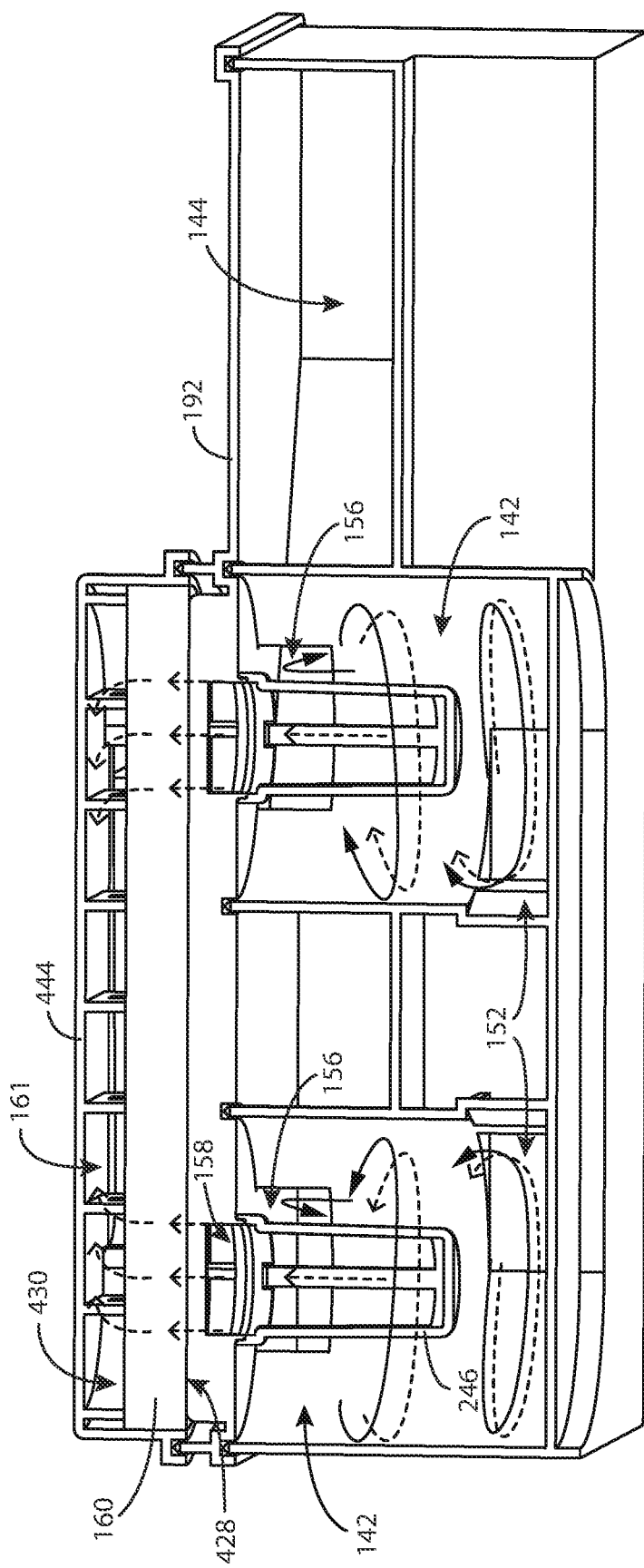
FIG. 77 is another cross-sectional view of the treatment unit of FIG. 75, taken in a plane orthogonal to the line 76-76.

Optionally, as illustrated in the embodiment of FIGS. 75-77, a uniflow cyclone can be configured with the cyclone chamber fluid inlet 152 at the bottom end, and the cyclone chamber air outlet 158 located at the upper end. This may help reduce the likelihood of liquid escaping the cyclone chamber 142 via the cyclone chamber air outlet 158.

In addition, the screen 246 that covers the cyclone chamber air outlet 158 can be arranged such that it extends downwardly from the upper end wall 192 of the cyclone chamber 142 (FIG. 76) but remains spaced apart from and does not contact the lower end wall 190. Providing a gap between the lower end of the screen 246 and the lower end wall 190 of the cyclone chamber 142, upon which liquid may accumulate while the cyclone chamber 142 is in use, may help prevent liquid from being drawing up the screen 246 and into the cyclone chamber air outlet 158.

While shown as part of a treatment unit 130 that includes two cyclone chambers 142 in parallel, the uniflow cyclone design could be used in treatment units that include only a single separator, and may be used in combination with any of the other features described herein.

Treatment Unit with Pre-Motor Filter

In accordance with another aspect, that may be used with one or more of the other aspects disclosed herein, the pre-motor filter chamber 161 may be included as part of the treatment unit 130 (see for example FIG. 72), and may be removable with the treatment unit 130 from the rest of the surface cleaning apparatus (as shown in FIG. 69). This may help facilitate the desired placement of the treatment unit and pre-motor filter chamber, and may in some embodiments allow the pre-motor filter chamber to be positioned in the surface cleaning head, while the suction motor is positioned either in the surface cleaning head or optionally on the upright section. This may also help ensure that the air exiting the treatment unit is relatively clean, which may reduce fouling of portions of the air flow path between the outlet of the treatment unit and the suction motor.

Figure 72:
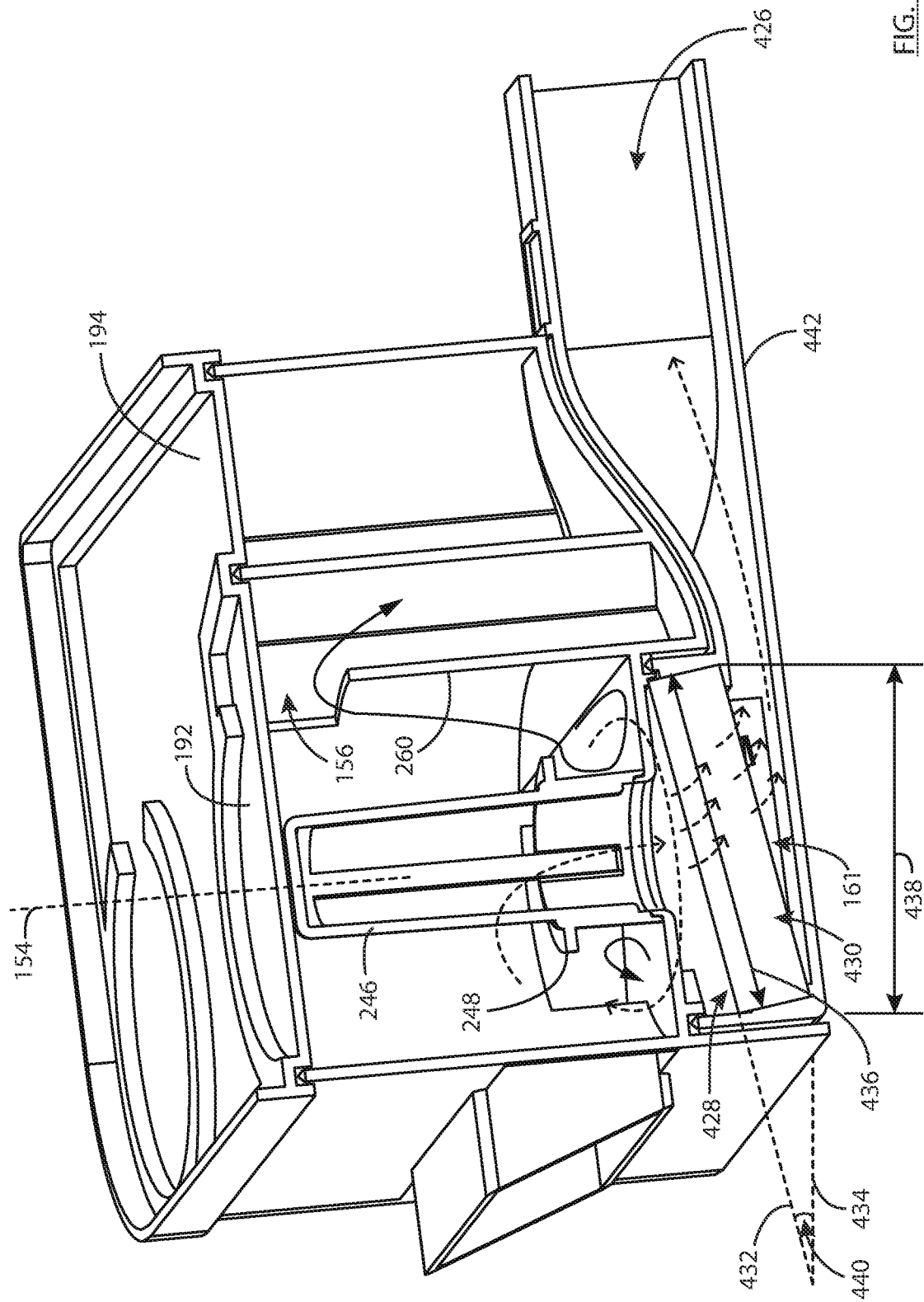
FIG. 72 is a cross-sectional view of the treatment unit of FIG. 69 taken along line 72-72.

In the example, of FIG. 72, the pre-motor filter chamber 161 is in communication with the cyclone chamber air outlets 158 from each cyclone chamber 142. After passing through the pre-motor filter chamber 161, the fluid can exit the separator stage 132 via a separator stage outlet passage 426, and continue downstream to the suction motor, additional separator stage or the like.

In the illustrated embodiment, the pre-motor filter 160 is a formed from a porous, physical filter media (e.g. foam, felt and the like) and has an upstream side 428 and an opposing downstream side 430. In this embodiment, the upstream side 428 is positioned below and generally faces the cyclone chamber air outlets 158 for each cyclone chamber 142. That is, both cyclone chambers 142 are in communication with a common pre-motor filter chamber 161 and air exiting both cyclone chambers 142 is treated by a common pre-motor filter.

Optionally, the upstream side 428 of the pre-motor filter 160 may be generally flat or planar, and may lie in a filter plane 432.

Separator with Inclined Pre-Motor Filter

In accordance with another aspect, that may be used with one or more of the other aspects disclosed herein, the filter plane 432 can be inclined relative to a reference plane 434 that is orthogonal to the direction of air flow through the pre-motor filter 160. In this example, the reference plane 434 is also generally orthogonal to the cyclone axes 154 and is generally horizontal as illustrated in FIG. 72, and the filter plane 432 is inclined at a filter angle 440, that is preferably between about 0 degrees and about 45 degrees. If the pre-motor filter 160 is inclined in this manner, the upstream side 428 may have a width 436 that is greater than the width 438 of the pre-motor filter chamber 161 in the same direction but measured in the reference plane 434. This configuration may allow the pre-motor filter 160 to be relatively larger, and for its upstream side to have a larger surfaced area than a non-inclined filter (i.e. a filter oriented such that its filter plane is parallel to the reference plane 434) positioned within the same pre-motor filter chamber 161. Providing a relatively larger filter, and upstream side surface area, may help improve air flow through the pre-motor filter 160 and/or may help extend the amount of time the pre-motor filter 160 can be used before becoming fouled or otherwise clogged.

Figure 73:
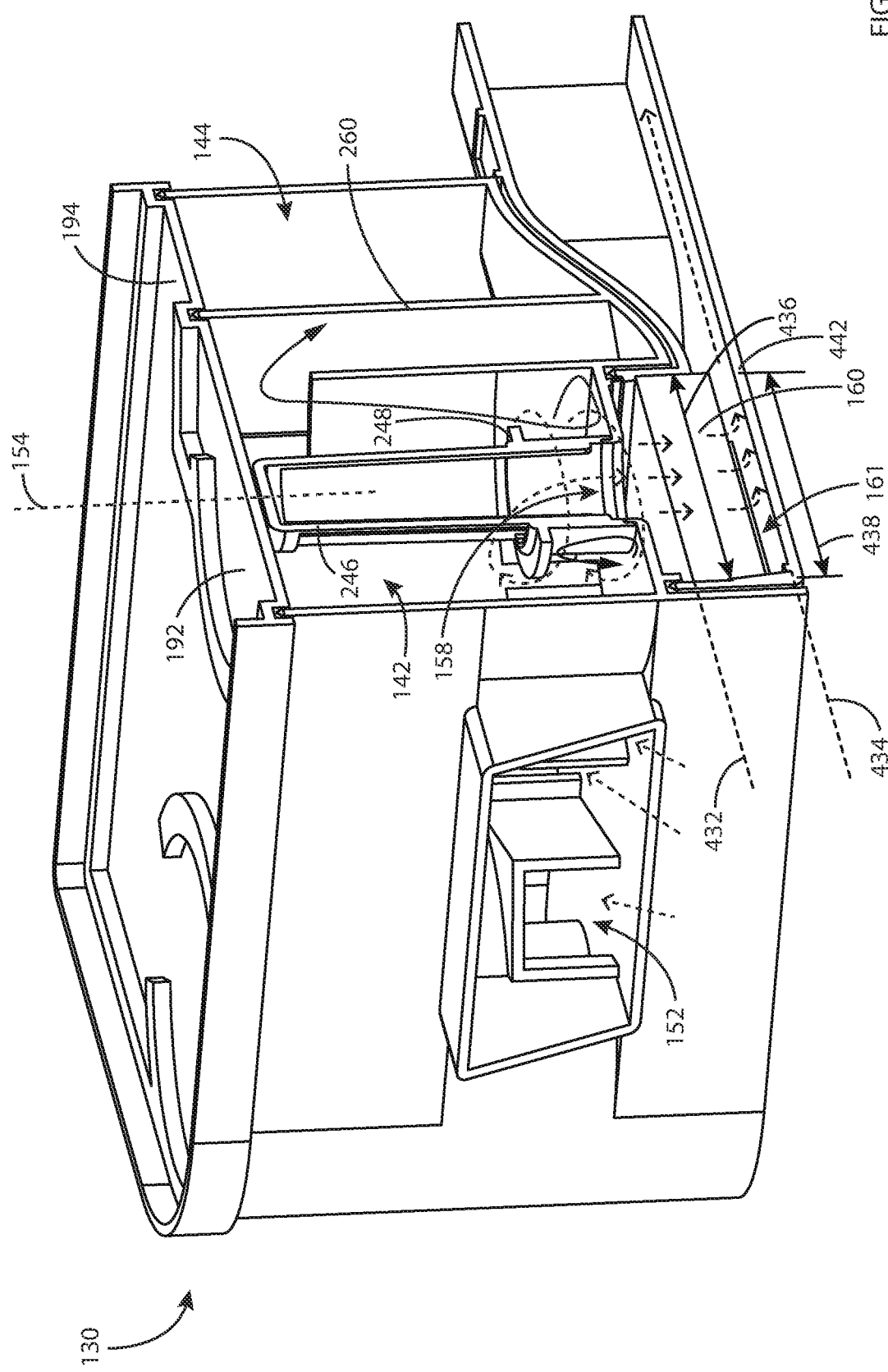
FIG. 73 is the cross-sectional view of FIG. 72, with a pre-motor filter in a different configuration.

Alternatively, as shown in the embodiment of FIG. 73, the pre-motor filter 160 may be arranged in a non-inclined manner, such that filter plane 432 is parallel to reference plane 434, and width 436 is approximately the same as width 438.

Single Stage Separator with Openable Filter Chamber

In accordance with another aspect, that may be used with one or more of the other aspects disclosed herein, the pre-motor filter chamber may be openable, optionally while the pre-motor filter chamber is installed in the surface cleaning apparatus or if the pre-motor filter chamber is included as part of the treatment unit (such as treatment unit 130) and is removable from the rest of the surface cleaning apparatus with the treatment unit and may be openable.

For example, at least one of the walls defining the pre-motor filter chamber may be removable or otherwise openable. Optionally, the pre-motor filter may remain in the pre-motor filter chamber when the chamber is opened, or alternatively the pre-motor filter may be removable with the openable wall portion (such that removing the wall also automatically extracts the pre-motor filter from the pre-motor filter chamber). Optionally, the treatment unit may be configured so that the upstream side of the pre-motor filter is visible to the use when the pre-motor filter chamber is opened. This may help a user easily visually inspect the condition of the pre-motor filter.

Referring to FIGS. 69-72 and 73, in these embodiments the pre-motor filter chamber 161 includes a detachable bottom wall 442 that can be separated from the cyclone separators 142 to provide access to the pre-motor filter 160. In these embodiments, the detachable bottom wall 442 also includes a portion of the air flow conduit that extends from the pre-motor filter chamber 161 and the separator stage outlet passage 426.

In the illustrated configuration, the pre-motor filter 160 is mounted on the openable bottom wall 442, and is removable from the treatment unit 130 with the bottom wall 442. In this arrangement, the upstream side 428 of the pre-motor filter 160 is revealed when the bottom wall 442 is detached. Alternatively, the treatment unit 130 could be configured to retain the pre-motor filter 160 while the bottom wall 442 is detached. In such embodiments, the downstream side 430 of the pre-motor filter 160 would be revealed when the bottom wall 442 is opened.

If a separation stage includes more than one cyclone chamber, then a common pre-motor filter 160 may be provided and may, e.g., underlie both cyclone chambers 142, and a portion of the fluid inlet passage provided therebetween and is forward of the solid collection chamber 144. In other embodiments, separate pre-motor filters 160, in respective pre-motor filter chambers 161 may be provided for each cyclone chamber 142.

Optionally, instead of being positioned below the cyclone chamber(s) 142, the pre-motor filter chamber 161 may be positioned above the cyclone chamber(s) 142. Referring to FIGS. 76-77, in this embodiment the dirty fluid enters the lower ends of the cyclone chambers 142 and the treated air exits out the upper end of the cyclone chamber 142. In this embodiment, the pre-motor filter chamber 161 overlies the upper ends of the cyclone chambers 142 and the upstream side 428 of the pre-motor filter 160 is generally downward facing and opposes the cyclone chamber air outlets 158. To access the pre-motor filter 160, the upper wall 444 of the pre-motor filter chamber 161 can be opened/detached. In this embodiment, the pre-motor filter 160 is mounted to the underside of the openable upper wall 444, and is removable from the treatment unit 130 with the upper wall 444. In this arrangement, the upstream side 428 of the pre-motor filter 160 is revealed when the upper wall 444 is detached. Alternatively, the treatment unit 130 could be configured to retain the pre-motor filter 160 while the upper wall 444 is detached. In such embodiments, the downstream side 430 of the pre-motor filter 160 would be revealed when the upper wall 444 is opened.

Separator with Flow Control Baffles

In accordance with another aspect, that may be used with one or more of the other aspects disclosed herein, instead of, or in addition to a porous, divider, the treatment unit 130 may include one or more flow limiting devices to help prevent back flow of liquid from the liquid collection container 148 into the cyclone chamber 142. The flow limiting device may be used with a combined collection chamber 144, 148 and may be configured to allow liquid to flow from the solid collection chamber 144 into the liquid collection container 148 and help prevent unwanted back-flow. It is also preferable that the flow limiting device can allow the liquid to be emptied from the liquid collection container 148 when desired.

Figure 33:
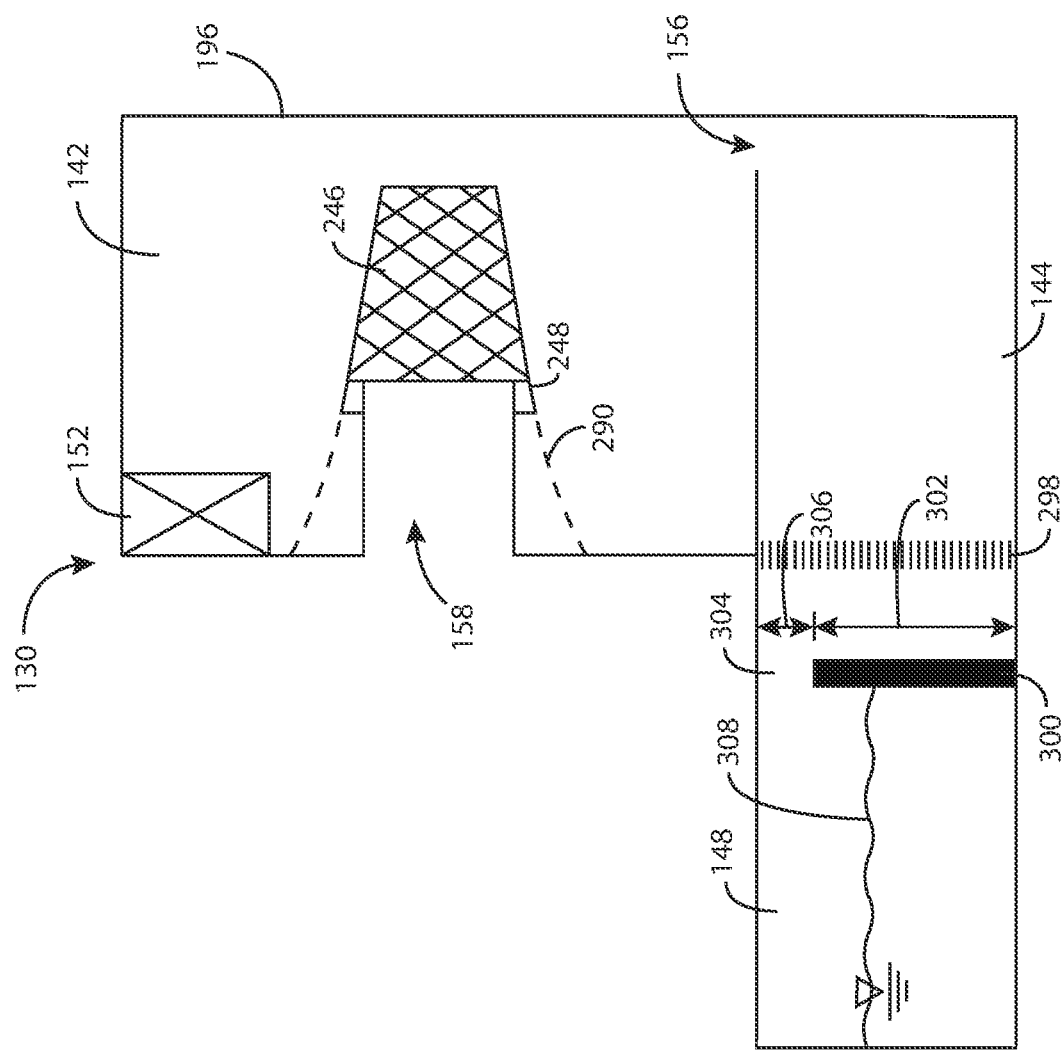

Referring to FIG. 33, another embodiment of a treatment unit 130 is illustrated in a generally horizontal position. This treatment unit includes a porous divider 298 that helps separate the solid collection chamber 144 from the liquid collection container 148, which underlies the solid collection chamber 144 when the treatment unit 130 is vertical (e.g. in the orientation shown in 32). In this embodiment, the treatment unit 130 also includes a flow limiting device that includes a solid baffle 300 extending inwardly from the rear sidewall of the liquid collection container 148. The baffle 300 has a width 302 in the lateral (vertical in the orientation of FIG. 33) direction, but stops short of the front wall of the liquid collection container 148 leaving a flow gap 304 having a gap width 306. The gap width 306 is selected to allow liquid to flow into the liquid collection container 148 when the treatment unit 130 is in an upright or inclined position.

The baffle width 302 is selected so that the baffle 300 is large enough to prevent the back flow of liquid, and to extend above a free surface 308 of the liquid when the liquid collection container 148 is filled to its predetermined "fill" line. In this configuration, the baffle 300 may substantially prevent the backflow of liquid when the treatment unit 130 is inclined with its rear end toward the floor (as shown). To empty the liquid collection container 148, the liquid collection container 148 can be provide with an openable drain to help remove the liquid.

Figure 34:
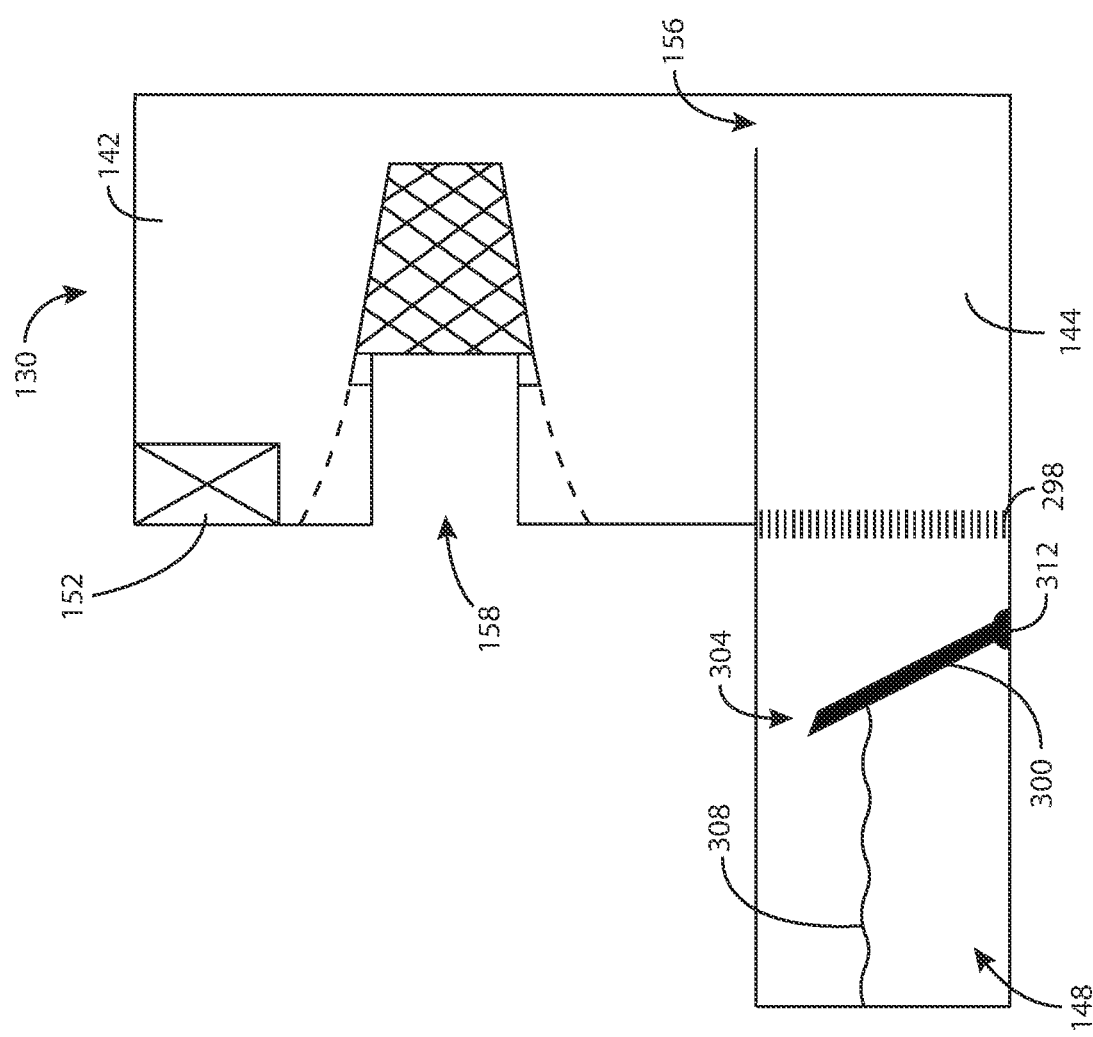
Figure 35:
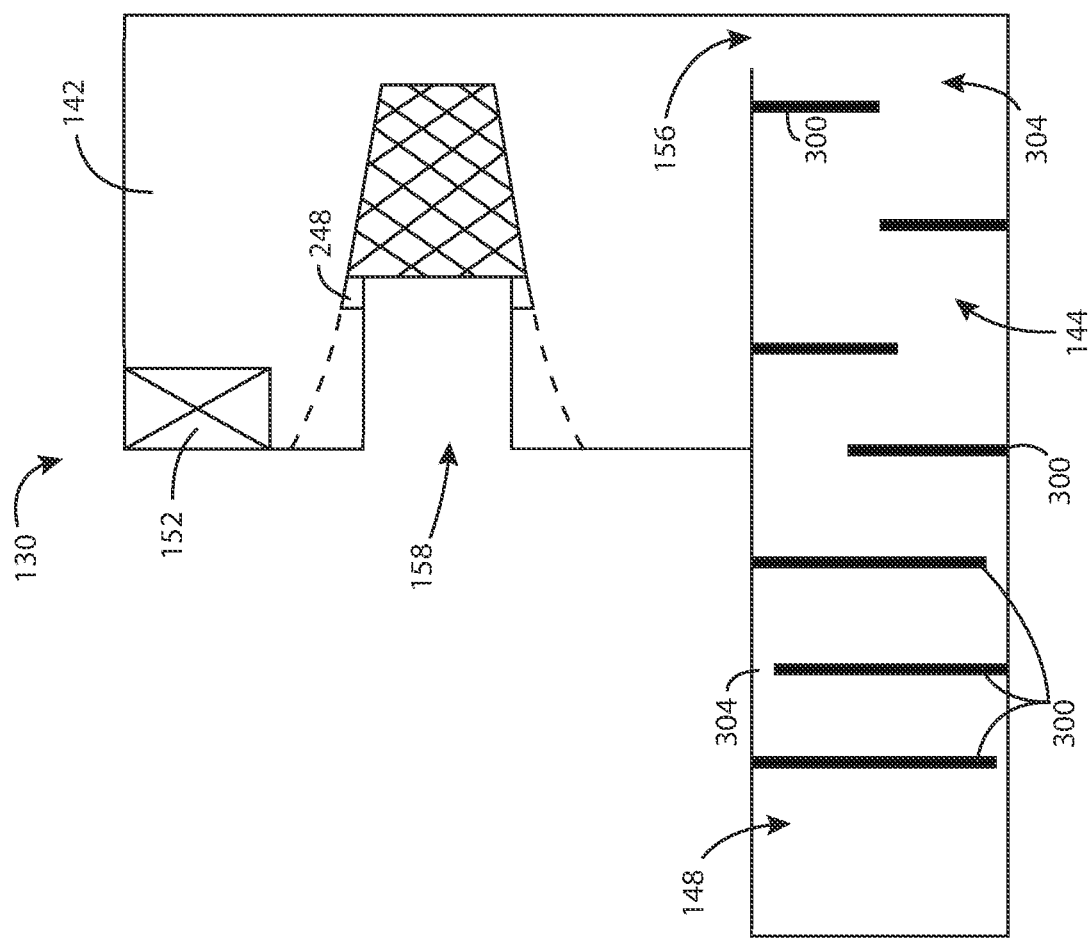

Referring to FIG. 34, in another embodiment, the baffle 300 can be movable within the liquid collection container 148, and can pivot about a pivot connection 310. For example, the baffle may be pivotally connected to a wall of the combined chamber 144, 148. This can allow the baffle 300 to open, e.g., pivot downwardly when the combined chamber 144, 148 is generally vertically oriented, which can widen the gap 304 and help facilitate the flow of liquid into the liquid collection container 148. When the treatment unit 130 is sufficiently inclined, the baffle 300 can be deployed (for example via a float, biasing member, actuator, manual switch and the like) to shrink the gap 304, extend above the free surface 308 and help retain the liquid.

A plurality of baffles 300 may also be provided. As exemplified in FIG. 35, alternating baffles 300, baffled provided on opposed sides of the combined collection chamber 144, 148, are provided in the solid collection chamber 144 and liquid collection container 148. Arranging the baffles 300 in this alternating manner can help create a torturous flow path for the liquid and may inhibit the back flow of liquid when the treatment unit 130 is inclined. Any suitable number of baffles 300, at any suitable spacing, may be used. It will be appreciated that one or more of the baffles may be pivotally mounted.

Figure 36:
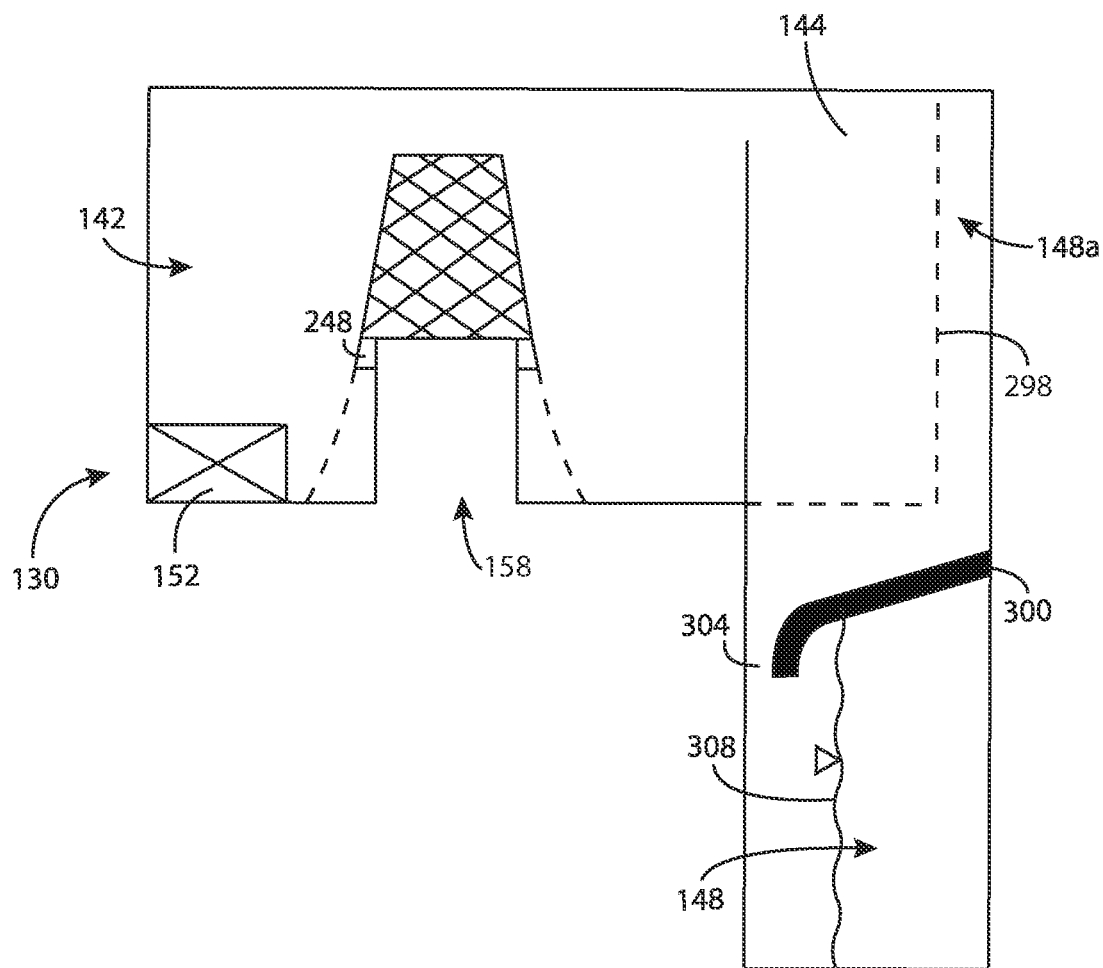

Optionally, as shown in the embodiment of FIG. 36, a baffle 300 may be used in combination with a divider 298 that extends both laterally and axially. Also, as shown in this embodiment, the baffle 300 may be inclined and/or curved in a downward direction (when viewed with the treatment unit 130 upright) to help promote the flow of liquid along the upper surface of the baffle 300 and into the flow gap 304 when the treatment unit 130 is in use. This may help prevent liquid from being trapped above the baffle 300.

The baffles 300 may be formed from any suitable material, including plastic, metal, open cell material, rubber, polymers and the like. The baffles 300 may be generally liquid impervious (i.e. generally non-porous such that they do not absorb liquid) or may be at least partially liquid pervious and/or absorbent. Configuring the baffles 300 to be absorbent may help the baffles 300 to absorb and sequester at least some of the liquid they contact, which may further help prevent splashing and sloshing of liquid within the liquid collection container 148. Optionally, one or more of the baffles 300 may include an open cell foam material, and may have properties that are analogous to those of the sponge 316 described herein. Analogous compression members may also be provided in some embodiments to compress the baffles 300 and help extract retained liquid, if suitable.

Remote Liquid Collection Container

In accordance with another aspect, which may be used with one or more of the other aspects disclosed herein, a separation stage may include a collection chamber that receives at least liquid and optionally both liquid and solid particulate matter (such as exemplified in FIG. 20) wherein a flow connection path is provided from the collection chamber to a separated liquid collection chamber. The separated liquid collection chamber may be remote from the separation stage (e.g., it may be located at a lower elevation) or in a separate part of the apparatus (e.g., the separator may be in an upright section 116 and the separated liquid collection chamber may be in a surface cleaning head). Alternately, the flow path may essentially subdivide a combined collection chamber 144, 148 into two distinct collection chambers whereby the separated liquid collection chamber is isolated from a solid collection chamber 144.

Optionally, the fluid flow path may include one or more flow limiting devices and/or may be configured as a generally one-way fluid flow path that can facilitate transfer of liquid from the solid collection chamber 144 to the liquid collection container 148 and inhibit and/or block flow in the opposite direction.

One advantage of this design is that the flow back of separated liquid may be reduced or essentially prevented. A second advantage is that the liquid may be stored at a lower elevation, thereby lowering the center of gravity of the apparatus when filled and also reducing the hand weight perceived by a user.

Figure 37:
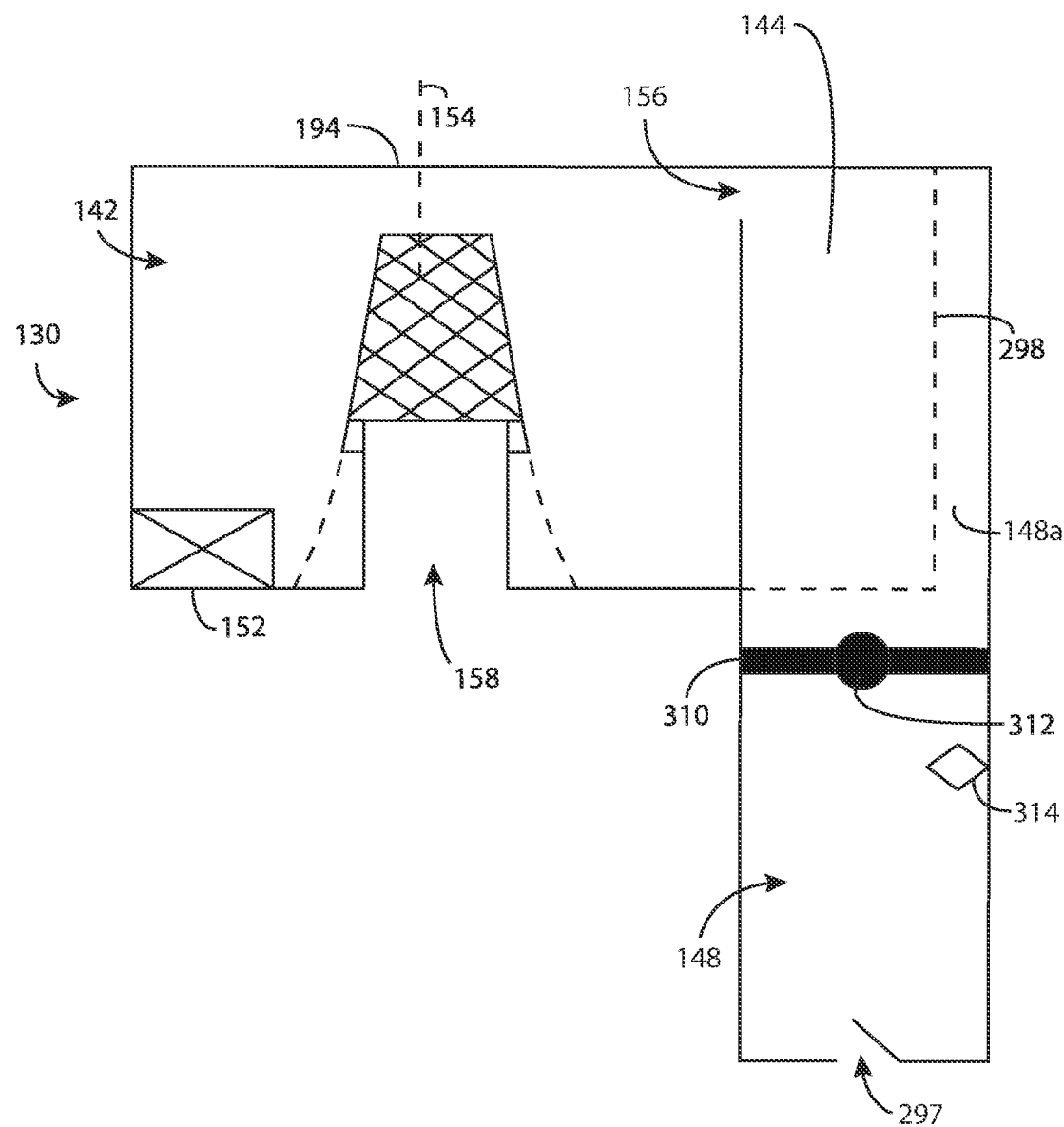

As exemplified in FIG. 37, the liquid collection container 148 is downstream from the solid collection chamber 144 and can be selectively, fluidically isolated from the solid collection chamber 144. In this example, the treatment unit has a flow limiting device that includes a valve 310 that can be opened when the treatment unit 130 is above a predetermined maximum incline angle to allow liquid to flow in the liquid collection container 148. The valve 310 can then be closed (FIG. 37), for example by pivoting about pivot connection 312, to seal the upper end of the liquid collection container 148. Optionally, the valve 310 may be manually controlled by a user. Alternatively, operation of the valve 310 can be automatic based on a variety of criteria, including, for example, if the treatment unit 130 passes a predetermined maximum incline angle, a float switch, a moisture sensor of the like. For example, the treatment unit 130 may include a sensor, such as an inclination sensor 314 that can detect when the treatment unit 130 is inclined past a predetermined threshold, such as when the cyclone axis 154 is within about, e.g., 25 degrees, about 20 degrees, about 15 degrees, about 10 degrees and/or less than 10 degrees of horizontal. When the sensor 314 senses that the treatment unit 130 has reached the inclination threshold, it can trigger operation of the valve 310 to seal the liquid collection container 148. To empty the liquid collection container 148 the valve 310, a drain port 297, or both can be opened.

It will be appreciated that the valve may also be a one-way valve which permits the flow of water into container 148 but inhibits the flow of water out of container 148 into container 144 (e.g., a check valve or one-way port). The valve may be open in a normal operating state but close when a sensor, float switch or the like determines that water is about to flow out of container 148 into container 144.

Optionally, the treatment unit 130 can be arranged so that when the surface cleaning apparatus is in the floor cleaning orientation, the separated liquid collection container 148 is positioned below the solid collection chamber 144. This may help facilitate the separated liquid passing from the solid collection chamber 144 to the separated liquid collection container 148 by gravity flow (e.g. FIGS. 36, 37 and 39).

Figure 38:
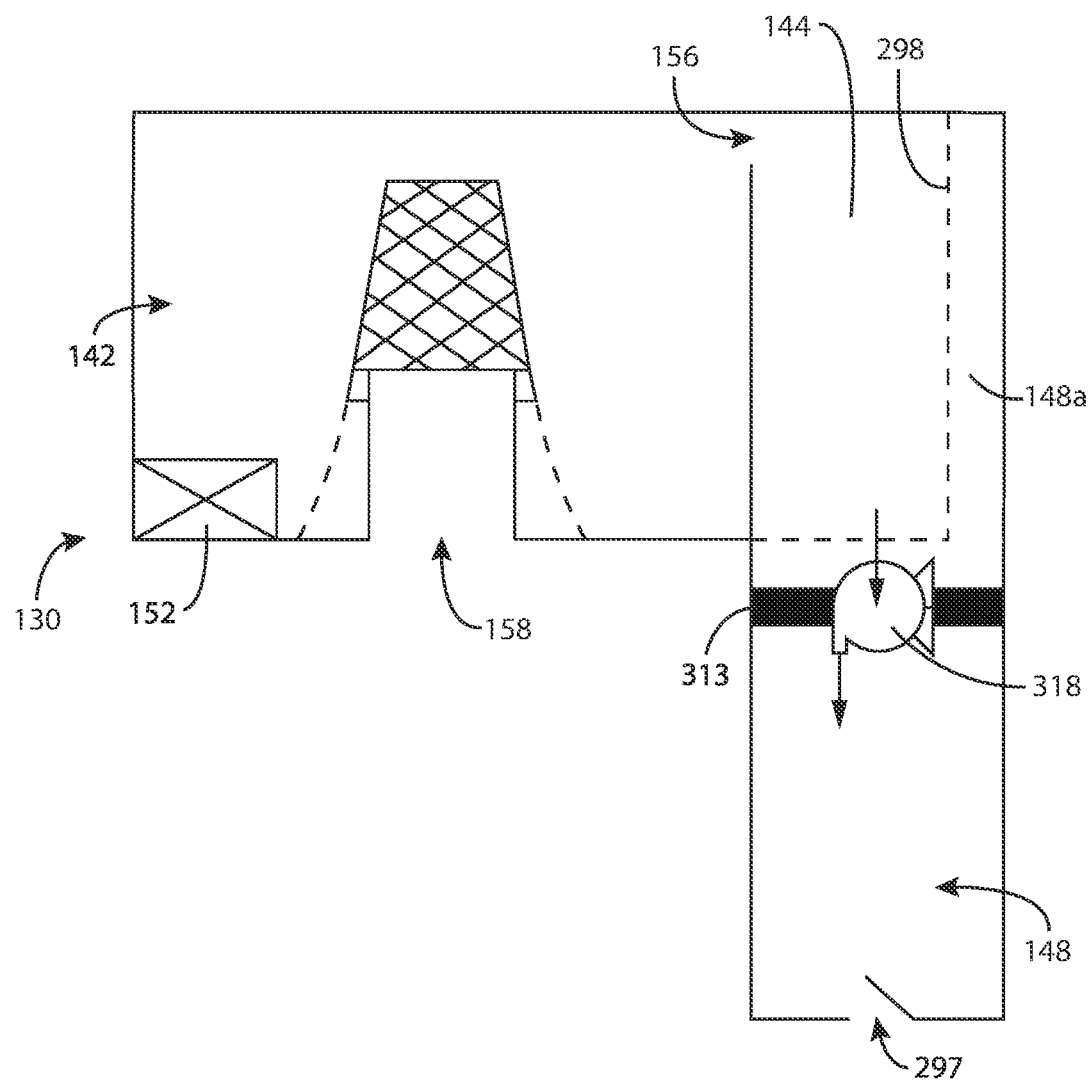

As exemplified in FIG. 38, a treatment unit 130 includes an optional divider 298 and a partition 313 that separates a lower portion of the liquid collection container 148 from the upright section 148a and the solid collection chamber 144, and helps provide a portion of the fluid flow path from the solid collection chamber 144 to the separated liquid collection container 148. The partition 313 can be provided with any suitable type of flow limiting devices, including a one-way flow device, such as a check valve or one-way port (FIG. 39) and the like to allow liquid to flow from the upright section 148a to the lower portion 148. As exemplified, partition 2313 includes a powered device, such as a pump 318 that can help draw liquid from the upright section 148a to the lower portion 148. The pump 318 may be configured to run continuously when the apparatus is actuated, may be controlled by a switch, may be configured to sense the presence of liquid in the upright section 148a and turn on accordingly and/or may be programmed to operate intermittently.

Figure 39:
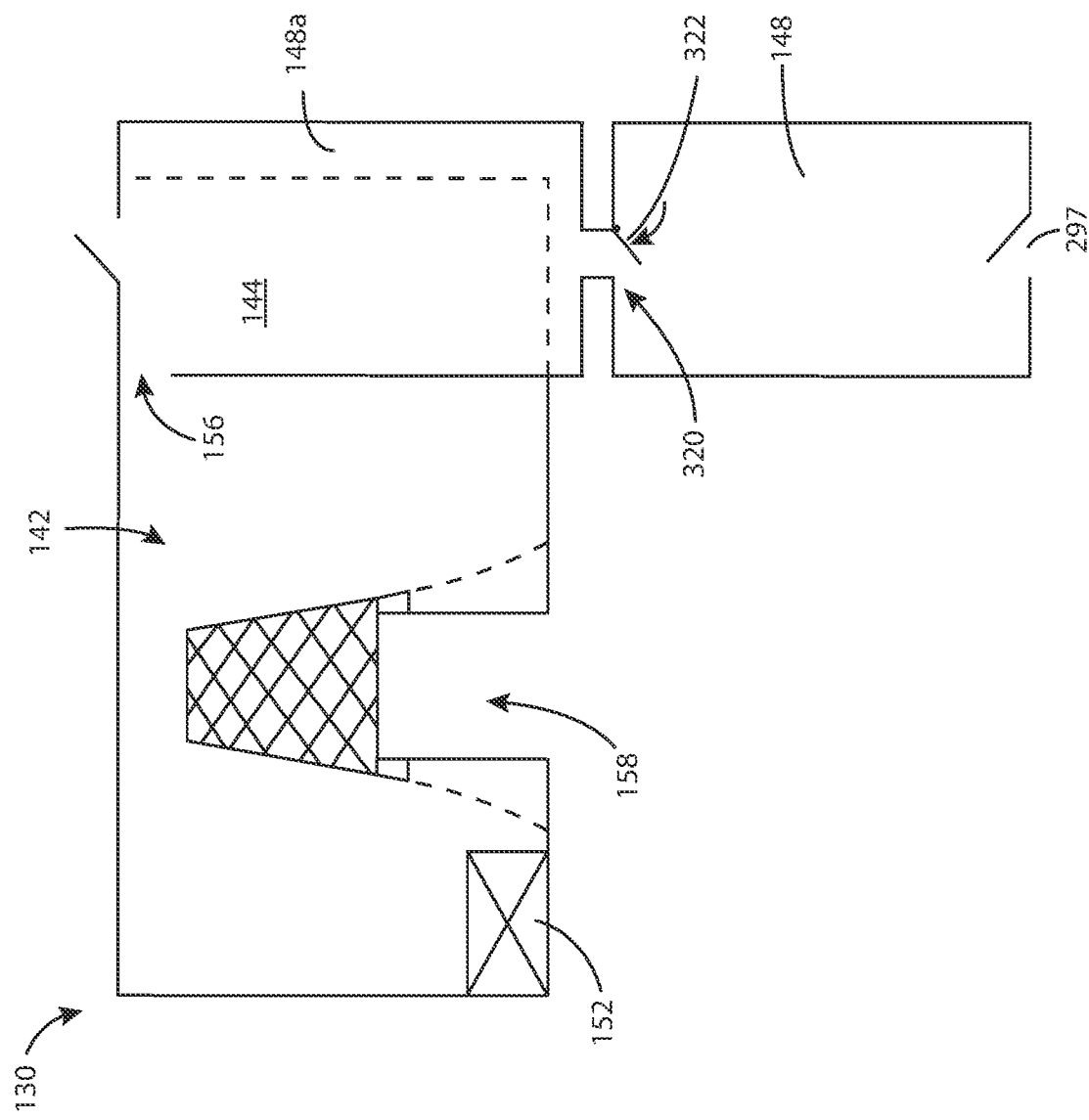

As exemplified in FIG. 39, a narrow port or passage may be provided between the upright section 148a and lower portion 148 which, optionally, may be blocked by valve that includes a flap 322 that is biased toward the closed position. The flap 322 may open under the weight of the liquid accumulating in the upright section 148a, but may be urged closed by its biasing force and the hydraulic pressure of liquid in the lower portion 148 when the treatment unit 130 is inclined. The lower portion of the liquid collection container 148 can be emptied by opening drain port 297, whereas the upright section 148a, and solid collection chamber 144, can be emptied when lid 194 is removed. Optionally, instead of the entire lid 194 being openable, it may be provided with an openable port.

Alternately, or in addition, the treatment unit 130 may be configured so that at least a portion of the liquid collection container 148 is provided in the surface cleaning head 102, or other suitable location, that is further remote from solid collection chamber 144 and cyclone chamber 142. For example, the cyclone chamber 142 and solid collection chamber 144 may be provided on the upright section 116, and optionally may be part of a removable cleaning unit 120, while at least a majority of the liquid collection region, including the liquid collection container 148 is provided as part of the surface cleaning head 102. This may help lower the centre of gravity of the apparatus 100, and may help reduce the weight that a user carries when holding and maneuvering the upright section 116. Liquid may be conveyed from the solid collection chamber 144 to the remote liquid collection container 148 using any suitable liquid flow conduit or passage, and may travel under the influence of gravity or be assisted, such as by a pump.

Figure 42:
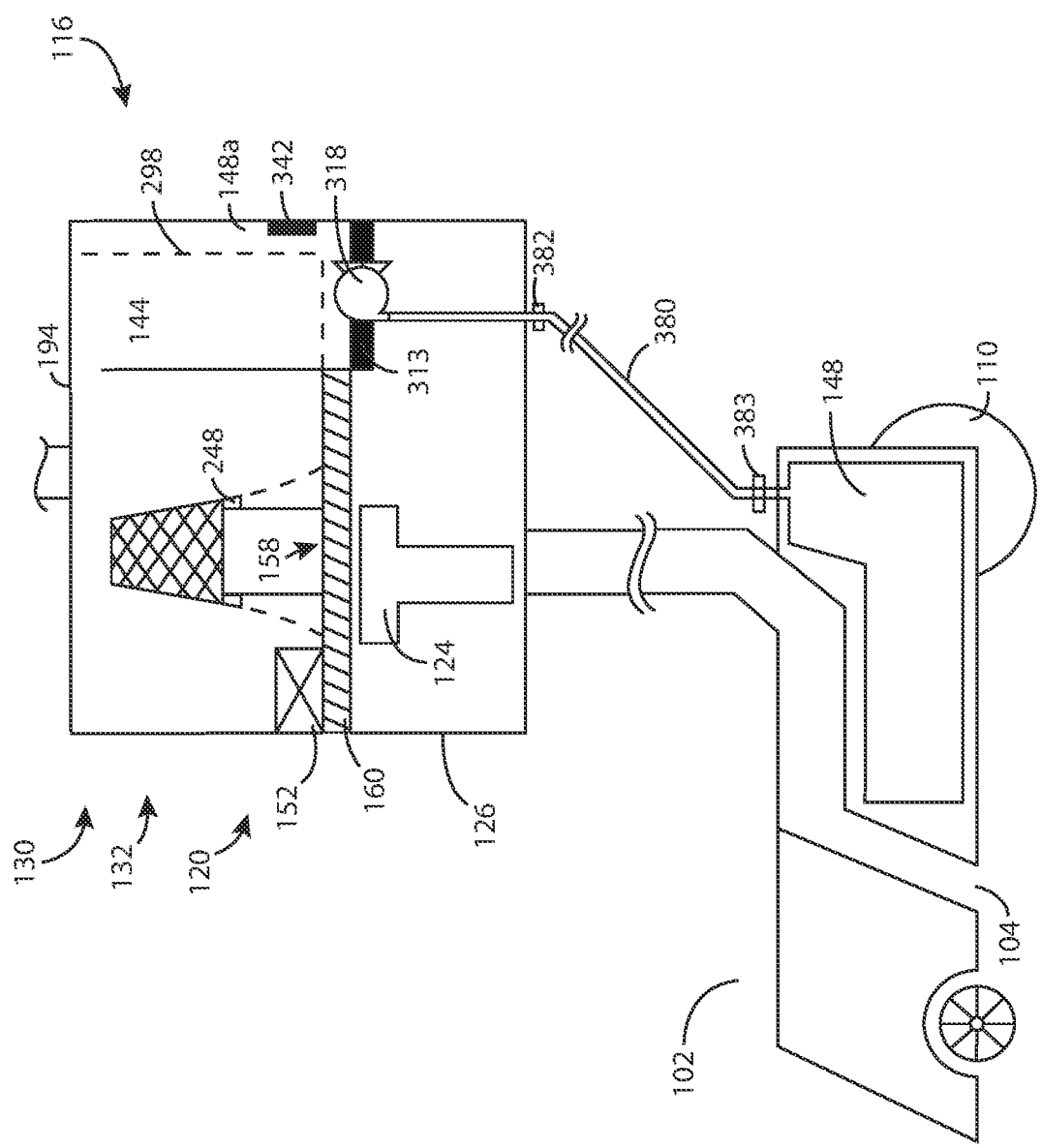
FIG. 42 is a schematic cross-sectional view of a portion of another embodiment of a surface cleaning apparatus.

Referring to FIG. 42, a portion of a surface cleaning apparatus 100 is illustrated, including a single stage separator 132 having a cyclone chamber 142 configured to separate liquid and solid debris. The solid collection chamber 144 is partially bounded by a porous divider 298, allowing liquid to flow form the solid collection chamber 144 into a relatively small upper liquid collection portion 148a. From the upright section 148a the liquid is pumped, via pump 318, through a liquid flow conduit 380 to the liquid collection container 148 that is provided in the surface cleaning head 102. This arrangement may also help prevent liquid from flowing back from the liquid collection container 148 into the solid collection chamber 144 when the upright section 116 is reclined because the pump 318 may pose a flow barrier, and because the surface cleaning head 102 will generally still be at a lower elevation that the solid collection chamber 144. Optionally, the liquid flow conduit 380 may include one or more suitable couplings 382, to allow the solid collection chamber 144 and cyclone chamber 142 to be separated from the liquid collection container 148.

Optionally, a moisture sensor, such as sensor 342 (FIG. 42) can be provided at a suitable location within the treatment unit 130, such as within the upper portion 148a of the liquid collection container and/or within the solid collection chamber 144. The sensor 342 can be used to detect when liquid is present in the treatment unit 130, and suitable controller may then automatically trigger the pump 318 (in the embodiments of FIGS. 15-16 and/or 42) or open a valve 310 (FIG. 37) or actuate any other suitable flow limiting device to help facilitate transfer of the liquid to the liquid collection container 148. Optionally, instead of, or in addition to being actuated by the moisture sensor 342, the pump 318 may be actuated when the liquid delivery system is activated (e.g. when liquid is sprayed via the nozzle 164) as it may be likely that the surface cleaning apparatus 100 will be used in a wet cleaning mode after liquid has been applied to the surface. In such embodiments, the pump 318 and liquid delivery system may be linked by a suitable controller. Optionally, the pump 318 may be configured so that it is always on when the surface cleaning apparatus 100 is in use, and is actuated when the surface cleaning apparatus 100 is actuated.

Figure 15:
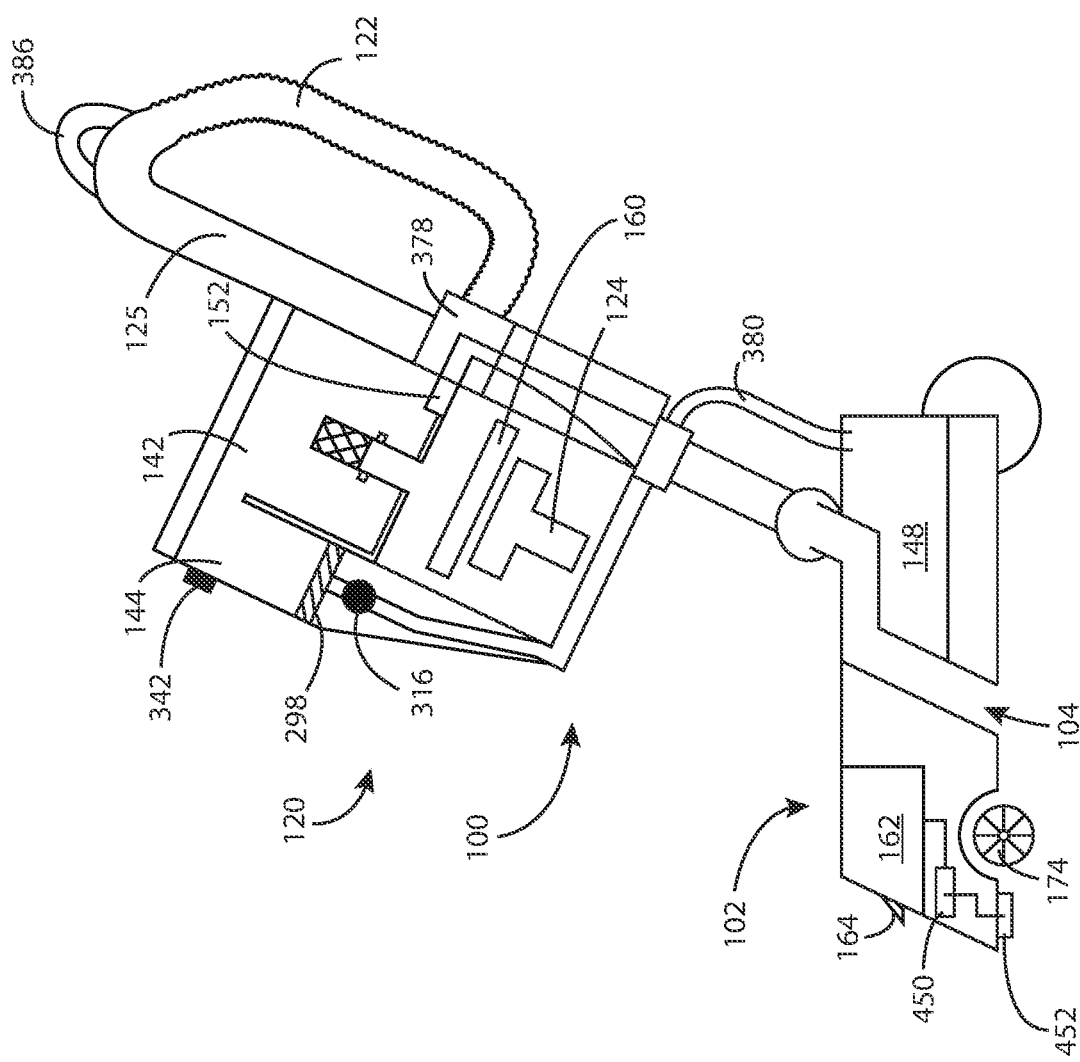
FIG. 15 is a schematic, cross-sectional view of yet another embodiment of an upright-style surface cleaning apparatus.
Figure 16A:
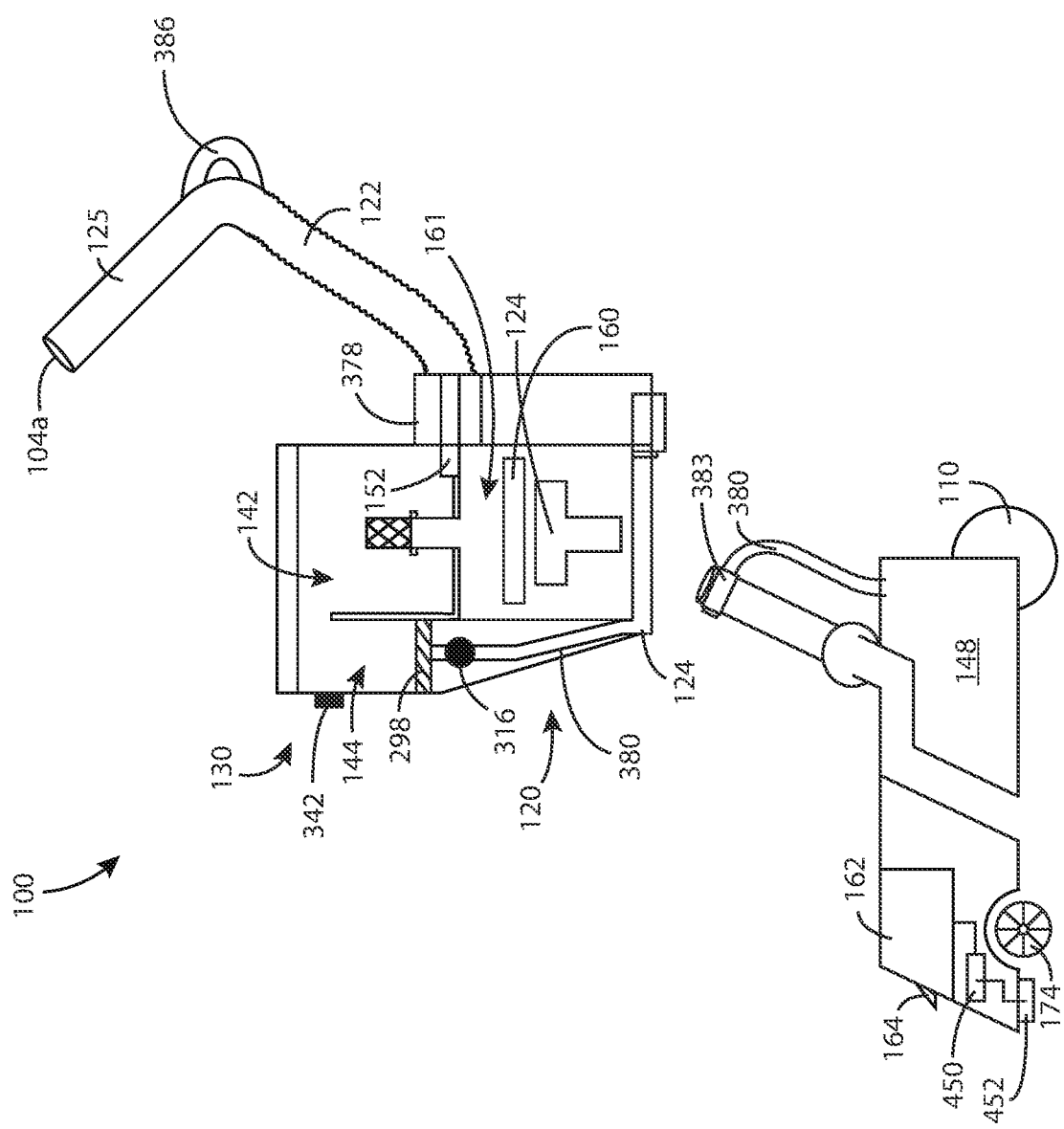
FIG. 16A is a schematic, cross-sectional view of the surface cleaning apparatus of FIG. 15, with a cleaning unit detached.

Optionally, the liquid flow conduit 380 may be of any suitable length and configuration and optionally may be separable into at least two portions connected by any suitable coupling, as shown in the embodiment of FIGS. 15 and 16A. In this embodiment, the fluid flow path between the solid collection chamber 144 and the liquid collection container 148 can be interrupted if the cleaning unit 120 is detached. The cleaning unit 120 may then be used in a dry-only mode, or optionally may be used in a wet-cleaning mode with the separated liquid being temporarily collected in the solid collection chamber 144 until it is emptied and/or until the liquid flow conduit 380 is re-connected to re-establish liquid communication with the liquid collection container 148.

Optionally, any suitable valve, such as the check valve 383 (FIGS. 16 and 42) may be provided in the fluid flow path between the solid collection chamber 144 and the liquid collection container 148 (e.g. along the length of flow conduit 380) to help prevent liquid from flowing back from the liquid collection container 148 and through the fluid flow path.

Optionally, the liquid collection container 148 can be removable from the surface cleaning apparatus 100 for emptying, and optionally may be configured as a disposable or single-use container. In such embodiments, one liquid collection container 148 containing dirty liquid can be discarded by a user, and a different, empty liquid collection container 148 can be inserted in its place. This may help reduce the chances of the dirty liquid spilling when the liquid collection container 148 is emptied.

Optionally, both the upper and lower ends of the treatment unit 130 can be openable, which may allow liquid to be removed from the bottom, while solid debris, retained above divider 298 is emptied via the top. In another embodiment, shown in FIG. 41, the treatment unit 130 may include an overflow region 326 connected to the liquid collection container 148, and positioned so that it is below, or at least at a lower elevation than, the liquid collection container 148 when the treatment unit 130 is inclined. In this arrangement, liquid in the liquid collection container 148 may flow down into the overflow region 326 rather than back into the solid collection chamber 144 or cyclone chamber 142. When the treatment unit is returned to its upright position, at least some of the liquid may flow back into the liquid collection container 148.

Liquid Sequestering Member in the Liquid Collection Container

In accordance with another aspect, which may be used with one or more of the other aspects disclosed herein, the treatment unit 130 may include one or more liquid sequestering members that can be configured to at least temporarily retain/sequester liquid that is collected in the liquid collection container 148, to help prevent backflow. Such liquid sequestering members may be formed from any suitable material(s), and may include open cell materials such as sponges and foams and/or absorbent materials such as polymers, fibrous materials and the like.

Optionally, the liquid sequestering member may be configured to be single-use members and optionally may generally permanently retain the liquid to which it is exposed. For example, the liquid sequestering member may include an absorbent material that absorbs water (e.g., it may swell when it absorbs water). When the surface cleaning apparatus 100 is in use, some or all of the water received in the liquid collection container 148 may be absorbed by the absorbent material, which may help reduce splashing or sloshing of the liquid and/or may help prevent liquid reentering the separator (e.g., cyclone chamber) from the liquid collection container 148. When the liquid collection container 148 is emptied, the absorbent material, containing the absorbed liquid, may be discarded and optionally replaced with fresh absorbent material. In these embodiments, the liquid sequestering member may also function as a baffle (similar in function to baffles 300) to help reduce the splashing and/or sloshing of liquid within the liquid collection container 148. For example, in some embodiments the liquid sequestering member may absorb some of the separated liquid that accumulates within the liquid collection container 148, while some of the liquid can remain unabsorbed (for example if the liquid sequestering member becomes saturated) and may flow within the liquid collection container 148 as it moves during use. The presence of the liquid sequestering member may act as at least a partial barrier to the flow of such liquid, in a manner analogous to the other examples of flow controlling baffles 300 described herein.

Alternatively, the liquid sequestering member may be re-usable (e.g. an open cell material), such that it can absorb a first quantity of liquid and then be drained, dried or otherwise regenerated such that it can absorb a second quantity of liquid.

Optionally, the liquid sequestering member may be generally rigid, and may retain a generally consistent shape during the different phases of its use. Alternatively, the liquid sequestering member may be deformable. This may help with insertion and removal of the liquid sequestering member within the liquid collection container 148. This may also help extract the liquid that has been retained within the liquid sequestering member. For example, a liquid sequestering member that is configured as a generally deformable open cell foam member may be deformed, e.g. squeezed, to help extract the liquid that has been absorbed by the open cell foam.

Optionally, the surface cleaning apparatus 100 may include an actuator to engage the liquid sequestering member and help dislodge and/or extract liquid that has been captured by the liquid sequestering member. For example, if the liquid sequestering member is deformable, the surface cleaning apparatus 100 may include a compression member that can be used to squeeze/compress the liquid sequestering member from an uncompressed state (in which liquid is retained) to a compressed state (whereby liquid is released from the liquid sequestering member). The compression member may be any suitable structure, including, for example a plate, plunger, piston, grill, screen and the like.

Figure 40:
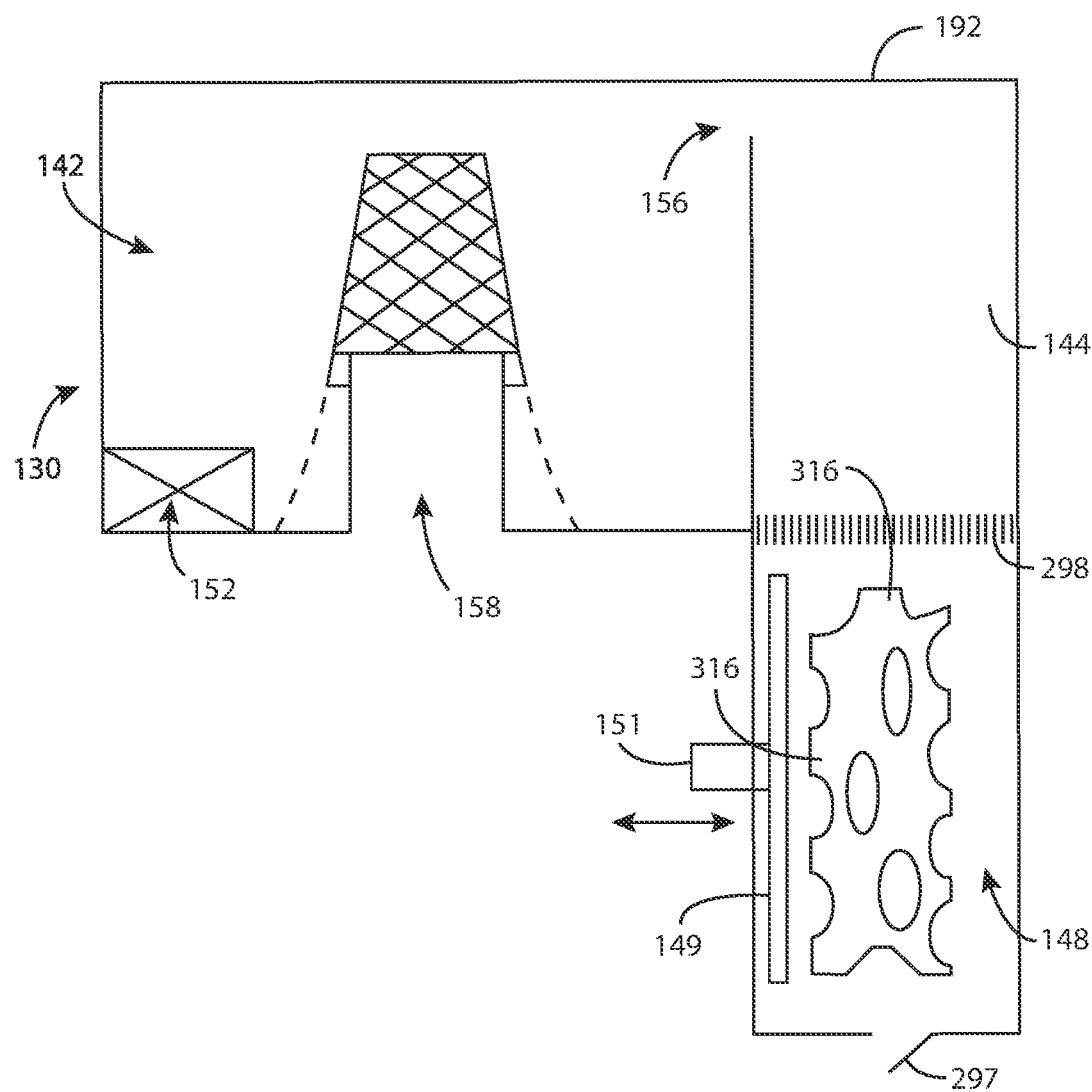
Figure 41:
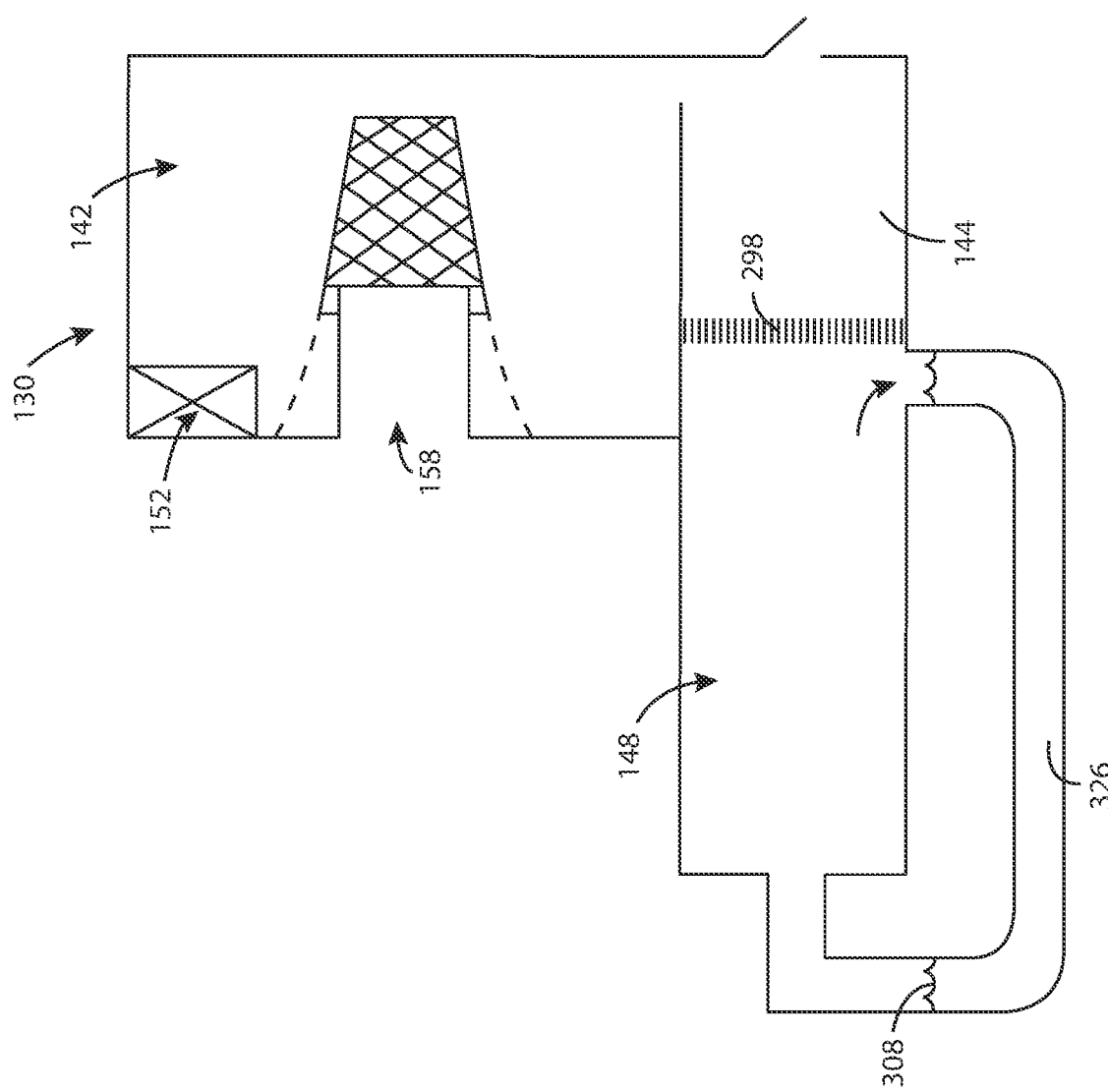

Referring to FIG. 40, this embodiment of the treatment unit 130 has a sequestering member that includes a porous, sponge 316 that is made from an open cell foam and is positioned inside the liquid collection container 148. The sponge 316 can absorb and at least temporarily retain liquid, and help prevent liquid from flowing freely out of the liquid collection container 148. To empty the liquid collection container 148, the container can be inverted and port 297 opened for a sufficient period of time for the liquid to eventually trickle out of the sponge 316. Alternatively, or in addition, the sponge 316 can deformable and can be squeezed to help dislodge the liquid. Optionally, the sponge 316 can be removed from the liquid collection container 148 and wrung out for re-use, or optionally replaced with a new sponge 316.

As exemplified in FIG. 40, the treatment unit 130 includes an optional compression member that can be used to compress the sponge 316 while it is within the liquid collection container 148. This may help a user squeeze the sponge 316 to extract liquid, without having to directly touch the sponge 316 or remove it from the liquid collection container 148. In this embodiment, the compression member includes a plunger 149 connected to a drive rod 151. By translating the drive rod 151, for example using a suitable motor or by manual engagement by a user, the plunger 149 can be moved toward the sponge 316 (to the right as illustrated in FIG. 40) to compress/deform the sponge 316 to squeeze out the liquid, and then moved away from the sponge 316 (to the left as illustrated) to decompress the sponge 316 and allow it to re-expand to absorb additional liquid.

Optionally, the help drain away liquid that has been squeezed out of the sponge 316, the liquid collection container 148 can include an optional liquid outlet that is located, e.g., at a lower elevation than the sponge 316 when the liquid collection container 148 is in an emptying configuration/orientation. In this arrangement, liquid that is squeezed out of the sponge 316 can fall downwardly under the influence of gravity, and then drain from the liquid collection container 148 via the liquid outlet. This may help prevent re-absorption of the liquid when the sponge expands after compression is terminated. In this embodiment, a drain port 297 is provided at the lower end of the liquid collection container 148 and can be selectively opened by the user (automatically and/or manually) to allow the liquid to drain. In this embodiment, when the liquid outlet is opened and the sponge 316 is compressed, liquid trapped in the sponge 316 can exit the separated liquid container 148 through the liquid outlet (port 297) while the sponge 316 remains in the separated liquid container 148. Port 297 may be opened automatically when the compression member is actuated, e.g., the port may be opened concurrently or sequentially with the actuation of the compression member.

While the drain port 297 shown as being positioned below, and underlying the sponge 316 in FIG. 40, in other embodiments the treatment unit 130 illustrated in this example may be intended to be oriented, e.g., horizontally when being emptied (i.e. rotated clockwise 90 degrees from the orientation shown). In such embodiments, the drain port 297 may be provided on the right sidewall of the liquid collection container 148 (as illustrated), such that the drain port 297 underlies the plunger 149 and sponge 316 when the treatment unit 130 is in the emptying position, but does not underlie the plunger 149 and sponge 316 when the treatment unit 130 is in the use position.

Alternatively, the treatment unit 130 may be intended to be inverted about 180 degrees when being emptied, for example by opening the lid 192. In such embodiments, the sponge 316 may be positioned above the open end of the solid collection chamber 144 and liquid collection container 148, and liquid that is squeezed from the sponge 316 may exit via the same opening that is used to drain the non-sequestered liquid and the dry dirt/debris (e.g. by flow through screen 298 and then out the open end of the solid collection chamber 144). This may eliminate the need for the separate drain port 297.

Optionally, the sponge 316 can be loosely received within the liquid collection container 148 such that it may be movable within the liquid collection container 148 while the treatment unit 130 is in use. Alternatively, the sponge 316, or any other suitable liquid sequestering member, may be mounted within the liquid collection container 148 (such as by using a frame, clips, fasteners and the like) so that it is held in a generally fixed position while the treatment unit 130 is in use. Alternately, it may be held in position by a friction fit.

Optionally, the sponge 316 can be configured such that it will remain in place within the liquid collection container 148 when the liquid collection container 148 is opened (such as by opening lid 192). This may allow a user to open the lid 192 without having to extract the sponge 316 from the liquid collection container 148. This may be helpful if, for example, a user wishes to open the lid 192 to inspect the interior of the treatment unit 130 but does not wish to touch the sponge 316 or empty the liquid. Alternatively, the sponge 316 may configured so that it is removed automatically when the lid 192 is opened. For example, the sponge 316 may be connected to, or mounted to an underside of the lid 192, such that when the lid 192 is opened the sponge 316 moves with it and is at least partially (and optionally entirely) removed from the liquid collection container 148. This may help facilitate access to the sponge 316, and may allow a user to remove the sponge 316 from the liquid collection container 148 by manipulating the lid 192 and without having to directly touch the sponge 316.

Flexible and/or Inflatable Liquid Collection Container

In accordance with another aspect, which may be used with one or more of the other aspects disclosed herein, a liquid reservoir, such as the liquid collection container 148, may be at least partially, and optionally entirely, formed from a generally flexible, pliable and/or expandable material. In some examples, the liquid collection container 148 may be configured as an inflatable, bladder like container that can have a relatively small volume/size when empty, and can be inflated/expand as it is filled with separated liquid. This may help reduce the overall size of the liquid collection container 148 when empty. Optionally, such a liquid collection container 148 may also be detachable, preferably as a sealed unit, and may be disposable (e.g. single use) without requiring the user to open or empty the separate liquid from the separated liquid container 148.

Figure 78:
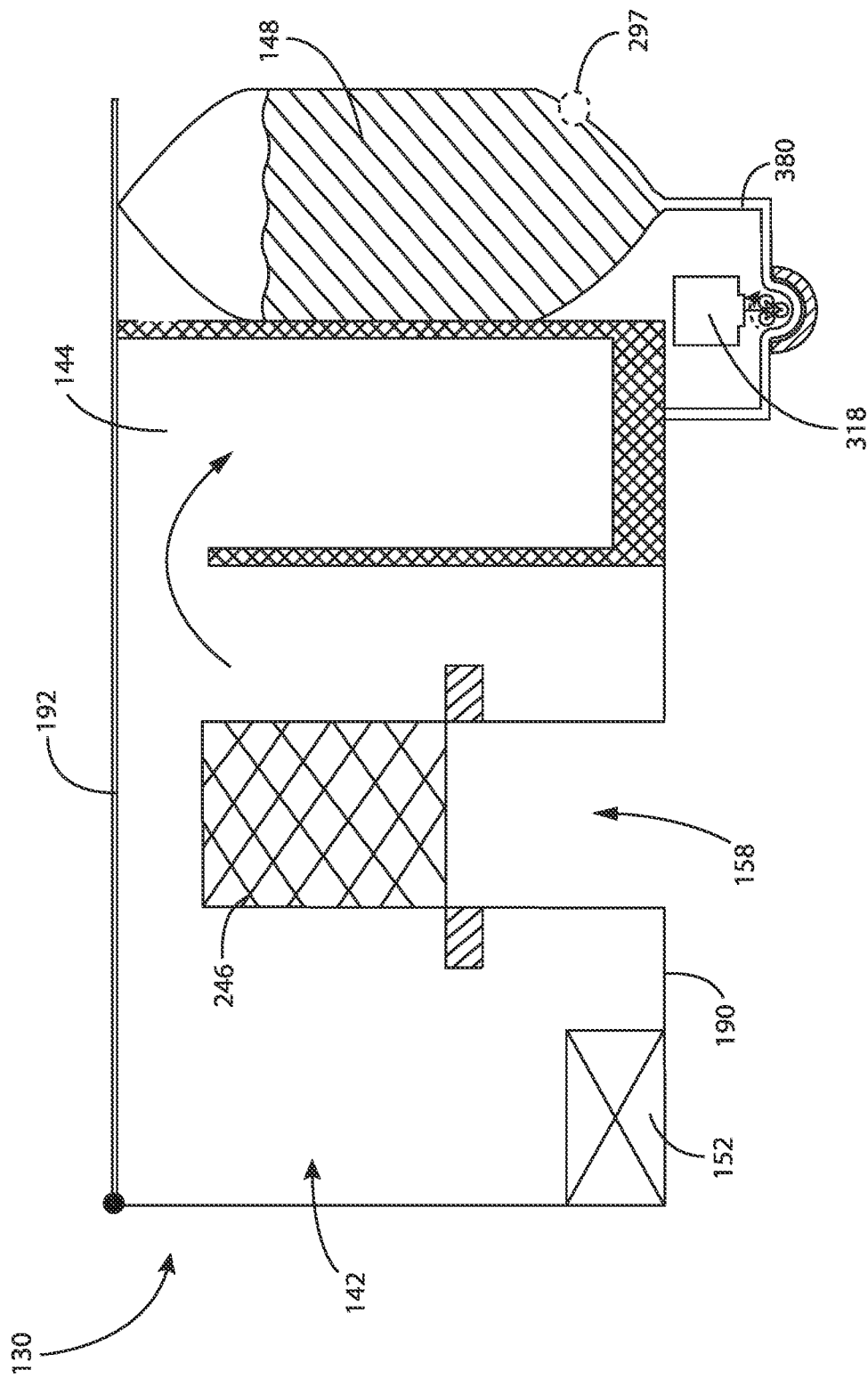
FIG. 78 is a cross-sectional, schematic representation of another embodiment of a treatment unit.

Referring to FIG. 78, one example of a separator 130 in which liquid that is separated by the cyclone chamber 142 passes through the divider 298 at the lower end of the solid collection chamber 144 and is pumped, via pump 318 and liquid flow conduits 380, into a liquid collection container 148 that is configured as an inflatable bladder. As more separated liquid is pumped into the bladder, it can expand. Optionally, the bladder may be detachable for disposal, or may include an optional drain port 297 for emptying.

In this example, opening the common upper wall 192 can provide simultaneous access to the interior of the cyclone chamber 142, the solid collection chamber 144 and the separate liquid container 148 for emptying/removal as desired.

Optionally, at least a portion of an inflatable liquid collection container 148 may be nested within one or more liquid reservoir tanks 200 or a cleaning solution tank. This may help reduce the overall size of the surface cleaning apparatus 100. As the liquid collection container 148 is nested within another liquid tank and is an expandable-type container, it will occupy relatively little volume when empty, and expand to occupy more volume within the reservoir tank 200 as more separated liquid is collected. As the surface cleaning apparatus 100 is in use, clean liquid may be dispensed from the reservoir tank 200, thereby reducing the volume of liquid retained in reservoir tank 200. As liquid is collected, the expandable liquid collection container 148 may expand into the interior of the reservoir tank 200, and may occupy some of the space that was previously occupied by clean liquid. This may allow the same volume/region within the apparatus 100 to be used for storing both clean liquid and dirty liquid, at different times. This may help reduce the overall size of the surface cleaning apparatus 100.

Figure 79:
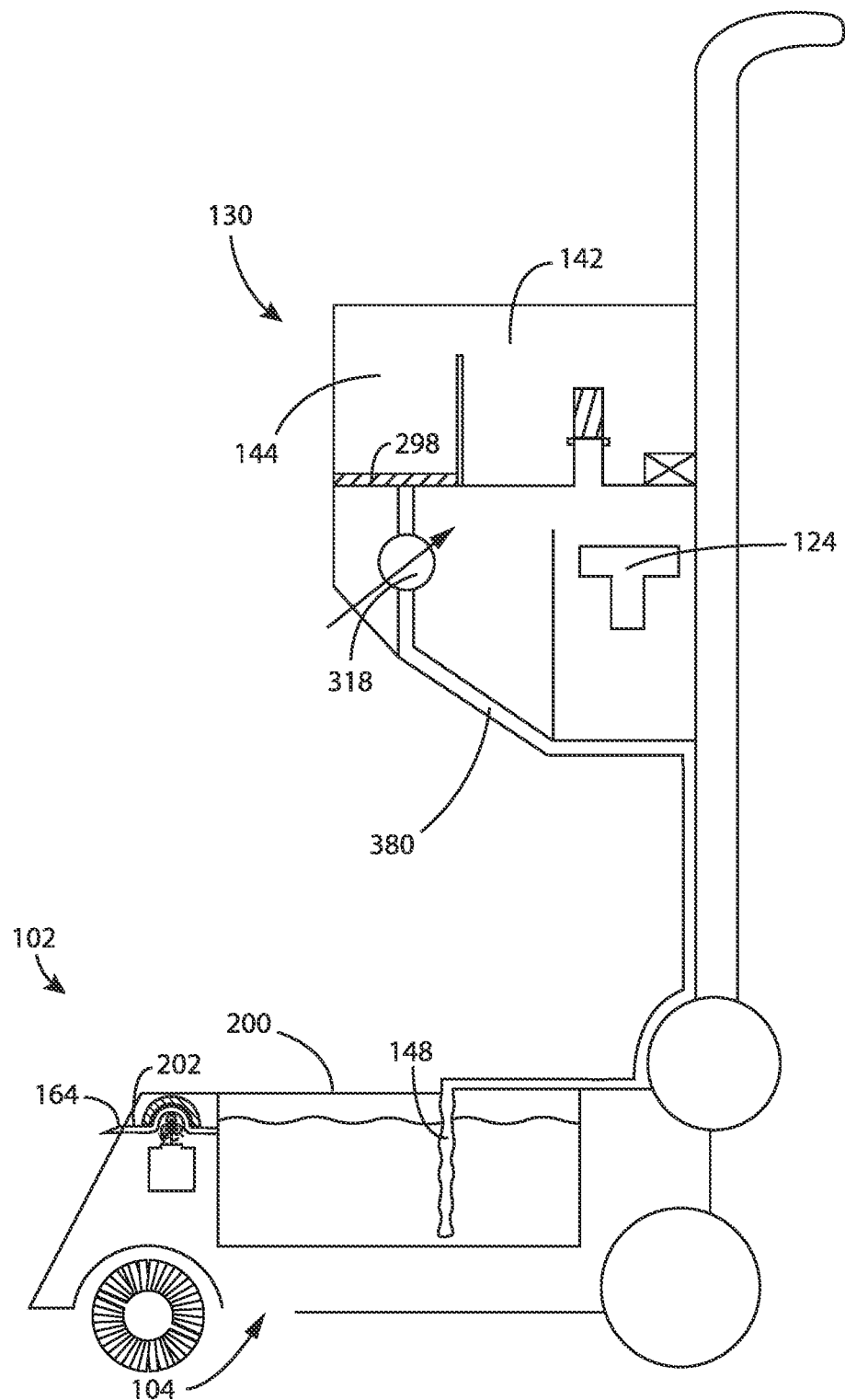
Figure 80:
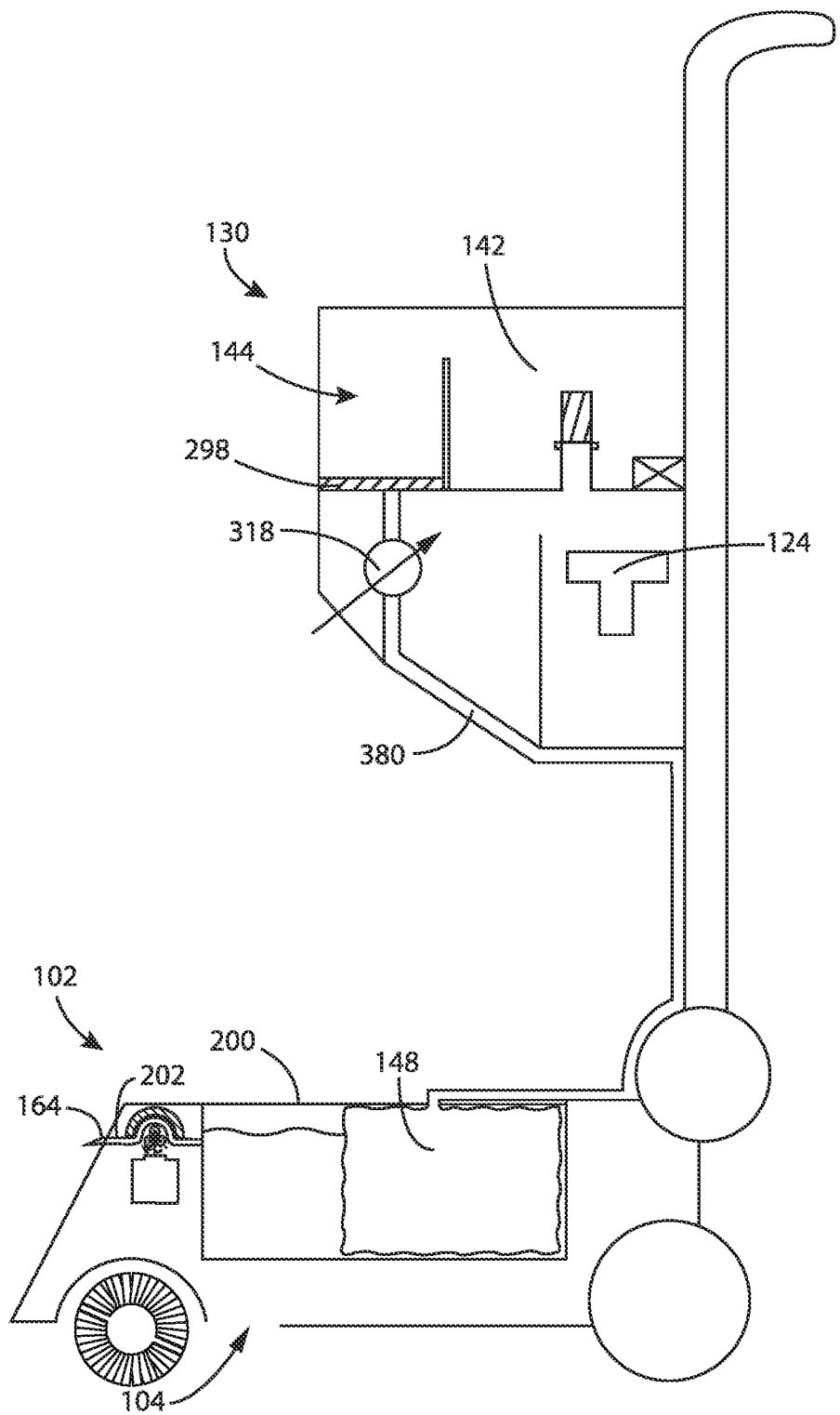
FIG. 80 is a schematic representation of the surface cleaning apparatus of FIG. 79 in a second configuration

Referring to FIGS. 79 and 80, in this example, the liquid collection container 148 is provided as an inflatable bladder that is entirely contained within the interior volume of a clean liquid reservoir tank 200 in the surface cleaning head. Prior to using the apparatus 100, the reservoir tank 200 may be substantially full of clean liquid (e.g., clean water or a cleaning solution), and the liquid collection chamber 148 is substantially empty and small (FIG. 79). When the apparatus 100 is in use, liquid can be dispensed from the reservoir tank 200 onto the floor (via nozzle 164) and then sucked up into dirty fluid inlet 104 and processed by the treatment unit 130. In the treatment unit 130, the separated liquid may pass through the solid collection chamber 144 and can be transported into the liquid collection container 148 via, e.g., pump 318 or gravity flow. During such usage the amount of clean liquid in the reservoir tank 200 will be reduced, and the liquid collection container 148 can expand into the interior of the evacuated interior of the reservoir tank 200 as it is filled. Under some operating conditions, the liquid recovery rate of the apparatus (e.g. the volume of liquid sucked up and separated as compared to the volume of liquid dispensed) may be less than 100%, which may help provide ample room within the reservoir tank 200 to accommodate the expansion of the liquid collection chamber 148.

Optionally, the expandable/inflatable liquid collection containers 148 may be formed from a resilient material, such as rubber, neoprene and the like, such that they may tend to resist expansion, and may tend to automatically shrink back to their deflated configuration when empty.

Liquid Delivery System, Optionally with an Externally Positioned Pumping Member

In any aspect disclosed herein, the surface cleaning apparatus 100 may also include a liquid delivery system for distributing water, a hard floor cleaning solution, a carpet cleaning solution and the like onto the surface to be cleaned. This liquid can then be extracted from the surface using the apparatus 100. Any such onboard liquid delivery system may be of any suitable configuration, and may include, for example, and suitable liquid reservoir(s), actuators such as pump(s), liquid conduits, mixing chamber(s), spray and application nozzle(s) and the like. Each component of the liquid delivery system may be at any location on apparatus 100. Various embodiments are disclosed herein.

The liquid delivery system may be configured to provide any suitable cleaning solution, including one or more of water, bleach, a hard floor cleaning solution, a carpet cleaning solution.

In the exemplified embodiment of FIG. 7, the liquid delivery system includes a single onboard liquid reservoir apparatus 162 that is provided on the upright section 116. The liquid reservoir apparatus 162 is fluidly connected to a delivery nozzle 164 via one or more liquid conduits (not shown), and liquid can be pumped and/or flow due to gravity from the liquid reservoir apparatus 162 to the delivery nozzle 164 by any suitable pump (not shown).

In this example, the liquid reservoir apparatus 162 is provided on the rear side of the cleaning unit 120, and at a higher elevation than the first separator 132. In this configuration, the liquid reservoir apparatus 162 will be positioned generally below the suction motor 124 and second separator 134 when the upright section 116 is reclined into the surface cleaning position (such as in FIG. 2).

The liquid reservoir apparatus 162 may also include any suitable pump (or optionally more than one pump) that can help convey the liquid from the liquid reservoir apparatus 162 to the delivery nozzle(s) 164. The pump may be any suitable type of pump, including, for example, a rotary lobe pump, a progressive cavity pump, a piston pump, a rotary gear pump, a diaphragm pump, a screw pump, a positive displacement pump (such as a peristaltic pump) and the like. The pump may be provided close to a tank of liquid reservoir apparatus 162, inside the tank, close to the delivery nozzle 164 or at any suitable location along the delivery line extending therebetween. The pump may optionally be attached to the same portion of the surface cleaning apparatus 100 as the tank (i.e., both in the cleaning unit 120, both in the surface cleaning head 102, etc.), or alternatively the tank and pump may be provided at different locations on the apparatus 100 (e.g., the tank may be in the cleaning unit 120, while the pump is provided in the surface cleaning head 102). Spacing the pump away from the tank may help reduce the overall size of the apparatus 100, and may help with the overall weight distribution of the apparatus 100. Optionally, the pump may be configured such that the pump components are exposed to the liquid being pumped. For example, the liquid may come into direct contact with a rotating pump impeller.

Alternatively, the pump may be configured so that it remains external the liquid flow, and the pump components do not come into direct contact with the liquid being pumped. Configuring the pump in this manner may help reduce contamination/fouling of the pump components. This may also help prevent the likelihood of cross-contamination between liquids, if a single pump is used, sequentially, to pump two or more different liquids. This may be preferable if the apparatus 100 can be configured to use different types of cleaning chemicals/solutions based on the nature of the surface to be cleaned. Some surfaces may be cleaned using an acidic cleaning solution, while others may be cleaned with, for example, a basic cleaning liquid. Exposing the internal components of the pump 204 to the liquid being pumped may lead to some degree of cross-contamination and/or chemical reaction if a basic liquid were to be introduced into a pump cavity containing traces of an acidic liquid—or vice versa. The use of a pump in which the pump components are not directly exposed to the liquid being pumped may help prevent such cross-contamination.

Figure 49:
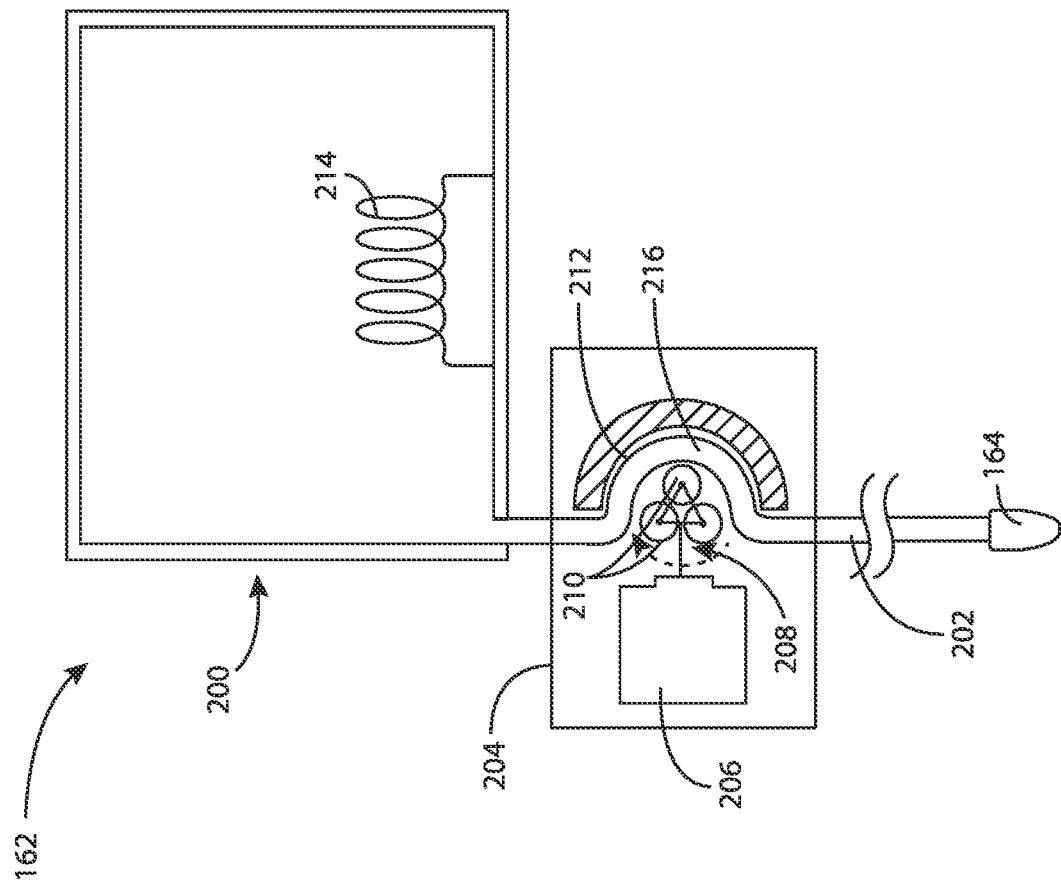
FIG. 49 is a schematic representation of one embodiment of a liquid reservoir unit.

FIG. 49 exemplifies the use of a pump which externally drive a fluid to flow between a reservoir tank and a delivery nozzle 164 As exemplified, reservoir tank 200 is adapted to hold any suitable liquid, such as water, a ready-to-use cleaning solution and the like. A liquid delivery line 202 extends between the reservoir tank 200 and any suitable liquid spray nozzle, such as delivery nozzle 164. While FIG. 49 shows a single nozzle, a plurality of the delivery nozzles 164 may be used and each delivery nozzle 164 may be any type know in the art and may be configured to distribute the liquid on the surface as a mist, stream, trickle/drip and in any other suitable manner.

In the embodiment shown in FIG. 49, the pump 204 is arranged as a peristaltic pump having a motor 206 that drives a rotor 208 having one or more rollers 210 attached thereto. As exemplified, a portion of the liquid delivery line 202, pumping portion 216, is configured to pass between the rollers 210 and an associated pump housing 212, where it can be squeezed against the housing 212 by the rotating rollers 210. In this configuration, the liquid within the delivery line 202 does not come into direct physical contact with the pump 204, and specifically its rollers 201 and housing 212. Any peristaltic pump may be utilized.

Optionally, the liquid reservoir apparatus 162 may include a heater to help heat the liquid before it is applied to the surface to be cleaned. The heater may be utilized to heat the liquid as it is held in the reservoir tank 200, and/or a heater may apply heat to the liquid delivery lines 202 that carry the liquid from the reservoir tank 200 to delivery nozzle 164. In the embodiment of FIG. 49, the liquid reservoir apparatus 162 includes an electrical resistance heater 214 that may be controlled by any suitable controller, may always be on when the apparatus 100 is powered and/or may be manually controllable by a user to adjust the liquid temperature.

Liquid Delivery System that can Apply Two Different Cleaning Solutions

In accordance with another aspect, which may be used with one or more of the other aspects disclosed herein, the liquid delivery system may be configured to be operable to alternately deliver two different liquids, such as a carpet cleaning solution and a hard floor cleaning solution and may include any suitable actuator so that the cleaning solution delivery system can be switched between a hard floor cleaning actuation mode in which the cleaning solution delivery system delivers the hard floor cleaning solution to at least one delivery nozzle 164, and in a carpet cleaning actuation mode, in which the cleaning solution delivery system delivers the carpet cleaning solution to the at least one delivery nozzle 164. It will be appreciated that each solution may be delivered to the same delivery nozzle(s) or that one liquid may be supplied to one delivery nozzle(s) and another solution may be delivered to another nozzle(s).

Optionally, the actuator used to change the mode of the liquid delivery system may be manually activated by a user, and may include a button, trigger, switch, lever and the like. Alternatively, the actuator may be automatically controlled by a suitable controller (microcontroller, PLC or the like) and may include a detector that is able to determine the type of surface that is being cleaned in order to select and apply the appropriate cleaning solution, e.g., an optical sensor.

Figure 55A:
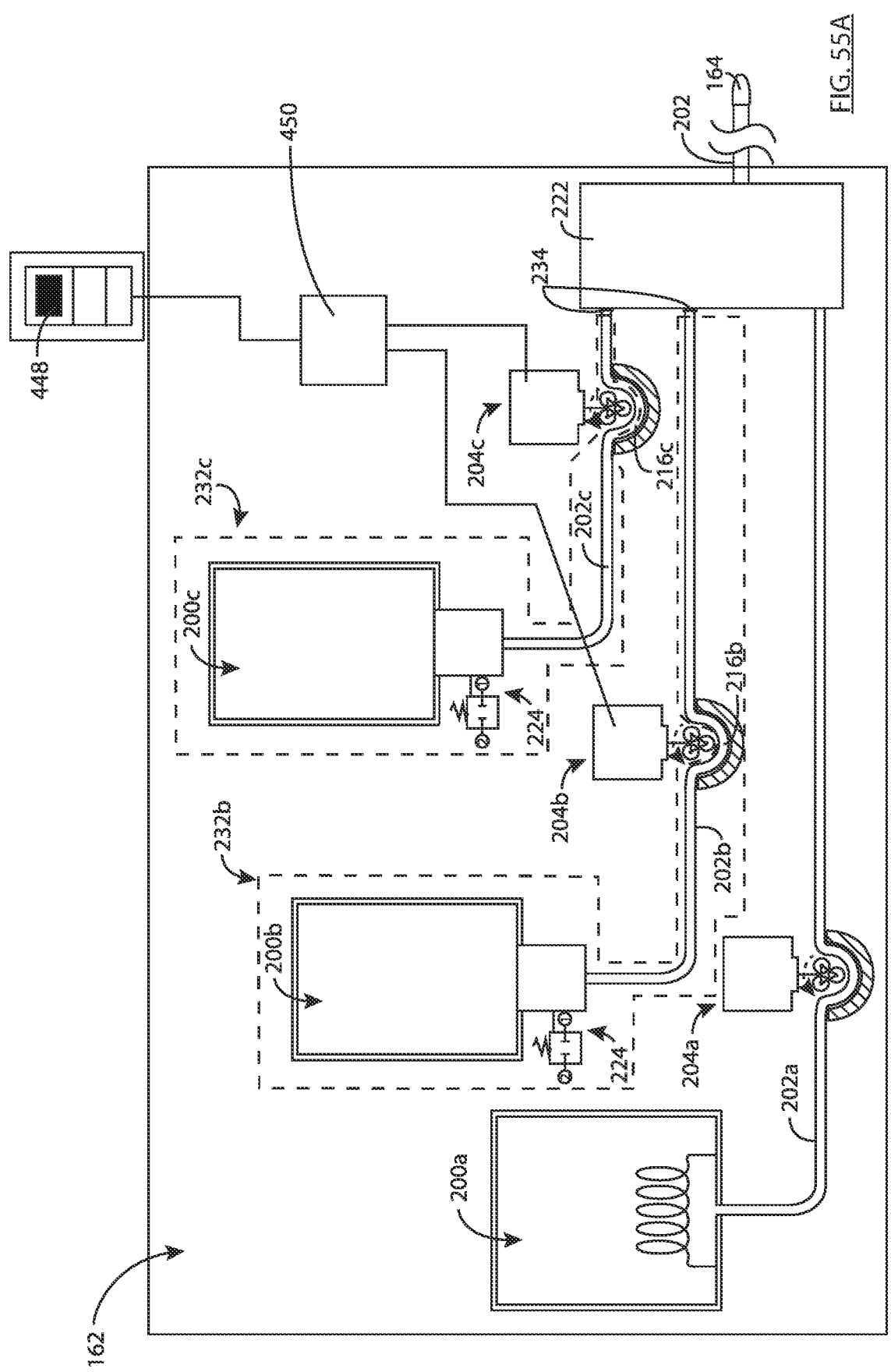
FIG. 55A is a schematic representation of yet another embodiment of a liquid reservoir unit.

Referring to FIG. 1, one example of an actuator that can be used to change the mode of the liquid delivery system is a three-position switch 448 that can be provided on the handle 386 as shown, or in any other suitable location (such as on the cleaning unit 120 as shown in FIG. 7 and on the surface cleaning head 102 as shown in FIG. 9). The switch 448 in this example may be movable between an "OFF" position in which no liquid is delivered to the surface, a "HARD FLOOR" position, in which the liquid deliver system delivers a hard floor cleaning solution and a "CAR- PET" position, in which the liquid deliver system delivers a carpet cleaning solution. This mode selection may be achieved by mechanical linkage, or by connecting the switch 448 to any suitable on board controller that can also be configured to control aspects of the liquid delivery system in response to inputs received from the switch 448. The switch 448 may be connected to two or more pumps, valves or the like to directly control the application of the different cleaning solutions (as shown in FIG. 51A), and/or may be connected to any suitable controller that can receive inputs from the switch 448 and control the liquid delivery system accordingly. FIG. 55A shows own example in which the switch 448 is connected to a liquid delivery controller 450, which may be a standalone controller as illustrated or may be integrated with another controller in the surface cleaning apparatus 100. For example, a single pump may be used to draw liquid from 2 or more tanks 200 and valves may be used to selectively fluidically connect the pump to a tank containing the desired liquid to be applied.

Optionally, instead of a switch 448, the actuator for the liquid delivery system may include a detector that can determine the type of surface that is being cleaned (i.e. distinguish between hard floor surfaces and carpets) and provide output signals to the liquid delivery controller 450. This may allow the liquid delivery system to automatically select an appropriate cleaning solution to deliver based on the type of floor being cleaned, without requiring manual user input. In the embodiment of FIGS. 15 and 16, the surface cleaning head 102 includes a downward facing optical sensor 452 that can determine, e.g., using light reflection, the type of surface underlying the surface cleaning head 102. The liquid delivery controller 450 is connected to the sensor 452 and, based on the outputs from the sensor 452, can determine if the surface being cleaned is a hard floor or a carpet. Based on this determination, liquid delivery controller 450 can control the liquid delivery system and Optionally, the switch 448 may also control the operation of other portions of the surface cleaning apparatus 100, including the suction motor, rotating cleaning brushes and the like. For example, the switch 448 may linked to a controller that also controls the suction motor 124 and rotating brushes 172 and 174.

Figure 50:
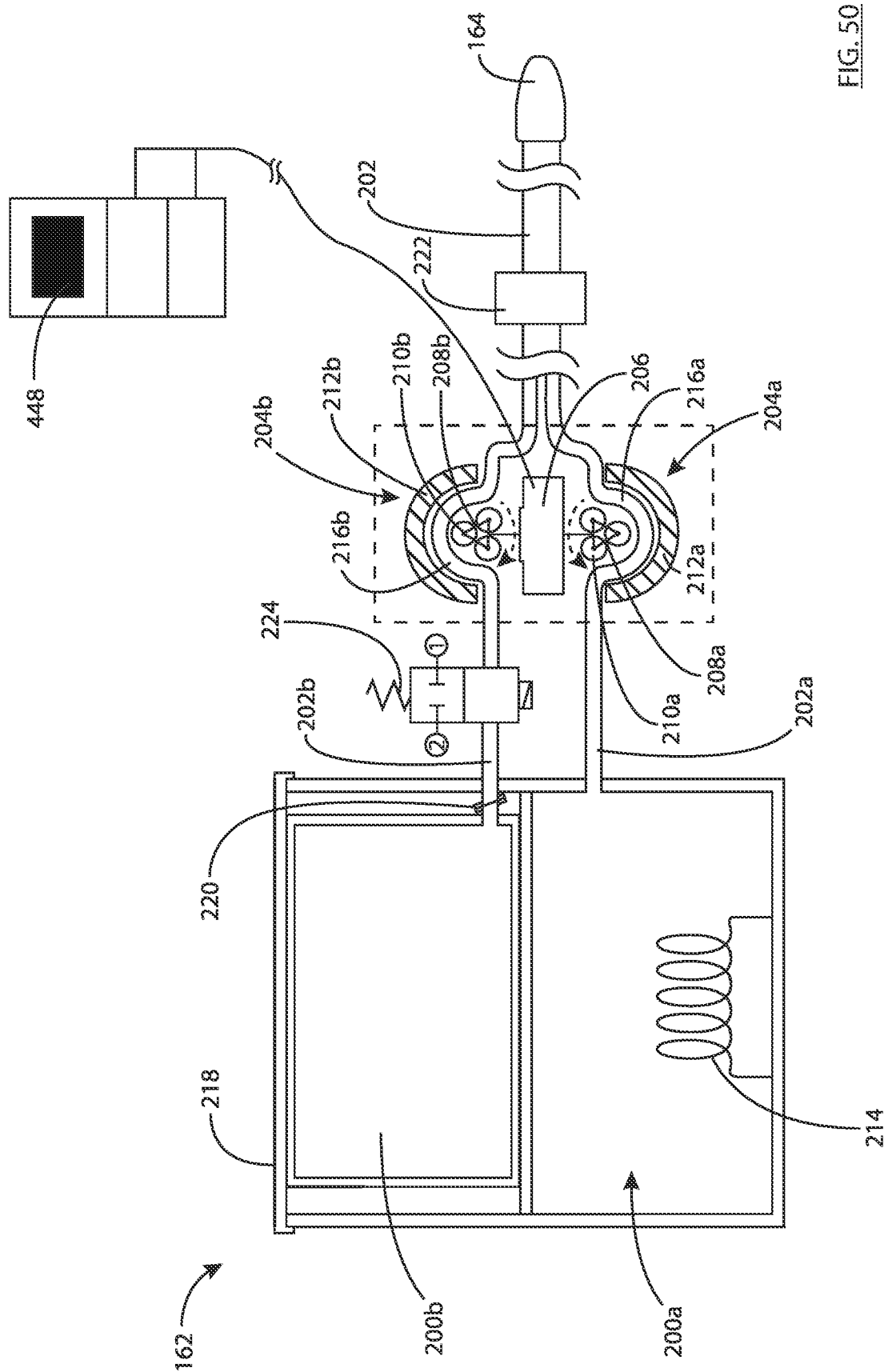
FIG. 50 is a schematic representation of another embodiment of a liquid reservoir unit.
Figure 51B:
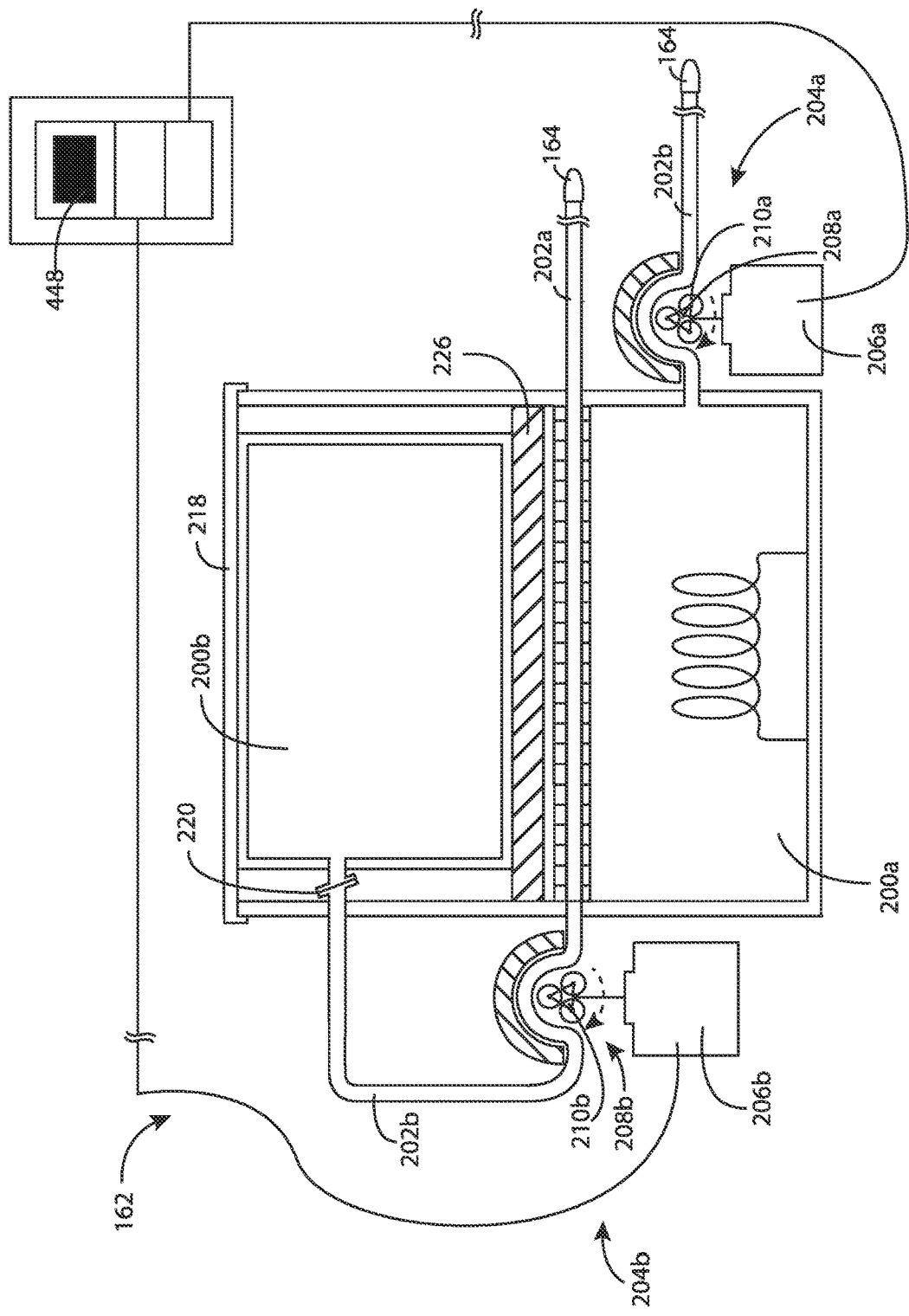
FIG. 51B is a schematic representation of another embodiment of a liquid reservoir unit.

As exemplified in FIGS. 50, 51A and 51B, other embodiments of a liquid reservoir apparatus 162, that can be used with any of the embodiments of the surface cleaning apparatus 100 described herein, the delivery system may utilize two separate reservoir tanks 200a and 200b, each connected to a respective liquid delivery lines 202a and 202b which engage respective peristatic pumps 204a and 204b. In the embodiment of FIG. 50, the rotors 208a and 208b are connected to and driven by a common motor 206. This can help reduce the overall size of the surface cleaning apparatus 100. Suitable gearing and/or transmission hardware (e.g., a gear box) may be used to allow each rotor 208a and 208b to be rotated independently of each other, optionally at different speeds, even while connected to a common motor 206. This may also help reduce the complexity and size of the liquid reservoir apparatus 162. In the embodiments of FIGS. 51A and 51B, each rotor 208 is driven by a respective motor 206. This may help facilitate independent operation of each pump 204a and 204b.

Optionally, the reservoir tank 200a, and its associated delivery line 202a may be used to hold carpet cleaning solution, while reservoir tank 200b, and its associated delivery line 202b may be used hold hard floor cleaning solution. It will be appreciated that tanks 200a, 200b may contain any liquids such a water, a hard floor cleaning solution, a carpet cleaning solution or an odor eliminating composition (e.g., Fabreeze™).

Optionally, one or more of the tanks 200a and 200b can be configured to be removable, from the rest of the apparatus 100, for filling, cleaning, replacement, inspection and the like. The tanks may be concurrently removable or individually removable. In the embodiment of FIG. 50, the tank 200a need not be removable while tank 200b may be configured as a removable tank that can be accessed by opening a cover 218. The cover 218 may be provided by another portion of the surface cleaning apparatus 100, such as a portion of the surface cleaning head 102, upright section 116, cleaning unit 120 and the like. The tank 200b may also include a detachable coupling 220 connecting it to its associated delivery line 202b.

It will be appreciated that tank(s) 200 may be refillable in situ and therefor need not be replaced. Alternately, tank(s) 200 may be disposable. In such an embodiment, a user may purchase a new tank 200 and insert the new tank into the housing or enclosure for the tank. Upon insertion, a seal may be broken or pierced to connect the interior of the tank with the delivery system (e.g., like a Tetra Pak™). It will be appreciated that tank 200 need not be a hard walled tank but may be made of a flexible material.

Optionally, tanks 200a and 200b may be configured to contain and dispense the same liquid. For example, both tanks 200a and 200b may hold water, the same pre-mixed cleaning solution and the like. Providing two tanks 200a and 200b could allow for increased liquid capacity and may allow one tank to hold hot water (tank 200a with heater 214) while the other tank 200b holds cold water, for example. Alternatively, the liquid reservoir apparatus 162 may be configured to hold different types of liquid.

For example, the tank 200a may be configured to hold a hard floor cleaning solution and the tank 200b may be configured to hold a carpet cleaning solution. By operating pump 204a, hard floor cleaning solution may be provided to the nozzle 164 and sprayed on a surface. By operating pump 204b (and not pump 204a), carpet cleaning solution may be provided to the nozzle 164 and sprayed on a surface.

Alternatively, tank 200a may be configured to hold water, while tank 200b contains a pre-mixed cleaning solution. By triggering the associated pumps 204a and 204b, a user could choose to apply water, cleaning solution or a combination of both to the surface being cleaned. The user may control the supply of each liquid independently, (e.g., by using different actuators or by using a multi-position switch) which may allow a user to first apply a cleaning solution from tank 200b, by operating only pump 204b, to the surface, operate the surface cleaning apparatus 100 in a cleaning mode and then apply water from tank 200a to the surface to perform a rinsing step.

Optionally, pumps 204a and 204b can be driven by the motor 206 at the same rate. Alternatively, any suitable gearing mechanism and/or transmission may be utilized between the motor 206 and the rotors 208a and 208b, such that the rotors 208a and 208b can be driven at different rates by the common motor 206. In some embodiments, the gearing ratios and/or transmission may be adjustable, such that the rotational speed of the rotors 208a and 208b can be independently adjusted while the apparatus 100 is in use. This may help facilitate independent control of the rate at which the liquids held in the tanks 200a and 200b are dispensed. This is one manner in which the mixing of the liquids may be manipulated.

Optionally, instead or varying the motor 206 or pump 204a and 204b operation, the liquid reservoir apparatus 162 may include one or more additional flow regulating devices to help control the flow of a liquid from one or more of the tanks 200a, 200b, etc. For example, the liquid reservoir apparatus 162 may include a valve, orifice plate and the like that can be used to modify the flow of liquid through the delivery lines 202a, 202b, etc. Referring to the embodiment of FIG. 50, the liquid reservoir apparatus 162 includes a variable flow control valve 224 that is provided in the delivery line 202b. This valve 224 can be actuated, by a user, controller and the like, to help regulate the flow of liquid out of tank 200b. A similar valve could be provided in the delivery line 202a, or any other suitable location. The valve 224 may be actuated be a solenoid, and may be biased (such as by a spring) toward one of its open and closed positions. The valve 224 may be a two-position, on/off valve, or may be a variable valve that can be operated to allow a plurality of different liquid flow rates. The operation of the valve 224 may be linked to the operation of the motor 206 (or motor 206a, 206b, etc. in other embodiments), or may be independently operated.

Optionally, instead of or in addition to using mechanical flow limiting devices, the deliver lines 202a, 202b, etc. may be configured to have different sizes and/or interior diameters, such that the flow rate through the lines will differ when subjected to similar operating pressures, pumps and the like. For example, a supply line carrying water may have a larger diameter than a supply line carrying cleaning solution concentrate or the like. By increasing the diameter of a delivery line 202, a higher flow rate may be achieved at the same rate of rotation of the pump.

Figure 52:
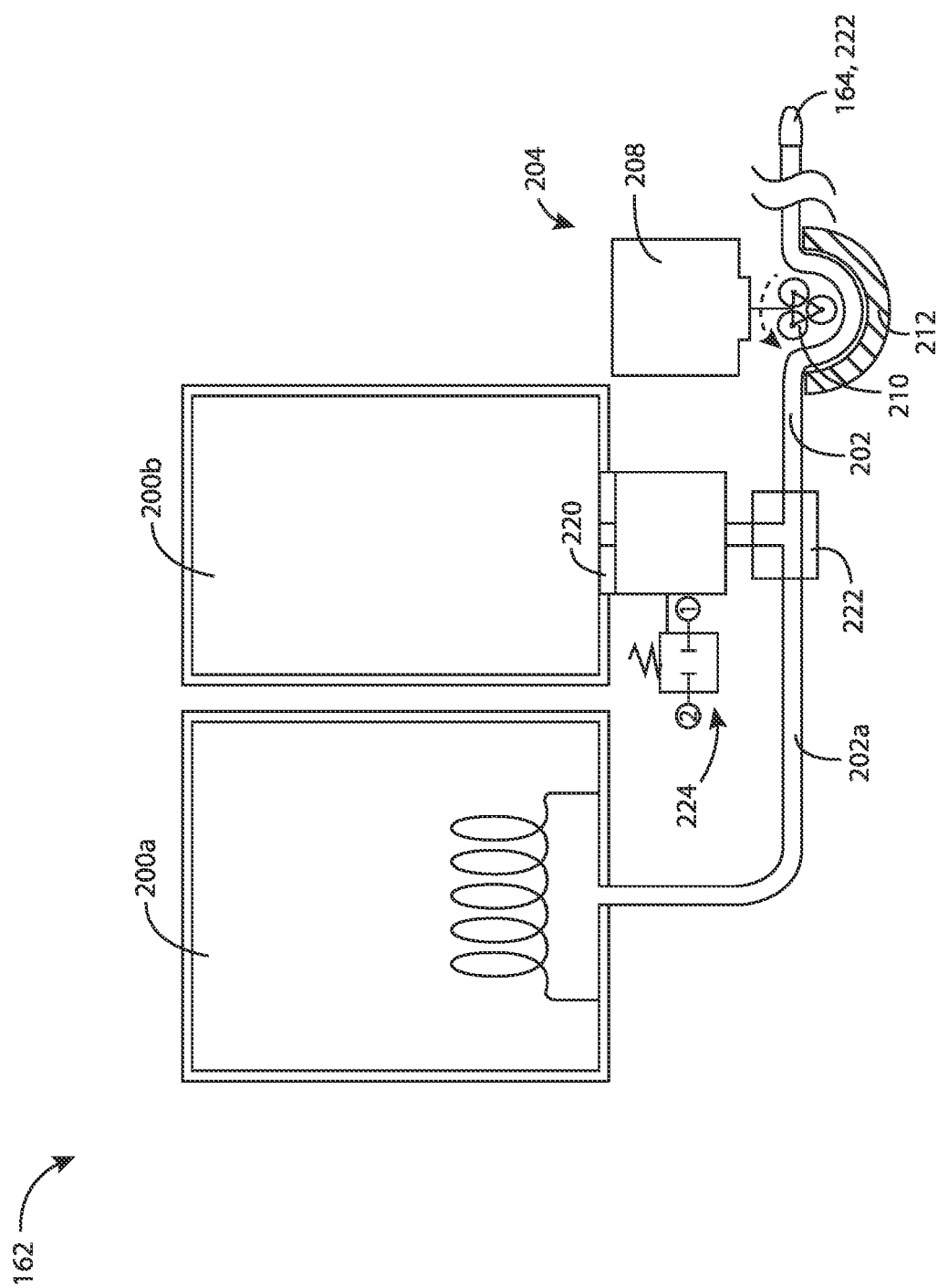
FIG. 52 is a schematic representation of yet another embodiment of a liquid reservoir unit.

Optionally, the delivery lines 202a and 202b connected to each tank 200a and 200b may extend in parallel substantially all the way to the delivery nozzle 164. Alternatively, the liquid reservoir apparatus 162 may be configured to include at least one intermediary mixing apparatus, such as a mixing nozzle or mixing chamber 222 that is located downstream from the tanks 200a and 200b and upstream from the delivery nozzle 164, or may in fact be the delivery nozzle 164. For example, the mixing chamber 222 may be integrally formed with the nozzle 164 (as shown in the embodiment of FIG. 52). Using a mixing chamber 222 may help facilitate mixing of the liquids being drawn from tank 200a and tank 200b before the combination of liquids is sprayed onto the surface to be cleaned. Providing mixing of this nature may help facilitate on-demand mixing of cleaning solutions and/or other liquids and/or may allow the concentration of a cleaning solution to be modified on demand by a user, or suitable controller provided on the surface cleaning apparatus 100.

For example, in the embodiment of FIG. 50 the liquid reservoir apparatus 162 of FIG. 50 may be configured to hold water in tank 200a, and a pre-mixed cleaning solution in tank 200b. For the purposes of this description, a pre-mixed cleaning solution can be understood to be a cleaning solution that is stored in tank 200b in a concentration in which it is intended to be applied to the floor. That is, it is suitable for spraying on the floor in a substantially "as is" condition, and without requiring substantial mixing or adjusting from the surface cleaning apparatus 100. In this embodiment, the cleaning solution from tank 200b can be applied to the floor independently from the supply of water in tank 200a. However, if the cleaning solution is considered to be too strong for a given application (such as a delicate floor covering, a secondary cleaning pass, etc.) it may be diluted by simultaneously dispensing water from the tank 200a, and mixing this liquids in the mixing chamber 222 before spraying the diluted cleaning solution via the delivery nozzle 164.

Optionally, as shown in the embodiment of FIG. 51A, the liquid delivery lines 202a and 202b may be almost entirely separate from each other, and may each extend from their respective tanks 200a and 200b to the nozzle 164. If the tanks 200a and 200b are removable, substantially all of their respective fluid delivery lines 202a and 202b could be removable with them, and replacement tanks 200 and lines 202 could be provided, and reconnected to the nozzle 164. In yet another configuration, the nozzle 164 may also be removable with the used fluid supply lines 202a and/or 202b, and a new nozzle may be provided with the new tanks and supply lines.

In other embodiments, such as shown in FIG. 51B, the liquid delivery lines 202a and 202b may remain separate from each other along their entire length, and may each terminate in a respective nozzle 164a and 164b. This may provide separate liquid flow paths from tank 202a to nozzle 164a, and from tank 202b to nozzle 164b. This configuration may eliminate cross-contamination between different cleaning solutions, as the contents of tank 202a need not mix with the contents of tank 202b (for example) at any point within the liquid delivery system. Nozzles 164a and 164b may be physically connected as part of a common nozzle assembly, or alternatively may be spaced apart from each other. The nozzles 164a and 164b may be located on the same portion of the surface cleaning apparatus 100 (such as both on the surface cleaning head 102), or alternatively may be provided in different locations. For example, one nozzle 164a may be provided on the surface cleaning head 102, while nozzle 164b is provided on the upright section 116, or vice versa.

In a particular embodiment, the nozzle is removable with line 202. Accordingly, when a line or a tank is replaced, an entire new delivery line and nozzle may be installed.

Liquid Delivery System with Water Reservoir and One or More Cleaning Solution Concentrates In accordance with another aspect, which may be used with one or more of the other aspects disclosed herein, instead of providing separate tanks 200 for storing different types of pre-mixed cleaning solutions (hard floor vs carpet, etc.), the liquid delivery system may include a water reservoir tank and one or more separate tanks holding cleaning solution concentrates (i.e. a cleaning solution in a form that is less suitable for direct application to a surface and that would typically be diluted with water before application). The system can then mix water from the water reservoir tank with an appropriate amount of a cleaning solution concentrate to provide the desired cleaning solution. In this arrangement, a common water reservoir source may be mixed with two or more different cleaning solution concentrates. Each cleaning solution concentrate material may be stored in suitable tank 200. Each concentrate tank 200 may be relatively smaller than a tank that would be used to hold the quantity of pre-mixed cleaning solutions that would provide the same amount of cleaning solution application. This may help eliminate the need to a provide full size tanks 200 for each time of pre-mixed cleaning solution, which may help reduce the overall size and weight of the surface cleaning apparatus 100.

For example, the liquid reservoir apparatus 162 of FIG. 50 may be configured to hold water in tank 200a, and a cleaning solution concentrate in tank 200b. As compared to a pre-mixed cleaning solution, the concentrate solution is a concentrated form of the cleaning ingredients that is not intended, and possibly not suitable, for direct application to the floor or surface to be cleaned "as is". Instead, the concentrate solution is intended to be diluted with water, or other suitable liquid, prior to application. In the example above, such dilution could have been performed prior to adding the liquid to tank 200*b*, which would provide tank 200*b* with the pre-mixed cleaning solution discussed. In contrast, in another embodiment the concentrate solution may be stored directly in tank 200*b*. This may allow tank 200*b* to be smaller than tank 200*a*, and smaller than it would otherwise need to be in order to carry an equivalent amount of pre-mixed cleaning solution.

In this example, the liquid reservoir apparatus 162 may be operated in a water only actuation mode to dispense water from tank 200*a* (for pre-soaking, rinsing, etc.) without drawing from tank 200*b*. When cleaning solution is desired, the liquid reservoir apparatus 162 may be operated in a second actuation mode in which it dispenses a relatively small (a metered) amount of the concentrate solution from tank 200*b*, simultaneously with a prescribed amount of water from tank 200*a*. The cleaning solution can then be mixed on-demand in mixing chamber 222 prior to spraying the solution on the floor. The ratio of water to concentrate solution may be determined by the characteristics of a given concentrate solution, but may be about 2:1 to 10:1 or 20:1 or more, but may be more or less in some embodiments.

In addition to mixing to a pre-set ratio, the amount of water dispensed to be mixed with the concentrate solution may be modified on the fly by a user or apparatus controller. Supply rate of the water (or other liquid) may be altered by providing different sized supply lines, changing the operating speed of one or both pump 204*a*, *b* (or the like—optionally manually or automatically based on apparatus operating conditions), using a valve or other such flow controlling mechanisms. By varying one or more of, e.g., the diameter of the delivery lines 202 and the speed of pump 204*a*,*b*, a desired mixing ratio may be obtained. The pump actuator may have a control to control the rate of rotation of one or both pumps 204*a*,*b* to obtain a desired missing ratio.

For example, the amount of water drawn from tank 200*a* could be reduced by operating the pump 204*a* at a slower rate if a stronger cleaning solution is desired (for a particularly soiled floor, etc.), and could be increased, by operating the pump 204*a* at a faster rate, if a relatively weaker cleaning solution is required (for a sensitive floor, etc.). This may allow a given concentrate solution to be used to provide a variety of different strength cleaning solutions, and be used for a variety of different cleaning jobs without requiring dedicated quantities of different strength cleaning solutions to be pre-loaded and carrier on the surface cleaning apparatus 100. Other embodiments of the liquid reservoir apparatus 162 described herein may also be operated in this manner.

Mixing the cleaning solution on-demand, that is just before it is to be applied to the floor, may also be advantageous if the cleaning solution includes one or more active ingredients or compounds that have a relatively short lifespan, and/or may tend to degrade or become less effective when stored for prolonged periods.

For example, some ingredients in a given concentrate may be configured to be activated when exposed to water, air or the like, but may remain relatively stable when in concentrate formulation (optionally in a modified atmosphere tank to help prolong shelf life). It may be desirable to mix such ingredients with water immediately prior to spraying the solution on the floor to help maximize the effect of the activated ingredients.

Optionally, instead of water, a cleaning solution may be provided in two-part format such that the solution becomes active when the parts are mixed. One part of the solution could be stored in tank 200*a* and the other component in 200*b*, with the components only being mixed immediately prior to application to the floor. For example, the solution components may combine to cause a time-limited chemical reaction (heating, cooling, bubbling, oxidizing and the like) that it is beneficial to occur on the floor, rather than in a holding tank.

Providing concentrate solution, instead of pre-mixed cleaning solution, may also reduce the volume of the cleaning solution that needs to be stored and carried in the liquid reservoir apparatus 162, which may help reduce the overall size and weight of the apparatus 100.

Optionally, as shown in the embodiment of FIG. 51A, each pump 204*a* and 204*b* may be provided with a separate motor 206*a* and 206*b*, rather than being driven by a common motor 206 as shown in FIG. 50. This may help facilitate independent control of the pumps 204*a* and 204*b* by directly controlling the speed, direction, etc. of the motors 206*a* and 206*b*, and may eliminate the need for additional gearing apparatus and/or transmissions in some embodiments.

Optionally, as shown in the embodiment of FIG. 51A, one or more layers of thermal insulation 226 may be provided around one or both of the tanks 200*a* and 200*b*, to help keep each tank at a desired storage temperature.

Optionally, if the liquid reservoir apparatus 162 is configured to utilize concentrate solution, as opposed to pre-mixed cleaning solutions, it may not be necessary in all embodiments for the liquid reservoir apparatus 162 to be configured to allow the concentrate solution (i.e. the contents of tank 200*b*) to be directly sprayed onto the surface without mixing with the water or other liquid in tank 200*a*. In such configurations, the delivery line 202*b* from tank 200*b* may merge with the delivery line 202*a* upstream from the pump(s) 204, and may not extend separately to the delivery nozzle 164.

Referring to FIGS. 52 and 53, another example of a liquid reservoir apparatus 162 is configured having a water tank 200*a* and removable tank 200*b* that contains a concentrate solution. In this example, the tank 200*b* is configured as a detachable cartridge that preferably comes pre-filled with a given concentrate solution, but alternatively may be fillable and/or re-fillable by a user.

The pre-filled cartridge may be of any suitable construction, and may be, for example, a rigid plastic container, a Tetra Pak™ type container, a flexible bag or bladder like container that is deformable and the like. If the cartridge is not intended to be self-supporting and/or visible when the apparatus 100 is in use, the liquid reservoir apparatus 162 may be provided with a suitable housing and/or compartment to receive and support the cartridge in a surface cleaning position (as shown in FIG. 52). In this example, the cartridge 200*b* is a sealed plastic container, with a fitting 228 (FIG. 53) that can be joined to a complimentary fitting on the liquid reservoir apparatus 162. Preferable, the fitting 228 is configured so that it will not leak when detached from fitting 230, but any suitable fitting can be used.

This embodiment also includes a flow control valve 224 that is illustrated as being non-removable, but could be integrated with and removable with the cartridge in some embodiments. Providing a fixed flow control valve 224 may be advantageous as it may allow the valve 224 to be used with multiple cartridges.

When this liquid reservoir apparatus 162 is in use, water can be drawn from tank 200*a* as a pre-determined amount of the solution concentrate is drawn from the cartridge 200*b*. The flows can mix in mixing chamber 222 (which is shown as a chamber, but may simply be the interior of one of the delivery lines 202), and then pump to the delivery nozzle 164.

Optionally, one or more replacement and/or substitute cartridges can be provided for use with the liquid reservoir apparatus 162, as shown using dashed lines in FIG. 53. For example, a second cartridge 200*b* containing the same concentrate solution may be provided to replace the first cartridge 200*b* when it is empty. In another example, a second cartridge 200*b* may contain a different concentrate solution. If a user wishes to use a different cleaning solution, the user may remove the initial cartridge 200*b* (whether empty or not) and replace it with the second cartridge 200*b* containing different chemicals. This may allow a user to change cleaning solutions on demand and/or on the fly, while utilizing a common water supply in tank 200*a* to form each different cleaning solution. The cartridges 200*b* may be exchanged without requiring access to tank 200*a*, without pouring out the unused contents of tank 200*a* and/or without having to refill tank 200*a* with a replacement liquid.

Optionally, the liquid reservoir apparatus 162 may be configured to include more than two separate tanks, and in some embodiments may be configured to include one common water tank, along with two or more cartridges of different concentrate solutions. This may help facilitate the on-demand mixing of two or more different types of cleaning solutions, using a common on-board water source.

Figure 54A:
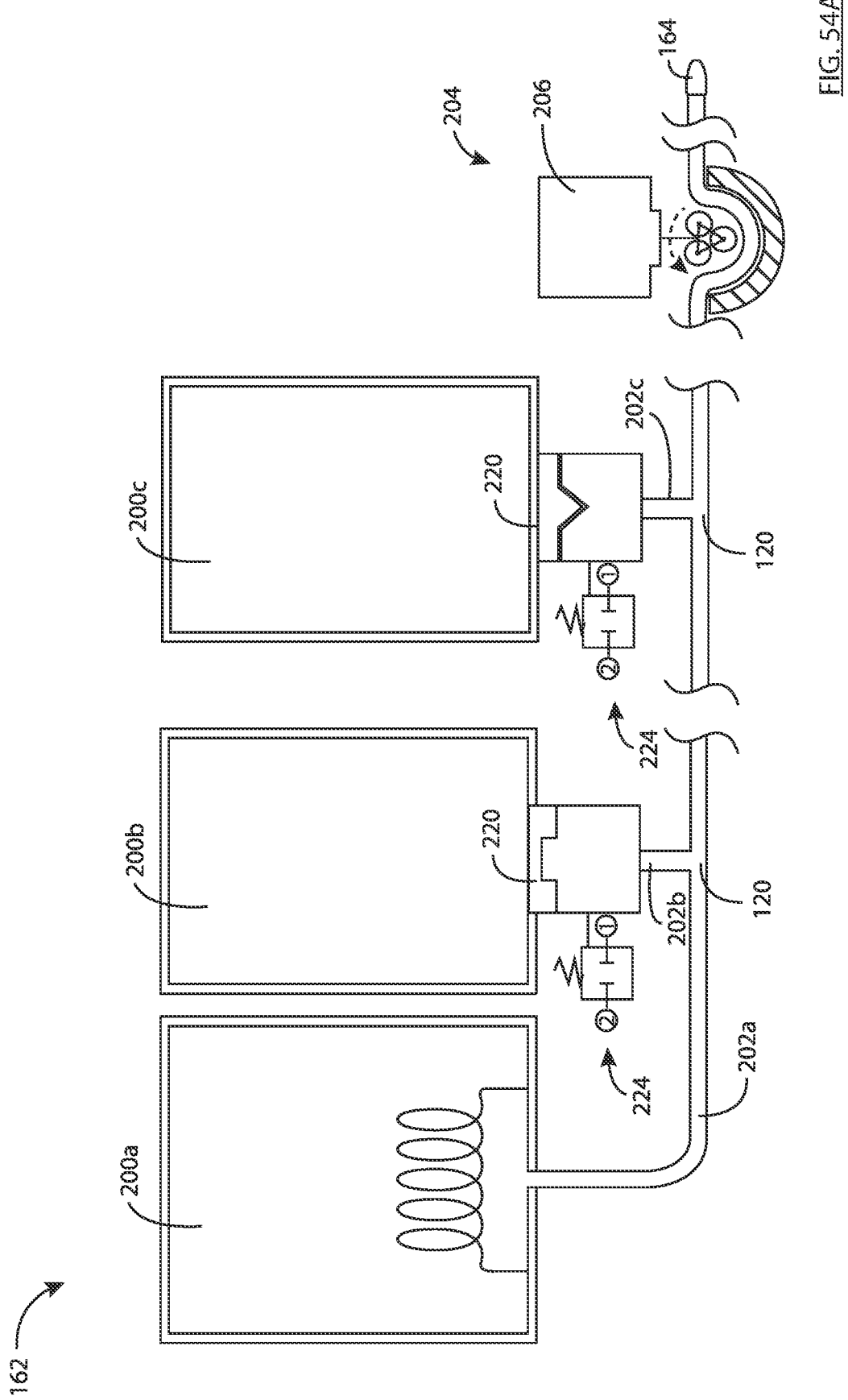
FIG. 54A is a schematic representation of yet another embodiment of a liquid reservoir unit.

Referring to FIG. 54A as an example, an embodiment of a liquid reservoir apparatus 162 includes a water tank 200*a*, and two cartridges 200*b* and 200*c* containing different concentrate solutions, such as chlorine based solutions, potassium hydroxide based solutions, hard floor cleaning solutions, carpet cleaning solutions and the like. For example, the cartridge 200*b* can be a hard floor cleaning concentrate container, containing a hard floor cleaning solution concentrate, and the cartridge 200*c* can be a carpet cleaning concentrate container, containing a carpet cleaning solution concentrate. This liquid reservoir apparatus 162 can then be operated to deliver two or more different types of cleaning solution by sequentially combining water (optionally at the same or different rates) with the different cleaning concentrate solutions. This may be manually managed by a user, or controlled by a suitable controller and the like. For example, the concentrate solution in cartridge 200*b* may be suitable for cleaning carpets while the concentrate solution in cartridge 200*c* is better suited for cleaning hard flooring. The liquid reservoir apparatus 162 may be configured to automatically draw from tanks 200*a* and 200*b* when the surface cleaning apparatus 100 is put into a carpet cleaning mode, and to draw from tanks 200*a* and 200*b* when the surface cleaning apparatus 100 is put into a hard floor cleaning mode. The flow control valves 224 may be independent operated to provide different amounts of the concentrate in tanks 200*b* and 200*c* to be mixed with a given flow rate of water (if necessary), to help ensure each cleaning solution is mixed to a desired concentration. Alternately, a user may manually select the concentrate to be used.

Optionally, at least a portion of the delivery lines 202*a*, 202*b*, 202*c*, etc. may be configured to be removable from the liquid reservoir apparatus 162 for servicing, replacement maintenance or other suitable reasons. The lines 202 may be configured to be removed independently of each other and/or of other components (such as tanks 200*a*, 200*b*, etc.) or may be configured to be removed in combination with other components. For example, at least a portion of the delivery line 202 corresponding to a given tank or cartridge 200 may be configured to be removed with the cartridge (e.g., line 202*b* may be removed with cartridge 200*b*), and a replacement delivery line may be provided with the replacement cartridge. This may help facilitate the switching of cartridges containing different chemicals, while helping to reduce the chances of cross-contamination or other issues that might arise if the different chemicals were carried through common delivery lines.

Figure 55B:
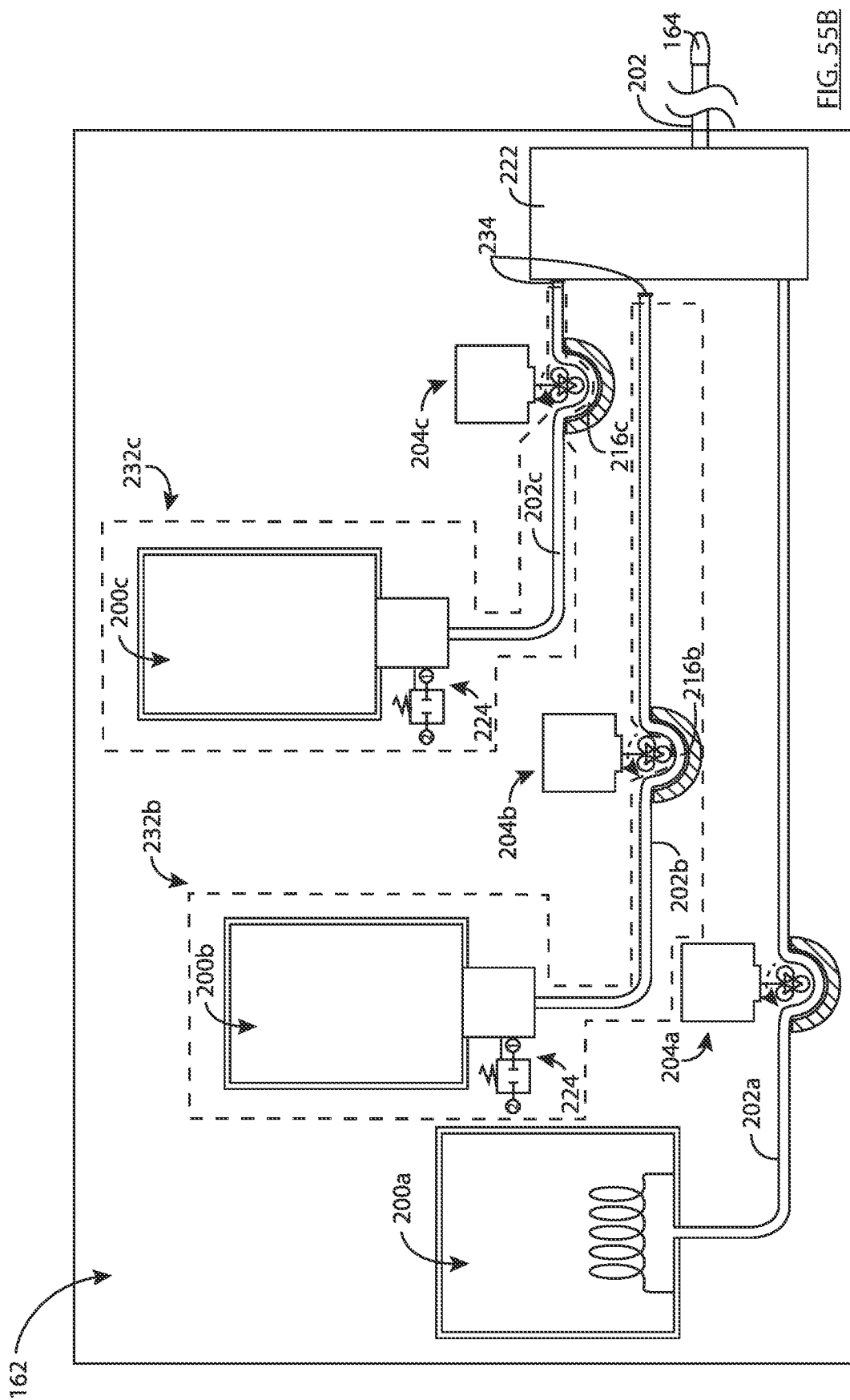
FIG. 55B is another schematic representation of the liquid reservoir unit of FIG. 55A.

Referring to FIGS. 55A and 55B, in the illustrated embodiment the liquid reservoir apparatus 162 is configured to so that the delivery line 202*b* is attached to, and removable with, the cartridge 200*b* when the cartridge 200*b* is to be removed or replaced. Together, the cartridge 200*b* and its respective delivery line 202*b* may be considered a cartridge assembly 232*b*, and optionally may also include a removable flow control valve 224 and other related hardware. Alternatively, the valves and other such hardware may remain in place. In this example, the removable/replaceable portion of the delivery line 202*b* extends from the cartridge 200*b*, and passes through the peristaltic pump 204 and is connected to the mixing chamber 222 using a detachable coupling 234 which is shown attached in FIG. 55A, and detached in FIG. 55B.

Is this embodiment, the delivery line 202*b* is formed from a relatively flexible material, and may be manipulated by the user such that the delivery line 202*b*, and notably pumping portion 216*b*, can be removed from the pump 204*a* when the delivery line 202*b* is removed, and the newly provided delivery line 202*b* can be inserted into the pump 204*b*. Downstream from the mixing chamber 222, a single delivery line 202 can extend to the delivery nozzle 164. The line 202 and/or delivery nozzle 164 may be replaceable for servicing, and optionally may be replaced if desired to help prevent unwanted mixing of previous and current chemicals.

Providing swappable cartridge assemblies 232*b* and 232*c* of this nature may help facilitate the changeover between different cleaning chemicals while reducing the amount of cleaning or rinsing of the delivery lines that may be required. This configuration may also allow the entire cartridge assembly 232*b* and 232*c* to be provided to the user as a generally closed, or sealed system that does not require a user to open the cartridge, fill the container or otherwise interact with the chemicals contained in the cartridges 200*b* and 200*c*, during either the insertion or removal process. This may be an advantage if some of the cleaning concentrate solutions are hazardous or ought not to be contacted by the user.

While shown with two cartridges 200*b* and 200*c*, and related assemblies, pumps, delivery lines and the like, other embodiments of the liquid reservoir apparatus 162 may include allow more than two cartridges to be installed at any given time.

Optionally, the liquid reservoir apparatus 162 can be operated in a line flush mode, in which only water is dispensed through the system to flush the lines, mixing chambers (if any) and nozzles 164 and substantially remove the traces of a first chemical or cleaning solution from the apparatus, before dispensing a second, different chemical or cleaning solution through the apparatus. This may help avoid mixing different chemicals or cleaning solutions together. Such a mode may be used to deliver unmixed water to a surface to be treated.

Optionally, in addition to operating the pumps and control valves as described herein, or as an alternative to such manipulations, the delivery lines leading from the different tanks 200a, 200b, 200c, etc. may be different sizes, to help facilitate different flow rates of different liquids in the liquid reservoir apparatus 162.

Liquid Delivery System with Non-Interchangeable Tanks

In accordance with another aspect, which may be used with one or more of the other aspects disclosed herein, if the liquid delivery system includes two or more tanks and/or cartridges that are intended to hold different cleaning solutions and/or cleaning solution concentrates, such as a hard floor cleaning solution cartridge and a carpet cleaning solution cartridge, the liquid delivery system may be configured to help ensure that each cartridge is connected to the liquid delivery system in a desired, appropriate manner. This may be achieved, e.g., by the cartridges or cartridge assemblies not being physically interchangeable or by the cartridges or cartridge assemblies being coded such that apparatus 100 will not operate if a cartridge or cartridge assembly is installed in the wrong location.

According to this aspect, the liquid reservoir apparatus 162 may be configured so that each removable tank or cartridge assembly has a different physical shape, size, connection mechanism and the like, such that a cartridge 200c cannot be unintentionally installed in place of cartridge 200a or 200b (e.g., it is not physically compatible with the housing, couplings or other features of the delivery lines 202a or 202b). For example, the liquid delivery system may be configured such that the hard floor cleaning solution cartridge has a different physical configuration and/or utilizes connectors or couplings that have a different configuration than the carpet cleaning solution cartridge such that the hard floor cleaning solution cartridge is physically incompatible with the compartment and/or coupling a carpet cleaning solution cartridge, and vice versa. This may help prevent unintentional mixing of the contents of the tanks 200a, 200b and 200c, and may help ensure that a cartridge 200c (containing a given type of cleaning chemical) is in the predetermined location such that upon actuation, the appropriate chemical is drawn through delivery line 202c.

Optionally, cartridges and/or tanks that are intended to be inserted into the liquid reservoir apparatus 162 may be coded, e.g., they may be provided with some type of identifying indicia, such as a bar code, QR code, RFID tag and the like. The surface cleaning apparatus 100 may be provided with any suitable type of reader, such that the surface cleaning apparatus 100 can identify a particular cartridge that is inserted into the liquid reservoir apparatus 162. Based on this information, the surface cleaning apparatus 100 may be operable to automatically adjust one or more of the parameters of the liquid reservoir apparatus 162 or other components. For example, the liquid reservoir apparatus 162 may automatically select an appropriate water supply rate, pump operation rate, and chemical supply rate based on the contents of a given cartridge, so that the cleaning solution is mixed to an appropriate concentration when dispensed.

Figure 54B:
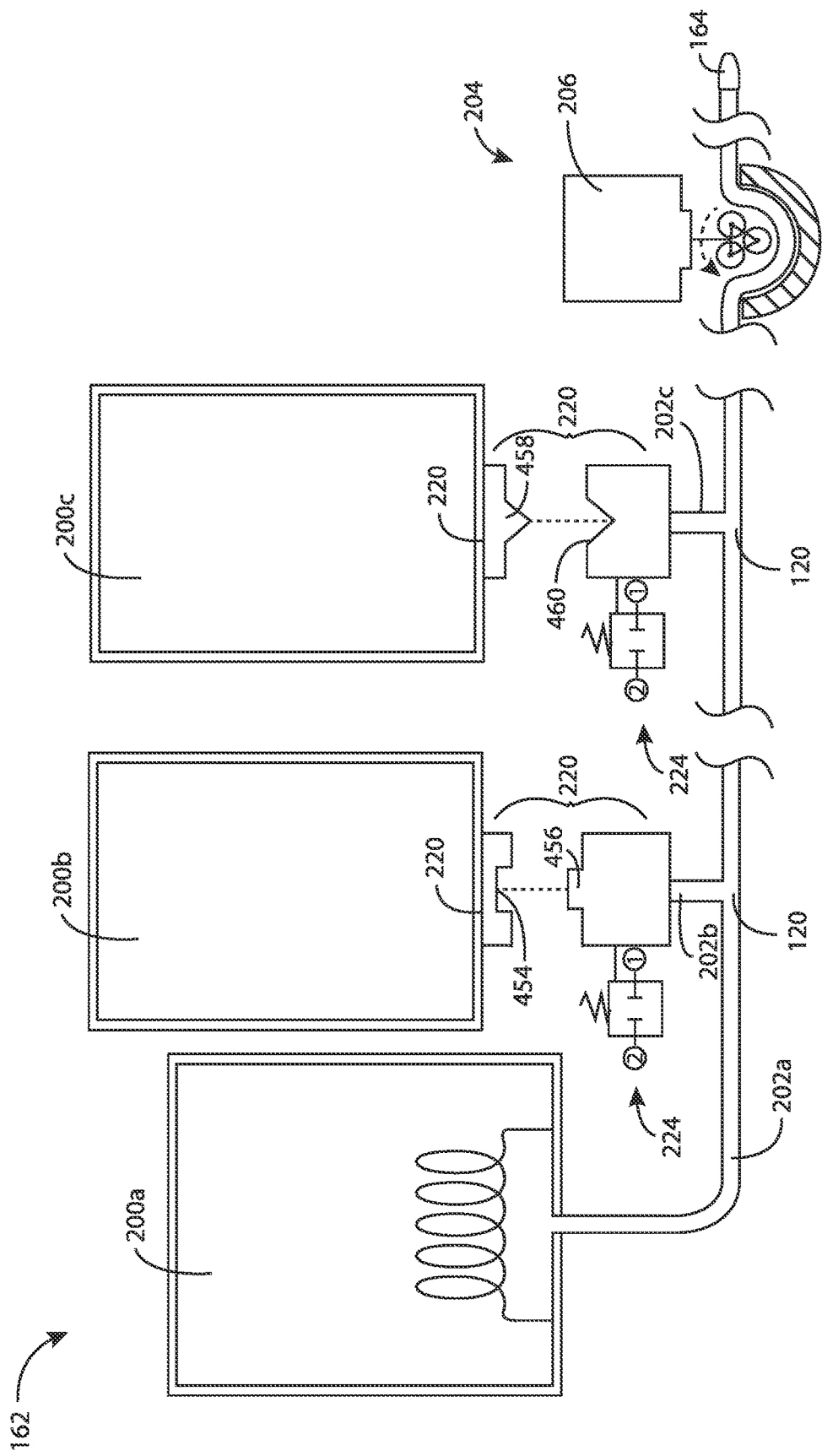
FIG. 54B is a schematic representation of the liquid reservoir unit of FIG. 54A with its cartridges removed.

Referring to FIGS. 54A and 54B, in this example liquid delivery system is configured so that the coupling 220 connecting the cartridge 200b to the supply line 202b is physically incompatible with the coupling connecting cartridge 200c to the supply line 202c. In this embodiment, the portion of the coupling 220 on cartridge 200b has a generally rectangular recess 454 that is configured to receive a complimentary rectangular protrusion 456 that is provided on the portion of the coupling connected to supply line 202b. In contrast, the portion of the coupling 220 on cartridge 200c has a generally conical protrusion 458 that is configured to be received in complimentary, conical recess 460 that is provided on the portion of the coupling connected to supply line 202c. In this arrangement, the cartridge 200b cannot be physically connected in to the liquid delivery system in the location intended to receive cartridge 200c. This may help prevent the unintentional swapping of the cartridges 200b and 200c. In other examples, the couplings 220 may include different types of alignment or keyed structures that are configured to accept one configuration of cartridge but cannot accept a differently configured cartridge, including, for example, coupling portions having different shapes (round vs square or triangular coupling portions), couplings that include pins, bosses or other types of protrusions that are to be registered with and inserted into only complimentarily located holes on the suitable cartridges, cartridges that have the same coupling design but are rigid and are differently shaped so as to only slide into corresponding housings/compartments provided on the surface cleaning apparatus (i.e. a square, rigid tank would not be able to be inserted into a compartment shaped to receive a triangular or cylindrical rigid tank), and the like.

Surface Cleaning Head with Two Rotating Agitators

In accordance with another aspect, which may be used with one or more of the other aspects disclosed herein, apparatus 100 may include two or more different types of brushes, each of which is intended for use with a different surface.

Figure 57:
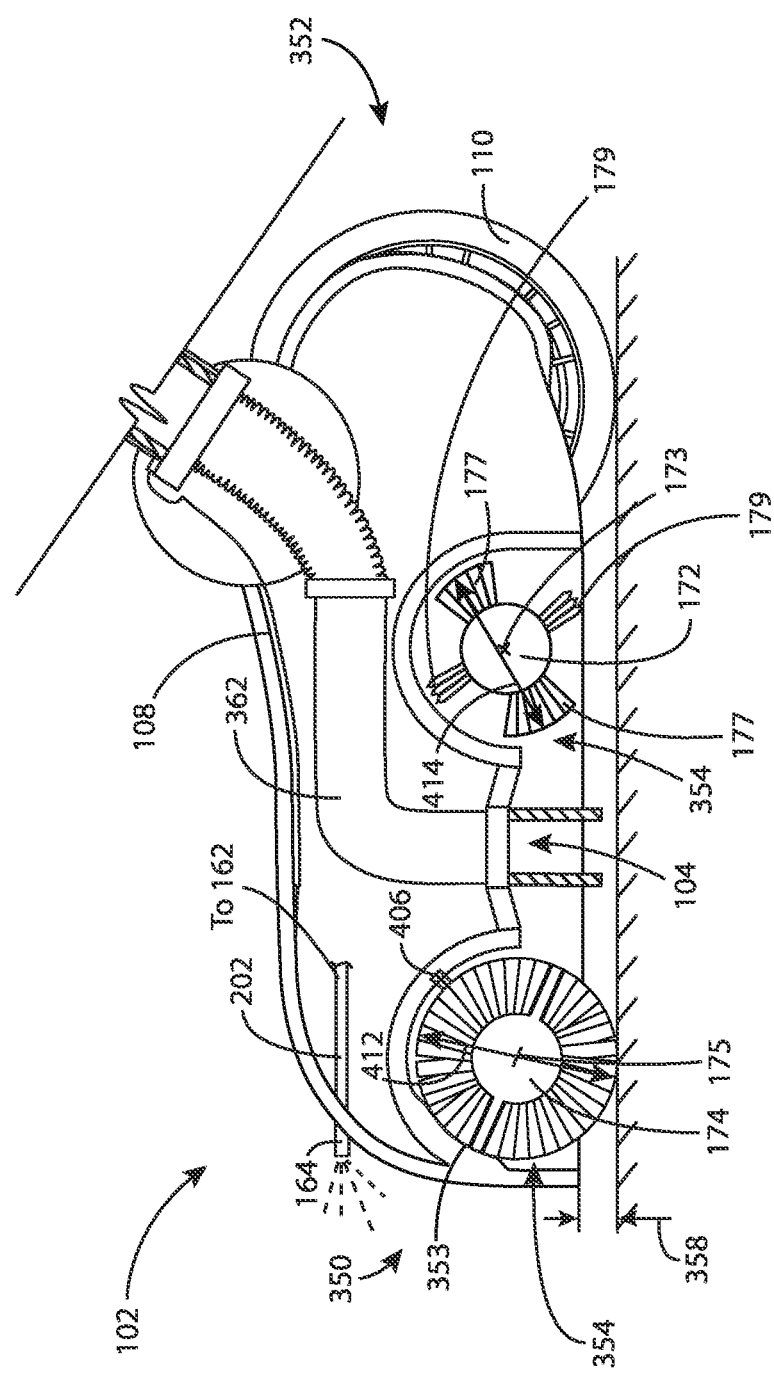
FIG. 57 is a schematic, cross-sectional representation of another embodiment of a surface cleaning head.
Figure 58:
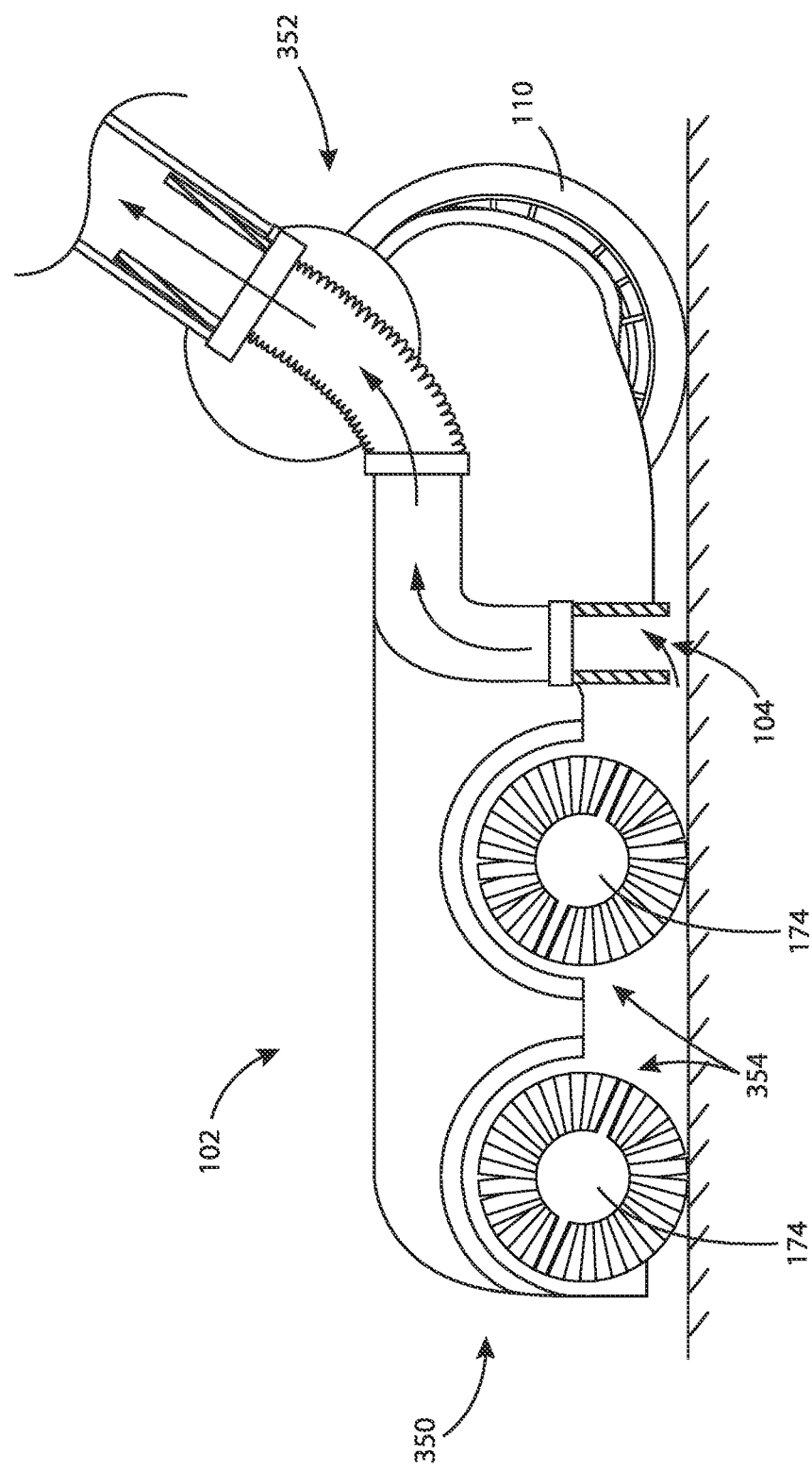
FIG. 58 is a schematic, cross-sectional representation of another embodiment of a surface cleaning head.
Figure 59:
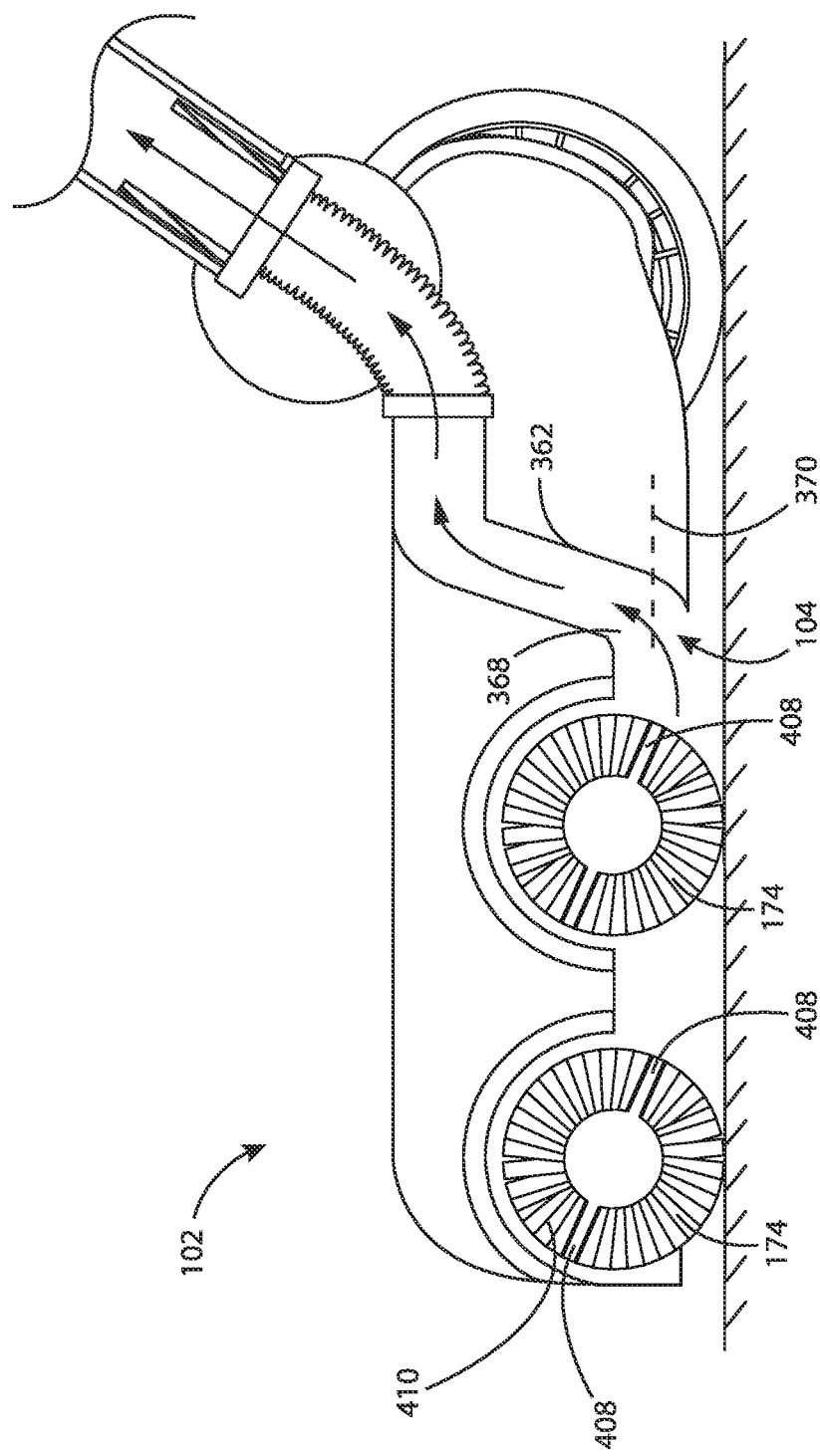

In the embodiments of FIGS. 5-9, 57-59, 61 and 67A-68, the surface cleaning head 102 includes two rotating agitators or members spaced apart from each other. The rotating agitators may be of the same type (for example as shown in FIGS. 58, 59 and 61) or may be of different types (for example as shown in FIGS. 5-9, 57 and 67A-68). In the embodiment of FIG. 57, the surface cleaning head 102 includes a rotating carpet cleaning brush 174, that rotates about a rotation axis 173 and a relatively soft, rotating hard floor cleaning brush 174 that rotates about a rotation axis 175. In the illustrated embodiments, the axes of rotation 173 and 175 are generally horizontal, laterally extending and substantially parallel with each other (if two agitators are present) when the surface cleaning head 102 is positioned on a generally horizontal floor. Each rotating agitator 172 or 174 may be driven by a suitable brush motor, or alternatively the rotating carpet cleaning brush 174 and a rotating hard floor cleaning brush 174 may be driven by a single brush motor (not shown).

Whether driven with separate brush motors, or using a single brush motor, the agitators 172 and 174 may optionally be rotated at the same speed while the surface cleaning head 102 is in use, or alternatively may be rotated at different speeds. In addition, which of the rotating agitators 174 and 172 is rotated during a cleaning operation may be based on the cleaning mode being utilized. For example, the surface cleaning head can be configured so that when it is in the hard floor cleaning actuation mode, the rotating hard floor cleaning brush 174 is rotated and the rotating carpet cleaning brush 174 is stationary and when it is in the carpet cleaning actuation mode, the rotating hard floor cleaning brush 174 is stationary and the rotating carpet cleaning brush 174 is rotated. Alternatively, in both the hard floor cleaning actuation mode and the carpet cleaning actuation mode, both the rotating carpet cleaning brush 174 and the rotating hard floor cleaning brush 174 may be rotated.

Optionally, the rotational rates of the rotating carpet cleaning brush 172 and the rotating hard floor cleaning brush 174 may be variable, and may be adjusted independently from each other. The rate of rotation for a given agitator 172 or 174 may be based on a variety of factors, including the type of surface being cleaned and the cleaning mode of the surface cleaning apparatus. For example, when the surface cleaning apparatus 100 is operated in the hard floor cleaning configuration, the rotating hard floor cleaning brush 174 may be rotated at a first rate of rotation (that may help prevent damage to a hard floor surface and/or reduce the likelihood of debris being scattered across the hard surface by the agitators), and when in the carpet cleaning configuration, the rotating hard floor cleaning brush 174 may be rotated at a second, faster rate of rotation that may help clean the carpet. For example, the rotating hard floor cleaning brush 174 (and/or optionally rotating carpet cleaning brush 174) may be rotated about its rotation axis 175 at a speed that is selected so that the radially outer portions of the rotating hard floor cleaning brush 174 (i.e. portions of its outer surface) have a tangential speed (i.e. velocity in the tangential direction) that is between about 75% and about 125% of the linear, forward travel speed of the surface cleaning head 102 as it travels across the surface.

The speed of rotation of the brushes may be adjusted based on the surface being cleaned. For example, if a carpet is being cleaned, then the speed of the rotating hard floor cleaning brush 174 may be selected so that it is approximately the same as the forward travel speed of the surface cleaning head 102 when travelling over a carpeted surface. Selecting a speed of this nature may reduce the relative movement between the outer portion of the rotating hard floor cleaning brush 174 and the carpeted surface (optionally to approximately zero), which may help reduce wear of the rotating hard floor cleaning brush 174. This may be automatically achieved by a sensor, e.g., a torque sensor that determines the torque applied to a rotating hard floor brush while the apparatus is in a carpet cleaning mode (it is used to clean a carpet). Similarly, if a hard floor is being cleaned, the speed of the rotating carpet cleaning brush 172 may be selected so that it is between about 75% and about 125% of the linear, forward travel speed of the surface cleaning head 102 when travelling over a hard floor surface.

When in the hard floor cleaning mode, the rotating hard floor cleaning brush 174, and optionally the rotating carpet cleaning brush 174, may be rotated at a rate of rotation of between about 1000 and about 2400 RPM, and when in the carpet cleaning configuration, the rotating hard floor cleaning brush 174, and optionally the rotating carpet cleaning brush 174, may be rotated at a rate of rotation of about 2400 and about 5000 RPM.

The different rotational speeds may be achieved by varying the speed of the brush motors (if two brush motors are provided) or altering a gearing ratio (if a single brush motor is provided) either manually (by a switch accessible to the user) or automatically based on a mode selection actuator or other suitable apparatus controller.

The rotating agitators may be helpful when cleaning carpets and other surfaces, and may be of any suitable configuration. The two rotating agitators may be configured so that the diameter 412 of the rotating hard floor cleaning brush 174 is between about 75% and about 125% of the diameter 414 of the rotating carpet cleaning brush 174, and optionally the diameters 412 and 414 may be approximately the same.

The rotating carpet cleaning brush 174 may be any carpet cleaning brush known in the art and may be provided with relatively stiff bristles, such as to help clean carpet, while the rotating hard floor cleaning brush 174 may be may be any hard floor cleaning brush known in the art, and may be provided with relatively softer bristles, such as to help clean hard floor surfaces.

Optionally, the rotating carpet cleaning brush 174 may include one or more rows of relatively stiff (i.e. generally self-supporting) bristles that are provided around the circumference of the brush 172. For example, the rotating carpet cleaning brush 174 in FIG. 57 includes two rows of relatively stiff bristles 177 that are spaced apart from each other and positioned circumferentially around rotating carpet cleaning brush 174 (approximately opposite each other as illustrated). In some embodiments, the rotating carpet cleaning brush 174 may include only a single type of bristles (such as bristles 177) but may have any suitable number of rows of bristles. Optionally, the rotating carpet cleaning brush 174 may include two or more different types of bristles that may have different sizes, lengths, diameters, stiffness, materials, colours and the like. This may help facilitate different types of cleaning using a common rotating carpet cleaning brush 174. For example, the rotating carpet cleaning brush 174 may include a plurality of spaced apart rows of bristles positioned circumferentially around the carpet brush 172 wherein a first group of the rows of bristles, such as the rows 177, have a relatively lower stiffness and a second group of the rows of bristles, such as rows 179 that have a relatively a higher stiffness.

Optionally, the rotating hard floor cleaning brush 174 may have an absence of stiff, self-supporting carpet cleaning bristles, and instead may have a generally continuous covering of relatively soft, flexible filaments, which in some embodiments may not be self-supporting. The surface may of the rotating hard floor cleaning brush 174 may have a generally soft, plush-like texture and may be similar to woven fabrics, microfiber, terrycloth or the like. In some embodiments, the rotating roller may include a plurality of generally radially extending elastomeric paddles that can be spaced apart from each other around the perimeter of the rotating hard floor cleaning brush 174, and may be interspersed between different types of flexible filaments or the like. The embodiment of FIG. 59 illustrates one example of a rotating hard floor cleaning brush 174 having a pair of elastomeric paddles 408 interspersed with a covering of flexible filaments 410 (e.g., a microfiber pad). In other embodiments, the roller 174 need not include the elastomeric paddles and may have a generally homogeneous outer surface.

Figure 56:
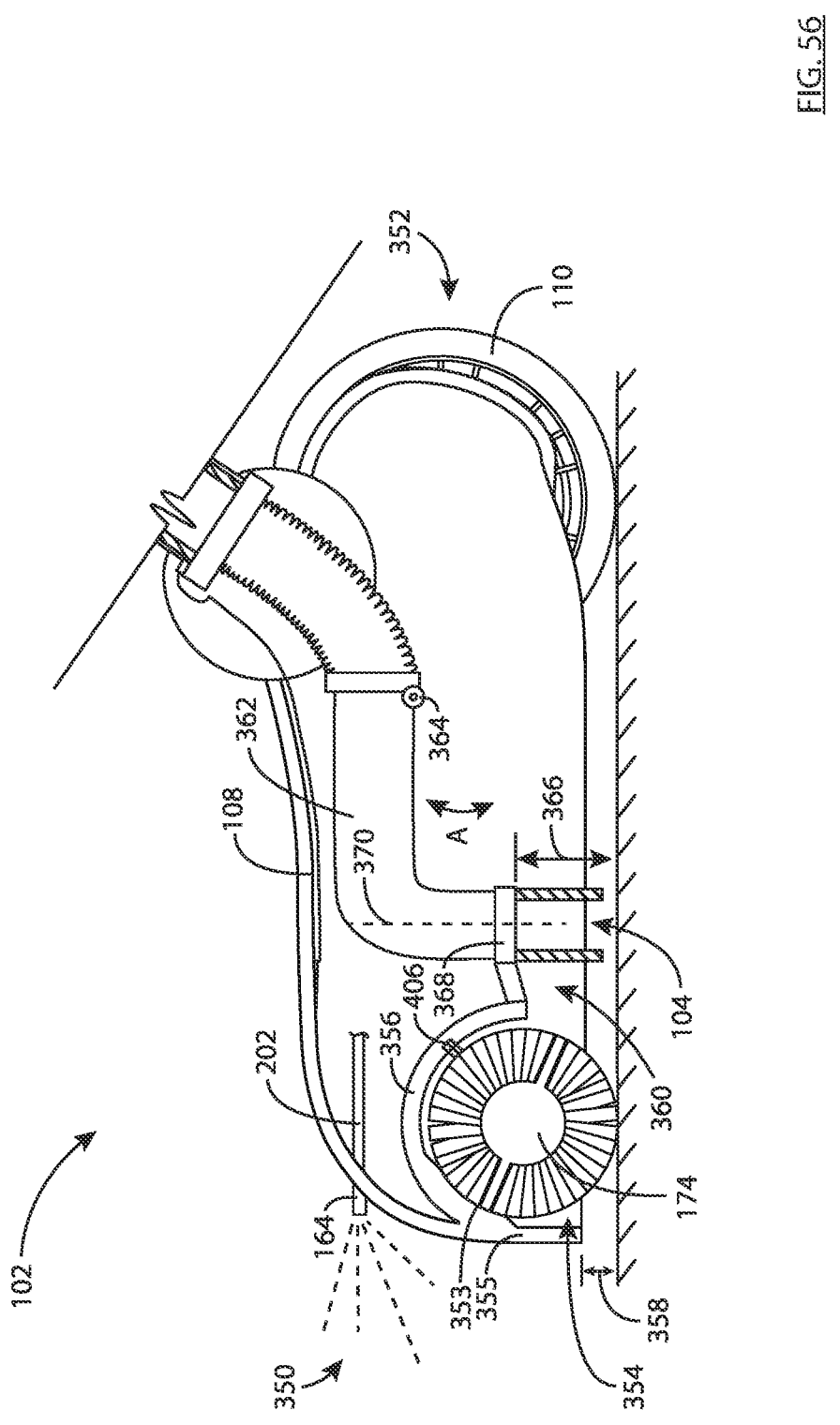

Optionally, one or more debriding members, such as a comb 406, can be provided to engage the surface of the soft roller 174 and to help remove debris from the roller 174. The debriding member(s) may be positioned in any suitable position relative to the soft roller 174 and may, for example, be positioned to extend generally forwardly and downwardly from the inner surface of the brush chamber 354, and may engage an upper, rearward portion of the rotating hard floor cleaning brush 174 as illustrated in the embodiments of FIGS. 56 and 57. Positioning the comb 406 in this position may help direct the dislodged debris into the dirty fluid inlet 104.

While shown as being different types of agitators, the two agitators shown may be the same, and may both be rotating brushes 172, rotating rollers 174 or other suitable agitators.

The rotating agitators 172 and 174 may be housed in a suitable brush chamber within the surface cleaning head 102 that has a generally downwardly facing opening. The opening to the brush chamber may provide the dirty fluid inlet 104, and both liquid and solid debris may pass through the brush chamber as they are sucked into dirty fluid flow path.

Figure 10:
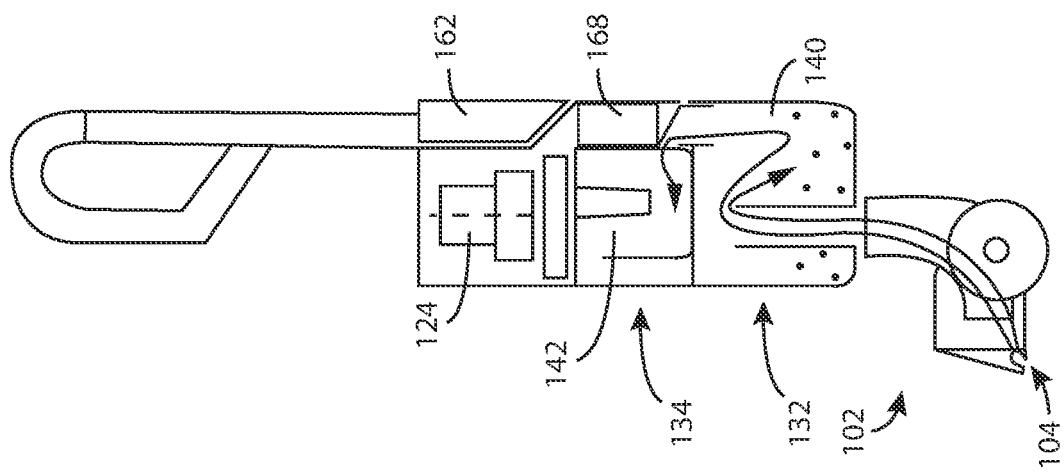
FIG. 10 is a schematic, cross-sectional view of yet another embodiment of a surface cleaning apparatus.

Alternatively, as shown in the embodiment of FIG. 10, the surface cleaning head 102 need not include rotating agitators or a brush chamber. Instead, the dirty fluid inlet 104 may be provided in the form of a relatively narrow slot or other such inlet passage. Such an embodiment may be beneficial if the apparatus is designed to be used solely as an extractor. Alternately, apparatus 100 may have a replaceable surface cleaning head and surface cleaning head of FIG. 11 may be a installed when the apparatus is to be used in a n extractor mode.

Figure 11:
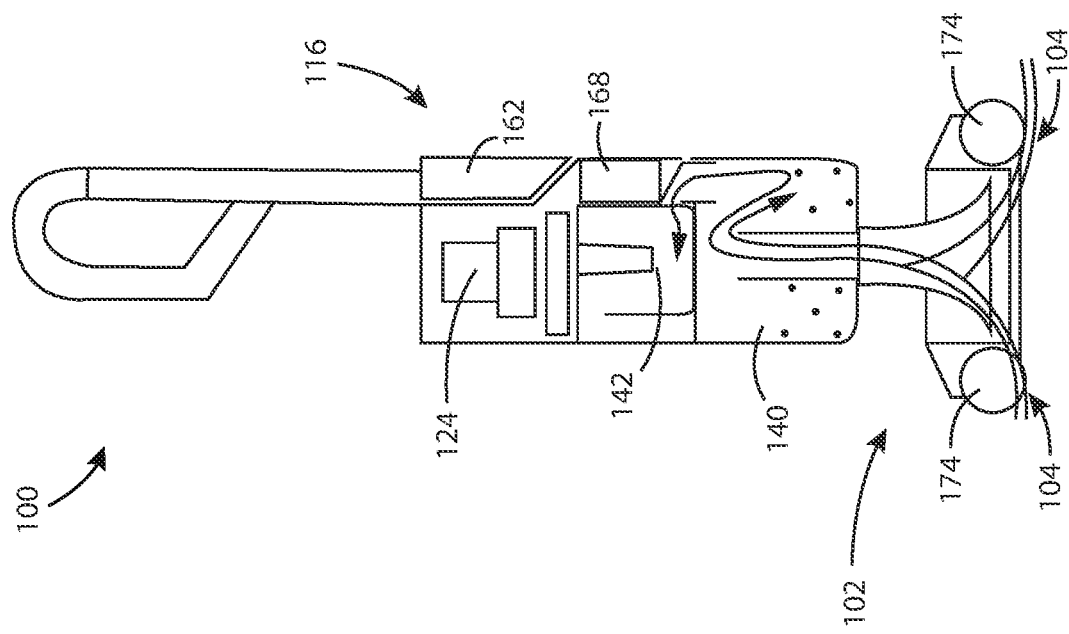
FIG. 11 is a schematic, cross-sectional view of yet another embodiment of a surface cleaning apparatus.

In another embodiment, shown in FIG. 11, the surface cleaning head 102 may have two dirty fluid inlets 104, one provided at the front end and one provided at the rear end of the surface cleaning head 102. Each dirty fluid inlet 104 can include a brush chamber, and rotating agitator therein (such as rollers 174). The fluid flow paths from each dirty fluid inlet 104 may converge (either within the surface cleaning head 102 or downstream from the surface cleaning head) before entering the treatment unit 130. Alternatively, the treatment unit 130 may have two inlets. It will be appreciated that each end may have a different dirty air inlet and rotating brush member. For example, the front end may have a carpet cleaning brush 172 and a suitable dirty air inlet and the rear end may have a hard floor roller 174 and a suitable dirty air inlet.

Figure 12:
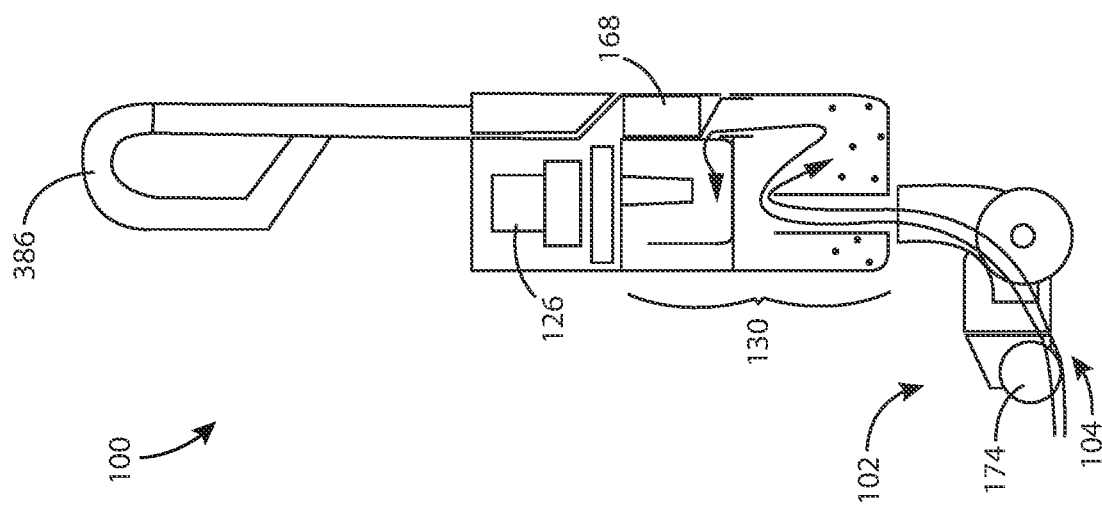
FIG. 12 is a schematic, cross-sectional view of yet another embodiment of a surface cleaning apparatus.

In yet another embodiment, as shown in FIG. 12, the surface cleaning head 102 may include only a single rotating agitator, such as roller 174 (or brush 172), instead of the two agitators shown in FIGS. 5-9.

Surface Cleaning Head with Front Roller

In accordance with another aspect, which may be used with one or more of the other aspects disclosed herein, a hard floor brush 174 may be used to reduce and preferably inhibit air from travelling rearwardly between roller 174 and the surface being cleaned at least when the apparatus 100 is used in an extractor mode. AN advantage of this design is that the apparatus may be used to remove larger debris from the floor while enhancing the suction at a location of the liquid intake rearward of the roller 174.

Referring to FIGS. 56 and 57, embodiments of a surface cleaning head 102 is shown in a schematic, cross-sectional view. The surface cleaning head 102 has a front end 350 and an opposing rear end 352 that includes the rear wheels 110. A hard floor brush chamber 354 is provided toward the front end 350, and includes a front wall 355 and an upper wall 356. The brush chamber 354 may be of any suitable configuration, and may be configured to hold any suitable type of agitator, including the rotating carpet cleaning brush 172 as shown in FIG. 57. The dirty fluid inlet 104 is provided behind the brush chamber 354, and in fluid communication with the brush chamber 354, so that debris that is dislodged by the rotating hard floor cleaning brush 174 can be conveyed into the dirty fluid inlet 104 for treatment.

If a front soft, rotating hard floor cleaning brush 174 is utilized, the rotating hard floor cleaning brush 174 can be positioned so that it extends to and engages the floor, including a hard floor surface, when the surface cleaning head 102 is positioned on a hard floor surface. This may help limit the about of air that can pass beneath the rotating hard floor cleaning brush 174. In this arrangement the front of the surface cleaning head may be defined in part by a forward side of the soft, rotating hard floor cleaning brush 174. Accordingly, the plastic casing of the surface cleaning head may terminate, e.g., part way down the front of the soft, rotating hard floor cleaning brush 174. An advantage of this design is that larger debris, e.g., popcorn, may pass under the soft, rotating hard floor cleaning brush 174 to allow the surface cleaning head to remove debris from a surface (i.e. a vacuum cleaning operation) prior to using water and/or a chemical solution to clean the surface. In such a case, the soft, rotating hard floor cleaning brush 174 may effectively form a seal with the floor, and or the surface cleaning head, thereby inhibiting air travelling into a dirty air inlet from in front of the surface cleaning head and thereby increase the draw of fluid from, e.g., carpet.

As exemplified, the front end 350 of the surface cleaning head 102 may be spaced above the floor by a front height 358. The front height 358 may be any suitable height and may be, for example, at least about 0.1 inches, about 0.2 inches, about 0.25 inches, about 0.3 inches, about 0.4 inches, about 0.5 inches, about 0.75 inches or more and may be less than about 3 inches, about 2.5 inches, about 2 inches, about 1.5 inches, about 1 inch or less. In some embodiments, the height 358 may be between about 0.25 inches and about 1.5 inches, between about 0.5 inches and about 1.25 inches and between about 0.75 inches and about 1 inch. Preferably, if the surface cleaning head 102 is configured to be used for both dry vacuuming and wet extracting, the front height 358 is selected so that the surface cleaning head 102 can be moved over common types of debris, such as dirt, sand and relatively larger objects that are on the floor. Providing a sufficient front height 358 may also help the surface cleaning head 102 to traverse changes in floor elevation, such as when moving onto a carpet, rug and/or across a transition to different flooring types.

When operating in an extractor mode to pick up liquid, it may be desirable to help create at least a partial seal around the dirty fluid inlet 104. Providing some sealing around the dirty fluid inlet 104 may help improve its liquid pick-up performance, and may help create faster air flow velocities. To help provide such, at least partial, sealing, this embodiment of the surface cleaning head 102 includes a rotating hard floor cleaning brush 174 that has a generally continuous covering of soft hair or fibers or other flexible bristle elements—as compared to a rotating carpet cleaning brush 174 that includes relatively discontinuous, discrete tufts of bristles (hard or soft). The surface cleaning head 102 may be configured to include only the rotating hard floor cleaning brush 174 (FIG. 56) or may include a rotating hard floor cleaning brush 174 toward the front of the surface cleaning head 102, and a rotating carpet cleaning brush 174 positioned rearward of the rotating hard floor cleaning brush 174.

The covering of the roller 174 may contact the floor across substantially the entire width of the roller 174, which may help seal the front end of the surface cleaning head 102. This may create a relatively sealed region 360 between the roller 174 and the dirty fluid inlet 104, which may help improve liquid pick-up. Because of the flexible, pliable nature of the roller 174, it may be able to provide at least some sealing, while retaining the ability to deform around and accommodate relatively large pieces of solid debris.

Optionally, the rotating hard floor cleaning brush 174 may also contact or otherwise engage at least a portion of the inner surface of the brush chamber 354 to help at least partially seal against the inner surface of the brush chamber 354. This may help prevent air from flowing around the upper portion of the rotating hard floor cleaning brush 174 and the inner surface of the brush chamber 354. Such engagement can be provided at any suitable point along the perimeter of the rotating hard floor cleaning brush 174, and preferably may be provided on a generally forward or upward facing portion of the rotating hard floor cleaning brush 174. For example, in the embodiment of FIG. 56, the spacing between the inner surface of the brush chamber 354 and the outer surface of the rotating hard floor cleaning brush 174 does not remain constant around the perimeter of the rotating hard floor cleaning brush 174. Instead, a generally forward portion 353 of the inner surface of the brush chamber 354 is positioned to engage the rotating hard floor cleaning brush 174. This can at least partially seal the space surrounding the rotating hard floor cleaning brush 174, and may essentially inhibit air travelling upwardly over the rotating hard floor cleaning brush 174 and into/through the brush chamber 354.

Movable Dirty Fluid Inlet

In accordance with another aspect, which may be used with one or more of the other aspects disclosed herein, the dirty air inlet may be adjustable to have an increased air flow velocity or suction proximate the surface of a carpet so as to be able to draw more fluid from carpet during operation of apparatus 100 as an extractor. Accordingly, at least a portion of the air flow path within the surface cleaning head 102 may be movable or otherwise re-configurable to help adjust the relative height of the dirty fluid inlet 104 above the floor, e.g., during operation of apparatus 100 as an extractor. This may help modify the suction performance of the surface cleaning head 102. For example, the dirty fluid inlet 104 may be positioned relatively close to the floor when extracting liquids, and may be positioned relatively farther from the floor when vacuuming solids.

In the embodiment of FIG. 56, a conduit 362 that forms part of the fluid flow path can be pivoted about pivot joint 364 (in the direction of arrows A), so as to change the distance 366 between and inlet end 368 of the conduit 362 (functioning as the dirty fluid inlet 104) and the floor. This pivoting may be done manually by a user, and/or may be automatically controlled based on the operation mode of the apparatus 100, the nature of the floor being cleaned and the like.

In this embodiment, a portion of the conduit 362 extends along a generally vertical inlet axis 370, and air entering the inlet end 368 may tend to travel generally parallel to the inlet axis 370.

The surface cleaning head 102 may optionally include the delivery nozzle 164 and a portion of the associated delivery lines 202, as shown in FIG. 56. The other surface cleaning heads 102 described herein may also be configured to include the delivery nozzle 164, and optionally other portions of the liquid reservoir apparatus 162.

Referring to FIG. 57, another embodiment of a surface cleaning head 102 includes a hard floor roller 174 positioned in a brush chamber 354 forward of the dirty fluid inlet 104, and a rotating carpet cleaning brush 174 positioned in a second carpet brush chamber 354 positioned behind the dirty fluid inlet 104. Alternatively, as shown in the embodiment of FIG. 58, the surface cleaning head 102 may include two brush chambers 354 positioned forward of the dirty fluid inlet 104, each including a suitable roller 174 as shown. It will be appreciated that this embodiment may use two carpet cleaning brushes 172, two hard floor brushes 174 or a hard floor brush 174 forward of a carpet cleaning brush 172, all forward of the dirty fluid inlet 104.

Optionally, instead of orienting the conduit 362 such that inlet end 368 is generally downward facing and the inlet axis 370 is generally vertical, as shown in FIGS. 56-58, the surface cleaning head 102 may be configured so that the inlet end 368 is generally forward facing and the inlet axis 370 is generally horizontal (i.e. extends in the front/back direction) as shown in the embodiments of FIGS. 59 to 61. This may help the dirty fluid inlet 104 to collect solid and liquid debris that is exiting the brush chambers 354.

Operating Components in the Surface Cleaning Head

In accordance with another aspect, which may be used with one or more of the other aspects disclosed herein, the surface cleaning apparatus 100 may be configured so that at least one or optionally some, or optionally all of the operating components of the treatment unit 130 and/or cleaning unit 120, may be provided in the surface cleaning head 102, instead of on the movable upright section 116. Providing one or more of the components within the surface cleaning head 102 may help reduce the amount of weight a user has to hold when maneuvering the apparatus 100 via the upright section 116. It may also help lower the overall centre of gravity of the apparatus 100. This configuration may also simplify some portions of the fluid flow path, and reduce the distance and/or height that liquid needs to be translated within the fluid flow path.

For example, one or more water containers (e.g., a clean water tank or clean solution tank 200 and/or a recovered liquid reservoir, may be provided as part of (e.g., in, on) the surface cleaning head 102. Accordingly, the weight of the liquid may be provided in the surface cleaning head, thereby lowering the hand weight of the drive handle of apparatus 100.

Figure 13A:
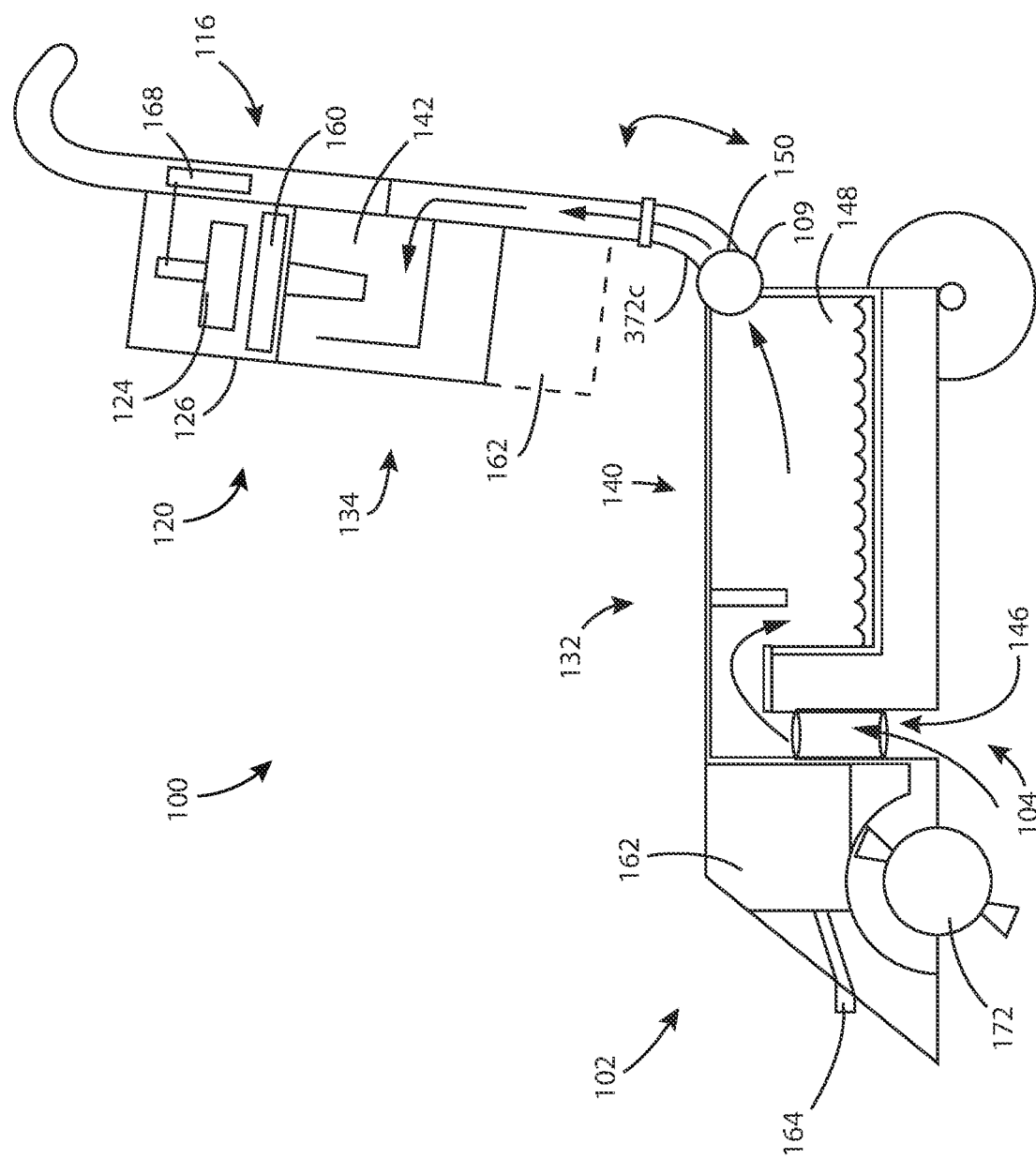
FIG. 13A is a schematic, cross-sectional view of yet another embodiment of a surface cleaning apparatus, with a separator in the surface cleaning head.
Figure 13B:
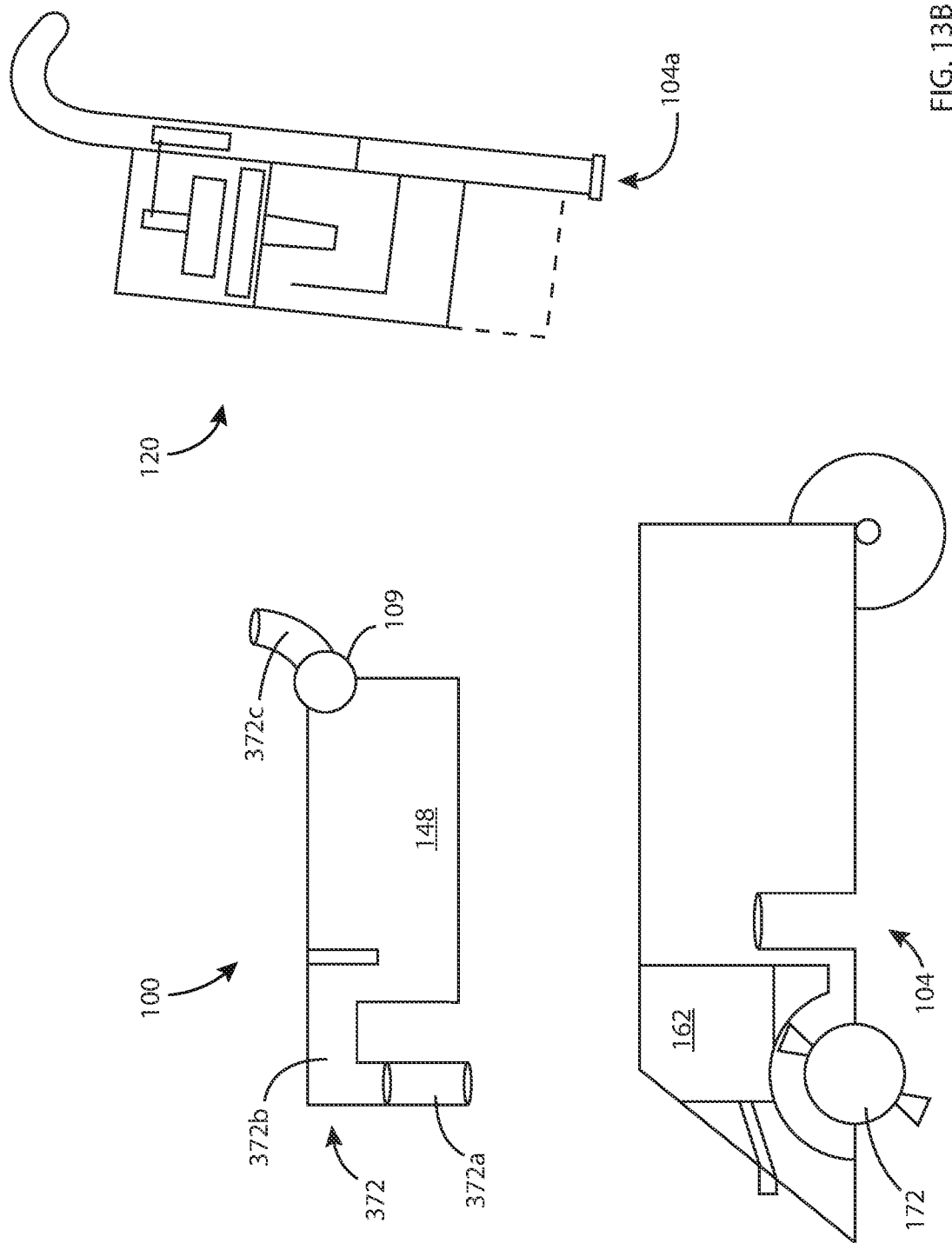
FIG. 13B is schematic, cross-sectional view of the embodiment of the surface cleaning apparatus of FIG. 13A in a different configuration.

As exemplified in FIGS. 13A and 13B, the first separator 132, i.e. momentum separator 140, is provided in the surface cleaning head 102, while the second separator 134 and suction motor 124 are provided in the cleaning unit 120 on the upright section 116. In this arrangement, the treatment unit 130 is split between the upright section 116 and the surface cleaning head 102. An advantage of this embodiment is that the water extracted from a surface need not be raised to the upper section and thereby reduce energy requirements, particularly in a battery operated version.

In the example of FIGS. 13A and 13B, the liquid reservoir apparatus 162 is also provided in the surface cleaning head 102, along with the delivery nozzle 164. This may help reduce the distance that the liquid from the liquid reservoir 162 needs to be pumped in order to reach the delivery nozzle 164 as well as the hand weight of the upper section. It will be appreciated that liquid reservoir apparatus 162 may be provided in the surface cleaning head 102 if all of the treatment unit 130 is located elsewhere (e.g., on upright section 116 as exemplified in FIGS. 16a-16f.

Alternatively, the liquid reservoir 162 could be provided on the upright section, as indicated using dashed lines.

Figure 14:
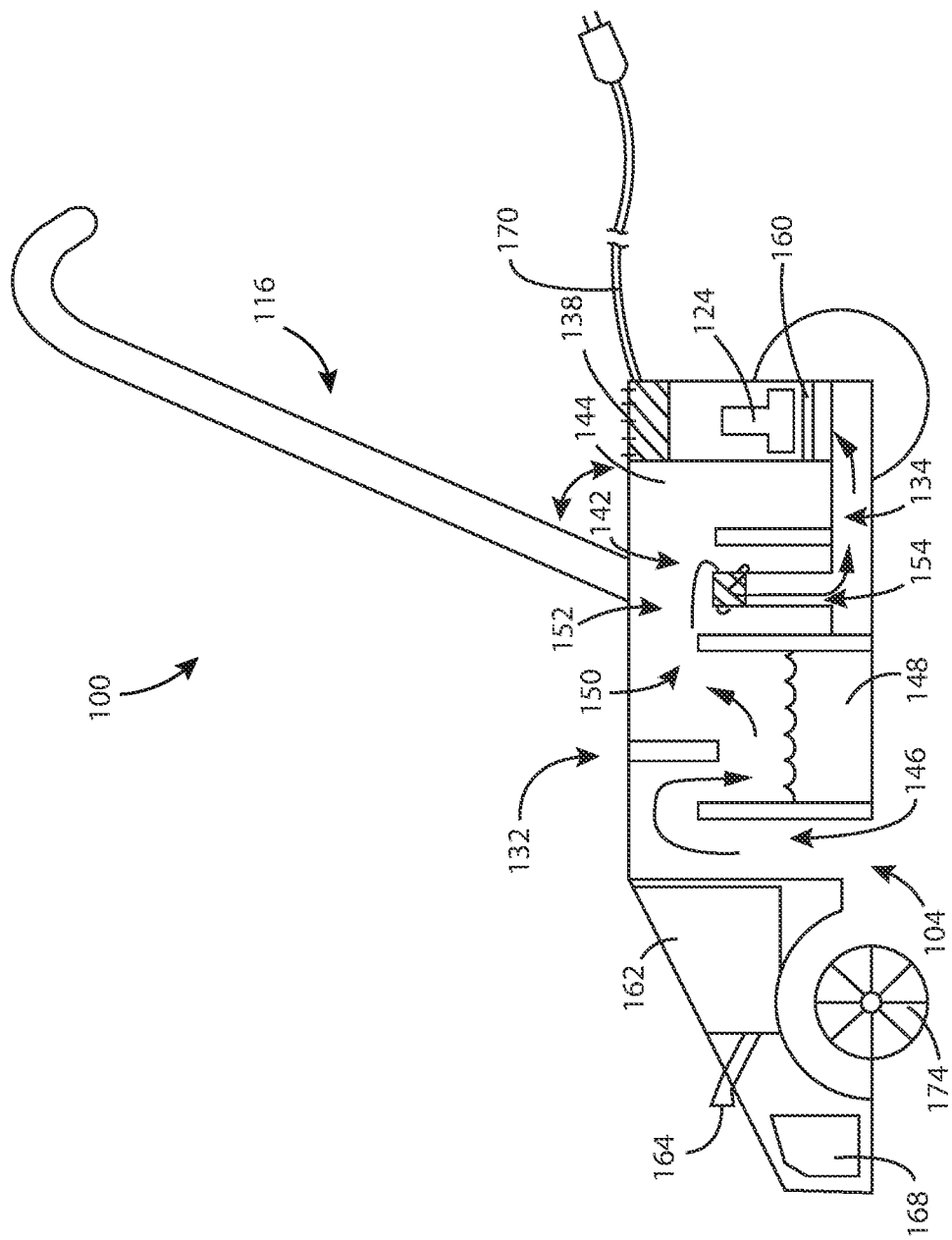
FIG. 14 is a schematic, cross-sectional view of an embodiment of an all in the head type surface cleaning apparatus, with the treatment unit and suction motor in the surface cleaning head.

FIG. 14 exemplifies an all-in-the-head type surface cleaning apparatus 100 wherein all of the functional components of the apparatus (first separator 132, second separator 134 and suction motor 124) are provided within the surface cleaning head 102. In this example, the cyclone chamber 142 is configured as a uniflow cyclone, in which the cyclone air inlet 152 is at one end of the cyclone chamber 142 (the upper end as shown) and the cyclone chamber air outlet 158 is at the opposing end of the cyclone chamber 142. Optionally, the treatment unit 130 may be removable from the surface cleaning head 102 in this embodiment, and may be removable in a closed or sealed configuration, but for the momentum separator fluid inlet 146 and the cyclone chamber air outlet 158. One or more of the upper wall, a side wall and a lower wall of the treatment unit 130 can then be openable to allow the liquid collection container 148 and solid collection chamber 144 to be emptied simultaneously. Alternately, a portion of the liquid collection container 148 and solid collection chamber 144 may be part of the exterior surface of the apparatus 100 and a wall (e.g., lid or upper housing) need not be opened to enable access to the liquid collection container 148 and solid collection chamber 144 for removal.

FIGS. 15 and 16a-16f exemplify providing the liquid collection container 148 in the surface cleaning head 102. In the embodiments of FIGS. 15 and 16a-16f, a single stage separator, which uses a cyclone chamber 142, is provided on the upright section 116, while the liquid collection container 148 is provided in the surface cleaning head 102. In this embodiment, the liquid collection container 148 is connected using suitable liquid flow conduit(s) 380 to allow liquid separated by the cyclone chamber 142 flow down to the liquid collection container 148. Optionally, a pump 318 or other suitable mechanism (gravity flow) can be included to help facilitate the liquid transfer to the liquid collection container 148. This embodiment is also arranged so that the liquid delivery system, including the liquid reservoir apparatus 162 and nozzle 164, is also included in the surface cleaning head 102, such that it is also separated from the cleaning unit 120 when the cleaning unit is detached.

Optionally, regardless of the position of momentum separator 140, the momentum separator 140 may be removable from the surface cleaning head 102 for emptying and/or maintenance. In some embodiments, regardless of the position of momentum separator 140, the momentum separator 140 may be removable with at least a portion of the fluid flow path between the dirty fluid inlet 104 and the momentum separator 140 may be removable for cleaning, and the surface cleaning head 102 may include a removable pipe, hose or other type of conduit. Optionally, the removable portion of the fluid flow path may be removable in unison with the momentum separator 140, or independently from the momentum separator 140.

Applying a Cleaning Solution to at Least One Agitation Member

In accordance with another aspect, which may be used with one or more of the other aspects disclosed herein, the apparatus may be configured so that a particular cleaning solution is provided to a particular brush. Accordingly, instead of, or in addition to, providing a nozzle 164 to apply the cleaning solution to the floor (such as by positioning it on the front end 350 of the surface cleaning head as exemplified in FIG. 6A), a surface cleaning apparatus 100 may be configured to apply the cleaning solution(s) to a selected one or more than one of the rotating agitators (such as roller 174 and/or brush 172). Accordingly, the surface cleaning head may be configured to include two rotating agitators, and may be operable to apply the cleaning solution selectively to a specific agitator. In accordance with this aspect, for example, a hard floor roller may have a hard floor cleaning solution applied to it and/or a carpet cleaning brush may have a carpet cleaning solution applied to it. This may help facilitate applying the cleaning solution to the areas of the floor that are engaged by the rotating agitator and/or may help prevent over use of the cleaning solution.

In accordance with this aspect, a hard floor cleaning solution may be applied to the roller 174 that is intended to be used when cleaning hard floors, whereas a carpet cleaning solution may be applied to the rotating carpet cleaning brush 174 that is intended to be used when cleaning carpets. This may help facilitate the application of an appropriate cleaning solution onto an appropriate agitator and/or onto a desired type of surface to be cleaned. A surface cleaning head may include a single liquid applicator/nozzle that could be reoriented and/or repositioned to independently apply a different cleaning solution to each of the rotating agitators, and/or may include at least one separate liquid applicator/nozzle for each rotating agitator. Providing separate applicators for each rotating agitator may help prevent cross-contamination and/or mixing of different cleaning solutions that are used with different rotating agitators. It may also facilitate applying liquids (optionally different liquids) simultaneously to each rotating agitator. The cleaning solution applicators may be connected to any of the liquid delivery systems described herein, or other suitable source of cleaning solution.

Referring to FIG. 67A, this embodiment of a surface cleaning head 102 includes a rotating hard floor cleaning brush 174 and a rotating carpet cleaning brush 172 that are spaced apart from each other. The surface cleaning head 102 also includes, in accordance with another aspect, portions of the liquid delivery system for the surface cleaning apparatus 100, including a pump 204a and associated motor 206a that can be used to supply liquid from any suitable reservoir (such as a reservoir tank 200a on the upright section 116) to a nozzle 164a, via the liquid delivery line 202a and a pump 204b and associated motor 206b that can be used to supply liquid from the same or a different reservoir to a nozzle 164b, via the liquid delivery line 202b. Each nozzle 164a, 164b is positioned within the brush chamber 354 containing a rotating brush 174, 172 and is toward the upper side of the brush chamber 354 in this example. Liquid, such as water or any other suitable hard floor cleaning solution can be transferred from the nozzle 164a to the rotating hard floor cleaning brush 174, such as by dripping, spraying a mist, spraying a stream of liquid and the like. The liquid can then be carried by the rotating hard floor cleaning brush 174 to the surface being cleaned. Similarly a liquid may be applied to the carpet cleaning brush 164b.

The rate at which a liquid is applied to either the rotating hard floor cleaning brush 174 or rotating carpet cleaning brush 172 may be variable (for example, by changing the operating speed of the pumps 204a and 204b), and may be any suitable amount. For example, liquid may be delivered to either agitator 172 or 174 at a rate of between about 10 to about 100 mL/minute or more than 100 mL/minute, or any other suitable rate.

The liquid may be applied at different rates to the different agitators 172 and 174. For example, in the hard floor cleaning mode, the cleaning solution may delivered at a first rate and in the carpet cleaning mode, the cleaning solution (either the same solution or a different solution) may be delivered at a second rate that is faster than the first rate. For example, liquids that are applied to the rotating hard floor cleaning brush 174 and intended for use in hard floor cleaning (e.g. hard floor cleaning solution) may be applied at a rate of between about 10 to about 100 mL/minute, while liquids that are applied to the rotating carpet cleaning brush 172 and intended for use in a carpet cleaning (carpet cleaning solutions) may be applied at a rate of at least 100 mL/minute.

Optionally, instead of providing separate nozzles 164a and 164b for each rotating agitator, the surface cleaning head 102 may include only a single nozzle, such as an exemplary embodiment of an optional nozzle 164a shown in dashed lines in FIG. 67A. The nozzle 164a may be movable, such as by pivoting about pivot joint 165, between a first position in which it is facing and can apply liquid to the rotating carpet cleaning brush 172 (as shown in FIG. 67A), and second position in which it is facing and can apply liquid to the rotating hard floor cleaning brush 174. The nozzle 164 may be moved between its first and second positions manually, for example using a lever or other actuator that can be accessed by a user, or automatically, such as by using an electric motor that is in communication with a suitable controller.

Figure 67B:
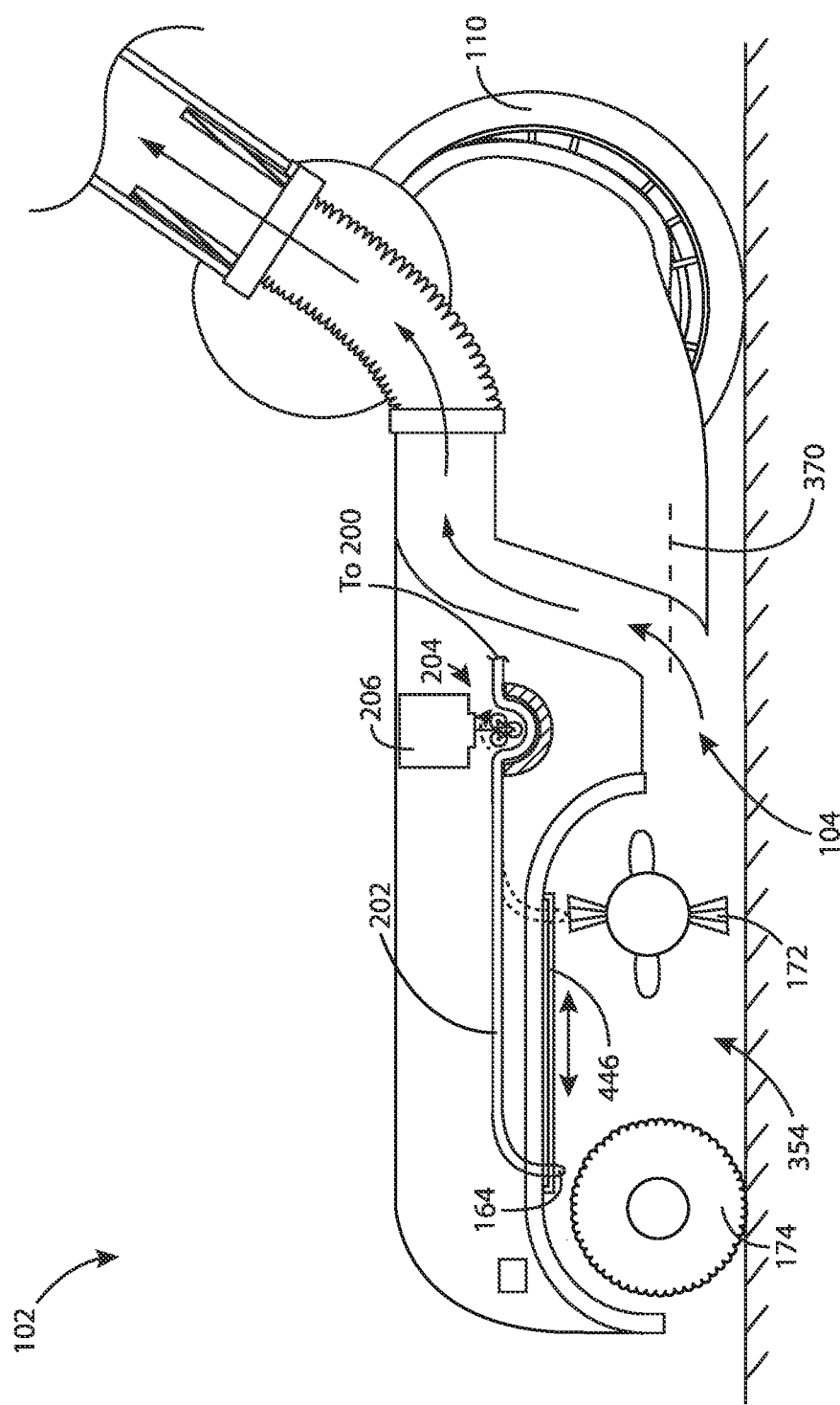
FIG. 67B is a cross-sectional view of another embodiment of a surface cleaning head.

Referring to FIG. 67B, in this embodiment, a single nozzle 164 is slidably mounted on a linear rail 446 that is provided within the brush chamber 254, such that the nozzle 164 can be moved between a first position in which it can spray liquid onto the rotating hard floor cleaning brush 174 (as shown in FIG. 67B), and a second position in which it can spray liquid onto the rotating carpet cleaning brush 172. In the illustrated example, the nozzle 164 can slide in the forward/rearward direction when moving between the first and second positions. The liquid supply line 202 may be extensible, flexible, or otherwise configured to help accommodate movement of the nozzle 164, while still maintaining a desired fluid connection to the tank 200. It will be appreciated that other translating mechanisms may be used.

If a single nozzle 164 is used, it may be connected to any suitable liquid delivery system and may optionally be selectably supplied with at least two different cleaning solutions. For example, a valve or other such mechanism may be provided upstream from the nozzle 164 and may be configured to selectably connect the nozzle 164 to a hard floor cleaning solution reservoir and a carpet cleaning reservoir. When the nozzle 164 is facing the rotating carpet cleaning brush 172 it may be connected to the carpet cleaning solution reservoir, and when it is moved to face the rotating hard floor cleaning brush 174 it may be connected to the hard floor cleaning solution reservoir. The operation of the valve may be manually, or may be linked to the orientation of the nozzle 164, the apparatus operating mode or the like and may be automatically controlled by a suitable controller.

FIG. 68 exemplifies another embodiment of a surface cleaning head 102 that includes two nozzles 164a and 164b. Instead of being connected to a remote liquid reservoir, as shown in FIGS. 67A and 68B, in this embodiment the liquid delivery system includes a hard floor cleaning solution reservoir tank 200a, that is connected to nozzle 164a via the supply line 202a. When motor 206a and pump 204a are activated, liquid can be drawn from the hard floor cleaning solution reservoir tank 200a and sprayed onto the rotating hard floor cleaning brush 174. When motor 206b and pump 204b are activated, liquid can be drawn from the hard floor cleaning solution reservoir tank 200b and sprayed onto the carpet cleaning brush 172. Optionally, as discussed herein, either or both of the tank 200a, 200b can be configured as a refillable reservoir container, or alternatively may be a single use, replaceable cartridge. If the tank 200a,b is removable, some or all of the supply line 202a, 202b may also be removable.

Optionally, the motor 206b and pump 204b may be activated independently from motor 206a and pump 204a, and vice versa. Optionally, the embodiments of FIGS. 67A and 67B may also include one or more liquid reservoir tanks 200 in the surface cleaning head 102.

Optionally, in the embodiments of FIG. 67A-68, the operation of the motors 206a and 206b may be linked to the rotational speed of the rotating hard floor cleaning brush 174 and/or rotating carpet cleaning brush 174, such that the pumps 204a and 204b operate a faster rate and supply more cleaning solution when the rotating hard floor cleaning brush 174 and/or rotating carpet cleaning brush 174 are rotating quickly, and the pumps 204a and 204b operate a relatively slower rate and supply less cleaning solution when the rotating hard floor cleaning brush 174 and/or rotating carpet cleaning brush 174 are rotating relatively slower. In such examples the pumps 204a and 204b may be driven by the same drive apparatus that drives the rotating hard floor cleaning brush 174 and/or the rotating carpet cleaning brush 174. Alternatively, the motors 206a and 206b may be sped up or slowed down by a suitable controller, based on the agitator rotation speed, thereby adjusting the pumps 204a and 204b operating rate. Any of the flow rates discussed herein may be used.

Removable Fluid Flow Path

In accordance with another aspect, which may be used with one or more of the other aspects disclosed herein, a fluid flow path has one or more openable and/or removable segments, which are upstream of the separator and may help facilitate maintenance and cleaning of the fluid flow path through which liquid travels. These embodiments of the fluid flow path may be used in combination with any of the other features and/or aspects of the surface cleaning apparatuses described herein, including any of the dual stage treatment units, single stage treatment units, recline limiting and/or mode controlling apparatuses, liquid delivery systems, surface cleaning heads, apparatuses with above floor cleaning mode(s) and/or lift away configurations, and may also utilize features described in relation to embodiments of the hand held surface cleaning apparatuses.

When drawing in liquid, the interior for the fluid flow path upstream of the wet separator become dirty, blocked or otherwise fouled. For example, when the apparatus 100 is used in an extractor mode, at least some of the dirty liquid being extracted may tend remain in parts of the fluid flow path and those portions may not dry out during normal use and storage. Accordingly, odors may build up in those portions of the fluid flow path. Optionally, to help facilitate cleaning of the fluid flow path, at least one portion of the fluid flow path upstream of the separator may be removable from the rest of the apparatus 100. Preferably, the removable portion(s) can include portions of the fluid flow path that are likely to retain liquid. In particular one or more portions of the air flow path that extend from the surface cleaning head 102 to the liquid separator portion of the treatment unit 130 maybe removable.

The removable portion of the fluid flow path may be a single, continuous portion or may include two or more removable segments. The two or more segments may optionally be configured to be independently removable, which may allow a user to remove some of the removable portion of the fluid flow path while leaving other segments in place.

In some embodiments, the removable portion of the fluid flow path may be limited to rigid conduits, pipes, flexible hoses and other such fluid conveying members, but need not include any of the separators 132, 134 or other functional components of the surface cleaning apparatus. In other embodiments, the removable portion of the fluid flow path may include one or more separators or other functional components. For example, a liquid separator 132 may be removable in unison with at least a portion of the fluid flow conduits that extend from the dirty fluid inlet 104 to the liquid separator inlet 146 or other portion of the surface cleaning head 102 (see FIGS. 63B and 13B for example). If a single stage treatment unit 130 is used, the removable portions of the fluid flow path may include the single stage separator (such as the cyclone chambers 142 described herein) along with at least a portion of the fluid flow path upstream from the cyclone fluid inlet 152. Optionally, substantially the entire portion of the fluid flow path that extends between dirty fluid inlet 104 and the inlet of the treatment unit (optionally either 146 or 152) can be removable.

Figure 63A:
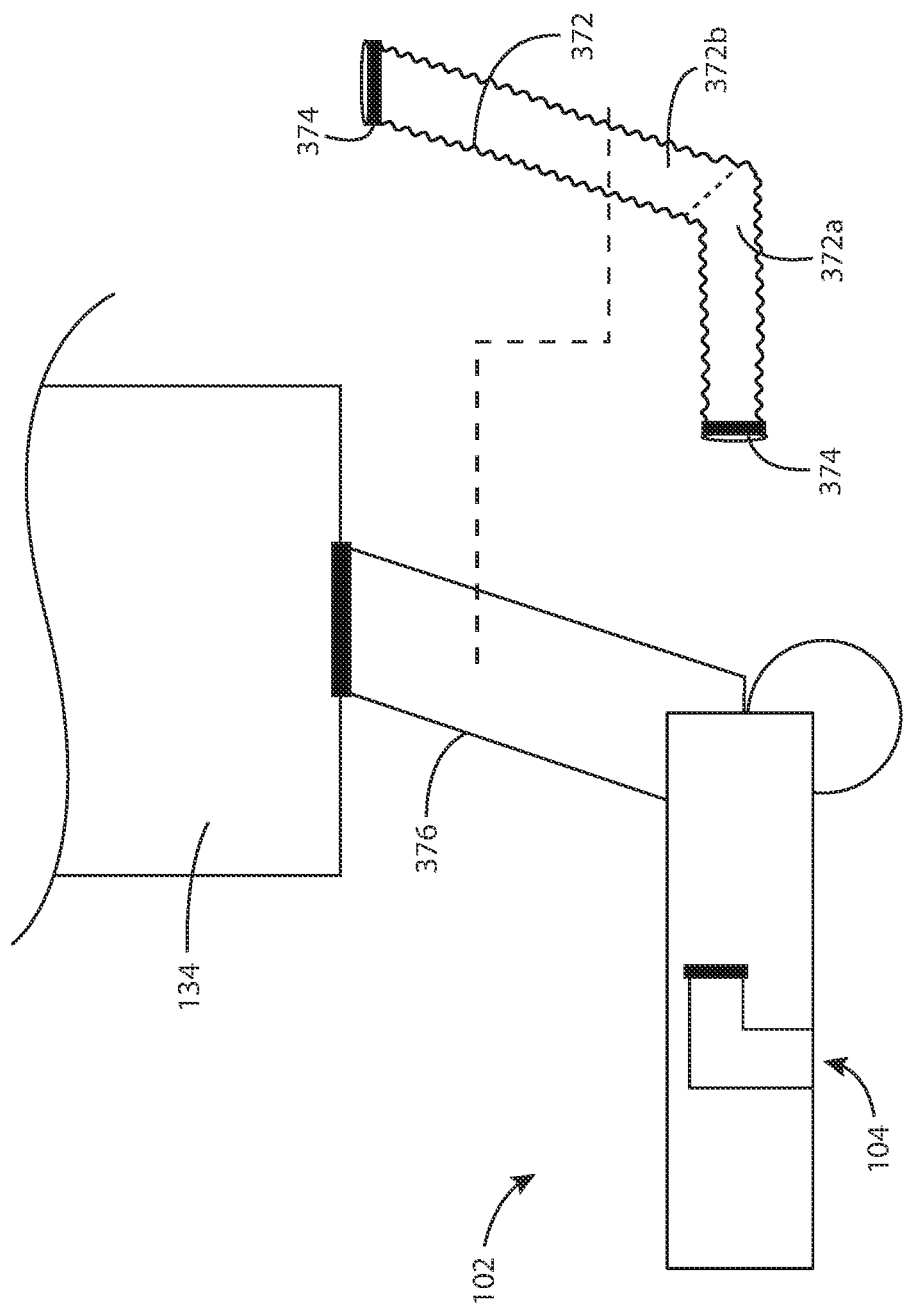
FIG. 63A is a schematic cross-sectional view the portion of the embodiment of a surface cleaning apparatus of FIG. 62, with an air flow path segment removed.

Referring to FIG. 62, a schematic example of a surface cleaning apparatus 100 includes a removable fluid flow path portion that forms the portion of the fluid flow path between the dirty fluid inlet 104 and the momentum separator 140. Referring also to FIG. 63A, the removable portion includes a hose 372 that can be connected to the apparatus using detachable couplings 374 and can be removed when desired. The hose 372 may be one continuous conduit, such as a continuous, flexible hose as illustrated, or may include two or more segments that are detachable from each other (illustrated as an optional lower segment 372a and separately removable upper segment 372b). If the removable portion includes two or more segments, they may have different configurations. For example, one segment may include rigid piping, while another segment may include a flexible hose. In the embodiment of FIGS. 13A and 13B, the removable segment 372 is substantially rigid (i.e. pipe-like configuration), and includes a rigid lower segment 372a connected (optionally removably) to a rigid upper segment 372b.

In this embodiment, the removable segment 372 need not form part of the structural support of the apparatus 100, and may be removably housed in corresponding frames 376 and extend through the pivot joint or other movable connection between the upright section 116 and the surface cleaning head 102.

Alternatively, some or all of the removable segments of the air flow path may be structural, load bearing components. For example, the removable portion may include rigid conduit sections that can be attached together to form part of the upright section 116, surface cleaning head 102, a movable connection joining and supporting the upright section 116 to the surface cleaning head 102. The segments may be joined using any suitable latches, threaded connections, couplings, clips and the like.

Optionally, the removable segment(s) 372 of the fluid flow path may include some, or the entirety of the movable joint that connects the upright section 116 to the surface cleaning head 102 (e.g. one or more pivot joints, rotatory joints and the like that are incorporated into the fluid flow path removable segment 372). Alternatively, removable segments 372 in the surface cleaning head 102 and upright section 116 (if any) may be independently removable, and may be coupled to a non-removable, movable joint. Referring to FIGS. 13A and 13B, in this embodiment the liquid separator 132 is removable from the surface cleaning head 102 as a unit with rigid, pipe-like sections 372 of the fluid flow path upstream from the liquid separator 132, as well as with the pivot joint 109 and a rigid conduit section 372c extending upwardly from the pivot joint 109 (to which the upright section 116 and auxiliary dirty fluid inlet 104a can be mounted). In this embodiment, at least some of the removable segments of the fluid flow path are provided in the surface cleaning head 102, and some removable segments 372a and 372b are upstream from the separator 132 while another removable segment 372c is downstream from the separator 132.

As exemplified in FIG. 13B, the liquid separator may be in the surface cleaning head. Accordingly, all of the flow path from the brush chamber to the liquid separator may be removed, optionally with the liquid separator or liquid reservoir 148 by, e.g., remove the parts upwardly from the surface cleaning head.

A removable portion may be provided in the fluid flow path of any suitable configuration of surface cleaning apparatus, including the embodiments shown in FIGS. 1-16 and 64-66.

Figure 63B:
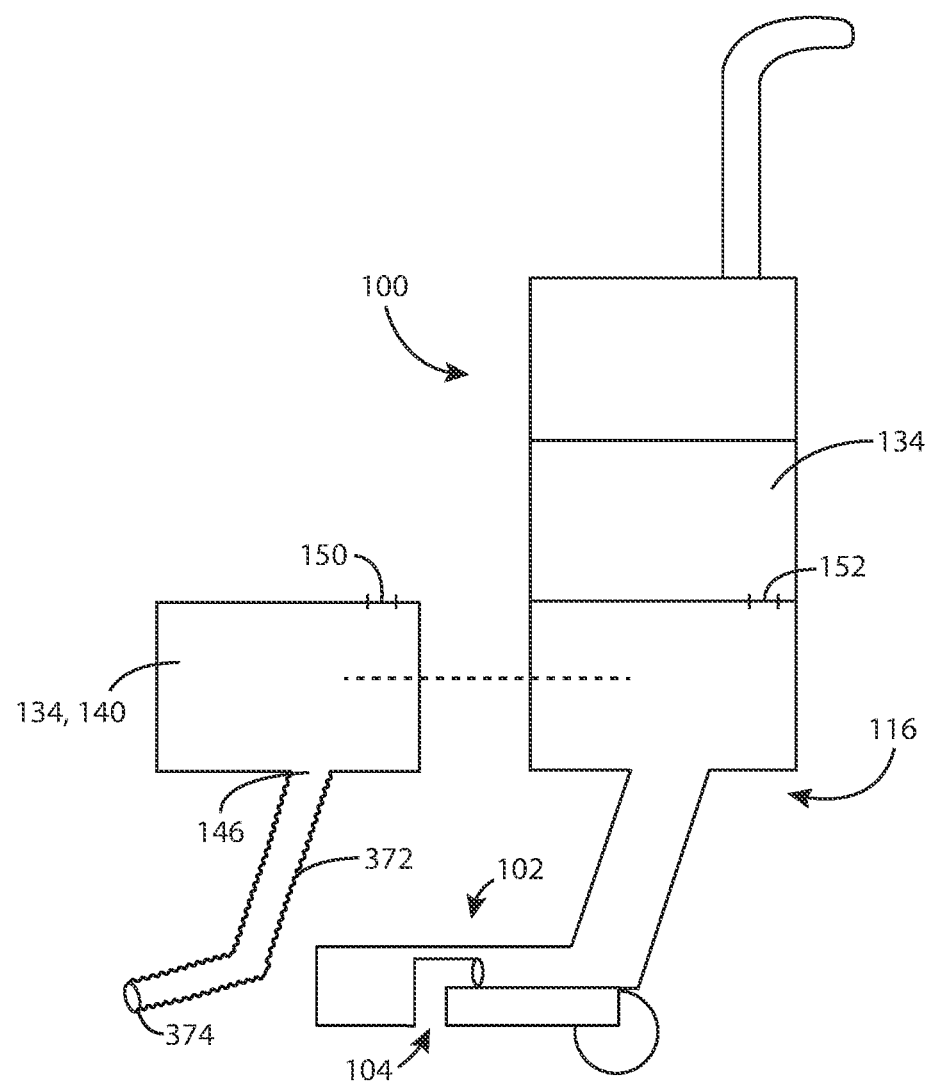
FIG. 63B is a schematic cross-sectional view the portion of the embodiment of a surface cleaning apparatus of FIG. 62, with a separator and an air flow path segment removed.

Optionally, as least some of the fluid flow path, and optionally at least some of the removable segments, such as a removable hose 372 in FIG. 63B can be transparent, which may help a user evaluate the condition of the interior of the fluid flow path without having to remove the segment(s) 372.

Above Floor Cleaning Mode(s)

In accordance with another aspect, which may be used with one or more of the other aspects disclosed herein, the apparatus may include an above floor cleaning mode. These embodiments may be used in combination with any of the other features and/or aspects of any of the dual stage treatment units, single stage treatment units, recline limiting and/or mode controlling apparatuses, liquid delivery systems, surface cleaning heads, apparatuses with openable fluid flow paths and/or above floor cleaning mode(s, and may also utilize features described in relation to embodiments of the hand held surface cleaning apparatuses.

In accordance with this aspect, the surface cleaning apparatus 100 may be operable in at least one above floor cleaning mode, in which air flow communication between the cleaning unit 120 and dirty fluid inlet 104 is interrupted, and one or more auxiliary dirty fluid inlets 104a are utilized as the inlet for the surface cleaning apparatus 100. This may help a user clean furniture, drapes, automobiles and other objects that are above the floor and/or for which the use of the surface cleaning head 102 is not required or desired.

The above floor cleaning mode(s) may be provided by reconfiguring at least a portion of the fluid flow path that was also utilized then operating in the floor cleaning mode (i.e. forms part of the air flow path between the dirty fluid inlet 104 and the cleaning unit 120) or by providing a different fluid flow path (i.e. portions of the fluid flow path between auxiliary dirty fluid inlet 104a and the cleaning unit 120 do not form part of the fluid flow path between the dirty fluid inlet 104 and the cleaning unit 120) or a combination of both.

In particular, an above floor cleaning wand and hose may not be part of the flow path when the apparatus is operated in an extractor mode. For example, when a user uses the apparatus to extract or pick up liquid, the wand and hose may be excluded from the flow path. One advantage of this design is that the wand and hose need not come into contact with water. This can prevent water being present in the wand and hose and causing fowling of the wand and hose and the buildup of odors therein. Also, the flow path to the separation unit may be shortened by excluding the wand and hose, which may reduce the energy required to draw liquid into the separator.

Figure 3:
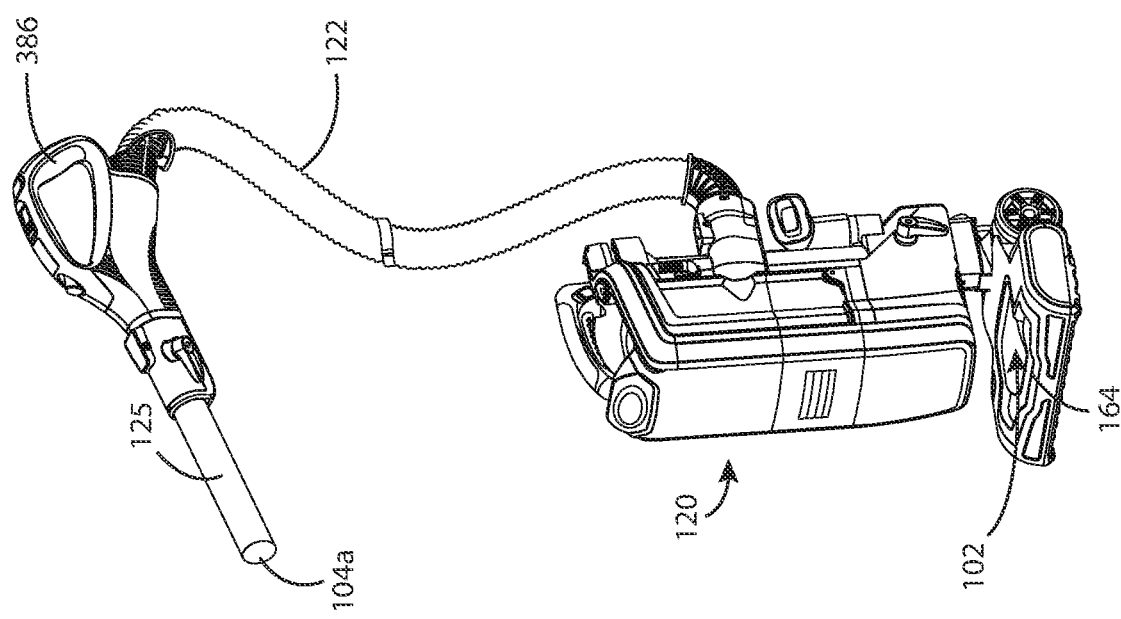
FIG. 3 is a front perspective view of the surface cleaning apparatus of FIG. 1, in an above floor cleaning configuration.

Referring to FIGS. 1-3, the illustrated embodiment of the surface cleaning apparatus 100 has a floor cleaning fluid flow path that is extends between the dirty fluid inlet 104 of the surface cleaning head 102 and the cleaning unit 120 (and the separators therein) and includes a rigid, floor cleaning wand 125 and a hose 122 downstream from the wand 125. In this embodiment, both the wand 125 and hose 122 form part of the floor cleaning airflow path from the surface cleaning head 102 to the clean air outlet 138 (and including the treatment unit 130 and suction motor 124) when arranged in an upright mode as shown in FIGS. 1 and 2.

For above floor cleaning, a user can detach an above floor cleaning member, which in this example includes the wand 125 and hose 122 (FIG. 3), which interrupts the fluid communication between the surface cleaning head 102 and the cleaning unit 120 and utilizes the upstream end of the wand 125 as the auxiliary dirty fluid inlet 104a. Reconfiguring the surface cleaning apparatus 100 in this manner creates an above floor fluid flow path that extends from the second, auxiliary dirty fluid inlet 104a to the clean air outlet 138 and that includes the treatment unit 130 and the suction motor 124. In this embodiment, if a nozzle 164 is provided on the wand, the apparatus 100 may still be used in both the wet and dry suction modes in both floor cleaning and above floor cleaning modes, as both the first and second separators 132 and 134 are included in both the floor cleaning and above floor fluid flow paths.

Figure 4:
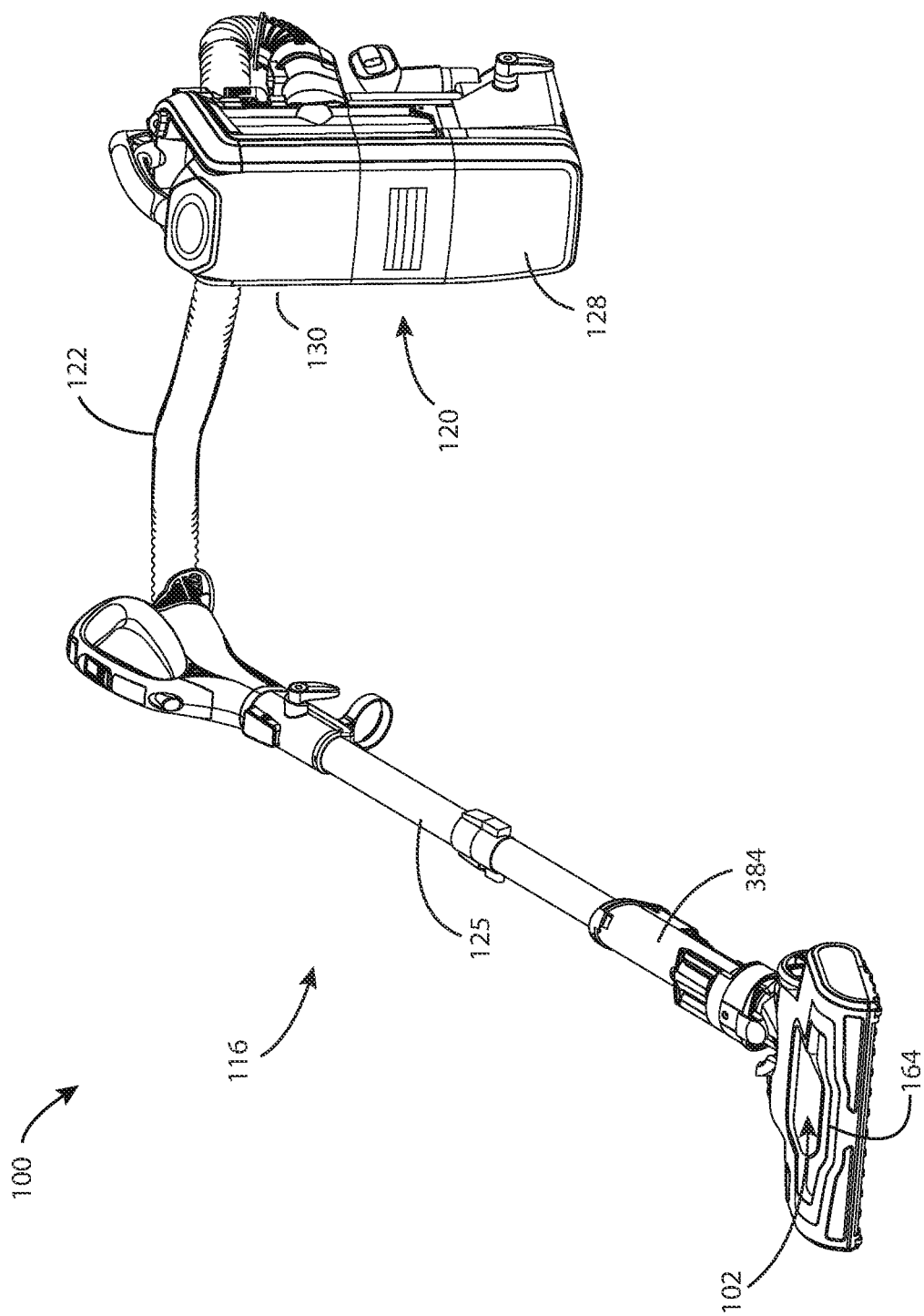
FIG. 4 is a front perspective view of the surface cleaning apparatus of FIG. 1, with a cleaning unit detached.

In this embodiment of FIG. 4, if the delivery system is provided in the surface cleaning head 102 or a cleaning fluid delivery conduit is provided along the length of the wand and hose, then the apparatus 100 may still be used in both the wet and dry suction modes in both floor cleaning and above floor cleaning modes, as both the first and second separators 132 and 134 are included in both the floor cleaning and above floor fluid flow paths.

Alternatively, as illustrated in the embodiment of FIGS. 5 and 6, the apparatus may include a mode selection valve 378 that can help direct the fluid flow through the apparatus 100, and may engage or disengage various portions of the fluid flow paths based on the operating mode. Optionally, the mode selection valve 378 may be provided upstream of the treatment unit 130 or, as shown, may be provided in the flow path between the first and second separators 132 and 134.

In this embodiment, the valve 378 is positioned between the fluid outlet 150 of the first separator 132 (liquid separator) and the inlet 152 of the second separator 134 (dry separator). When operating in a floor cleaning mode (FIG. 5) the valve 378 can be arrange to provide a fluid flow path between the first separator 132 and the second separator 134, but isolate the wand 125 and hose 122 from the floor cleaning fluid flow path. In this example, the apparatus 100 may be used in either a wet or dry operating mode when in the floor cleaning mode as the floor cleaning fluid flow path extends the dirty fluid inlet 104, through the first separator 132 and to an outlet end that is proximate the inlet of the valve 378 (i.e. upstream from the second separator 134) through which the fluid can continue to the second separator 134.

When a user wishes to switch to an above floor cleaning mode (FIG. 6) the user may detach the wand 125, to expose auxiliary dirty fluid inlet 104a, and change the position of the valve 378 (either automatically when the wand is removed or manually) to interrupt the fluid connection between the first separator fluid outlet 150 and the second separator inlet 152 and establish fluid communication between the second separator inlet 152 and auxiliary dirty fluid inlet 104a (including the wand 125 and hose 122). In this embodiment, the above floor fluid flow path extends from the auxiliary dirty fluid inlet 104a on the wand 125, through the hose 122 to an outlet end that is proximate an inlet of the valve 378 through which the fluid can enter the second separator 134 (dry separator), but the first separator 132 is isolated from the above floor fluid flow path.

In this arrangement, the above floor cleaning mode may be limited to generally dry, vacuuming rather than wet suction/extraction, as the liquid separating portion of the treatment unit 130 has been removed from the above floor fluid flow path. The embodiments of the surface cleaning apparatus 100 in FIGS. 15-16A utilizes a single stage treatment unit 130 and can be operated in a similar manner. That is, this embodiment has a mode selection valve 378 that can be positioned in a floor cleaning mode to provide direct fluid communication between the surface cleaning head 102 and the cyclone fluid inlet 152 (FIG. 15). When in this mode, the apparatus can be used for both wet and dry cleaning. To operate in an above floor cleaning mode, the wand 125 can be detached and the mode selection valve 378 can be re-positioned to provide fluid communication between the hose 122 and the cyclone fluid inlet 152 (FIG. 16A). Optionally, this embodiment may be operable in both generally dry, vacuuming and wet suction/extraction when in the above floor cleaning mode as the first separator 132 remains connected and can handle both liquid and solid debris. In this embodiment, the wand 125 and hose 122 are not part of the floor cleaning suction fluid flow path, but are included in the above floor cleaning flow path and can be subjected to wet extraction fluid flows. The wand 125 and hose 122 may optionally be removable for cleaning.

Figure 16C:
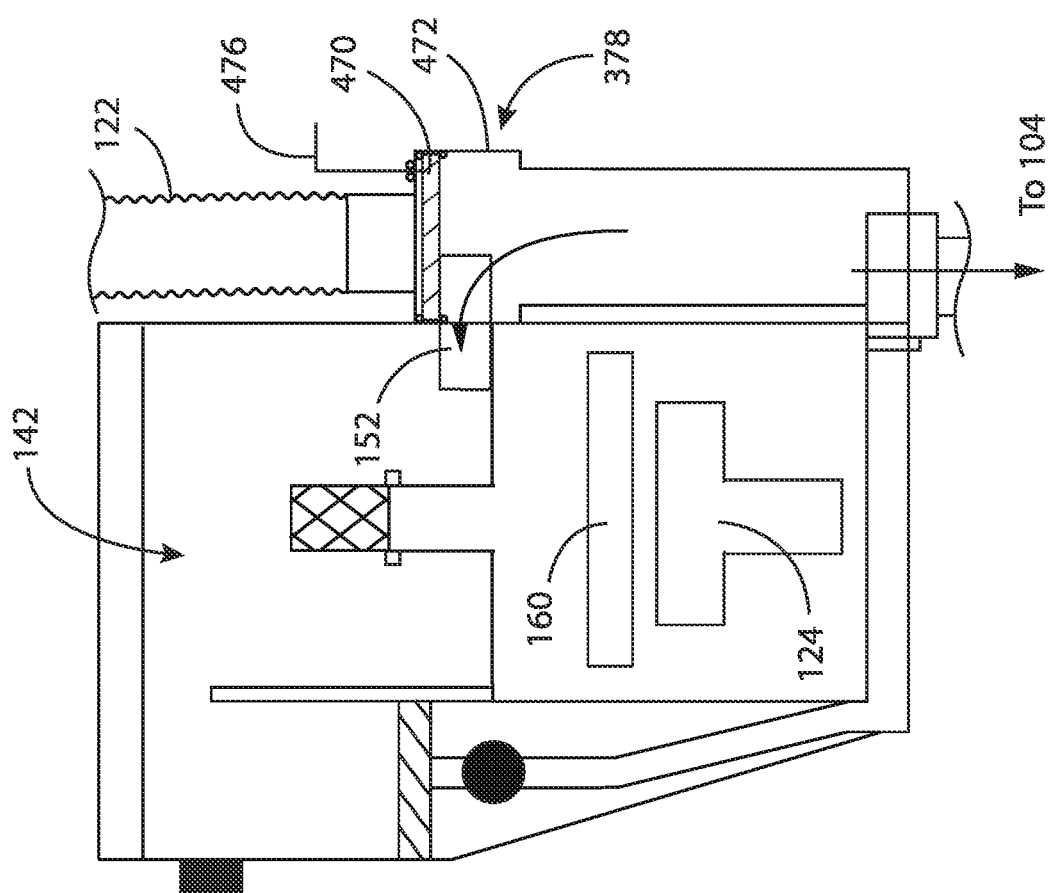
FIG. 16C is a schematic, cross-sectional view of FIG. 16B, with the valve in a second configuration.

Optionally, in any suitable embodiment (including those described herein), the mode selection valve 378 may be manually actuated by a user. Referring to FIGS. 16B and 16C, one embodiment of a valve 378 that is suitable for use with the apparatus 100 described herein is configured as a manually actuated valve. In this example, the valve 378 includes a movable gate 470 that can translate within a housing 472, between a lower position for above floor cleaning (FIG. 16B) in which the cyclone air inlet 152 is in communication with the hose 122, and a second position for floor cleaning (FIG. 16C) in which the cyclone air inlet 152 is in communication with the dirty fluid inlet 104. In this example, the gate 470 is connected to manual valve actuator that includes a driving rod 474, that a user can manually grasp and raise/lower via tab 476.

Figure 16D:
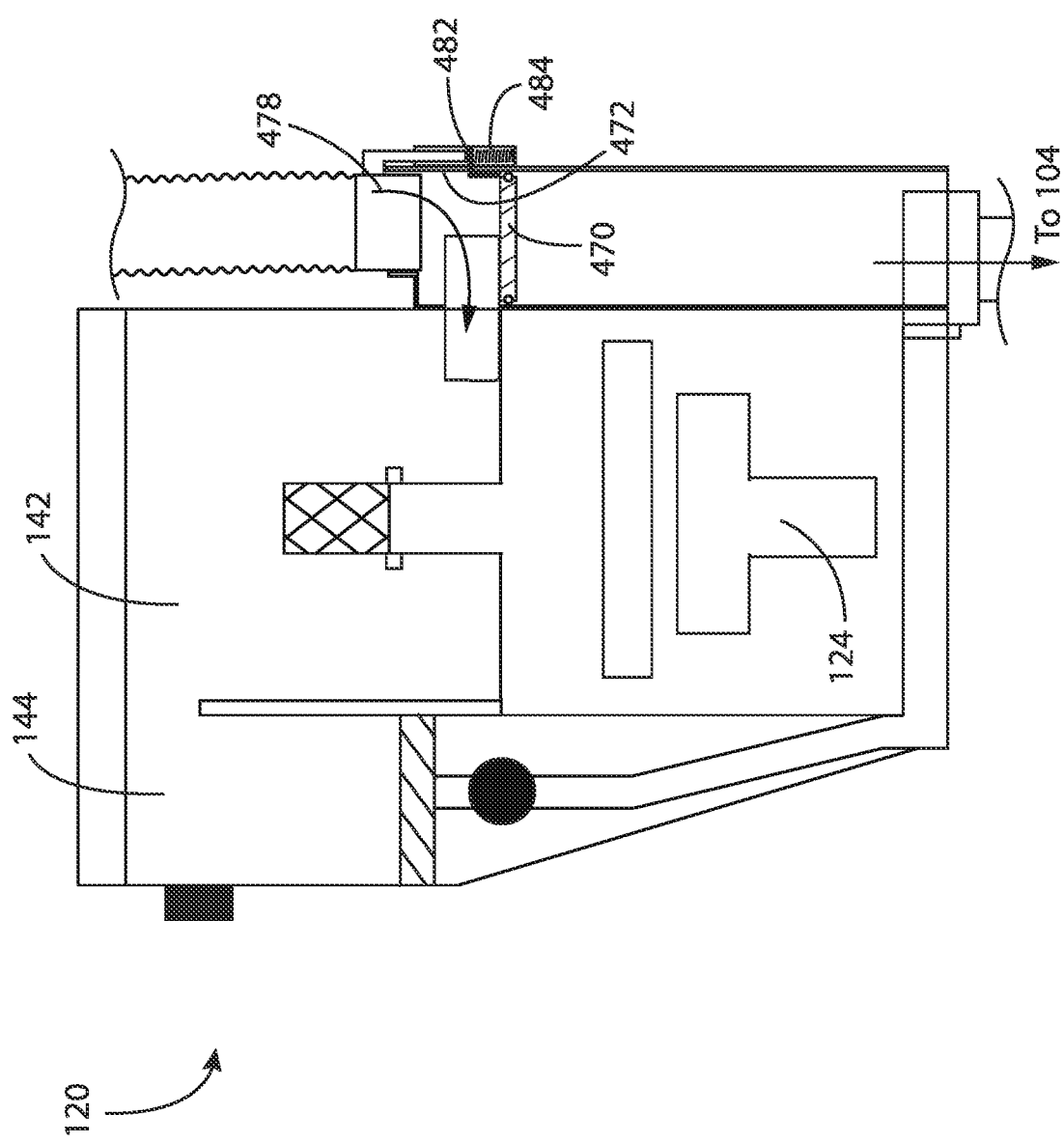
FIG. 16D is a schematic, cross-sectional view of a portion of the surface cleaning apparatus of FIG. 5 with an alternate valve in a first configuration.
Figure 16E:
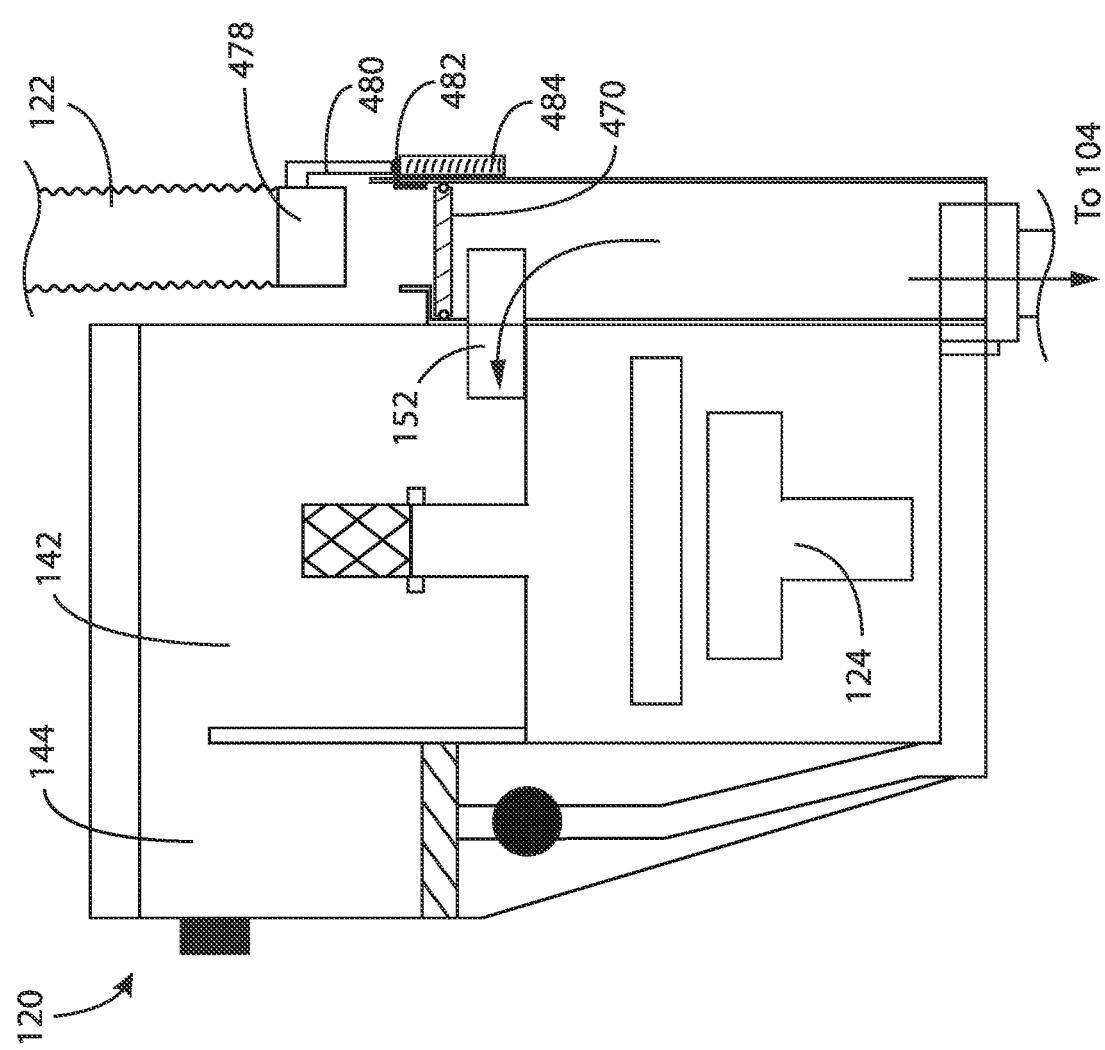
FIG. 16E is a schematic, cross-sectional view of FIG. 16D, with the valve in a second configuration.

Optionally, the mode selection valve 378 may be configured to be automatically actuated by attaching and/or detaching a portion of the surface cleaning apparatus 100, such as a hose, wand, auxiliary cleaning tool and the like. For example, connecting a flexible hose to the cleaning unit 120 or moving the downstream end of a hose, such as for use with above floor cleaning, may automatically re-configured the mode selection valve 378 into an above floor cleaning position, in which air flow communication is established between the hose and the separator, from the floor cleaning position, in which air flow communication is established between the dirty fluid inlet on the surface cleaning head and the separator. Referring to FIGS. 16D and 16E, one example of an automatically actuated mode selection valve 378 includes a movable gate 470 that can translate within a housing 472, between a lower position for floor cleaning (FIG. 16D) in which the cyclone air inlet 152 is in communication with the surface cleaning head 102, and a second position for above floor cleaning (FIG. 16E) in which the cyclone air inlet 152 in communication with the hose 122. In this example, the downstream end of the hose 122 includes a coupling member 478 with a protruding drive member 480. When the coupling member 478 is mounted on an upper end of the housing 472, the drive member 480 bears against a flange 482 that is connected to the gate 470. As the coupling member 478 is seated, the drive member 480 presses on the flange 482 driving it downwardly (as illustrated in this example), thereby shifting the gate 470 downward to its lower position (FIG. 16E) and interrupting air flow between the cyclone inlet 152 and the dirty fluid inlet 104. When the hose coupling member 478 is removed, the gate 470 may be returned to its upper position (FIG. 16D), thereby re-establishing air flow between the dirty fluid inlet 104 and the cyclone air inlet 152.

Optionally, as shown in this example, the mode selection valve 378 may be biased toward one of its operating positions, such as the floor cleaning position as shown in FIG. 16E. In this example, the mode selection valve 378 includes a biasing member in the form of a spring 484 that is compressed when the gate 470 is moved to the above floor cleaning position (FIG. 16E). When the hose coupling member 478 is removed, the biasing force of the spring 484 may help automatically return the gate 470 to the floor cleaning position (FIG. 16D).

Figure 16F:
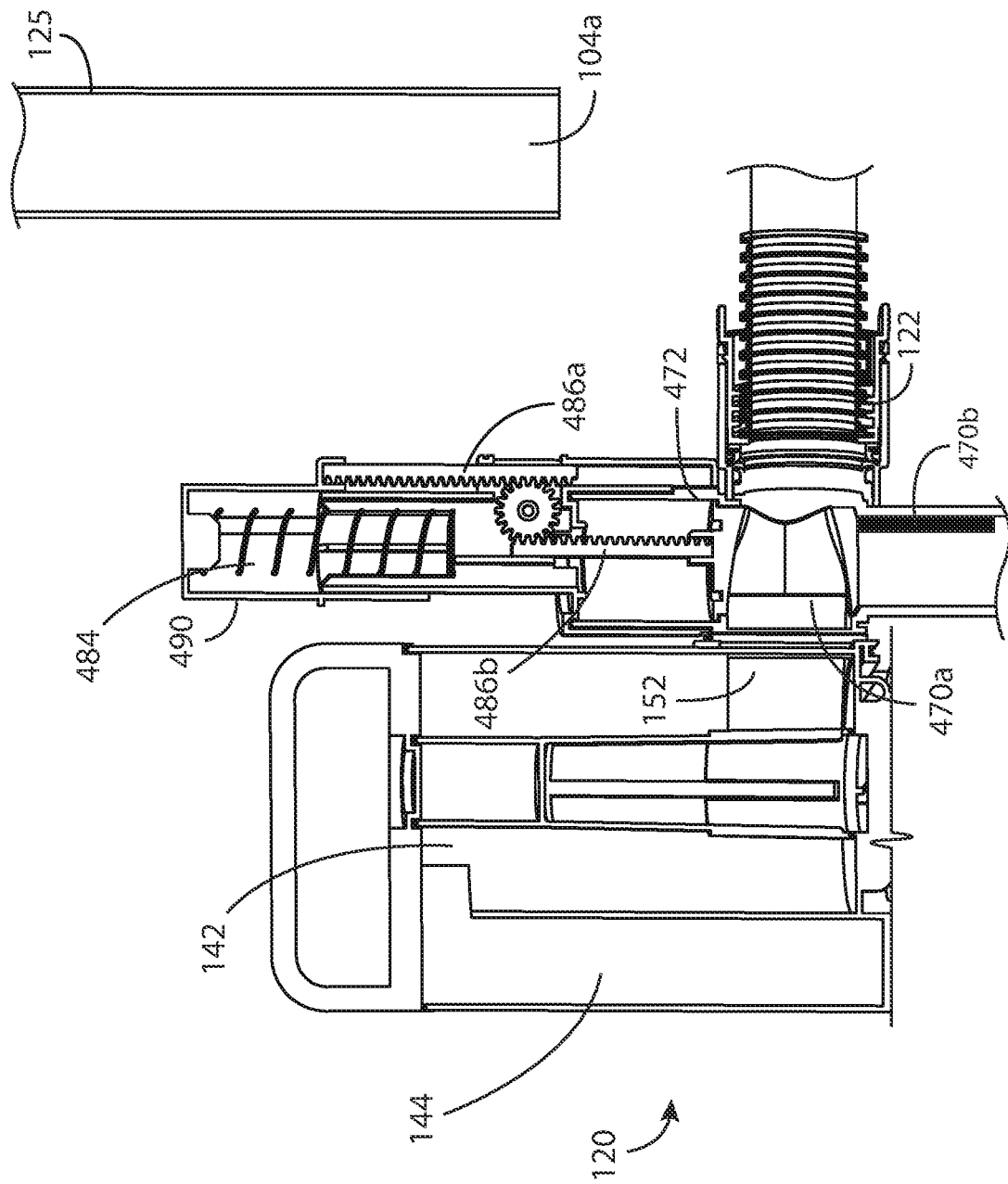
FIG. 16F is a schematic, cross-sectional view of a portion of the surface cleaning apparatus of FIG. 5 with an alternate valve in a first configuration.
Figure 16G:
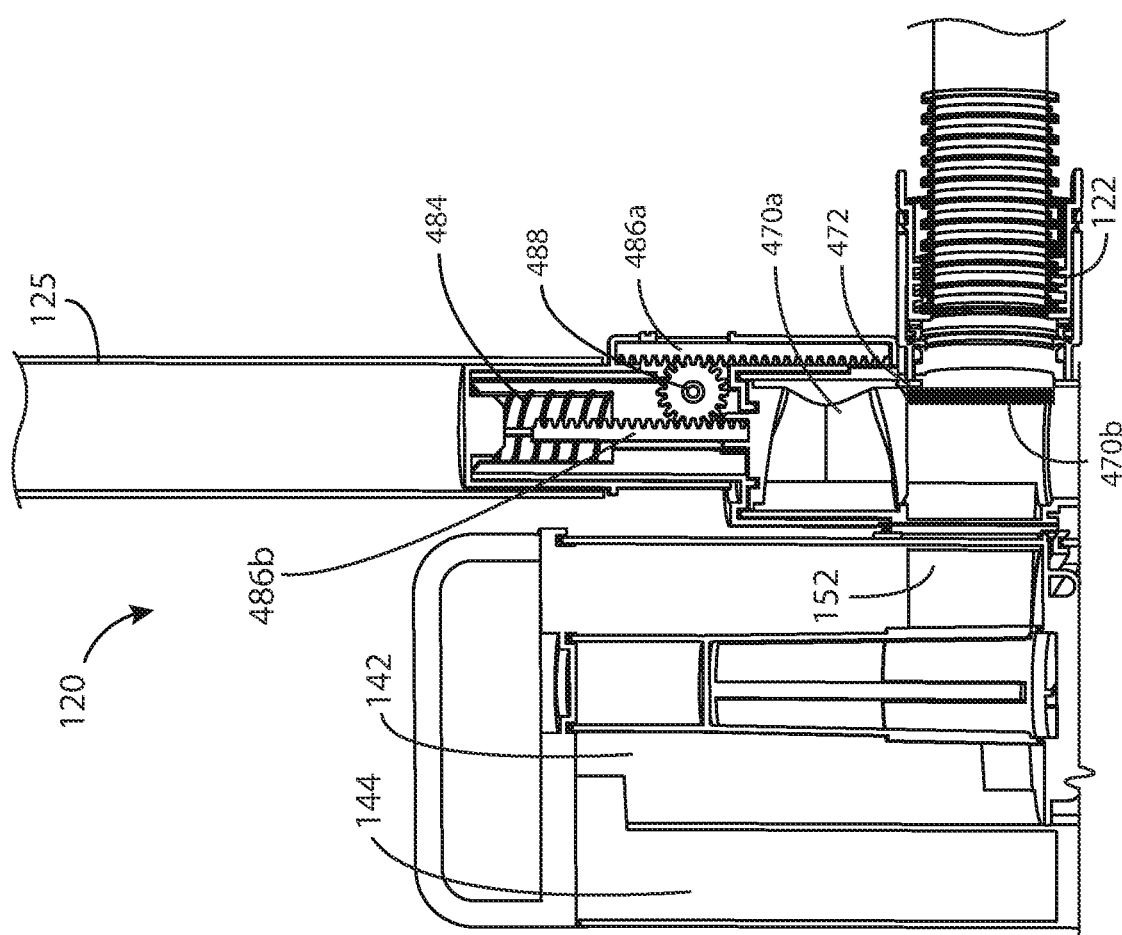
FIG. 16G is a schematic, cross-sectional view of FIG. 16F, with the valve in a second configuration.

Alternatively, the mode selection valve 378 may include a valve actuator that is drivingly connected to the valve 378 and the above floor cleaning member, such as the wand 125 can also be drivingly connected to the valve actuator. Referring to FIGS. 16F and 16G, one example of a mode selection valve 378 is shown can be moved to a floor cleaning position in which the at least the second separator 134 is in flow communication with the first dirty fluid inlet 104 when an inlet, upstream end of the wand 125 is mounted to the upright surface cleaning apparatus (FIG. 16G) and the valve 378 is automatically moved to an above floor cleaning position in which the at least the second separator 134 is in flow communication with the auxiliary dirty fluid inlet 104*a* when the inlet end of the wand 125 is removed from the upright surface cleaning apparatus (FIG. 16F).

In this example, the valve 378 includes a movable gate 470 that can translate within a housing 472, between an lower position for above floor cleaning (FIG. 16F) in which the cyclone air inlet 152 is in communication with the hose 122, and a second, raised position for floor cleaning (FIG. 16G) in which the cyclone air inlet 152 is in communication with the dirty fluid inlet 104. In this example, the gate 470 includes a movable, hollow conduit portion 470*a* and an optional blocking wall 470*b* extending therefrom. When the gate 470 is in the lower position (FIG. 16F) the conduit 470*a* establishes air flow communication between the cyclone air inlet 152 and the downstream end of the hose 122, while concurrently blocking the up flow duct extending to the surface cleaning head and dirty fluid inlet 104. When in the raised position, the conduit 470*a* is removed from the air flow path, providing air flow communication between the dirty fluid inlet and the cyclone air inlet 152, and the blocking wall 470*b* occludes the downstream end of the hose 122, thereby isolating the hose 122 and wand 125 from the fluid flow path. It will be appreciated that a blocking wall 470*b* may not be required to inhibit air flow into the downstream end of hose 122. For example, in the configuration shown in FIG. 16G, the inlet, upstream end of the wand 125 (i.e. auxiliary dirty fluid inlet 104*a*) is mounted to collar 490 (discussed further below), which may effectively seal that end of wand 125 and hose 122. Thus, the downstream end of the hose 122 may be the only opening into the interior of wand 125 and hose 122. Since there is no effective inlet for air entering the upstream end of the hose 122, air may be effectively inhibited or prevented from being drawn out from the downstream opening (outlet) of the hose, even in the absence of a blocking wall 470*b*.

In this example, the gate 470 is moved automatically when the upstream end of the wand 125, which may form the auxiliary air inlet 104*a*, is attached or detached from the cleaning unit 120. This may help automatically reconfigure the air flow path through the apparatus 100 based on whether a user has detached the wand 125 for above floor cleaning, or replaced the wand 125 to resume floor cleaning. In this embodiment, the actuator for changing the configuration of the mode selection valve 378 includes a rack and pinion linkage, having racks 486*a* and 486*b* that engage a common pinion 488. A movable collar 490 is connected to the rack 486*a* and is configured to engage the upstream end of the wand 125. When the wand 125 is in place, it urges the collar 490 downwardly to the position shown in FIG. 16G. When the wand 125 is removed, the collar 490 can be moved upwardly. This moves the rack 486*a* upwardly, which in turn drives the pinion 488 and causes a corresponding, downward movement of rack 486*b* which is coupled to the gate 470. When the collar 490 is fully raised (FIG. 16F), the gate 470 has been moved into its above floor cleaning position. Replacing the wand 125 causes the reverse operation to occur.

Alternatively, a hollow conduit portion 470*a* may not be provided. Instead, blocking wall 470*b* may be configured to pivot. For example, when the movable gate is in a lower position for above floor cleaning, blocking wall 470*b* may be in a generally horizontal orientation in which it occludes the up flow duct extending to the surface cleaning head and dirty fluid inlet 104, while permitting air flow to the cyclone air inlet 152 from the hose 122 (e.g. as shown in FIG. 16F, but with blocking wall 470*b* oriented generally perpendicular to its illustrated orientation). When the movable gate is in a raised position for floor cleaning, blocking wall 470*b* may pivot to a generally vertical orientation, in which the up flow duct is not occluded by the blocking wall 470*b* and the cyclone air inlet 152 is in communication with the dirty fluid inlet 104 (e.g. as shown in FIG. 16G).

Optionally, as shown in this example, the mode selection valve 378 may be biased toward one of its operating positions, such as the floor cleaning position as shown in FIG. 16G. In this example, the mode selection valve 378 includes a biasing member in the form of a spring 484 that is compressed when the gate 470 is moved to the above floor cleaning position (FIG. 16G). When the wand 125 is removed, the biasing force of the spring 484 may help automatically return the gate 470 to its floor cleaning position (FIG. 16F).

It will be appreciated that, in a two stage separation system, the valve may be located at the inlet to the liquid separator and not the inlet to the second stage separator.

Lift Away

In accordance with another aspect, which may be used with one or more of the other aspects disclosed herein, the floor cleaning apparatus may include a detachable cleaning unit 120 that includes a suction motor and at least one separator (optionally the entire treatment unit 130), such that the cleaning unit 120 can be operational as a cleaning apparatus when detached from the rest of the surface cleaning apparatus 100. These embodiments may enable a user to separate the cleaning unit 120 from other portions of the surface cleaning apparatus, such as the surface cleaning head, liquid delivery system, liquid collection container and the like, which may reduce the amount of weight the user has to carry. Optionally, the cleaning unit 120 may be operable in both wet and dry cleaning modes, or in only one of the modes. The modes the cleaning unit 120 can be operated in may depend on the nature of the treatment unit 130, and or individual separators 132 and 134 that are contained in, and removable with the cleaning unit 120. These embodiments having a detachable cleaning unit 120 may be used in combination with any of the other features and/or aspects of any of the dual stage treatment units, single stage treatment units, recline limiting and/or mode controlling apparatuses, liquid delivery systems, surface cleaning heads, apparatuses with openable fluid flow paths and/or above floor cleaning mode(s, and may also utilize features described in relation to embodiments of the hand held surface cleaning apparatuses.

Referring to FIG. 4, this embodiment of the surface cleaning apparatus 100 is configured so that the cleaning unit 120, containing the suction motor 124, in housing 126, and entire treatment unit 130 (whether two stage or one stage) is detachable from the upright section 116 as a portable surface cleaning unit. In this embodiment, both the cleaning unit 120 and wand 125 are mounted to a common support member 384, and may be individually detached (see wand 125 detached while cleaning unit 120 remains attached FIG. 3). This configuration may allow the cleaning unit 120 to remain attached during some above floor cleaning modes (FIG. 3) and to be detached from the upright section 116 while remaining fluidly connected to the surface cleaning head 102 (and without interrupting the fluid communication during the attaching and detaching process). In this arrangement, the surface cleaning apparatus can be used in both wet and dry modes, whether the cleaning unit 120 is attached (FIG. 2) or detached (FIG. 4). This configuration may also reduce the chances of liquid flowing from the momentum separator 140 into the cyclone chamber 142 when the upright section 116 is reclined, as the cleaning unit 120 is physically spaced from the momentum separator 140 and need not be inclined to the same degree as the momentum separator 140 and wand 125. For example, the cleaning unit 120 may remain generally upright, while the wand 125 is reclined (FIG. 4).

Figure 6A:
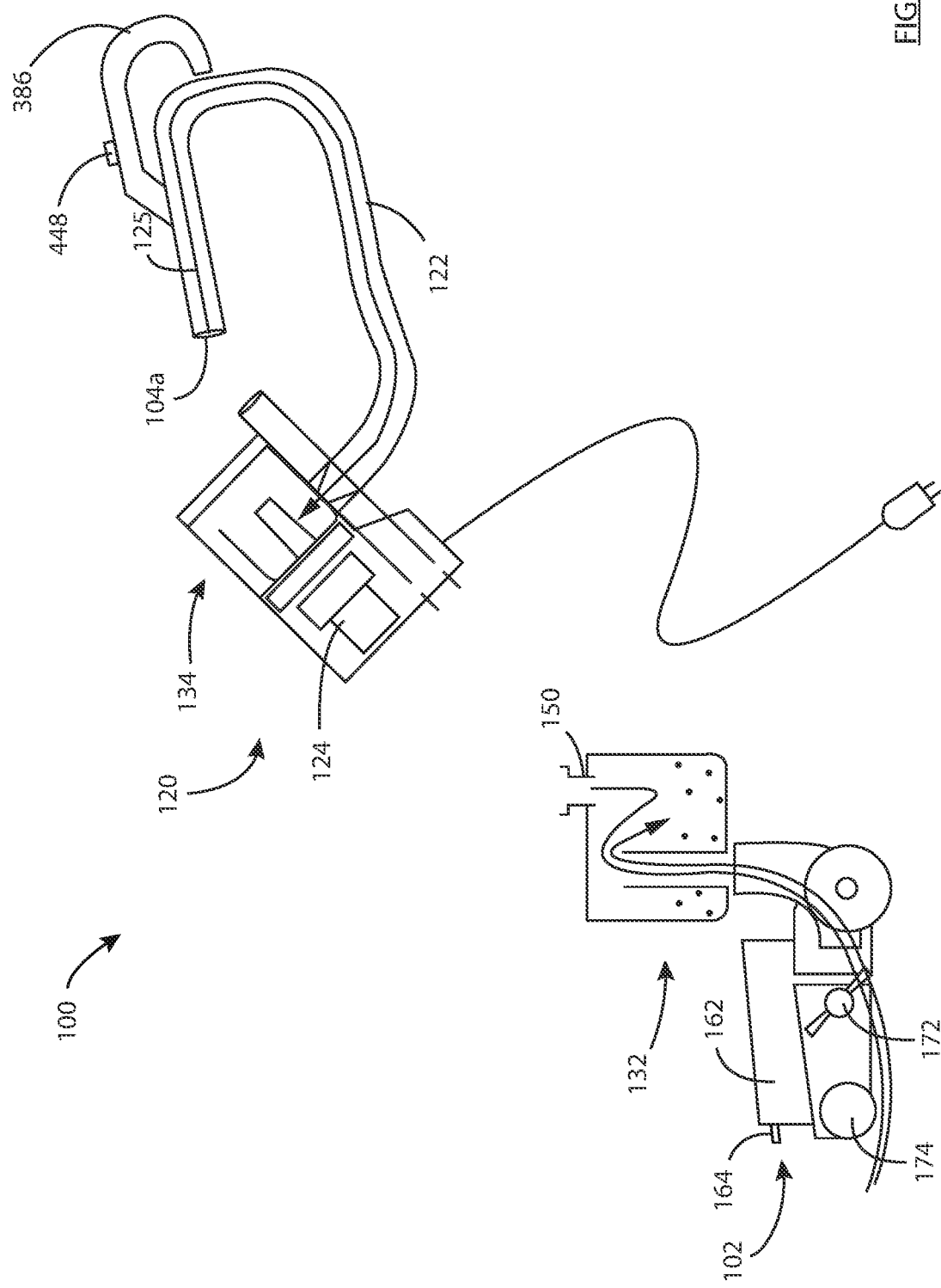
FIG. 6A is a schematic, cross-sectional view of the surface cleaning apparatus of FIG. 5, with a cleaning unit detached.

Referring to FIGS. 6 and 6*a*, another embodiment of a surface cleaning apparatus 100 is configured to have a portable surface cleaning unit 120. In this embodiment, the cleaning unit 120 includes the suction motor 124 and second separator 134 (configured to include a cyclone chamber 142 and solid collection chamber 144) but does not include the first separator 132 (the momentum separator 140). That is, the cleaning unit 120 includes only a portion of the treatment unit, and removing it severs the fluid flow connection between the first and second separators 132 and 134. In this configuration, the relatively heavy liquid that has been collected in the first separator 132 (as well as optionally the clean fluid reservoir(s)) remains attached to and supported by the surface cleaning head 102, while a user can detach and carry only the relatively lighter second, dry separator 134. In this embodiment, the cleaning unit 120 is usable for dry vacuuming, but may not be well suited to wet, liquid extraction as the cleaning unit 120 does not include a wet-type separator. Optionally, this embodiment could be modified to provide the first separator 132, and liquid collection chamber 148, as part of the surface cleaning head 102 instead (such as having the configuration shown in FIG. 13) rather than being provided above the pivot joint on the upright section 116. Such a configuration may help improve the stability of the portions of the surface cleaning apparatus 100 that are left behind when the cleaning unit 120 is removed.

The lift away embodiments may use any of the above floor cleaning embodiments.

Alternately, or in addition, the free end of the wand 125 (including the auxiliary dirty fluid inlet 104*a*) could be configured so that it can be connected to the first separator fluid outlet 150 when the cleaning unit 120 is detached. This may allow the cleaning unit 120 to re-establish fluid communication with the surface cleaning head 102 and first separator 132, while being independently held by the user. This may allow the apparatus 100 to again be used in a wet, extractor mode when the cleaning unit 120 is detached, as the liquid would first be separate by the momentum separator 140 before the incoming dirty fluid travels through the wand 125 and hose 122 and reaches the cyclone chamber 142 in the cleaning unit 120. This configuration may also reduce the chances of liquid flowing from the momentum separator 140 into the cyclone chamber 142 when the upright section 116 is reclined, as the cleaning unit 120 is physically spaced from the momentum separator 140 and need not be inclined to the same degree as the momentum separator 140 and wand 125.

Optionally, the embodiment of FIGS. 5-6*a* may also include any suitable liquid supply system, including those described herein. Portions of the liquid supply system may be mounted in any suitable locations on the surface cleaning apparatus 100, including the upright section 116 and/or surface cleaning head 102. As shown schematically in FIG. 6*a*, this embodiment can be also arranged so that the liquid delivery system, including the liquid reservoir apparatus 162 and nozzle 164, is also included in the surface cleaning head 102. In this configuration, when the portable surface cleaning unit 120 is detached, as shown in FIG. 6*a*, the liquid supply system and first separator 132 can both be left behind. This may further reduce the weight of the cleaning unit 120.

Referring to FIGS. 13A and 13B, this embodiment of the surface cleaning apparatus 100 is configured with the first stage separator 132 (including momentum separator 140) and liquid reservoir apparatus 162 in the surface cleaning head, with the second stage separator 134 (including cyclone chamber 142) and suction motor 124 (i.e. the cleaning unit 120) mounted on the upright section 116. In this arrangement, the upright section 116 can be detached from the surface cleaning head 102 (FIG. 13B) exposing an auxiliary dirty fluid inlet 104*a* on the lower end of the rigid conduit that forms part of the upright section 116. In this arrangement, the portable cleaning unit 120 can be used when separated from the surface cleaning head 102, and the exposed auxiliary dirty fluid inlet 104*a* may be used to directly clean a surface and/or may be connected to any suitable auxiliary cleaning tool, hose, other type of surface cleaning head (e.g. a separate head that does not include the first stage separator 132 and liquid reservoir apparatus 162) or the like.

Referring to FIGS. 15 and 16, this embodiment of the surface cleaning apparatus 100 has a detachable cleaning unit 120 that includes treatment unit 130 with a single stage separator, including cyclone chamber 142, and the suction motor 124, but the liquid collection container 148 and liquid delivery system (including liquid reservoir apparatus 162 and nozzle 164) are provided on and remain with the surface cleaning head 102. In this configuration, removing the cleaning unit 120 interrupts the fluid flow connection between the surface cleaning head 102 (i.e. dirty fluid inlet 104) and the cyclone chamber 142 and also interrupts the liquid communication between the solid collection chamber 144 and the liquid collection container 148. This may help reduce the weight of the cleaning unit 120, as the heavy liquid collection container 148 remains in the surface cleaning head 102. This may further reduce the weight of the cleaning unit 120 when used in a lift-away mode.

Hand Held Surface Cleaning Apparatus

Figure 64:
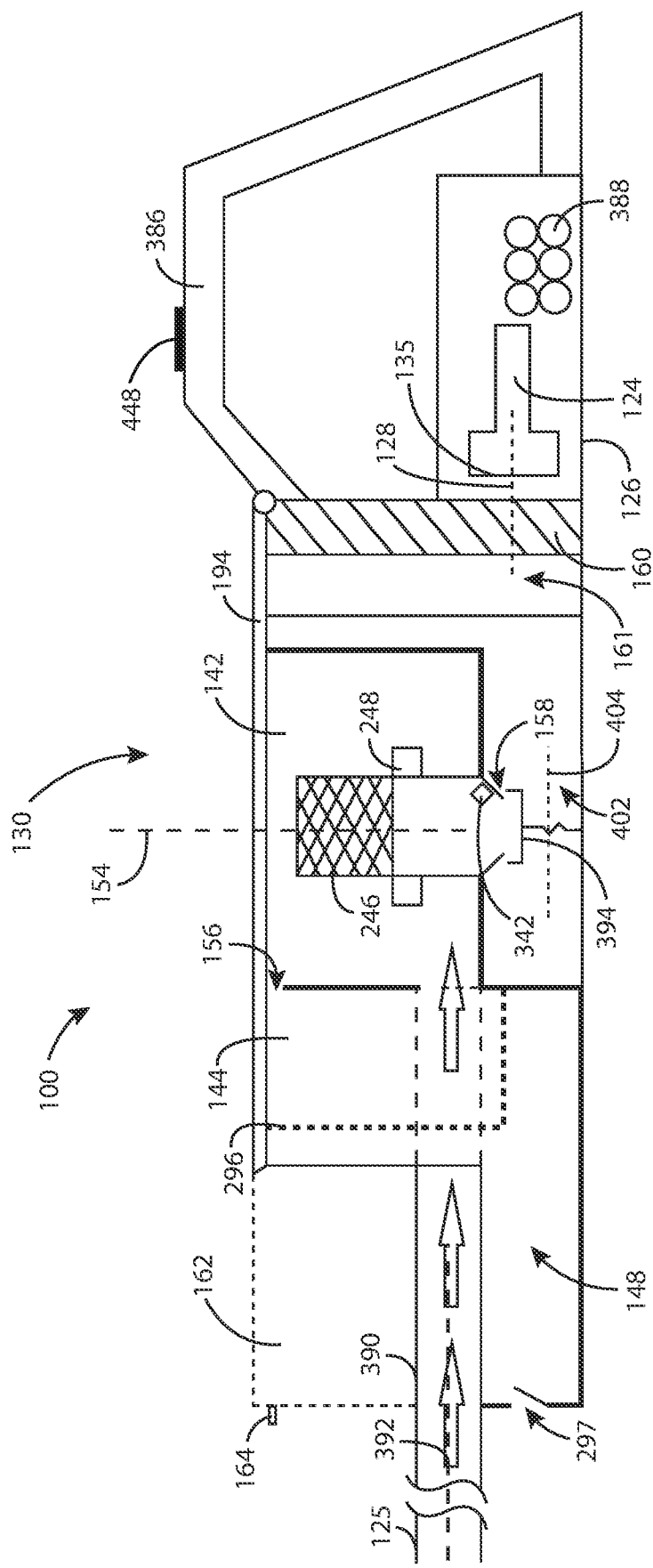
FIG. 64 is a schematic, cross-sectional view of one embodiment of a hand held surface cleaning apparatus.
Figure 65:
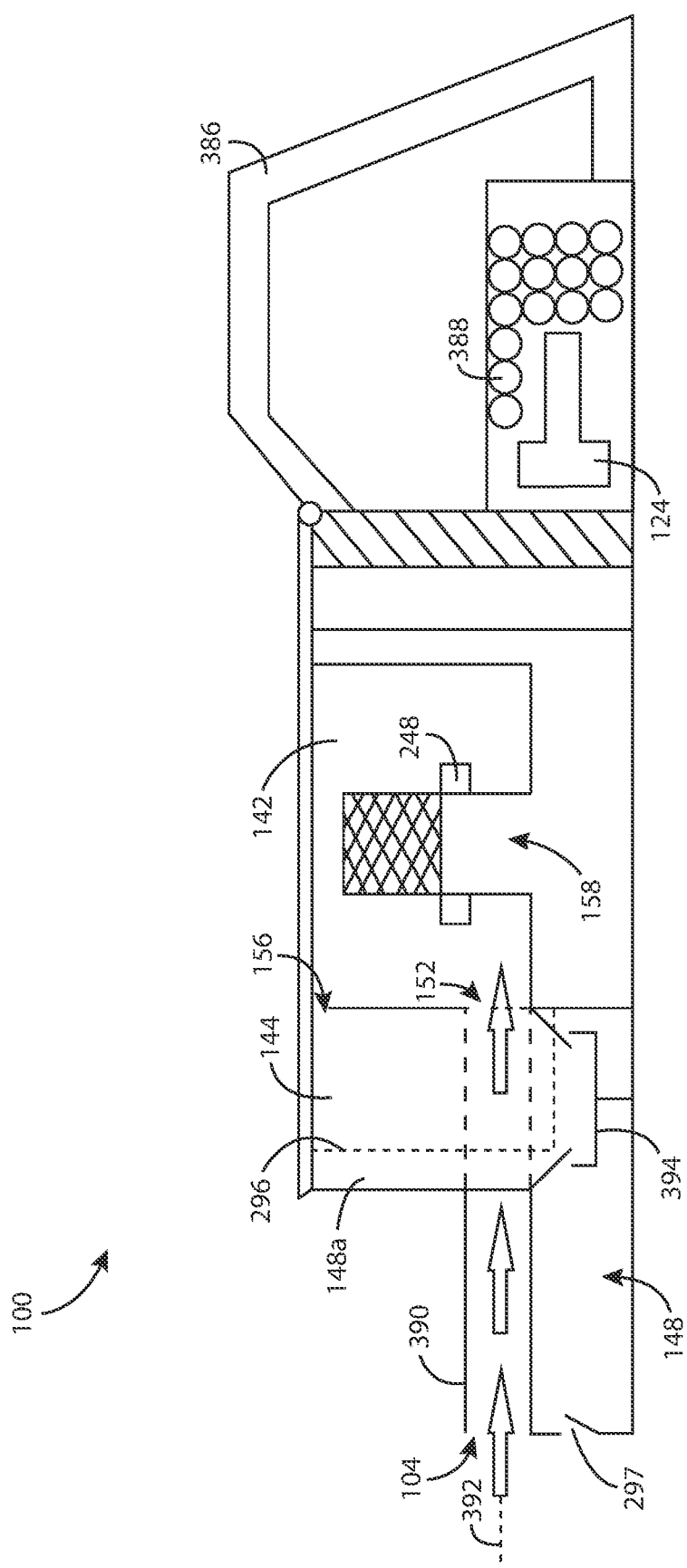
FIG. 65 is a schematic, cross-sectional view of another embodiment of a hand held surface cleaning apparatus.

In accordance with another aspect, which may be used with one or more of the other aspects disclosed herein, the surface cleaning apparatus 100 may be configured as a hand held or hand held surface cleaning apparatus. Some embodiments of hand held surface cleaning apparatuses are illustrated in FIGS. 64 to 66, may have cleaning units 120 and may utilize one or more of the aspects and features described herein, including the treatment units 130 and the like. The hard carryable surface cleaning apparatuses may optionally be connectable to an upper end of wand, such as wand 125 that can be also be connected to a surface cleaning head 102. This may allow the hand held apparatuses to be used in a floor cleaning mode. Optionally, a liquid delivery system may be provided in the surface cleaning head 102 used in combination with the hand held surface cleaning apparatuses illustrated, which may eliminate the need for the weight and complexity of the liquid reservoir apparatus 162 to be incorporated into the hand held structure.

Referring to FIG. 64, a hand held surface cleaning apparatus 100 includes a single stage treatment unit 130, having a cyclone chamber 142 that is suitable for wet separation (e.g. with blocking collar 248), a solid collection chamber 144 and a liquid collection container 148. The suction motor 124 and pre-motor filter 160 are positioned rearward (with respect to the inlet 104) of the treatment unit 130, and a handle 386 provided at the rear end of the apparatus 100. Batteries 388, or any other suitable on board power source, can also be provided to enable cordless operation, or the apparatus may be operated on household current using a power cord. In the illustrated example, the batteries 388 are positioned rearward of the treatment unit 130, and the suction motor 124. This may help provide a desired hand feel to a user and may help reduce the overall size of the hand held surface cleaning apparatus. In other embodiments, the on board power source may be in a different location.

In this embodiment, the dirty fluid inlet 104 is provided at the front end of the surface cleaning apparatus 100, while the handle 386 is provided toward an opposing, rear end of the surface cleaning apparatus (to the right as illustrated in FIG. 64). In this arrangement, the suction motor 124 is positioned rearward of the separator that includes the cyclone chamber 142. This embodiment is also arranged so that the liquid collection container 148 is positioned at the front of the surface cleaning apparatus 100 and the solid collection chamber 144 is positioned rearward of at least a portion, and in the illustrated example, of more than 50% of the liquid collection container 148. When oriented horizontally as exemplified in FIG. 64, the solid collection chamber 144 overlies a portion of the liquid collection container 148. In other embodiments, the solid collection chamber may be entirely rearward of the liquid collection container 148.

The front end of the apparatus includes an inlet passage that includes an inlet conduit 390, extending along an inlet flow axis 392. The inlet conduit 390 may include the dirty fluid inlet 104, and/or may be configured to be connected to the wand 125 and surface cleaning head 102. As exemplified, the inlet flow axis 392 may extend in the generally front/back direction, and is orthogonal to the cyclone axis 154.

The top of the apparatus 100 can include the openable lid 194, which may be opened to provide simultaneous access to the cyclone chamber 142, solid collection chamber 144 and liquid collection container 148. An optional drain 297 may also be provided to assist with emptying the liquid collection container 148. Alternately, the separation unit and/or the collection chambers 144, 148 may be removable.

In the embodiments shown in FIGS. 64-66, the cyclone chamber 142 is oriented so that the rotation axis 154 of the cyclone chamber is generally vertical when the inlet flow axis 392 is generally horizontal. In this arrangement, the cyclone chamber 142 can be considered to be generally vertically oriented when the surface cleaning apparatus 100 is positioned so that the inlet flow axis 392 is horizontal (as illustrated in FIG. 64). When in this position, the separated element outlet 156 maybe located toward the upper end/top of the cyclone chamber 142, and the other operating components of the surface cleaning apparatus 100 (such as the suction motor 124, batteries 388) may be positioned below the separated element outlet 156.

In the embodiment of FIG. 64, the air flow path through the surface cleaning apparatus 100 includes an upstream portion (between the dirty fluid inlet and the cyclone chamber 142) and a downstream portion that extends from the cyclone chamber air outlet 158 to the suction motor 124. This downstream portion can include a pre-motor filter chamber 161 and a pre-motor filter 160, and may have a generally rearwardly extending conduit portion 402 that may extend along a flow axis 404 and air travelling through the conduit portion 402 may therefore tend to travel in the axial direction. As in the illustrated embodiment, the flow axis 404 may be generally parallel to the inlet flow axis 392 and to the axis of rotation 128 of the suction motor 124.

In any embodiment, and preferably in a hand surface cleaning apparatus embodiment, to help prevent inhibit backflow from the treatment unit 130 into the suction motor, a blocking member, such as the valve 394 (which may be a one way valve such as a check valve) in FIG. 64 can be provided in the fluid flow path upstream from the suction motor 124. The valve 394 can be operable to automatically close and seal the fluid flow path under given conditions. In this embodiment, the valve 398 is provided at the cyclone chamber air outlet 158 from the cyclone chamber 142, and can be triggered if a sensor, e.g., a moisture sensor 342, detects a threshold level of moisture or liquid in the fluid exiting the cyclone chamber 142 or if a float switch or other orientation sensor detects that the apparatus is in an orientation in which liquid may flow from reservoir 148 into the cyclone chamber.

Alternatively, as shown in the embodiment of FIG. 65, the blocking valve 394 may be provided in the liquid collection container 148 to help prevent the back flow of liquid from the liquid collection container 148 into the upright section 148a and/or solid collection chamber 144. Alternately, the blocking member may be provided in solid collection chamber 144.

Optionally, as shown in the embodiments of FIGS. 64-66A, the hand held surface cleaning apparatus can be configured such that the separated element outlet 156 is at or at least located toward the upper end of the cyclone chamber 142, and toward the upper end of the hand held cleaning apparatus 100 when it is resting on a horizontal surface (as illustrated in the Figures). In this configuration, the separated element outlet 156 may be position above most, if not all of the other operating components of the hand held cleaning apparatus 100. That is, the other operating components, such as the suction motor 124, cyclone chamber 142, separated liquid collection container 148 (or at least substantial portions thereof), inlet passage 390 and the like are at a position that is generally below the separated element outlet 156. This may help reduce the likelihood of solid and/or liquid debris passing backward through the separated element outlet 156 (i.e. back into the cyclone chamber 142) when the hand held cleaning apparatus 100 is in a horizontal orientation.

Hand Held Surface Cleaning Apparatus with Enlarged Liquid Collection Container

Alternately or in addition to having a blocking member, a hand held apparatus may have a liquid collection reservoir with an overflow tank portion to store recovered liquid when the apparatus is inclined during use.

Figure 66A:
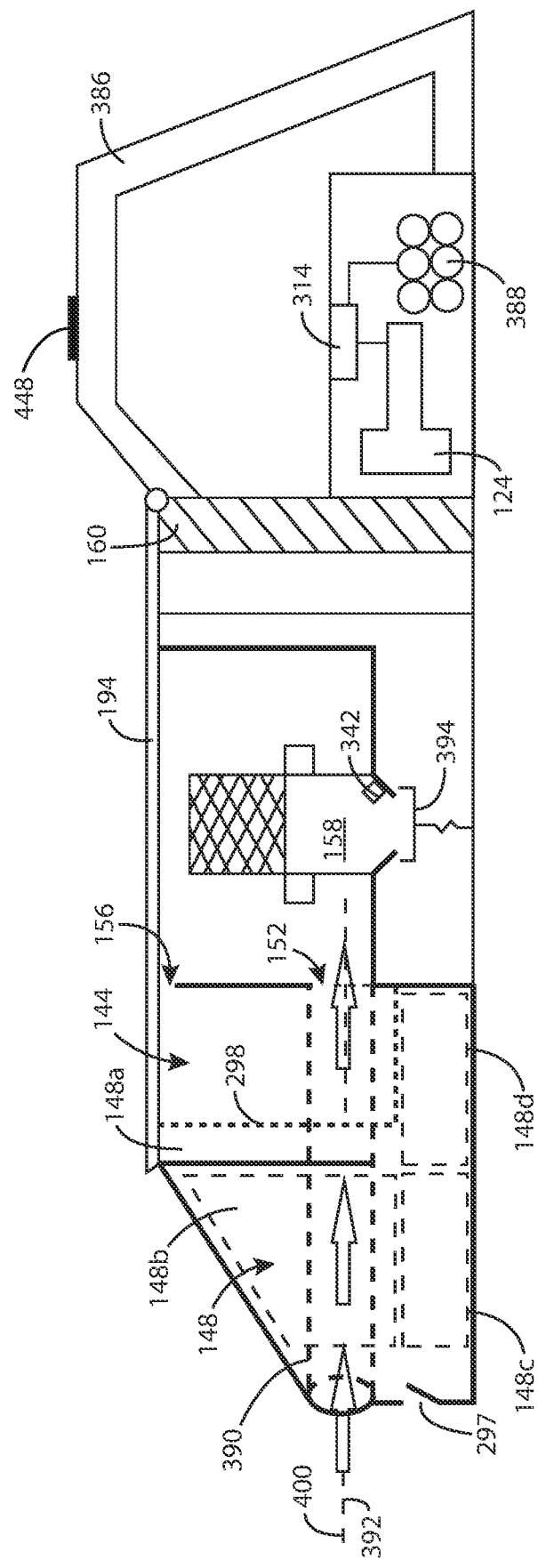
FIG. 66A is a schematic, cross-sectional view of yet another embodiment of a hand held surface cleaning apparatus.
Figure 66B:
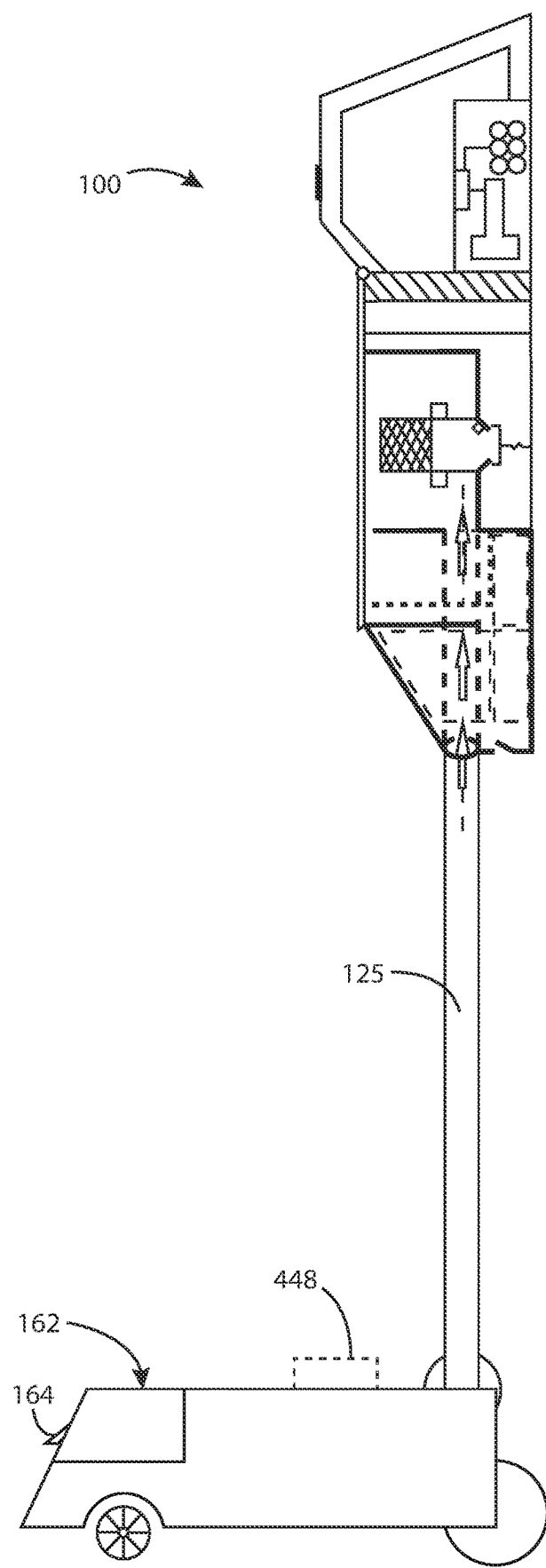
FIG. 66B is a schematic cross-sectional view of the hand held surface cleaning apparatus of FIG. 66A in an upright storage configuration.
Figure 66C:
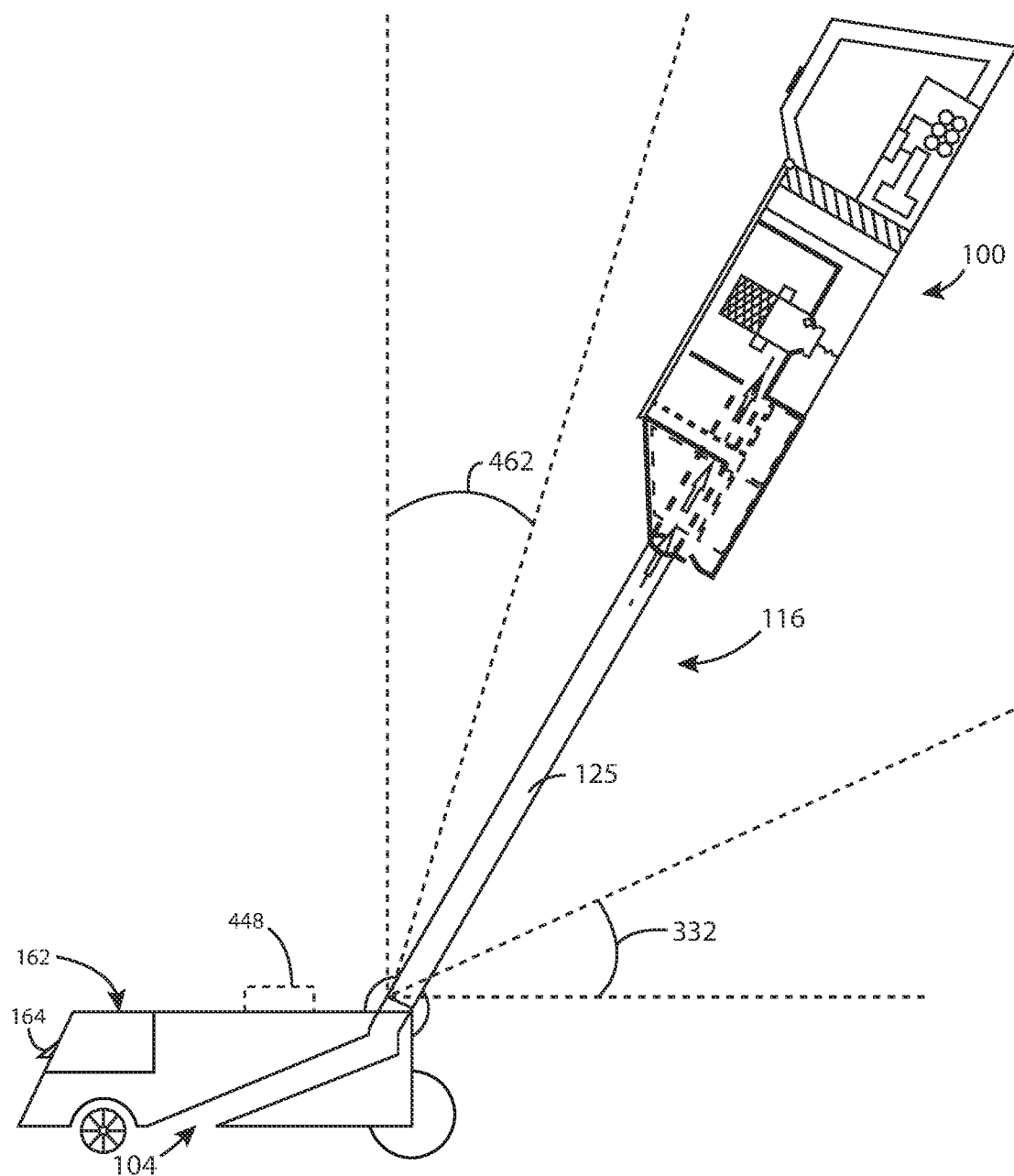
FIG. 66C is a schematic cross-sectional view of the hand held surface cleaning apparatus of FIG. 66A in a floor cleaning configuration.

Referring to FIGS. 66a-66c, another embodiment of a hand held surface cleaning apparatus 100 is similar to the embodiment of FIG. 64, but includes an enlarged liquid collection container 148. In this embodiment, the liquid collection container 148 includes a first portion 148b that is positioned toward the front of the apparatus 100, a second portion 148c and a third portion 148d. In this embodiment, the liquid collection container 148 is configured so that when the hand held surface cleaning apparatus 100 is in a generally vertical orientation (e.g. when the inlet flow axis 392 is generally vertical and/or when the cyclone axis 154 is generally horizontal), the first portion 148*b* is positioned to underlie the separator (i.e. cyclone chamber 142), the second portion 148*c* would be laterally (rearwardly) spaced from the first portion and positioned below (i.e. at a lower elevation but optionally not underlying) the separator and the third portion 148*d* would be positioned above the second portion 148*c* (and extends along a side of the solid collection chamber 144). To help facilitate this arrangement, the inlet conduit 390 may extend through, or may at least be partially surrounded by the liquid collection container 148.

The first, second and third portions 148*b*, 148*c* and 148*d* may be provided as generally separate chambers or volumes that are connected by ports, apertures, flow lines and the like. Alternatively, some or all of the first, second and third portions 148*b*, 148*c* and 148*d* can be portions of a substantially contiguous volume (as illustrated in this embodiment), and need not be separated by walls or other sub-divided structures.

In this embodiment, if the hand held surface cleaning apparatus 100 is used in a floor cleaning mode, the front end will tend to be downward facing when in use. When the hand held surface cleaning apparatus 100 is used in this manner, the separated liquid may tend to collect primarily win the first portion 148*b* and the second portion 148*c*, after having passed through the solid collection chamber 144, divider 298 and third portion 148*c*. the upper end of portions 148*b* and *c* may define or have marked thereon a "maximum fill line". This is an indication to a user not to operate the apparatus when the portions 148 *b* and 148*c* are full. If the hand held surface cleaning apparatus 100 is moved in to a generally vertical storage position (FIG. 66B), the collected liquid may tend to collect primarily win the first portion 148*b* and the second portion 148*c*. As the apparatus is reclined rearwardly, liquid will tend to flow rearwardly and some of the liquid in portion 148*b* will tend to fill portion 148*d*. If the apparatus is further reclined into a generally horizontal position (as shown in FIG. 66A, with the cyclone axis 154 generally vertical), such as being rested on a surface or table, separated liquid that was retained in portion 148*b* when the apparatus is in the vertical orientation will collect in the third portion 148*d*. Accordingly, providing a third portion in this manner may help serve as an overflow region in the liquid collection container 148, and may help prevent separated liquid from flowing from the first portion 148*b* back into the solid collection chamber 144 and/or cyclone chamber 142.

Optionally, the liquid collection container 148 can be configured so that the volumes of the first and third portions 148*b* and 148*d* are generally the same, or are within about 10%, about 20%, about 25%, about 30%, about 40% and/or about 50% of each other. That is, the third portion 148*d* may be configured so that it has at least 50%, 60%, 70%, 80%, 90% and/or 100% of the volume of the first portion 148*b*. In the illustrated embodiment, the third portion 148*d* has about the same volume as the first portion 148*b*. This means that if the combination of the first portion 148*b* and second portion 148*c* is substantially filled when the hand held surface cleaning apparatus 100 is in use (i.e. generally vertical or reclined in use), the separated liquid may tend to flow into, and can substantially entirely be accommodated within the combination of the second portion 148*c* and the third portion 148*d* if the apparatus 100 is rested on a horizontal surface (such as for storage). This may help prevent the liquid from flowing back into the upright section 148*a* and/or solid collection chamber 144. For example, if when the surface cleaning apparatus 100 is in a vertical orientation and the first and second portions 148*b* and 148*c* are full with separated liquid the third portion 148*d* may be substantially empty. This may be considered to be a "full" liquid collection container 148 (i.e. triggering an alert to the user and/or disabling the suction motor 124), even though some space remains in the third portion 148*d*. When the surface cleaning apparatus 100 is then moved to a horizontal orientation, the separated liquid can be contained in the second and third position 148*c* and 148*d* such that an upper surface of the separated liquid is positioned below the separated element outlet 156.

In this embodiment, substantially all of the primary portion 148*b* of the liquid collection container 148 is located forward of the solid collection chamber 144 and the cyclone chamber 142. In this embodiment, a plane 400 that extends in the generally forward/rearward direction will intersect the liquid collection container 148, the solid collection chamber 144 and the cyclone chamber 142, as well as the handle 386 and a portion of the housing containing the suction motor 124. In other embodiments, the plane 400 may also intersect the motor 124 and batteries.

Optionally, in addition to having a liquid collection container 148 that includes the first, second and third portions 148*b*, 148*c* and 148*d* as illustrated, this embodiment of the surface cleaning apparatus 100 may also include a valve that is the liquid flow connection between the solid collection chamber 144 and the liquid collection container 148, such as by incorporating the valve 394 (which may be a one way valve such as a check valve) that is shown in such a position in the embodiment of FIG. 65. In such a configuration, the valve 394 may provide flow communication between the solid collection chamber 144 and the third portion 148*d* of the liquid collection container 148. The valve 394 may be configured to automatically close as the surface cleaning apparatus 100 approaches a horizontal orientation (using a mechanical actuator and/or in response to a signal issued by the inclination sensor 314), which may provide an additional barrier to the separate liquid flow backward from the liquid collection container 148 and into the solid collection chamber 144 and/or cyclone chamber 142.

Hand Held Surface Cleaning Apparatus with Liquid Delivery System

Optionally, a surface cleaning apparatus 100 that is configured as a hand held surface cleaning apparatus may also include a liquid delivery system for delivering liquid to the surface to be cleaned. In such embodiments, the hand held cleaning apparatus may include any suitable liquid reservoir apparatus 162, delivery nozzle 164, actuator (such as a switch 448) and the like.

For example, in the embodiment of FIG. 64A the hand held surface cleaning apparatus 100 is illustrated with an optional liquid reservoir apparatus 162 (which may be provided at the front end of the hand held surface cleaning apparatus 100) and deliver nozzle 164 that is provided at the front end of the hand held surface cleaning apparatus 100, adjacent the inlet conduit 390 (inlet conduit 390 may extend through reservoir 162. In this configuration, the liquid delivery system may be removable from a wand 125 and carryable with the hand held surface cleaning apparatus 100, and may be used when the hand held surface cleaning apparatus 100 is used for above floor cleaning and the like.

In another embodiment, as shown in FIGS. 66A-66C, the hand held surface cleaning apparatus 100 may be configured so that the liquid delivery system, or at least the liquid reservoir apparatus 162 and delivery nozzle 164, may be provided on the surface cleaning head 102 that is configured to be used in combination with the hand held surface cleaning apparatus 100 and rigid extension wand 125. In this arrangement, the weight of the liquid reservoir apparatus 162 can be supported by the surface cleaning head 102, which may reduce the weight felt by the user manipulating the hand held surface cleaning apparatus 100. The actuator for controlling the liquid delivery system, such as the switch 448, may be provided on the hand held surface cleaning apparatus 100 (as shown in FIGS. 66A and 64) or alternatively, a switch or other such actuator may be provided on the surface cleaning head 102, such as shown by optional switch 448 shown in FIGS. 66B and 66C. Optionally, the switch 448 on the surface cleaning head 102 may be configured as a foot-actuated lever, button or the like such that at use can trigger the liquid delivery system using her foot.

Any of the embodiments of the liquid delivery systems described herein may be used in combination with any of the hand held cleaning apparatuses described herein.

Recline Limiter System

In accordance with another aspect, which may be used with one or more of the other aspects disclosed herein, an apparatus 100 may include a recline limiter system that can be used in upright-style surface cleaning apparatuses to help limit degree of inclination of the upright section of the apparatus. These recline limiter systems may be used in combination with any of the other features and/or aspects of the surface cleaning apparatuses described herein, including any of the dual stage treatment units, single stage treatment units, liquid reservoir units, surface cleaning heads, apparatuses with openable fluid flow paths, above floor cleaning mode(s) and/or lift away configurations, and may also utilize features described in relation to embodiments of the hand held surface cleaning apparatuses.

In upright embodiments, the treatment unit 130, and specifically the liquid collection container 148, may be provided on the movable, upright section 116 of the surface cleaning apparatus 100. In such embodiments, it may be desirable in some instances to limit how much the upright section 116 is inclined when the apparatus is in use, as the farther the upright section 116 is inclined the chances of unwanted liquid flowing back into the separator, and then to the suction motor, may increase, and/or the efficiency and functionality of the treatment unit 130 (including a cyclonic separator and/or a momentum separator or the like).

Optionally, the desired degree of inclination may be based on the operating mode of the apparatus, and/or the presence or absence of liquid in the liquid collection container 148. For example, the upright section 116 may be permitted to recline to a first position when operating in a dry, vacuum mode, but may be limited to a smaller amount of recline to a second position when operating in a wet pick-up or extractor mode, or if liquid is being held in the liquid collection container 148.

The recline limiter system may include mechanical components, electrically actuated components and a combination of both, including one or more blocking members that can be triggered/deployed to inhibit rearward inclination of the upright section 116 beyond a particular recline angle. The recline limiter system may be automatically controlled, for example based on the inclination or position of the upright section 116 or the presence of moisture, and/or may be manually engagable by a user.

Figure 43:
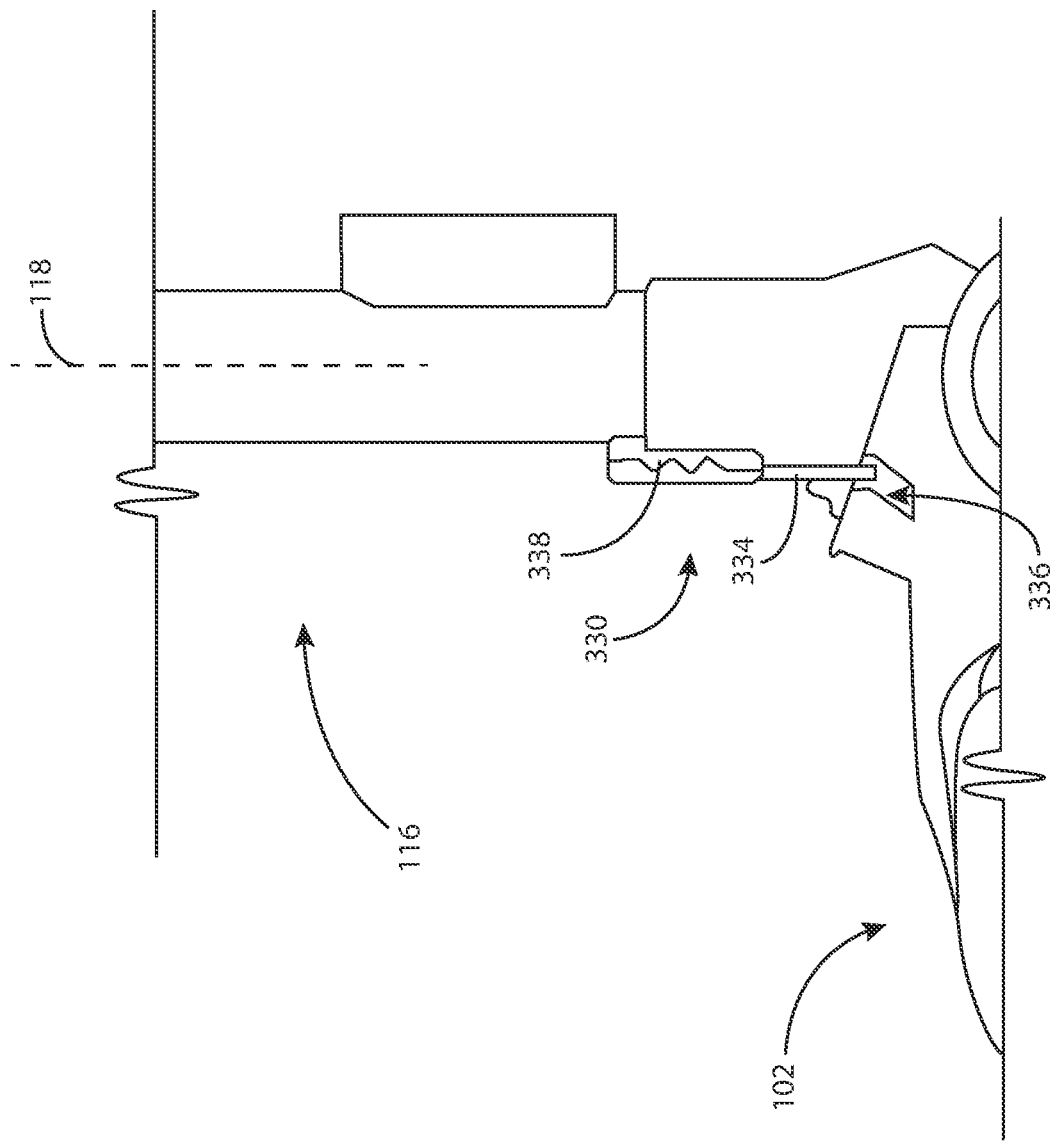
FIG. 43 is a schematic cross-sectional view of a portion of another embodiment of a surface cleaning apparatus in an upright position.
Figure 44:
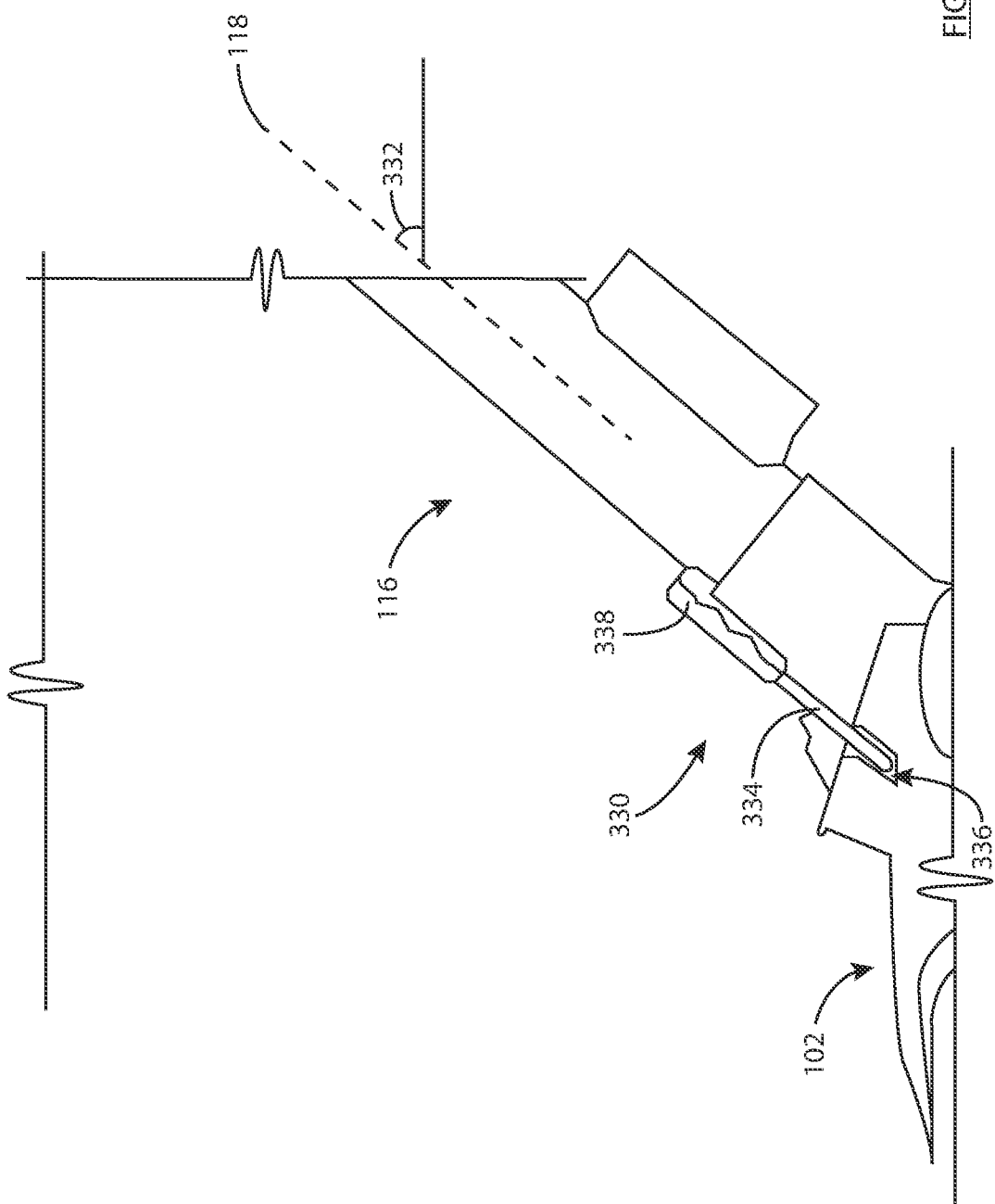
FIG. 44 is a schematic cross-sectional view of the portion of the embodiment FIG. 43, with the upright section in a reclined position.

Referring to FIG. 43, portions of one embodiment of a surface cleaning apparatus are shown having a recline limiter system 330 that can be engaged when the upright section 116 reaches a pre-determined recline angle threshold, i.e. when the recline angle 332 (FIG. 44) reaches a pre-determined value, such as about 45 degrees, about 30 degrees, about 22 degrees, about 20 degrees, about 15 degrees or about 10 degrees from the floor. When using the apparatus 100 in an extractor mode (i.e. to suck up liquids), the recline angle may be limited to about 22.5 degrees.

In this embodiment, the recline limiter system 330 includes a deployable blocking member in the form of a movable pin 334 that is mounted to the upright section 116 that can be inserted into a corresponding slot 336 on the surface cleaning head 102 (or the location of the pin 334 and slot 336 can be reversed). The pin 334 is biased using a suitable biasing mechanism, such as spring 338, such that when the upright section 116 reaches the predetermined recline angle 332, the pin 334 is aligned with and is extended into the slot 336 (FIG. 44) by the spring thereby inhibiting further reclining of the upright section 116 is inhibited. The spring may be set to automatically deploy the pin 334 when the unit is reclined to a set angle. Alternately, a user may be able to adjust the mechanism (e.g., the apparatus is being used only as a vacuum cleaner) so that the spring will not deploy the pin 334 (e.g., the spring may be disengaged from pin 334).

Figure 45:
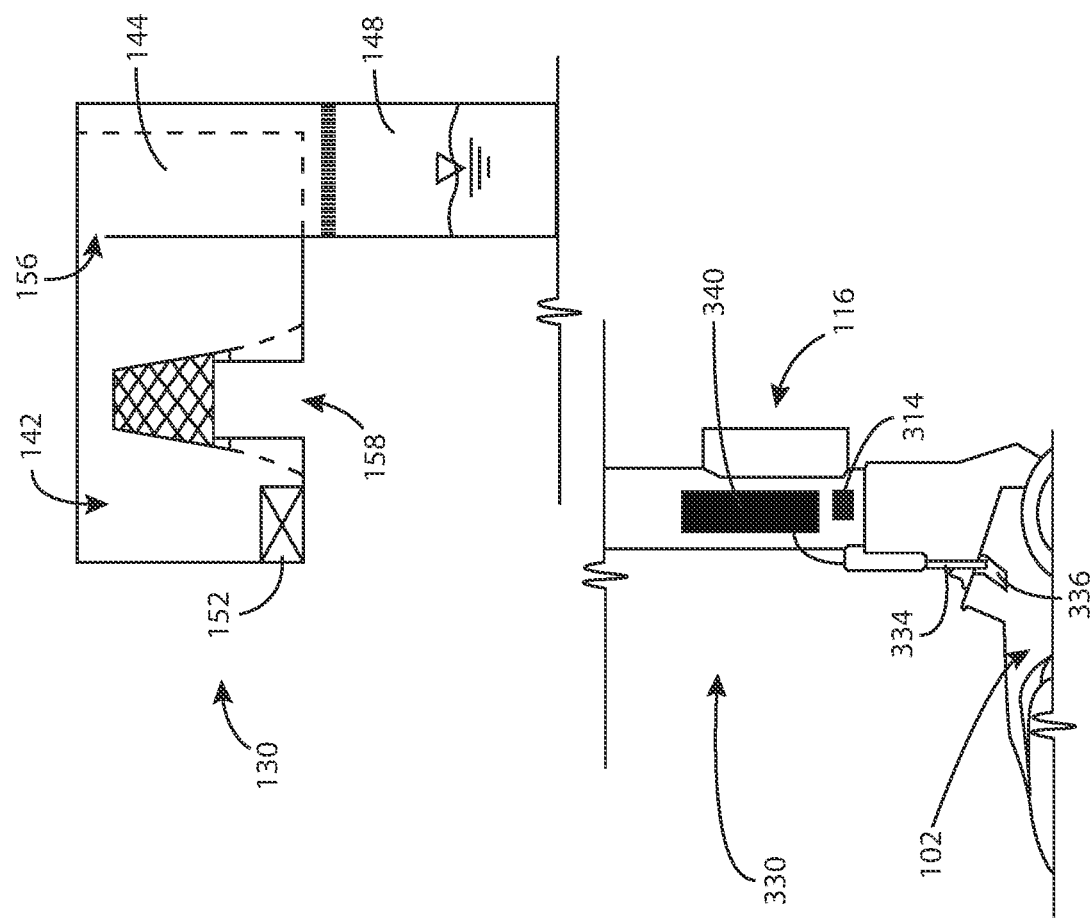
FIG. 45 is a schematic cross-sectional view of a portion of another embodiment of a surface cleaning apparatus in an upright position.
Figure 46:
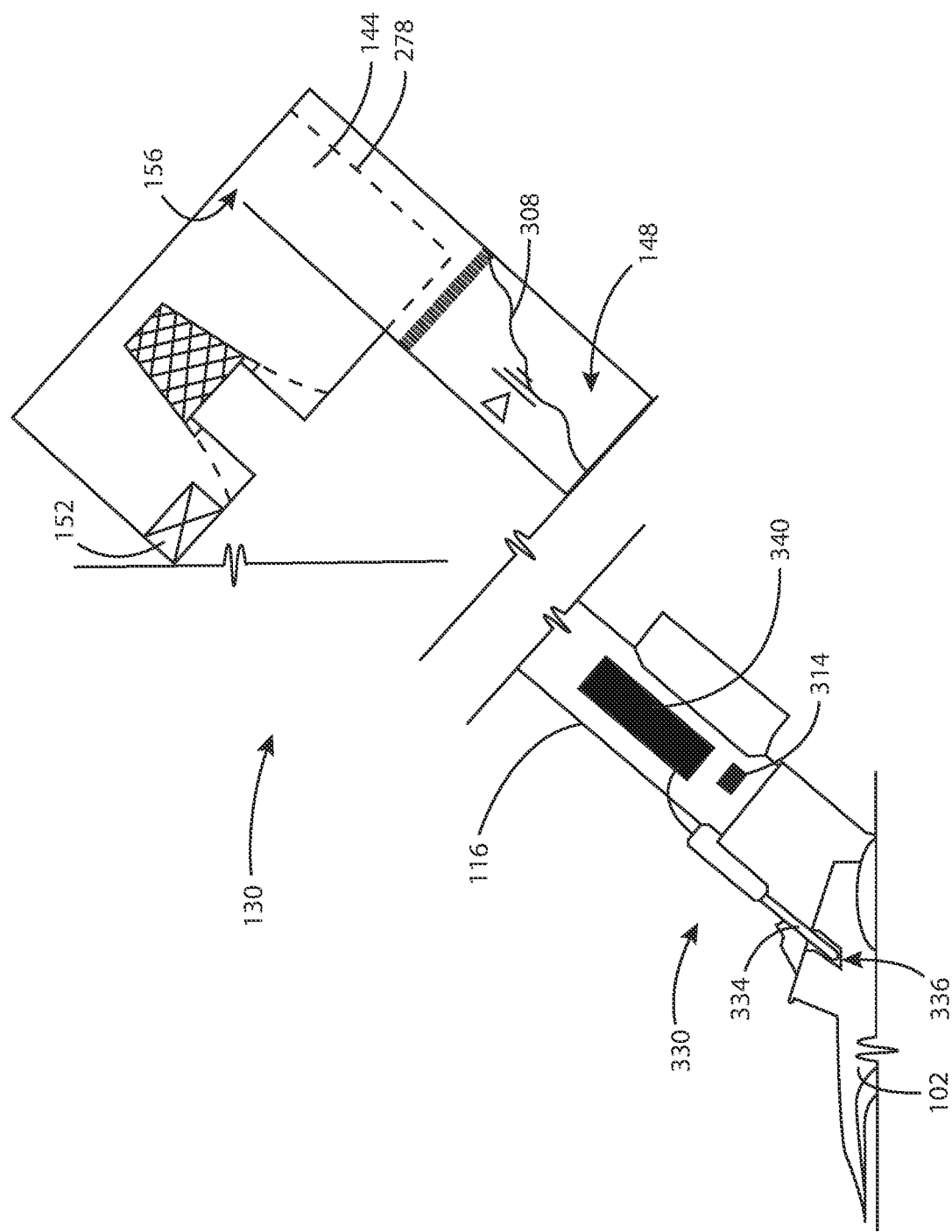
FIG. 46 is a schematic cross-sectional view of the portion of the embodiment FIG. 45, with the upright section in a reclined position.

Referring to FIGS. 45 and 46, in another embodiment the recline limiter system 330 can include a controller 340, instead of the spring 338. In this embodiment, the controller 340 can activate the locking pin 334 when a recline limiting event occurs which causes controller 340 to receive a recline limiting signal. For example, the controller can include a mode detector (e.g., a manually operated switch or a user actuates the liquid delivery system, or if the cleaning solution delivery system has been actuated or used by a user during a given cleaning session) that that can determine if the treatment unit 130 is being operated in a vacuum (i.e. dry only) or extractor mode (suctioning liquid). Alternately or in addition, the recline limiting system may also include an inclination sensor 314 (FIG. 46) to determine the recline angle of the upright section 116, a liquid level sensor for the reservoir 148 (e.g., a float switch, a moisture sensor in the reservoir 148) to determine the liquid level in the reservoir and/or a moisture sensor to determine if the apparatus is or has been used to extract water. The inclination sensor 314 (FIG. 46) may be integrated into the controller 340 as shown, or provided in a separate location if desired. A reclining limiting signal may be issued if, e.g., the inclination sensor detects that the upright section 116 has been reclined to a certain angle, the inclination sensor detects that the upright section 116 has been reclined to a certain angle and a liquid level sensor determines that a predetermined amount of water is in the reservoir 148, a moisture sensor determines that the apparatus has or is being used to collect liquid, the inclination sensor detects that the upright section 116 has been reclined to a certain angle and a moisture sensor determines that the apparatus has or is being used to collect liquid, the inclination sensor detects that the upright section 116 has been reclined to a certain angle and a mode sensor determines that the unit is being used as an extractor, or a mode sensor determines that the unit is being used as an extractor. If the controller 340 receives a recline limiting signal from a sensor, it may automatically deploy the locking pin 334 so it engages the slot 336 when the upright section 116 is reclines to a predetermined angle (the recline limit angle) that aligns the pin 334 with the slot 336, or when the controller 340 receives a signal from the inclination sensor 314 that corresponds to when the upright section 116 reaches the pre-determined recline limit (e.g. a recline angle of about 22.5 degrees).

Alternatively, if the controller 340 determines that the apparatus 100 is operating in a dry, vacuum-only mode, (for example if the cleaning solution delivery system has not been actuated) the controller 340 may not activate the locking pin 334, thereby permitting further reclining of the upright section 116 (past the extractor mode recline limit angle).

The liquid fill sensor may operate with the controller 340 to monitor the amount of liquid in the liquid collection container 148 and compare the current amount to a pre-determined recline liquid threshold amount. The controller 340 may then be operable to restrict the reclining of the upright section 116 if the liquid collection container 148 is filled to a level where backflow of the liquid may be likely—optionally, regardless of the current operating mode of the apparatus 100.

Figure 47:
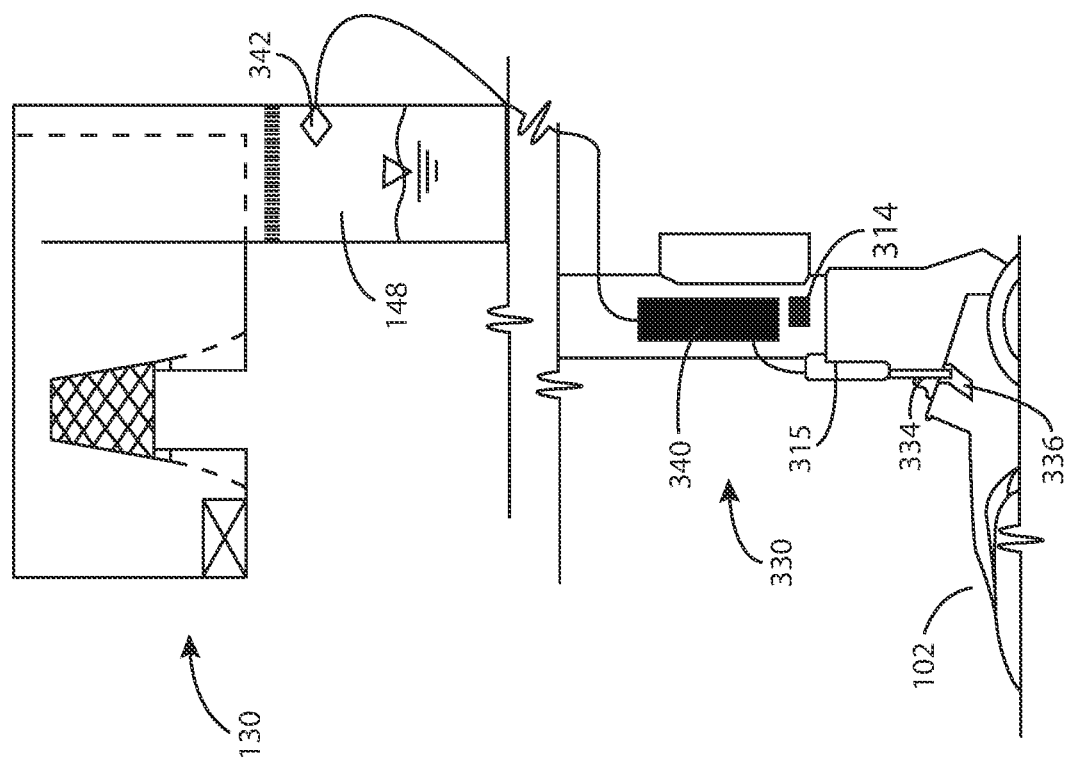
FIG. 47 is a schematic cross-sectional view of a portion of another embodiment of a surface cleaning apparatus in an upright position.
Figure 48:
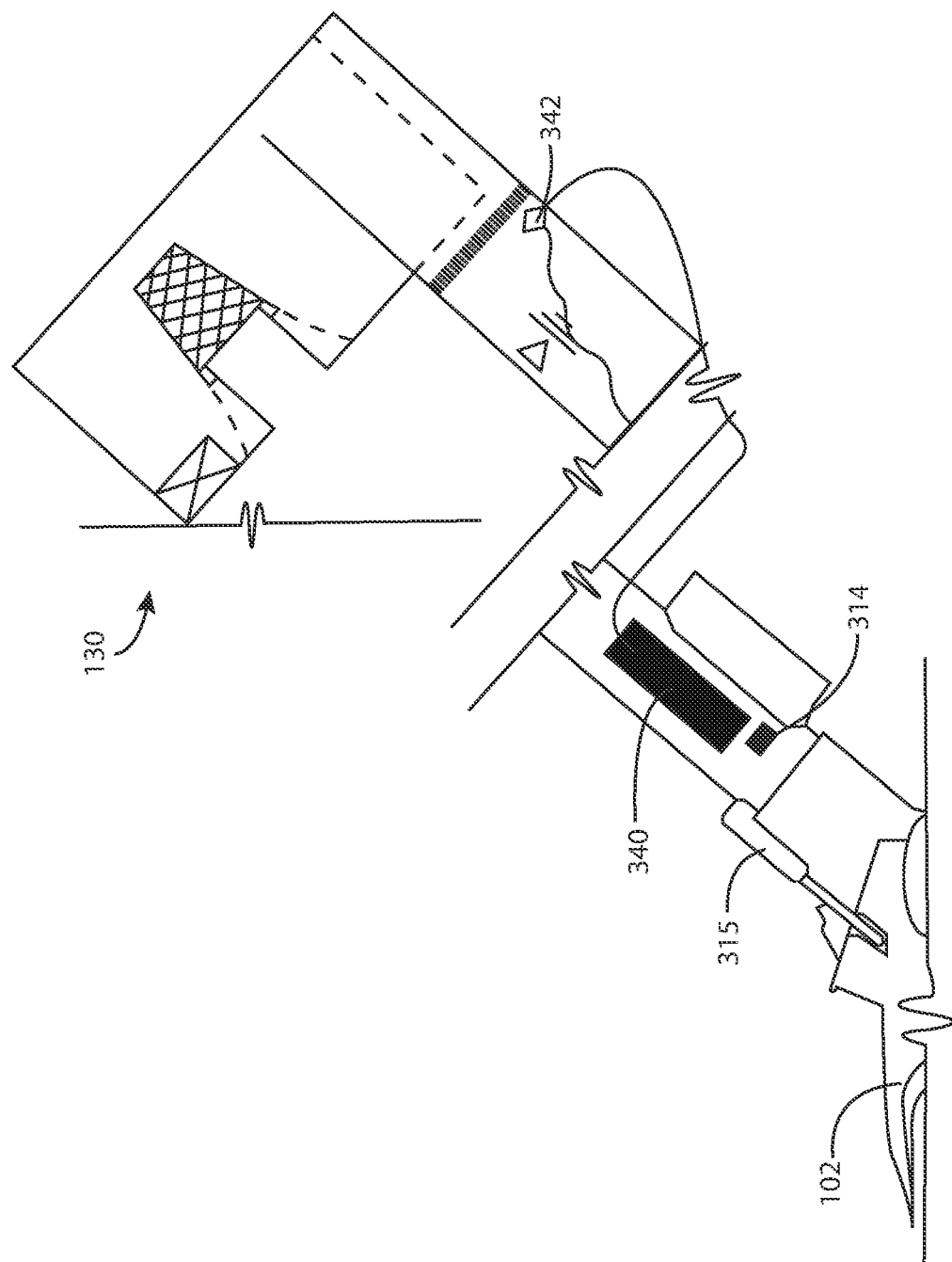
FIG. 48 is a schematic cross-sectional view of the portion of the embodiment FIG. 47, with the upright section in a reclined position.

As exemplified in FIGS. 47 and 48, the recline limiter system 330 includes a liquid level sensor, such as a moisture sensor 342 that can issue a water detection signal upon detecting water. Optionally, as discussed previously, the recline limiter system 330 may include both a moisture sensor 342 and an inclination sensor 314 (as shown in FIGS. 47 and 48), and the controller 340 can be operable to limit the reclining of the upright section 116 based on the signals issued from the moisture sensor 342, the inclination sensor or both.

Optionally, the recline limiter system 330 may also include a user feedback apparatus, such as a light, display screen, audible transducer or speaker and the like, to alert a user then the reclining of the upright section 116 has been limited, and optionally identifying the reason for such limitation. For example, the controller 340 in the embodiment of FIGS. 45 and 46 includes a user feedback apparatus that can alert a user, via a light, that reclining of the upright section 116 has been limited because the treatment unit 130, and/or overall apparatus, is operating in an extractor mode or that the liquid collection container 148 is holding too much liquid to allow further reclining. As exemplified, the sensor 342 may be positioned toward the upper end, and toward the rear side of the liquid collection container 148 where it may detect the liquid flowing along the rear wall as the treatment unit 130 is reclined (moving from the position of FIG. 47 to the position of FIG. 48). The sensor 342 can provide feedback to the controller 340, and may be used in combination with any other suitable controller features, including the mode detection apparatus, user feedback apparatus and angular position sensor. In the embodiments utilizing a controller 340 or the like, the pin 334 may be driven using a solenoid 315 (as shown in FIGS. 47 and 48) and/or any other suitable mechanical or electro-mechanical driving mechanism.

While some other operating components of the surface cleaning apparatus 100, such has the treatment unit 130, are shown schematically in FIGS. 43-48, the particular configuration of the surface cleaning apparatus 100 that incorporates the recline limiter system may differ in different examples, and may include upright-type surface cleaning apparatus (such as that shown in FIGS. 1-4), a hand held surface cleaning apparatus 100 connected to an elongate wand section (such as the embodiments shown in FIGS. 64-66).

While using a blocking member, such as pins 334, is one example of a mechanism that can be used to inhibit movement of the upright section, other embodiments of the recline limiter system 330 may include other types of limiting mechanisms. For example, the recline limiter system 330 may include intermeshing gears on the upright section 116 and surface cleaning head 102 that rotate with each other as the upright section 116 is reclined. The recline limiter system 330 may be able to lock or otherwise impede rotation of one at least one of the gears in response to a control signal (or physical actuator) to inhibit further rotation of the upright section 116 relative to the surface cleaning head 102. In other embodiments, the upright section 116 may include a rotor that rotates with the upright section 116, and the recline limiter system 330 may include caliper or other such apparatus that can be actuated to engage and prevent rotation of the rotor (e.g. a disc brake type system), thereby inhibiting movement of the upright section 116.

In another embodiment, a rearwardly extending groove may be provided instead of a slot 336. Accordingly, the pin 334 may be deployed onto the groove as soon as a condition is detected which causes the pin 334 to be deployed. Alternately, the pin 334 may be deployed into a rearwardly extending groove at all times and only withdrawn from the groove if the controller 340 does not detect an incline limiting event as a user moves to recline the unit past the recline limit.

Mode Control System

Optionally, as an alternative to limiting the reclining of the upright section 116, or in addition thereto, the apparatus 100 may be configured so that its operating modes are restricted when the upright section 116 is in a given orientation or moves past a given orientation. For example, controller 340 may be configured to both detect and optionally control the operating mode of the apparatus 100, and/or automatically shut off the suction motor 124 to help prevent liquid damage to the suction motor 124 upon receipt of a signal.

Optionally, the embodiments of FIGS. 45-48 may utilize a controller 340 that can automatically switch the apparatus 100 from an extractor or wet pick-up mode, to a dry, vacuum only mode or shut the apparatus off when the upright section 116 reaches the pre-determined recline angle or if another recline limiting event discussed previously occurs. This may include alerting the user, modifying the operation of the suction motor or other components, changing the air flow path, changing the operation of the surface cleaning head, deactivating the cleaning solution delivery system (to limit the dispensing of liquids) and the like.

The user feedback apparatus may be used to communicate this information to the user, and inform the user why the wet mode functionality is restricted or why the apparatus has switched off. It may also, optionally, prompt the user to raise the upright section 116 if the user would like to resume wet mode operations.

In accordance with this aspect, an auto shut off system (which includes controller 340) can be configured so that the controller 340 will automatically turn off the suction motor 124 upon the occurrence of a recline limiting event (e.g., prior to the upright section 116 reclining to a position at which recovered water contained in the liquid collection container 148 will flow back and enter the separator, e.g. cyclone chamber 142, or reach the suction motor 124).

In some embodiments, such as a hand held apparatus, which may be mounted on a wand 125 as the embodiments shown in FIG. 66C), the auto shut off system may be actuated in more than one range of motion. As exemplified in FIG. 66c, if wand 125 or the hand held apparatus when disconnected from wand 125 is pivoted rearwardly to the predetermined recline angle 332 the mode control system may automatically turn-off and/or inhibit activation of the suction motor 124. In this embodiment, an inclination sensor 314 maybe provided in the hand held surface cleaning apparatus 100 and may be operable to control the operation of the suction motor 124.

Optionally, it may also be desirable to limit the operation of the surface cleaning apparatus 100 when it is in a storage position (such as shown in FIG. 66B) and optionally until the upright section 116 has been reclined to a minimum floor cleaning angle, such as angle 462 measured from a vertical reference axis (FIG. 66C). That is, in the embodiment of FIG. 66C, the hand held surface cleaning apparatus 100 may be configured such that the suction motor 124 is rendered inoperable (i.e. automatically shut off or cannot be actuated) until the upright section is pivoted rearwardly past the minimum floor cleaning angle 462, and the inclination sensor 314 issues a corresponding inclination signal. The hand held surface cleaning apparatus 100 may then be usable in either the wet or dry operating modes until it reaches the predetermined recline angle 332.

If a recline limiting event has occurred, e.g., the hand held surface cleaning apparatus 100 has been used for wet cleaning (for example if a water detection signal has been produced by moisture sensor 342) the suction motor 124 may be automatically shut off when the upright section 116 reaches the predetermined recline angle 332 (e.g., when an inclination signal is issued by the inclination sensor 314). Alternatively, if a recline limiting event has not occurred (e.g., the hand held surface cleaning apparatus 100 has not been used for wet cleaning, for example if moisture has not been detected by moisture sensor 342) the hand held cleaning apparatus 100 may continue to operated when the upright section 116 reaches and/or passes the predetermined recline angle 332.

On Board Power Supply

In accordance with another aspect, which may be used with one or more of the other aspects disclosed herein, the surface cleaning apparatus 100 may include an onboard power supply, such as in the form of a battery pack 168 and can be operated as a cordless apparatus (see for example FIG. 9). The battery pack 168 may be relatively heavy as compared to some other components in the apparatus 100, and may be positioned toward the rear of the cleaning unit 120. This may help lower the overall centre of gravity of the cleaning unit 120 when reclined in the surface cleaning position. In the embodiment of FIG. 9, the battery pack 168 is located below a liquid reservoir apparatus 162, rearward of the second cleaning state 134 (i.e. cyclone chamber 142) and above the first separator 132.

In order to enhance the operational time of an apparatus 100 when battery operated, the apparatus may be configured in one or more of the following ways.

Optionally, the surface cleaning apparatus 100, and/or cleaning unit 120, can be arranged so that the suction motor housing 126 (containing the pre-motor filter 160, a pre-motor filter chamber 161 and suction motor 124) is immediately downstream from the treatment unit 130, meaning that there are no intervening structures or functional components of the surface cleaning apparatus 100 positioned in the fluid flow path between with cleaning unit 120 and motor housing 126, other than optionally one or more pre-motor filters. Optionally, the first separator 132 and second separator 134 may be arranged so that the second separator 134 is immediately downstream from the first separator 132, such that there are no intervening components in the fluid flow path between the first and second separators 132, 134. In some embodiments, such as, for example, the treatment unit 130 shown in FIG. 7, the second separator 134 may be directly adjacent and/or connected to the first separator 132, which may help reduce the length of the fluid flow path, and number of turns and changes of direction therein, between the first and second separators 132 and 134. This may help reduce backpressure in the system and/or may help reduce the weight of the treatment unit 130 by helping to reduce the length of conduits required to provide the fluid flow path. Reducing the back pressure enables an on board power supply to power the apparatus for a longer period of time.

Optionally, the first stage separator or a combined liquid and solid separator may be in the surface cleaning head. An advantage of such a design is that the water extracted from a surface need not be raised as high and this reduces the power required to operate the apparatus.

Optionally, the cleaning unit 120 may be removably mounted to, e.g., the upright section. In such a case, the first stage momentum separator, which may be in the surface cleaning head (see for example FIG. 13) or the upper section, may not be removable with the remainder of the cleaning unit. In such a case, battery pack 168 may be used to operate the cleaning unit as a vacuum cleaner in a portable operating mode.

Optionally, the wand and hose may only be used in an above floor cleaning mode.

The choice of power supply for a given apparatus may be based on a variety of criteria, including suction motor size and power requirements, desired run time, desired portability, desired overall weight and the like. While some embodiments are illustrated with battery packs and others with electrical cords, it is understood that any of the embodiments described herein may be provided with a battery pack, a power cord or optionally both.

What has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. An upright surface cleaning apparatus comprising:
   a) a surface cleaning head having a dirty fluid inlet;
   b) an upright section moveably mounted to the surface cleaning head, the upright section moveable between an upright storage position and a reclined surface cleaning position;
   c) a separator and a liquid collection chamber that receives recovered water, wherein the liquid collection chamber is provided on the upright section;
   d) a fluid flow path extending from the dirty fluid inlet to a clean air outlet, the first fluid flow path including the separator and a suction motor; and,
   e) a recline limiter system adapted to inhibit the upright section reclining to a positon at which recovered water enters the separator.

2. The upright surface cleaning apparatus of claim 1, wherein the recline limiter system comprises a moisture sensor which issues a signal upon detecting water and a blocking member which, upon issuance of the signal, deploys to inhibit rearward inclination of the upright section further than a particular inclination.

3. The upright surface cleaning apparatus of claim 2, wherein the particular rearward inclination of the upright section is an angle of from 15 to 30° from the floor.

4. The upright surface cleaning apparatus of claim 1, wherein the recline limiter off control system comprises an inclination sensor which issues a signal upon detecting a particular rearward inclination of the upright section and a blocking member which, upon issuance of the signal, deploys to inhibit rearward inclination of the upright section further than a particular inclination.

5. The upright surface cleaning apparatus of claim 4, wherein the particular rearward inclination of the upright section is an angle of from 15 to 30° from the floor.

6. The upright surface cleaning apparatus of claim 4, further comprising a cleaning solution delivery system comprising at least one spray nozzle that delivers at least one cleaning solution and the recline limiter system is actuated when the cleaning solution delivery system is actuated.

7. The upright surface cleaning apparatus of claim 1, wherein the recline limiter system comprises a moisture sensor which issues a water detection signal upon detecting water and an inclination sensor which issues an inclination signal upon detecting a particular rearward inclination of the upright section and the recline limiter system deploys a blocking member that inhibits rearward inclination of the upright section further than a particular inclination upon issuance of the signals.

8. The upright surface cleaning apparatus of claim 7, further comprising a solenoid which is actuated to deploy the blocking member upon issuance of the signals.

9. The upright surface cleaning apparatus of claim 1, wherein the separator comprises an inverted cyclone comprising, when the surface cleaning apparatus is in a floor cleaning orientation, a lower end and an upper end, the lower end having a cyclone fluid inlet and a cyclone fluid outlet and the upper end has a separated element outlet in communication with the collection chamber.

10. A surface cleaning apparatus comprising:
a) a surface cleaning head having a dirty fluid inlet;
b) an upright section moveably mounted to the surface cleaning head, the upright section moveable between an upright storage position and a reclined surface cleaning position;
c) a separator and a liquid collection chamber that receives recovered water,
wherein the liquid collection chamber is provided on the upright section and
surface cleaning apparatus is in a floor cleaning orientation, a lower end and an upper end, the lower end having a cyclone fluid inlet and a cyclone fluid outlet and the upper end has a separated element outlet in communication with the collection chamber;
d) a fluid flow path extending from the dirty fluid inlet to a clean air outlet, the first fluid flow path including the separator and a suction motor; and,
e) an auto shut off control system adapted to shut the suction motor off prior to the upright section reclining to a positon at which recovered water enters the separator.

11. The surface cleaning apparatus of claim 10, wherein the auto shut off control system comprises a moisture sensor which issues a signal upon detecting water and the auto shut off control system de-actuates the suction motor upon receipt of the signal.

12. A surface cleaning apparatus comprising:
a) a surface cleaning head having a dirty fluid inlet;
b) an upright section moveably mounted to the surface cleaning head, the upright section moveable between an upright storage position and a reclined surface cleaning position;
c) a separator and a liquid collection chamber that receives recovered water, wherein the liquid collection chamber is provided on the upright section;
d) a fluid flow path extending from the dirty fluid inlet to a clean air outlet, the first fluid flow path including the separator and a suction motor; and,
e) an auto shut off control system adapted to shut the suction motor off prior to the upright section reclining to a positon at which recovered water enters the separator,
wherein the auto shut off control system comprises an inclination sensor which issues a signal upon detecting a particular rearward inclination of the upright section and the auto shut off control system de-actuates the suction motor upon receipt of the signal.

13. The surface cleaning apparatus of claim 12, wherein the particular rearward inclination of the upright section is an angle of from 15 to 30° from the floor.

14. The surface cleaning apparatus of claim 12, further comprising a cleaning solution delivery system comprising at least one spray nozzle that delivers at least one cleaning solution and the auto shut off control system is actuated when the cleaning solution delivery system is actuated.

15. A surface cleaning apparatus comprising:
a) a surface cleaning head having a dirty fluid inlet;
b) an upright section moveably mounted to the surface cleaning head, the upright section moveable between an upright storage position and a reclined surface cleaning position;
c) a separator and a liquid collection chamber that receives recovered water, wherein the liquid collection chamber is provided on the upright section;
d) a fluid flow path extending from the dirty fluid inlet to a clean air outlet, the first fluid flow path including the separator and a suction motor; and,
e) an auto shut off control system adapted to shut the suction motor off prior to the upright section reclining to a positon at which recovered water enters the separator,
wherein the auto shut off control system comprises a moisture sensor which issues a water detection signal upon detecting water and an inclination sensor which issues an inclination signal upon detecting a particular rearward inclination of the upright section and the auto shut off control system de-actuates the suction motor when both signals are issued.

16. The surface cleaning apparatus of claim 10, further comprising a cleaning solution delivery system comprising at least one spray nozzle that delivers at least one cleaning solution and the auto shut off control system comprises an inclination sensor which issues a first inclination signal that inhibits the actuation of the suction motor until the upright section has been reclined beyond an initial angular degree of rotation of the upright section from the upright storage position.

17. The surface cleaning apparatus of claim 16, wherein the auto shut off control system comprises a moisture sensor which issues a water detection signal upon detecting water and the inclination sensor issues a second inclination signal upon detecting a particular rearward inclination of the upright section and the auto shut off control system de-actuates the suction motor when both the water detection signal and the second inclination signals are issued.

18. The surface cleaning apparatus of claim 17, wherein the inclination sensor comprises a single inclination sensor which issues both the first and second inclination signals.

19. The surface cleaning apparatus of claim 17, wherein the surface cleaning apparatus is a hand held surface cleaning apparatus.

* * * * *